US011442059B2

(12) United States Patent
Dong et al.

(10) Patent No.: US 11,442,059 B2
(45) Date of Patent: Sep. 13, 2022

(54) METHOD FOR TREATING A CHRONIC ITCH CONDITION BY ADMINISTERING SMALL MOLECULE MRGPRX4 ANTAGONISTS

(71) Applicant: The Johns Hopkins University, Baltimore, MD (US)

(72) Inventors: Xinzhong Dong, Clarksville, MD (US); Chirag Vasavda, Baltimore, MD (US); Solomon H. Snyder, Baltimore, MD (US); James Meixiong, Baltimore, MD (US); Yingying Cheng, Baltimore, MD (US); Nathachit Limjunyawong, Baltimore, MD (US); Xintong Dong, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 65 days.

(21) Appl. No.: 16/623,279

(22) PCT Filed: Jun. 15, 2018

(86) PCT No.: PCT/US2018/037870
§ 371 (c)(1),
(2) Date: Dec. 16, 2019

(87) PCT Pub. No.: WO2018/232316
PCT Pub. Date: Dec. 20, 2018

(65) Prior Publication Data
US 2020/0173985 A1    Jun. 4, 2020

Related U.S. Application Data

(60) Provisional application No. 62/520,812, filed on Jun. 16, 2017.

(51) Int. Cl.
*C07K 14/72* (2006.01)
*G01N 33/50* (2006.01)
*C12N 15/64* (2006.01)
*G01N 33/15* (2006.01)
*G01N 33/74* (2006.01)

(52) U.S. Cl.
CPC ....... *G01N 33/5041* (2013.01); *C07K 14/723* (2013.01); *C12N 15/64* (2013.01); *G01N 33/15* (2013.01); *G01N 33/74* (2013.01); *G01N 2333/726* (2013.01)

(58) Field of Classification Search
CPC .... G01N 33/15; G01N 33/5041; G01N 33/74; G01N 2333/726; C07K 14/723; C12N 15/64
See application file for complete search history.

(56) References Cited

FOREIGN PATENT DOCUMENTS

| WO | 2010046706 A1 | 4/2010 |
| WO | 2014/202515 A1 | 12/2014 |
| WO | 2016/019246 A1 | 2/2016 |
| WO | 2016118632 A1 | 7/2016 |
| WO | 2020198537 A1 | 10/2020 |

OTHER PUBLICATIONS

Tiwari, "Mas-Related G Protein-Coupled Receptors Offer Potential New Targets for Pain Therapy," from http://www.ncbi.nlm.nih.gov/pubed/26900065, 2016.
Kiatsurayanon et al., "Angiogenic Peptide Activates Human Keratinocytes to Produce Cytokines/Chemokines and to Migrate and ProliferateviaMrgX Receptors," Journal of Dermatological Science, 83:3, pp. 190-199, 2016.
Wang et al., "Salusin @b is a Surrogate Ligand of the Mas-Like G Protein-Coupled Receptor MrgA1," European Journal of Pharmacology, Elsevier Science, 539:3,pp. 145-150, 2006.
Lembo et al., "Proenkephalin A Gene Products Activate a New Family of Sensory Neuron-Specific," Nature Neuroscience, Nature America, Inc., 5:3, pp. 1097-6256, 2002.
Grazzini et al., "Sensory Neuron-Specific Receptor Activation Elicits Central and Peripheral Nociceptive Effects in Rats," Proceedings of the National Academy of Sciences, 101:18, pp. 7175-7180, 2004.
Sang-Kyou Han et al., "Orphan G Protein-Coupled Receptors MrgA1 and MrgC11 are distinctively Activated by RF-Amide-Related Peptides through the Galphq/11 Pathway," Proceedings of the National Academy of Sciences, National Academy of Sciences, 99:23, pp. 14740-14745, 2002.
Azimi Ehsan et al., "Substance P Activates Mas-Related G Protein-Coupled Receptors to Induce Itch," Journal of Allergy and Clinical Immunology, 140:2, p. 447, 2017.
Meixiong et al., "MRGPRX4 is a G Protein-Coupled Receptor Activated by Bile Acids that May Contribute to Cholestatic Pruritus," Proceedings of the National Academy of Sciences, 116:21, pp. 10525-10530, 2019.
Takashi et al., "Itching as a Systemic Disease," Journal of Allergy and Clinical Immunology, 144:2, pp. 375-380, 2019.
Shtessel et al., "MRGPRX2 Activation Causes Increased Skin Reactivity in Patients with Chronic Spontaneous Urticaria," Journal of Investigative Dermatology, pp. 1-5, 2020.
Perner, et al., "Substance P Release by Sensory Neurons Triggers Dendritic Cell Migration and Initiates the Type-2 Immune Response to Allergens," Immunity, Cell Press, Amsterdam, 53:5, p. 1063, 2020.
Meixiong, "Identification of a Bilirubin Receptor that may Mediate a Component of Cholestatic Itch," pp. 1-24, 2019.
European Search Report dated Apr. 27, 2021 from Corresponding EP Application No. 18816786.0, pp. 1-21.
Kroeze, WK et al., "PRESTO-TANGO: an open-source resource for interrogation of the druggable human GPCR-ome." Nature Structural and Molecular Biology, May 2015, Epub Apr. 20, 2015, vol. 22, No. 5; pp. 362-369 (21 pages).

(Continued)

*Primary Examiner* — Robert S Landsman
(74) *Attorney, Agent, or Firm* — Fox Rothschild LLP

(57) ABSTRACT

The present invention relates to cells and methods for detecting compounds that affect G protein coupled receptor mediated conditions. The invention also relates to methods for treating adverse drug reactions, autoimmune disorders, and pruritus.

3 Claims, 73 Drawing Sheets

Specification includes a Sequence Listing.

(56) References Cited

OTHER PUBLICATIONS

International Search Report and Written Opinion of International Application No. PCT/US18/37870, dated Nov. 7, 2018 (15 pages).
Aoki Junken et al, Special Lecture 2, Identification and functional analysis of GPCRs responsive to oxidized phospholipids, Vitamins (Japanese), vol. 89, No. 7, pp. 359-360, 2015.
Office Action from countepart Japanese Patent Application No. 2019-569449, dated Jul. 14, 2022, 8 pages.

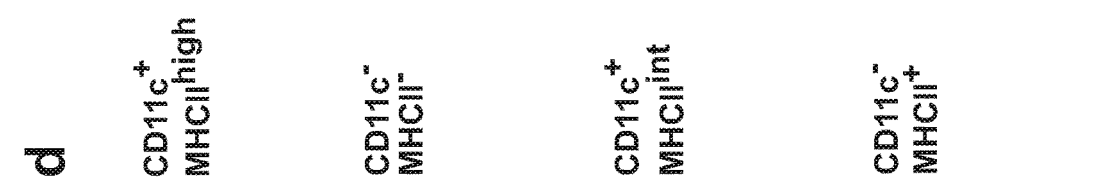

FIG. 22

| | Hematin (100nM) | Bilirubin 100µM | Bilirubin 50µM | Stercobilin 1mM | Urobilinogen 1mM | Conjugated Bilirubin 1mM | Deoxycholic Acid 100µM | Morphine 1.75mM | DAMGO 1mM |
|---|---|---|---|---|---|---|---|---|---|
| mrgprA1 | + 40-50% | - | + 40-50% | + 60-70% | - | + 15-20% | - <1% | - | - <1% |
| mrgprA3 | - | - | - | - | - | - | - | - | - |
| MRGPRX1 | - | - | - | - | - | - | - | - | - |
| MRGPRX4 | - | + 10-15% | + >80% | + 40-50% | + 60-70% | + 50-60% | + >80% | - | - | e-2

Urobilinogen

↑ *Bacterial Dehydrogenases*

Stercobilin

↑ *Bacterial Oxidases*

FIG. 29A a

```
WT  55  GCAGGGTTTCTAGCCCTAAACACATCGGCCTCGCCAACAGCACCCAC  101
A1      GCAGGGTTTCTAGCCCTAAA--CATCGGCCTCGCCAACAGCACCCAC
        *******************   ************************
```

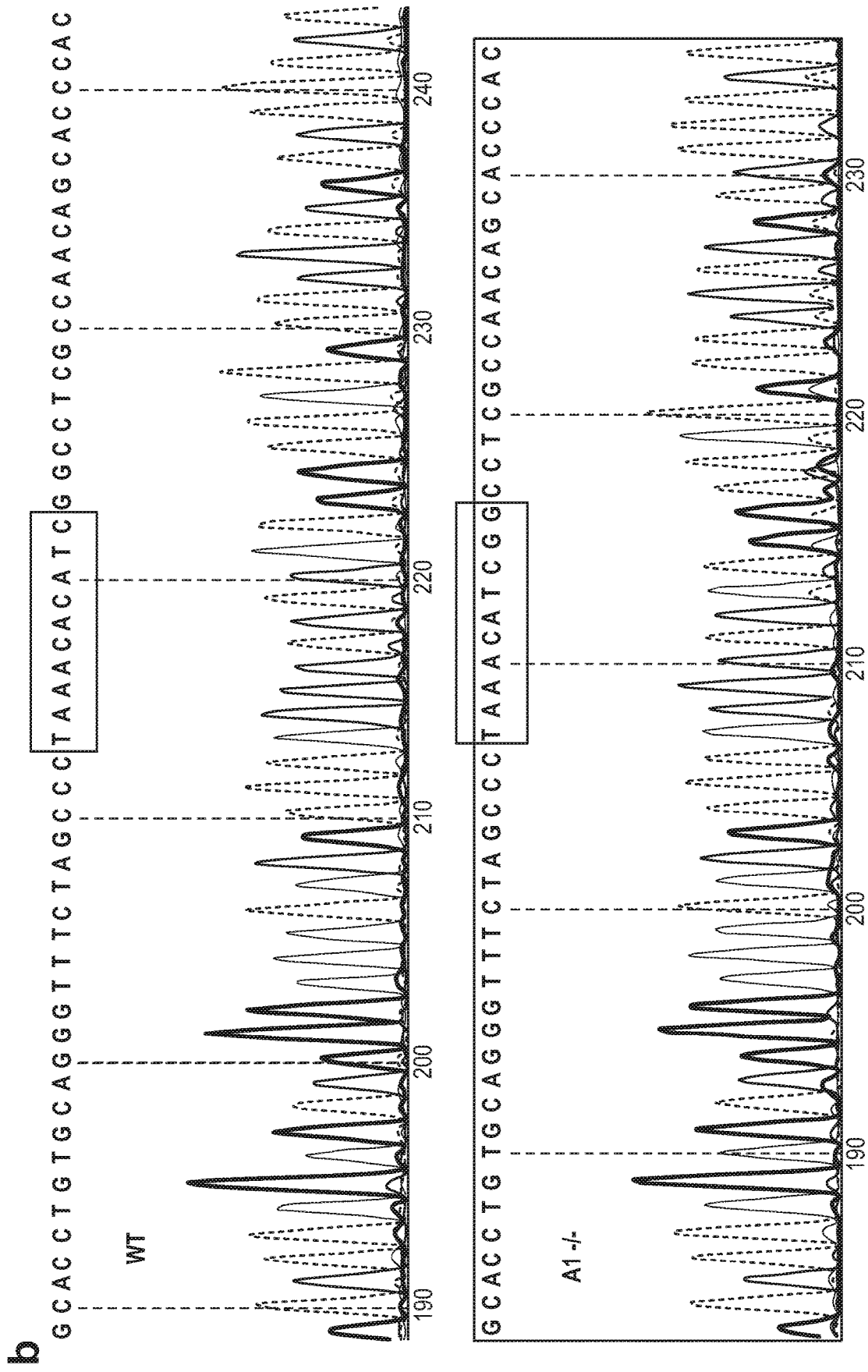

FIG. 29C c

A1-/-  atgggggaaagcagcagcacctgtgcagggtttctagccctaaacatcggcctcgccaacagcaccacaacactaa
       taccccctttcgtcgtggacacgtcccaaagatcgggattgtagccggagcggttgtcgtggtgttgttgatt
       Met Gly Glu Ser Ser Thr Cys Ala Gly Phe Leu Ala Gly Phe Leu Ala Leu Asn Ile Gly Leu Ala Asn Ser Thr His Asn Asn * a b a b c

METHOD FOR TREATING A CHRONIC ITCH CONDITION BY ADMINISTERING SMALL MOLECULE MRGPRX4 ANTAGONISTS

RELATED APPLICATIONS

This application is national stage application, filed under 35 U.S.C. § 371 of International Application No. PCT/US18/37870, filed Jun. 15, 2018, which claims the benefit of priority to U.S. Provisional Application No. 62/520,812 filed on Jun. 16, 2017. The entire contents of these applications are incorporated herein by reference in their entirety.

STATEMENT AS TO FEDERALLY SPONSORED RESEARCH

This invention was made with government support under R01NS054791 and MH18501 awarded by the National Institutes of Health. The government has certain rights in the invention.

INCORPORATION BY REFERENCE OF SEQUENCE LISTING

The contents of the text file named "048317-539001WO sequence listing 08022018_ST25.TXT," which was created on Aug. 2, 2018, and is 1,807 bytes in size, are hereby incorporated by reference in their entireties and for all purposes.

BACKGROUND

G protein coupled receptor mediated disorders including chronic itch (e.g., pruritus), inflammation disorders, autoimmunity, skin disorders, and adverse drug reactions cause suffering. Much is unknown regarding the pathology of G protein coupled mediated disorders. There is an unmet need for treating G protein coupled receptor mediated disorders.

SUMMARY INVENTION

The invention is based, in part, on the identification of a novel G protein-coupled receptor: human MrgprX4 and mouse MrgprA1. MrgprX4 and MrgprA1 are expressed in a specific type of innate immune cell and mediate Stevens Johnson Syndromes (SJS) and are likely involved in autoimmune diseases. MrgprX4 and MrgprA1 are activated by many SJS causing drugs including lamotrigine and allopurinol. In addition, MrgprX4 and MrgprA1 are also expressed in sensory neurons and are important for itch sensation and cholestatic pruritus. In some embodiments, MrgprX4 and MrgprA1 are receptors for bilirubin. As described herein, prior to this discovery, no bilirubin receptor has been identified. In some embodiments, human MrgprX4 is a drug target for SJS, autoimmune diseases such as multiple sclerosis, cholestatic pruritus and other chronic itch conditions. As described herein, a role of MrgprX4 in any biological process and disease was completely unknown prior to this discovery. In some embodiments, MrgprX4 expressing cell-based assays (MrgprX4 cell line and cDNA, and MrgprA1 mutant mouse line) are used to screen and test drugs targeting these reactions. As described herein, MrgprX4-expressing cell lines are completely novel and used for high through-put screening for drug screening. In some embodiments, blocking MrgprX4 is a novel way to treat SJS; autoimmune diseases such as multiple sclerosis; and cholestatic pruritus and other chronic itch conditions.

In a preferred aspect, provided is a method for screening for drug agents that modulate one or more G protein coupled receptor-mediated conditions or disorders, the method comprising: (1) contacting one or more cells expressing a G protein coupled receptor with a candidate drug agent; and (2) detecting a response of the one or more cells to thereby select the candidate drug agent for evaluation to modulate a G protein coupled receptor-mediated condition or disorder. Suitably, a response of the cells is detected as activation of the G protein coupled receptor. The method may further comprises determining whether the candidate drug agent modulates a G protein coupled receptor-mediated condition or disorder.

The invention is also based, in part, on the discovery that human MrgprX3 and its mouse homologue MrgprA6 are expressed in keratinocytes, epithelial cells, and primary sensory neurons in dorsal root ganglion (DRG). It was also discovered that antimicrobial peptides defensin and cathelicidin are agonists of MrgprX3 and MrgprA6. Defensins and cathelicidin may play roles in multiple diseases and conditions including wound healing, chronic inflammation, malignant transformations, skin diseases such as psoriasis and dermatitis, airways disorders, intestinal and GI tract disorders, pain, and itch. In some embodiments, targeting MrgprX3 and MrgprA6 treats wound healing, chronic inflammation, malignant transformations, skin diseases such as psoriasis and dermatitis, airways disorders, intestinal and GI tract disorders, pain, and itch. As described herein, the role of MrgprX3 in any biological process and disease was previously unknown. In some embodiments, MrgprX3 expressing cell-based assays and MrgprA6 mutant mice are used to screen and test drugs targeting these reactions. As described herein, MrgprX3-expressing cell lines are novel and used for high through-put screening for drug screening.

Further provided herein are methods for using MrgprX3 and MrgprX4 expressing cell-based assays to screen for drugs targeting these receptors. The present invention also provides for MrgprX3- and MrgprX4-expressing cell lines for high through-put screening for drug candidates. In some embodiments, blocking MrgprX4 treats adverse drug reactions (e.g., SJS), cholestatic pruritus and other chronic itch conditions, and autoimmune diseases (e.g., multiple sclerosis). In some embodiments, blocking MrgprX3 treats wound healing, chronic inflammation, malignant transformations, skin diseases such as psoriasis and dermatitis, airway and GI tract disorders, pain and itch.

The invention is also based, in part, on an isolated cell comprising a recombinant nucleic acid that expresses mas-related G-protein coupled receptor member X3 (MrgprX3) or MrgprX4. For example, the recombinant nucleic acid expresses MrgprX3. Alternatively, the recombinant nucleic acid expresses MrgprX4. In other cases, the recombinant nucleic acid that expresses MrgprX3 comprises one or more mutations. For example, the one or more mutations produce an MrgprX3 protein incapable of activating a signal transduction pathway. Alternatively, the recombinant nucleic acid that expresses MrgprX4 comprises one or more mutations. For example, the one or more mutations produce an MrgprX4 protein incapable of activating a signal transduction pathway. In some embodiments, the cell is selected from immune cells, nerve cells, and skin cells. In some embodiments, the immune cells are selected from innate immune cells. In some embodiments, the cells are selected from stem cells. In some embodiments the cells are selected from a cell line. In some embodiments, the cells are primary cells. In some embodiments, the cells are obtain from a mammal. In some embodiments, the nerve cells consist of primary sensory neurons in dorsal root ganglia. In some embodiments, the immune cells consist of dendritic cells. In some embodiments, MrpgrX4 or MrpgrA1 are expressed in dendritic cells and primary sensory neurons in dorsal root ganglion. In some embodiments, the skin cells are keratinocytes.

The invention is also based, in part, on a recombinant nucleic acid that expresses mas-related G-protein coupled receptor member X3 (MrgprX3) or MrgprX4. For example, the recombinant nucleic acid is an expression vector and expresses MrgprX3. Alternatively, the recombinant nucleic acid expresses MrgprX4. In other cases, the recombinant nucleic acid that expresses MrgprX3 comprises one or more mutations. For example, the one or more mutations produce an MrgprX3 protein incapable of activating a signal transduction pathway. Alternatively, the recombinant nucleic acid that expresses MrgprX4 comprises one or more mutations. For example, the one or more mutations produce an MrgprX4 protein incapable of activating a signal transduction pathway. In some embodiments, a vector comprises a nucleic acid sequence encoding a mas-related G-protein coupled receptor member X3 (MrgprX3) or MrgprA6. In some embodiments, a vector comprises a nucleic acid sequence encoding MrgprX3 nucleic acid sequence comprising one or more mutations. In some embodiments, a vector comprises a nucleic acid sequence encoding a MrgprA6 nucleic acid sequence comprising one or more mutations. In some embodiments, a vector comprises a nucleic acid sequence encoding a mas-related G-protein coupled receptor member X4 (MrgprX4) or MrgprA1. In some embodiments, a vector comprises a nucleic acid sequence encoding a MrgprX4 nucleic acid sequence comprising one or more mutations. In some embodiments, a vector comprises a nucleic acid sequence encoding a MrgprA1 nucleic acid sequence comprising one or more mutations.

Provided herein are methods for screening for drugs that modulate G protein coupled receptor-mediated conditions or disorders comprising: contacting a cell expressing a G protein coupled receptor with a candidate drug; detecting the activation of the G protein coupled receptor; determining whether the candidate drug modulates the G protein coupled receptor-mediated condition or disorder. In some embodiments, the G protein coupled receptor is selected from MrgprX4 and MrgprX3. In some embodiments, the G protein coupled receptor-mediated condition is selected from adverse drug reactions, autoimmune disorders, multiple sclerosis, pain, pruritus, cholestatic pruritus, inflammation disorders, malignant transformations, skin disorders, and wound healing. In some embodiments, the cell is selected from immune cells, nerve cells, and skin cells. In some embodiments, the immune cells are selected from innate immune cells. In some embodiments, the cells are selected from stem cells. In some embodiments the cells are selected from a cell line. In some embodiments, the cells are primary cells. In some embodiments, the cells are obtain from a mammal. In some embodiments, the nerve cells consist of primary sensory neurons in dorsal root ganglia. In some embodiments, the immune cells consist of dendritic cells. In some embodiments, MrpgrX4 or MrpgrA1 are expressed in dendritic cells and primary sensory neurons in dorsal root ganglion. In some embodiments, the skin cells are keratinocytes. In some embodiments, activation of MrgprX3 or MrgprX4 is detected by identifying an increase in intracellular calcium.

Also provided herein are methods of treating a G protein coupled receptor-mediated condition in a subject, the method comprising administering an MrgprX3 or MrgprA6 antagonist to the subject, thereby treating the G protein coupled receptor-mediated condition. In some embodiments, the G protein coupled receptor-mediated condition is selected from pain, pruritus, cholestatic pruritus, inflammation disorders, malignant transformations, skin disorders, and wound healing.

Further provided are methods of treating a G protein coupled receptor-mediated condition in a subject, the method comprising administering an MrgprX3 or MrgprA6 agonist to the subject, thereby treating the G protein coupled receptor-mediated condition. In some embodiments, the G protein coupled receptor-mediated condition is selected from pain, pruritus, cholestatic pruritus, inflammation disorders, and skin disorders (e.g. psoriasis and atopic dermatitis).

In some embodiments of such methods, the antagonist or agonist comprises an antibody or fragment thereof, a binding protein, a polypeptide, or any combination thereof. In some embodiments, the antagonist or agonist comprises a small molecule. In some embodiments, the antagonist or agonist comprises a nucleic acid molecule. In some embodiments, the nucleic acid molecule comprises double stranded ribonucleic acid (dsRNA), small hairpin RNA or short hairpin RNA (shRNA), or antisense RNA, or any portion thereof. In some embodiments of such methods, the antagonist or agonist is administered prior to, simultaneously with, or subsequent to administering the compound to the subject. In some embodiments, the antagonist or agonist is administered topically, orally, via inhalation, or via injection.

Also provided herein are methods of treating a G protein coupled receptor-mediated condition in a subject, the method comprising administering an MrgprX4 or MrgprA1 antagonist to the subject, thereby treating the G protein coupled receptor-mediated condition. In some embodiments of such methods, the G protein coupled receptor-mediated condition is selected from adverse drug reactions such as Stevens-Johnson Syndrome (SJS) and toxic epidermal necrolysis (TEN), autoimmune disorders, multiple sclerosis, pain, pruritus, and cholestatic pruritus.

Further provided are methods of treating a G protein coupled receptor-mediated condition in a subject, the method comprising administering an MrgprX4 or MrgprA1 agonist to the subject, thereby treating the G protein coupled receptor-mediated condition. In some embodiments of such methods, the G protein coupled receptor-mediated condition is selected from adverse drug reactions, autoimmune disorders, pruritus, and cholestatic pruritus.

In some embodiments of such methods, the antagonist or agonist comprises an antibody or fragment thereof, a binding protein, a polypeptide, or any combination thereof. In some embodiments, the antagonist comprises a small molecule. In some embodiments, the antagonist or agonist comprises a nucleic acid molecule. In some embodiments, the nucleic acid molecule comprises double stranded ribonucleic acid (dsRNA), small hairpin RNA or short hairpin RNA (shRNA), or antisense RNA, or any portion thereof. In some embodiments, the antagonist or agonist is administered prior to, simultaneously with, or subsequent to administering the compound to the subject. In some embodiments of such methods, the antagonist or agonist is administered topically, orally, via inhalation, or via injection.

Also provided herein are methods for reducing the severity of an adverse drug reaction in a subject that is induced by administering a compound, the method comprising: administering the compound to a subject; administering an MrgprA1 or MrgprX4 antagonist or agonist to the subject, thereby reducing the severity of an adverse drug reaction in the subject.

Also provided herein are methods for determining whether a subject has an increased risk of developing an adverse drug reaction to a compound, the method comprising: obtaining a test sample from a subject having or at risk of developing an adverse drug reaction to a compound; determining the expression level of at least one G protein coupled receptor gene in the test sample; comparing the expression level of the G protein coupled receptor gene in the test sample with the expression level of the G protein coupled receptor gene in a reference sample; and determining that administering the compound to the subject will induce an adverse drug reaction if the expression level of the G protein coupled receptor gene in the test sample is differentially expressed as compared to the level of the G protein coupled receptor gene in the reference sample. In some embodiments, the G protein coupled receptor gene is MrgprA1 or MrgprX4. In some embodiments, the MrgprA1 or MrgprX4 is a mutant.

Also provided herein are pharmaceutical compositions for the treatment of a G protein coupled receptor-mediated condition or disorder, the composition comprising an effective amount a G protein coupled receptor antagonist or agonist. In some embodiments, the G protein coupled receptor antagonist is an MrgprX4 or MrgprX3 antagonist or dual/multivalent antagonist of MrgprX3, MrgprX4, and other Mrgpr members. In certain other embodiments, the G protein coupled receptor agonist is an MrgprX4 or MrgprX3 agonist. In some embodiments, the antagonist or agonist is selected from the group comprising an antibody or fragment thereof, a binding protein, a polypeptide, a small molecule, a nucleic acid, or any combination thereof. In some embodiments, the antagonist or agonist is administered topically, orally, via inhalation, or via injection. In some embodiments, the G protein coupled receptor condition or disorder is selected from adverse drug reactions, autoimmune disorders, multiple sclerosis, pain, pruritus, cholestatic pruritus, inflammation disorders, malignant transformations, skin disorders, and wound healing.

Further provided are kits that comprise 1) a pharmaceutical composition as disclosed herein and 2) written instructions for treating the G protein coupled receptor condition or disorder. The pharmaceutical composition suitably may comprise an effective amount a G protein coupled receptor antagonist such as an MrgprX4 or MrgprX3 antagonist. In other embodiments, the pharmaceutical composition suitably may comprise an effective amount a G protein coupled receptor antagonist such as an MrgprX4 or MrgprX3 agonist. The written instructions may be for example a label or packaging insert that disclose use of the pharmaceutical composition to treat for example adverse drug reactions, autoimmune disorders, multiple sclerosis, pain, pruritus, cholestatic pruritus, inflammation disorders, malignant transformations, skin disorders, and/or wound healing.

Also provided herein are compositions of an isolated cell comprising a recombinant nucleic acid that expresses mas-related G-protein coupled receptor member X3 (MrgprX3) or MrgprA6. In some embodiments, the recombinant nucleic acid expresses MrgprX3. In some embodiments, the recombinant nucleic acid expresses MrgprA6. In some embodiments, the recombinant nucleic acid that expresses MrgprX3 comprises one or more mutations. In some embodiments, the one or more mutations produces an MrgprX3 protein incapable of activating a signal transduction pathway. In some embodiments, the recombinant nucleic acid that expresses MrgprA6 comprises one or more mutations. In some embodiments, the one or more mutations produces an MrgprA6 protein incapable of activating a signal transduction pathway. In some embodiments, the isolated cell comprises a human embryonic kidney 293 (HEK 293) cell.

Also provided herein are compositions of an isolated cell comprising a recombinant nucleic acid that expresses mas-related G-protein coupled receptor member X4 (MrgprX4) or MrgprA1. In some embodiments, the recombinant nucleic acid expresses MrgprX4. In some embodiments, the recombinant nucleic acid expresses MrgprA1. In some embodiments, the recombinant nucleic acid that expresses MrgprX4 comprises one or more mutations. In some embodiments, the one or more mutations produce an MrgprX4 protein incapable of activating a signal transduction pathway. In some embodiments, the recombinant nucleic acid that expresses MrgprA1 comprises one or more mutations. In some embodiments, the one or more mutations produce an MrgprA1 protein incapable of activating a signal transduction pathway. In some embodiments, the isolated cell comprises a human embryonic kidney 293 (HEK 293) cell.

Also provided herein are methods for identifying an antagonist of MrgprX3 or MrgprA6 comprising: contacting the isolated cell (e.g. an isolated cell comprising a recombinant nucleic acid that expresses mas-related G-protein coupled receptor member X3 (MrgprX3) or MrgprA6) with a compound that induces a pseudo-allergic-type reaction, contacting the isolated cell with a candidate antagonist, detecting activation of MrgprX3 or MrgprA6, wherein a decrease in activation of MrgprX3 or MrgprA6 relative to the activation of MrgprX3 or MrgprA6 in the absence of the compound determines that the candidate compound is an antagonist.

Further provided are methods for identifying an agonist of MrgprX3 or MrgprA6 comprising: contacting the isolated cell (e.g. an isolated cell comprising a recombinant nucleic acid that expresses mas-related G-protein coupled receptor member X3 (MrgprX3) or MrgprA6) with a compound that induces an adverse drug reaction, contacting the isolated cell with a candidate agonist, detecting activation of MrgprX3 or MrgprA6, wherein an increase in activation of MrgprX3 or MrgprA6 relative to the activation of MrgprX3 or MrgprA6 in the absence of the compound (i.e. control) determines that the candidate compound is an agonist. Preferably, a candidate agonist increases activation of MrgprX3 or MrgprA6 by at least 1, 2, 3, 4 or 5 percent relative to a test assay in the absence of the candidate agonist (control), more preferably a candidate agonist increases activation of MrgprX3 or MrgprA6 in a test assay by at least 7, 10, 15, 20, 25, 30, 40 50 60, 70, 80, 90 or 100 percent relative to the same test assay in the absence of the candidate agonist (control). Preferred test assays for assessing a candidate agonist include an assay of Example 9, which follows where activation can be assessed by calcium imaging or inositol phosphate detection.

Also provided herein are methods for identifying an antagonist of MrgprX4 or MrgprA1 comprising: contacting the isolated cell (e.g. an isolated cell comprising a recombinant nucleic acid that expresses mas-related G-protein coupled receptor member X4 (MrgprX4) or MrgprA1) with a compound that induces an adverse drug reaction, contacting the isolated cell with a candidate antagonist, detecting activation of MrgprX4 or MrgprA1, wherein a decrease in activation of MrgprX4 or MrgprA1 relative to the activation of MrgprX4 or MrgprA1 in the absence of the compound (i.e. control) determines that the candidate compound is an antagonist. Preferably, a candidate antagonist decreases activation of MrgprX4 or MrgprA1 by at least 1, 2, 3, 4 or 5 percent relative to a test assay in the absence of the candidate antagonist (control), more preferably a candidate antagonist decreases activation of MrgprX4 or MrgprA1 in a test assay by at least 7, 10, 15, 20, 25, 30, 40 50 60, 70, 80, 90 or 100 percent relative to the same test assay in the absence of the candidate antagonist (control). Preferred test assays for assessing a candidate antagonist include an assay of Example 9, which follows where activation can be assessed by calcium imaging. Activation also can be assessed by inositol phosphate detection.

Further provided are methods for identifying an agonist of MrgprX4 or MrgprA1 comprising: contacting the isolated cell (e.g. an isolated cell comprising a recombinant nucleic acid that expresses mas-related G-protein coupled receptor member X4 (MrgprX4) or MrgprA1) with a compound that induces an adverse drug reaction, contacting the isolated cell with a candidate agonist, detecting activation of MrgprX4 or MrgprA1, wherein an increase in activation of MrgprX4 or MrgprA1 relative to the activation of MrgprX4 or MrgprA1 in the absence of the compound (i.e. control) determines that the candidate compound is an agonist. Preferably, a candidate agonist increases activation of MrgprX4 or MrgprA1 by at least 1, 2, 3, 4 or 5 percent relative to a test assay in the absence of the candidate agonist (control), more preferably a candidate agonist increases activation of MrgprX4 or MrgprA1 in a test assay by at least 7, 10, 15, 20, 25, 30, 40 50 60, 70, 80, 90 or 100 percent relative to the same test assay in the absence of the candidate agonist (control). Preferred test assays for assessing a candidate agonist include an assay of Example 9, which follows where activation can be assessed by calcium imaging or inositol phosphate detection.

Provided herein are methods for reducing the severity of a G protein coupled receptor-mediated condition in a subject that is induced by administering a compound by administering the compound to a subject; administering an MrgprX4 antagonist, an MrgprX3 antagonist, or a combination thereof to the subject, thereby reducing the severity of a G protein coupled receptor-mediated condition in the subject.

Further provided are methods for reducing the severity of a G protein coupled receptor-mediated condition in a subject that is induced by administering a compound by administering the compound to a subject; administering an MrgprX4 agonist, an MrgprX3 agonist, or a combination thereof to the subject, thereby reducing the severity of a G protein coupled receptor-mediated condition in the subject.

Also provided are methods for reducing the severity of an adverse drug reaction in a subject that is induced by administering a compound by administering the compound to a subject; administering an MrgprX4 antagonist to the subject, thereby reducing the severity of an adverse drug reaction in the subject.

Also provided are methods for reducing the severity of wound healing, chronic inflammation, malignant transformations, skin diseases such as psoriasis and dermatitis, airways and GI tract disorders, pain and itch in a subject; administering an MrgprX3 antagonist to the subject, thereby reducing the severity of wound healing, chronic inflammation, malignant transformations, skin diseases such as psoriasis and dermatitis, airways and GI tract disorders, pain and/or itch in a subject.

Also provided are methods for reducing the severity of wound healing, chronic inflammation, malignant transformations, skin diseases such as psoriasis and dermatitis, airways and GI tract disorders, pain and itch in a subject; administering an MrgprX3 agonist to the subject, thereby reducing the severity of wound healing, chronic inflammation, malignant transformations, skin diseases such as psoriasis and dermatitis, airways and GI tract disorders, pain and/or itch in a subject.

For example, the methods described herein prevent or reduce the severity of a G protein coupled receptor-mediated condition by at least 1%, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

The subject is preferably a mammal in need of such treatment or prophylaxis, e.g., a subject that has been diagnosed with a pseudo-allergic-type reaction or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

The inhibitors or antagonists or agonists may include but are not limited to nucleic acids, peptides, antibodies, or small molecules that bind to their specified target or the target's natural ligand and modulate the biological activity.

In some cases, the antagonist or agonist comprises a small molecule. A small molecule is a compound that is less than 2000 Daltons in mass. The molecular mass of the small molecule is preferably less than 1000 Daltons, more preferably less than 600 Daltons, e.g., the compound is less than 500 Daltons, less than 400 Daltons, less than 300 Daltons, less than 200 Daltons, or less than 100 Daltons.

Small molecules are organic or inorganic. Exemplary organic small molecules include, but are not limited to, aliphatic hydrocarbons, alcohols, aldehydes, ketones, organic acids, esters, mono- and disaccharides, aromatic hydrocarbons, amino acids, and lipids. Exemplary inorganic small molecules comprise trace minerals, ions, free radicals, and metabolites. Alternatively, small molecules can be synthetically engineered to consist of a fragment, or small portion, or a longer amino acid chain to fill a binding pocket of an enzyme. Typically small molecules are less than one kilodalton.

In some cases, the antagonist or agonist comprises a nucleic acid molecule. For example, ribonucleic acid (RNA) or deoxyribonucleic acid (DNA) inhibits the expression of MrgprX3 or MrgprX4 polypeptide, thereby inhibiting the activity of MrgprX3 or MrgprX4. In some cases, the nucleic acid comprises small interfering RNA (siRNA), RNA interference (RNAi), messenger RNA (mRNA), small hairpin RNA or short hairpin RNA (shRNA), double stranded ribonucleic acid (dsRNA), antisense RNA or microRNA, or any portion thereof. However, the skilled artisan could readily identify additional nucleic acids that inhibit/antagonize or activate/agonist MrgprX3 or MrgprX4.

As discussed, the antagonist or agonist can be an antibody, for example a monoclonal or polyclonal MrgprX3 or MrgprX4 antibody. For instance, MrgprX3 or MrgprX4 antibodies that may be employed as an antagonist include monoclonal polyclonal antibodies, such as mouse, rabbit, primate (e.g. monkey) or humanized antibodies (e.g., commercially available Novus Biologicals rabbit polyclonal MrgprX4 antibody No. NLS2429; Abcam's rabbit polyclonal MrgprX4 antibody b97784; Abcam's rabbit polyclonal MrgrpX4 antibody ab188740; and Thermo Fischer's anti-MrgprX3 polyclonal antibody PA5-3395). Fragments of such monoclonal antibodies also can be suitable antagonists or agonists, including fragments of the noted commercially available antibodies. Suitable and preferred antibody fragments for use as an MrgprX3 or MrgprX4.antagonist or agonist can be readily identified by the assays disclosed herein. Suitable fragments may have contain a sequence that has at least 30, 40, 50, 60, 70, 80, 90 or 95 sequence identity with the corresponding antibody such as the noted commercially available antibodies. Such fragments may be the entire agent that is used an MrgprX3 or MrgprX4.antagonist or agonist or may be covalently linked to another sequence or other molecule, for instance to form a fusion molecule containing the antibody fragment sequence, or containing a sequence having a suitable sequence identify with the corresponding antibody such as the noted commercially available antibodies.

As also discussed herein, suitable and preferred MrgprX4 and MrgprX3 antagonist and agonists including small molecules, polypeptides, antibodies and antibody fragments, and nucleic acids can be readily identified including by the assays disclosed herein, The antagonist or agonist is administered prior to, simultaneously with, or subsequent to administering the compound to the subject.

A variety of administration routes are available. For example, the antagonist or agonist is administered topically, orally, via inhalation, or via injection.

The effective amount of the antagonist or agonist is from 0.001 mg/kg to 250 mg/kg body weight, e.g., 0.001 mg/kg, 0.05 mg/kg 0.01 mg/kg, 0.05 mg/kg, 1 mg/kg, 5 mg/kg, 10 mg/kg, 25 mg/kg, 50 mg/kg, 75 mg/kg, 100 mg/kg, 125 mg/kg, 150 mg/kg, 175 mg/kg, 200 mg/kg, 225 mg/kg, or 250 mg/kg body weight. Ultimately, the attending physician or veterinarian decides the appropriate amount and dosage regimen.

In some cases, the antagonist or agonist is administered at least once per day, at least once per week, or at least once per month. The antagonist or agonist suitably may be administered for a duration of one day, one week, one month, two months, three months, six months, 9 months, or one year. In some cases, the antagonist is administered daily, e.g., every 24 hours. Or, the antagonist is administered continuously or several times per day, e.g., every 1 hour, every 2 hours, every 3 hours, every 4 hours, every 5 hours, every 6 hours, every 7 hours, every 8 hours, every 9 hours, every 10 hours, every 11 hours, or every 12 hours.

Methods for determining whether a compound induces an adverse drug reaction are carried out by contacting the isolated cell described herein with a candidate compound, detecting activation of MrgprX4, wherein activation of MrgprX4 determines that the candidate compound induces an adverse drug reaction.

For example, activation of MrgprX3 or MrgprA6 is detected by identifying an increase in intracellular calcium relative to the level of intracellular calcium in the absence of the compound. In some cases, the level of intracellular calcium increases by at least 1%, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. Intracellular calcium concentration is determined utilizing the methods described herein or those available to the skilled artisan.

For example, activation of MrgprX4 or MrgprA1 is detected by identifying an increase in intracellular calcium relative to the level of intracellular calcium in the absence of the compound. In some cases, the level of intracellular calcium increases by at least 1%, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. Intracellular calcium concentration is determined utilizing the methods described herein or those available to the skilled artisan.

A candidate MrgprX4 antagonist is screened to confirm that it counteracts or inhibits, decreases, or suppresses the biological activity of a MrgprX4 polypeptide. A candidate MrgprX3 antagonist is screened to confirm that it counteracts or inhibits, decreases, or suppresses the biological activity of a MrgprX3 polypeptide.

Also provided are methods for identifying an antagonist of MrgprX4 or MrgprX3 comprising contacting the isolated cell described herein with a compound that induces a pseudo-allergic-type reaction, contacting the isolated cell described herein with a candidate antagonist, detecting activation of MrgprX3 or MrgprX4, wherein a decrease in activation of MrgprX3 or MrgprX4 relative to the activation of MrgprX3 or MrgprX4 in the absence of the candidate antagonist determines that the candidate compound is an antagonist. Preferably, a candidate antagonist decreases activation of MrgprX3 or MrgprX4 by at least 1, 2, 3, 4 or 5 percent relative to a test assay in the absence of the candidate antagonist (control), more preferably a candidate antagonist decreases activation of MrgprX3 or MrgprX4 in a test assay by at least 7, 10, 15, 20, 25, 30, 40 50 60, 70, 80, 90 or 100 percent relative to the same test assay in the absence of the candidate antagonist (control). Preferred test assays for assessing a candidate antagonist include an assay of Example 9, which follows where activation can be assessed by calcium imaging or inositol phosphate detection.

Also provided are methods for identifying an agonist of MrgprX4 or MrgprX3 comprising: contacting the isolated cell described herein (e.g. an isolated cell comprising a recombinant nucleic acid that expresses mas-related G-protein coupled receptor member X3 (MrgprX3) or MrgprX4) with a compound that induces a pseudo-allergic-type reaction, contacting the isolated cell described herein with a candidate agonist, detecting activation of MrgprX3 or MrgprX4, wherein an increase in activation of MrgprX3 or MrgprX4 relative to the activation of MrgprX3 or MrgprX4 in the absence of the candidate agonist determines that the candidate compound is an agonist. Preferably, a selected candidate agonist decreases activation of MrgprX3 or MrgprX4 by at least 1, 2, 3, 4 or 5 percent relative to a test assay in the absence of the candidate antagonist (control), more preferably a selected candidate agonist decreases activation of MrgprX3 or MrgprX4 in a test assay by at least 7, 10, 15, 20, 25, 30, 40 50 60, 70, 80, 90 or 100 percent relative to the same test assay in the absence of the candidate antagonist (control). Preferred test assays for assessing a candidate agonist include an assay of Example 9, which follows where activation can be assessed by calcium imaging or inositol phosphate detection.

Also provided herein are methods for treating autoimmune disease (e.g., multiple sclerosis) in a subject comprising identifying a subject suffering from or at risk of developing autoimmune disease and administering to the subject an effective amount of a composition comprising an MrgprX4 antagonist, thereby treating or preventing autoimmune disease (e.g., multiple sclerosis) in a subject.

Exemplary autoimmune diseases are selected from the group consisting of celiac disease, diabetes mellitus type 1, Graves disease, inflammatory bowel disease, multiple sclerosis, psoriasis, rheumatoid arthritis, and systemic lupus erythematosus (SLE or lupus).

Also provided herein are methods for treating wound healing in a subject comprising identifying a subject experiencing or at risk of experiencing wound healing and administering to the subject an effective amount of a composition comprising an MrgprX3 antagonist, thereby treating or aiding wound healing in a subject.

Also provided herein are methods for treating skin disorders in a subject comprising identifying a subject suffering from or at risk of developing skin disorders and administering to the subject an effective amount of a composition comprising an MrgprX3 antagonist, thereby treating or preventing skin disorders in a subject.

Further provided are methods for treating skin disorders in a subject comprising identifying a subject suffering from or at risk of developing skin disorders and administering to the subject an effective amount of a composition comprising an MrgprX3 agonist, thereby treating or preventing skin disorders in a subject.

Exemplary skin disorders treated by such methods include psoriasis, dermatitis, skin ulcers, and carcinoma (e.g., melanoma).

Also provided herein are methods for treating inflammation (e.g., chronic inflammation) in a subject comprising identifying a subject suffering from or at risk of developing inflammation and administering to the subject an effective amount of a composition comprising an MrgprX3 antagonist, thereby treating or preventing inflammation (e.g., chronic inflammation) in a subject.

Examples of inflammation are selected from the group consisting of chronic inflammation, appendicitis, bursitis, colitis, cystitis, dermatitis, phlebitis, reflex sympathetic dystrophy/complex regional pain syndrome (rsd/crps), rhinitis, tendonitis, tonsillitis, acne vulgaris, reactive airway disorders such as asthma and airway infections, autoimmune diseases, autoinflammatory diseases, celiac disease, chronic prostatitis, diverticulitis, glomerulonephritis, hidradenitis suppurativa, hypersensitivities, intestinal disorders including epithelial intestinal disorders such as inflammatory bowel diseases such as irritable bowel syndrome and colitis, interstitial cystitis, otitis, pelvic inflammatory disease, reperfusion injury, rheumatic fever, rheumatoid arthritis, sarcoidosis, transplant rejection, and vasculitis.

Also provided herein are methods for treating malignant transformation (e.g., cancer) in a subject comprising identifying a subject suffering from or at risk of developing a malignant transformation and administering to the subject an effective amount of a composition comprising an MrgprX3 antagonist, thereby treating or preventing a malignant transformation (e.g., cancer) in a subject.

Exemplary cancers are selected from the group consisting of carcinoma, sarcoma, tumors, solid tumors, blood cancer, leukemia, lymphoma, skin cancer, melanoma, breast cancer, ovarian cancer, uterine cancer, prostate cancer, testicular cancer, colorectal cancer, stomach cancer, intestinal cancer, bladder cancer, lung cancer, non-small cell lung cancer, pancreatic cancer, renal cell carcinoma, kidney cancer, liver cancer, hepatocarcinoma, brain cancer, head and neck cancer, retinal cancer, glioma, lipoma, throat cancer, thyroid cancer, neuroblastoma, endometrial cancer, myeloma, and esophageal cancer.

The composition described herein are administered via oral administration, intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

Definitions

Unless defined otherwise, all technical and scientific terms used herein have the meaning commonly understood by a person skilled in the art to which this invention belongs. The following references provide one of skill with a general definition of many of the terms used in this invention: The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Antibodies and fragments thereof described herein include, but are not limited to, polyclonal, monoclonal, chimeric, dAb (domain antibody), single chain, Fab, Fab' and F(ab')2 fragments, Fv, scFvs. A fragment of an antibody possess the immunological activity of its respective antibody. In some embodiments, a fragment of an antibody contains 1500 or less, 1250 of less, 1000 or less, 900 or less, 800 or less, 700 or less, 600 or less, 500 or less, 400 or less, 300 or less, 200 or less amino acids. For example, a protein or peptide inhibitor contains 1500 or less, 1250 of less, 1000 or less, 900 or less, 800 or less, 700 or less, 600 or less, 500 or less, 400 or less, 300 or less, 200 or less, 100 or less, 80 or less, 70 or less, 60 or less, 50 or less, 40 or less, 30 or less, 25 or less, 20 or less, 10 or less amino acids. For example, a nucleic acid inhibitor of the invention contains 400 or less, 300 or less, 200 or less, 150 or less, 100 or less, 90 or less, 80 or less, 70 or less, 60 or less, 50 or less, 40 or less, 35 or less, 30 or less, 28 or less, 26 or less, 24 or less, 22 or less, 20 or less, 18 or less, 16 or less, 14 or less, 12 or less, 10 or less nucleotides.

General methods in molecular and cellular biochemistry can be found in such standard textbooks as Molecular Cloning: A Laboratory Manual, 4th Ed. (Sambrook et al., Cold Spring Harbor Laboratory Press 2012); Short Protocols in Molecular Biology, 5th Ed. (Ausubel et al. eds., John Wiley & Sons 2002); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (μ), respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. e al. Nucl. Acids Res. 28:219-221 (2000)). Optionally, the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_H$ when numbered in accordance with AHo; Honneger, A. and Plunkthun, A. J. Mol. Biol. 309:657-670 (2001)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Also provided are variable domain antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332: 323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a $C_L$ and at least heavy chain constant domains, $C_H 1$, $C_H 2$ and $C_H 3$. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, Fc$_\epsilon$RI.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H 1$). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H 1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

As used herein, an antibody that "internalizes" is one that is taken up by (i.e., enters) the cell upon binding to an antigen on a mammalian cell (e.g., a cell surface polypeptide or receptor). The internalizing antibody will of course include antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

As used herein, an antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and in certain embodiments, HuM2e antibody specifically binds to M2e if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (Ann. N.Y. Acad. Sci. USA 51:660 (1949)).

Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

The term "antagonist antibody" is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "1-Rs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the term "epitope" includes any protein determinant capable of specific binding to an immunoglobulin, an scFv, or a T-cell receptor. Epitopic determinants consist of chemically active surface groupings of molecules such as amino acids or sugar side chains and have specific three dimensional structural characteristics, as well as specific charge characteristics. For example, antibodies may be raised against N-terminal or C-terminal peptides of a polypeptide, linear or non-linear peptide sequences of a protein, as well as epitopes that comprise amino acids of a first antigen and those of a second antigen.

As used herein, the term "immune cells" generally includes white blood cells (leukocytes) which are derived from hematopoietic stem cells (HSC) produced in the bone marrow "Immune cells" includes, e.g., lymphocytes (T cells, B cells, natural killer (NK) cells) and myeloid-derived cells (neutrophil, eosinophil, basophil, monocyte, macrophage, dendritic cells). In some embodiments, the immune cells comprise chimeric antigen receptors. The term "chimeric antigen receptor" or "CAR" as used herein refers to an antigen-binding domain that is fused to an intracellular signaling domain capable of activating or stimulating an immune cell, and in certain embodiments, the CAR also comprises a transmembrane domain.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (Nature 361: 186-87 (1993)). The ratio of $K_{off}/K_{on}$ enables the cancellation of all parameters not related to affinity, and is equal to the dissociation constant $K_d$. Davies et al. (1990) Annual Rev Biochem 59:439-473). An antibody of the present invention is said to specifically bind to an antigen or epitope described herein (e.g., a CTLA, PD1, PDL1, or other immune inhibitory protein and/or tumor antigen) when the equilibrium binding constant ($K_d$) is ≤1 µM, preferably ≤100 nM, more preferably ≤10 nM, more preferably ≤1 nM, and most preferably ≤100 pM to about 1 pM, as measured by assays such as radioligand binding assays or similar assays known to those skilled in the art.

The invention also comprises polypeptides and nucleic acid fragments, so long as they exhibit the desired biological activity (i.e., antagonize MrgprX3 or MrgprX4) of the full length polypeptides and nucleic acid, respectively. A nucleic acid fragment of almost any length is employed. For example, illustrative polynucleotide segments with total lengths of about 10,000, about 5000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

Polynucleotides, polypeptides, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a synthetic complementary DNA (cDNA), a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

The term "vector" is used to refer to a carrier nucleic acid molecule into which a heterologous nucleic acid sequence can be inserted for introduction into a cell where it can be replicated and expressed. The term further denotes certain biological vehicles useful for the same purpose, e.g. viral vectors and phage—both these infectious agents are capable of introducing a heterologous nucleic acid sequence An "expression vector" is a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. The term "promoter" is used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Other elements that may be present in an expression vector include those that enhance transcription (e.g., enhancers) and terminate transcription (e.g., terminators), as well as those that confer certain binding affinity or antigenicity to the recombinant protein produced from the expression vector.

By a "candidate compound" is meant a chemical, be it naturally-occurring or artificially-derived. Candidate compounds may include, for example, peptides, polypeptides, synthetic organic molecules, naturally occurring organic molecules, nucleic acid molecules, peptide nucleic acid molecules, and components and derivatives thereof.

The term "pharmaceutical composition" is meant any composition, which contains at least one therapeutically or biologically active agent and is suitable for administration to the patient. Any of these formulations can be prepared by well-known and accepted methods of the art. See, for example, Remington: The Science and Practice of Pharmacy, 20th edition, (ed. A. R. Gennaro), Mack Publishing Co., Easton, Pa., 2000.

By "G protein-coupled receptors (GPCR)" is meant a protein receptor that senses molecules outside a cell and activates, inside the cell, signal transduction pathways and, ultimately, cellular responses. GPCRs are called seven-transmembrane receptors because they pass through the cell membrane seven times.

By "agonist" is meant a chemical that binds to a receptor and activates the receptor to produce a biological response. Whereas an agonist causes an action, an "antagonist" blocks the action of the agonist and an inverse agonist causes an action opposite to that of the agonist. As used herein, the terms "antagonist" and "inhibitor" are used interchangeably to refer to any molecule that counteracts or inhibits, decreases, or suppresses the biological activity of its target molecule. In some embodiments, an agonist is a "superagonist" when it induces or increases the biological activity of its target molecule (e.g., MrgprX4 or MrgprX3). In some embodiments, an antagonist is a "superantagonist" when it counteracts or inhibits, decreases, or suppresses the biological activity of its target molecule (e.g., MrgprX4 or MrgprX3). Suitable MrgprX3 antagonists, MrgprX4 antagonists, MrgprX3 agonists and/or MrgprX4 agonists include soluble receptors, peptide inhibitors, small molecule inhibitors, ligand fusions, and antibodies.

By "wild type" or "WT" is meant the phenotype of the typical form of a species as it occurs in nature. Alternately, the wild type is conceptualized as a product of the standard, "normal" allele at a locus, in contrast to that produced by a non-standard, "mutant" allele.

The term "administering," as used herein, refers to any mode of transferring, delivering, introducing, or transporting an MrgprX3 or MrgprX4 antagonist or an MrgprX3 or MrgprX4 agonist, for example, to a subject in need of treatment for a disease or condition. Such modes include, but are not limited to, oral, topical, intravenous, intraperitoneal, intramuscular, intradermal, intranasal, and subcutaneous administration.

By "MrgprX3 or MrgprX4 antagonist" is meant any small molecule, chemical compound, antibody, nucleic acid molecule, or polypeptide, or fragments thereof that is capable of blocking, preventing, lessening, or altering MrgprX3's or MrgprX4's ability to activate a signal transduction pathway.

By "MrgprX3 or MrgprX4 agonist" is meant any small molecule, chemical compound, antibody, nucleic acid molecule, or polypeptide, or fragments thereof that is capable of increasing, activating or altering MrgprX3's or MrgprX4's ability to activate a signal transduction pathway. An MrgprX3 agonist or MrgprX4 agonist can be identified by protocols disclosed herein, such as in Example 9 which follows.

By "alteration" is meant a change (increase or decrease) in the activity of polypeptide, e.g., MrgprX3 or MrgprX4, as detected by standard methods known in the art such as those described herein. As used herein, an alteration includes a 10% or more change in expression levels or activity of a gene or polypeptide, preferably a 25% change, more preferably a 40% change, and most preferably a 50% or greater change in activity of polypeptide.

As used herein an "alteration" also includes a 2-fold or more change in expression levels or activity of a gene or polypeptide, for example, 5-fold, 10-fold, 20-fold, 30-fold, 40-fold, 50-fold, 100-fold, 500-fold, 1000-fold or more.

By "ameliorate" is meant decrease, suppress, attenuate, diminish, arrest, or stabilize the development or progression of a disease such as, for example, a pseudo-allergic-type reaction.

By "amplify" is meant to increase the number of copies of a molecule. In one example, the polymerase chain reaction (PCR) is used to amplify nucleic acids.

By "binding" is meant having a physicochemical affinity for a molecule. Binding is measured by any of the methods of the invention, e.g., a drug/compound with a receptor expressed on a cell.

In this disclosure, "comprises," "comprising," "containing," "having," and the like can have the meaning ascribed to them in U.S. Patent law and can mean "includes," "including," and the like; the terms "consisting essentially of" or "consists essentially" likewise have the meaning ascribed in U.S. Patent law and these terms are open-ended, allowing for the presence of more than that which is recited so long as basic or novel characteristics of that which is recited are not changed by the presence of more than that which is recited, but excludes prior art embodiments.

"Detect" refers to identifying, either directly or indirectly, the presence, absence, or amount of MrgprX3 or MrgprX4 activation of a signal transduction pathway to be detected.

By "effective amount" is meant the amount required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "recombinant" is meant nucleic acid molecules formed by laboratory methods of genetic recombination (such as molecular cloning) to bring together genetic material from multiple sources, creating sequences that would not otherwise be found in biological organisms.

A "heterologous promoter" is a promoter which is different from the promoter to which a gene or nucleic acid sequence is operably linked in nature. The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence. A "heterologous polynucleotide" or a "heterologous gene", as used herein, is one that originates from a source foreign to the particular host cell, or, if from the same source, is modified from its original form.

By "reduces" is meant a negative alteration of at least 10%, 25%, 50%, 75%, or 100%.

By "reference" is meant a standard or control condition.

Unless specifically stated or obvious from context, as used herein, the terms "a," "an," and "the" are understood to be singular or plural. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1A is a diagram of genomic loci showing mouse and human Mrgpr genes. Mouse Mrgpra3, Mrgprc11, and their human orthologue MRGPRX1 are specifically expressed in sensory neurons in dorsal root ganglion (DRG) and functions as itch receptors in response to itchy substances including chloroquine (CQ) and BAMS-22 (BAM). Mouse Mrgprb2 and its human orthologue MRGPRX2 are receptors for basic secretagogues (e.g., compound 48/80 and PAMP) specifically expressed in mast cells and mediate drug-induced anaphylactic reactions. The MRGPRX4 orthologue Mrgpra1 is described in this study. Saal1, Ptpn5, and Zdhhc13 are unrelated genes in the loci. In FIG. 1D the lamotrigine concentrations were $2.0 \times 10^{-8}$, $4.0 \times 10^{-8}$, $8.0 \times 10^{-8}$, $1.6 \times 10^{-7}$, and $3.2 \times 10^{-7}$ mol $l^{-1}$, respectively. KD lamotrigine=$(4.17 \pm 0.24) \times 10^{-7}$ mol $l^{-1}$. Every result was repeated more than three times.

FIG. 2A is an illustration demonstrating how to generate a mouse where Mrgpra1's open reading frame was replaced by GFP. FIG. 2B is a photograph demonstrating that after 7 to 10 days of oral ingestion of LTG 50 mg kg$^{-1}$ body weight, WT mice developed mucosal secretion in their eyes and blister bleeding in their paws, similar to symptoms seen in patients suffering from SJS, whereas Mrgpra1 KO mice did not have these symptoms. FIG. 2C and FIG. 2E are photographs and graphs demonstrating that at day 7 of treatment with LTG, WT and HET Mrgpra1$^{\pm/GFP}$ mice developed conjunctival secretions, not in saline treated WT mice or LTG treated KO mice. H&E staining showed near the junction of the epidermis and conjunctiva local tissue defects, and some inflammatory cell infiltration in WT and HET mice not in saline and KO mice. WT and HET mice's conjunctiva also had increased staining for the apoptotic cell marker TUNEL (LTG WT: 40.45±2.58%, LTG HET: 40.39±1.45%), while saline and KO mice did not exhibit this increased cellular death (saline WT: 7.08±1.99%, LTG KO: 13.56±1.74%), (, p<0.01). FIG. 2D and FIGE are photographs and graphs demonstrating that at day 9 of treatment with LTG, WT and HET mice's symptoms progressed further, they showed significant edema and blister bleeding in their paws (FIG. 2D), not in saline and KO mice. H&E staining showed a large number of erythrocytes and inflammatory cells infiltration in the dermis of WT and HET mice not in saline and KO mice. The tissue in black dashed rectangle is enlarged in FIG. 6A-FIG. 6F. The TUNEL assay detected lots of dead epithelial cells (green) in WT and HET mice (LTG WT: 48.74±5.94%, LTG HET: 45.99±1.84%), (, p<0.01), not in saline and KO mice (saline WT:10.56±1.45%, LTG KO: 6.10±1.63%). Scale bar, FIG. 6F, 100 µm, FIG. 6C, FIG. 6D, 50 µm, FIG. 2F is a graph demonstrating that ELISA results show the quantification of Granzyme B and TNF-α expression in paw skin after 9 days treated with LTG. **, p<0.01 (n=5 per genotype).

FIG. 3A is an immunoblot demonstrating that RT-PCR showed Mrgpra1 only express in spleen, lymph node of WT mice not in KO mice. FIG. 3B is a cell sorting plot demonstrating that flow cytometry showed GFP cells were CD11c$^+$ and MHCII$^+$, markers of dendritic cells. FIG. 3C and FIG. 3D are immunoblots and micrographs demonstrating that CD11C+ and MHCII high cells, CD11c– and MHCII– cells, CD11c+ and MHCII int cells, CD11c– and MHCII+ cells were sorted from the spleens of WT and KO mice, for the detection of RT-PCR (FIG. 3C) and calcium imaging (FIG. 3D). As depicted in FIG. 3C, RT-PCR showed only CD11C+ and MHCII high cells of WT express Mrgpra1. As depicted in FIG. 3D, calcium imaging showed the responses at 10 s (before addition of LTG), 60 s (after addition of LTG), 180 s (LTG washed out) in four different cells sorting from the spleen of WT mice. The yellow arrow indicates that LTG induced the increase in [Ca2+]i of two cells in CD11C+ and MHCII high cells at 60 seconds. Scale bar, 25 µm. Right, representative imaging traces. Each line is a response from a unique cell. Only CD11C+ and MHCII high cells had good respond to LTG (0.05 mg/L). FIG. 3E is a graph demonstrating the quantification of calcium imaging assays (n=3 per genotype, >100 cells counted for each experiment, **, p<0.01). FIG. 3F is a photograph demonstrating that isolated MHCII+ and CD11c+ dendritic cells (DCs) from WT or KO mice, injected 2.5 million cells into Mrgpra1 KO mice via tail vein injection (n=6, each group). After 7 days of LTG intake (50 mg kg−1 body weight), mice received WT DCs forming conjunctival secretions. Mice who received A1KO DCs did not have any phenotype.

FIG. 4A is a n immunoblot demonstrating that the RT-PCR results of human Dendritic Cells (hDCs) showed MRGPRX4 expressed in hDCs. FIG. 4B is a graph demonstrating the representative images from immunostaining of hDCs treated with medium, medium with dye, LTG (3 μM), LTG with dye (3 μM) for 15 min at 37° C. LTG (labeled with dye, red) only internalized into the cell that express MRGPRX4 (green). Scale bar, 100 μm. FIG. 4C is a graph demonstrating the example traces showing changes in $[Ca^{2+}]i$, as measured by ratiometric Fura-2 imaging, from human dendritic cells (hDCs) exposed to 0.1 mg/L LTG (duration indicated by black line). Each trace is a response from a single cell. FIG. 4D is a photomicrograph demonstrating the percentage of responding cells from hDCs treated with LTG after received control siRNA (scramble siRNA) and MRGPRX4 siRNA application. Human DCs were transfected with siRNA against MRGPRX4 or control siRNA. Forty-eight hours later, the cells were treated with LTG and subjected to calcium imaging. The activation of hDCs was significantly reduced in MRGPRX4 siRNA treated cells, compared to control group. Group data were expressed as mean±s.e.m. Two-tailed unpaired Student's t-test was used to determine significance in statistical comparisons (n=4 per genotype; >100 cells counted per experiment. **, p<0.01). FIG. 4E demonstrates the analysis of MRGPRX4 gene from SJS patient and tolerant people showing that MRGPRX4 G/G mutation is more likely to occur in patients with SJS. The percentage of G/G mutation in tolerant people is 7.14%, while in SJS patient is 50%.

FIG. 6A is a graph demonstrating that the body weight change which shows that WT and HET mice lose weight after treatment with LTG 10 days (WT: −3.89±0.47 g; HET: −4.48±0.89 g), while saline and KO group gain weight (saline WT: 0.84±0.3 g; KO: 1.07±0.69 g). FIG. 6B is a graph demonstrating that the survival proportion shows the survival ratio of mice after treatment with LTG for 14 days. At day 14, only 30% of mice survived in the LTG treated WT and HET groups, while no mouse died in the saline and KO groups. FIG. 6C is photomicrograph depicting the H&E staining showed the subcutaneous tissue under microscope with x40 lens in rectangular of WT and KO that was shown in FIG. 2D. The red blood cells and inflammatory cells could be found only in WT dermis. Scale bar, 50 μm. FIG. 6D is a photomicrograph depicting immunofluorescence double staining that demonstrated the CD8 positive and CD3 positive cells in the eyelid of mice that were treated with LTG for 9 days. Scale bar, 50 μm. FIG. 6E is a graph demonstrating the number of CD8 positive and CD3 positive cells in eyelid were counted (naïve WT: 3.67±1.20, LTG WT: 25±8.34, LTG HET: 25±2, LTG KO: 5.67±0.88; **, p<0.01; n=5 per genotype). FIG. 6F is a photomicrograph demonstrating the IHC staining of Granzyme B in the paw skin of mice at day 9 after being treated with LTG and saline. The blue shading displays the location of Granzyme B. Scale bar, 100 μm.

FIG. 8A is an illustration depicting the treatment scheme of 129S1 WT mice receiving rat monoclonal antibodies against mouse CD4 and CD8 i.p. injection 3 times to deplete CD4 or CD8 T cells at day −2, 0 and 3. Then, the mice were treated with LTG for 14 days after receiving antibody a second time. FIG. 8B is a flow cytometry plot to confirm there is no CD4 or CD8 T cells in mice. At day 7 and day 14, peripheral blood and spleen samples were collected from mice for flow cytometry. FIG. 8C is a photograph of mice experiencing LTG treatment. At day 9, mice receiving saline injection (the left panel labeled with "WT") developed conjunctival secretion in their eyes and blister bleeding in their paws, but these phenotypes were not found in CD8 or CD4 T cells depletion groups.

FIG. 9A is a flow cytometry plot depicting that Mrgpra1 KO mice was Mrgpra1's open reading frame replaced by GFP. Flow cytometry was used to characterize GFP+ cells from Mrgpra1 GFP/GFP mice; splenocytes and lymph nodes cells were stained with different antibodies such as CD4, CD8a, CD11b, CD45, CD317, CD370, F4/80, I-A/I-E, Ly6C, Ly6G, XCR1, CD3, and CD11c. Then cell acquisition was performed on an LSR-II flow cytometer (BD Biosciences). The results showed GFP+ cells were highly express CD11c and MHC-II. FIG. 9B is a photomicrograph depicting the immunofluorescence staining which shows GFP cells were CD11c+ cells not CD3+ cells in A1KO mouse spleen. Scale bar, 50 μm. FIG. 9C is a flow cytometry plot of lymph nodes cells demonstrating that Mrgpra1 GFP/GFP cells were MHC-II+ and CD11c+.

FIG. 13A is a graph depicting the results for mice that were given either vehicle (olive oil) or 25 mg/kg ANIT per os daily. On day five, spontaneous itch was assessed. Mice were videotaped in a test chamber for thirty minutes, and the number of scratching bouts was counted. All mice are male, 8-12 week old, littermates. A blind study was conducted regarding genotype throughout treatment and scoring. n=10 per treatment and genotype except for vehicle treated cluster KO which was n=6. FIG. 13B is a graph depicting the results when serum was collected by cardiac puncture after pruritus was assessed. Total bilirubin was measured by the animal pathology lab at JHU. FIG. 13C is a graph depicting the results for liver weight post treatment. FIG. 13D is a graph depicting the results for serum bile acid levels. n=4 for control, n=10 for WT treated, n=7 for KO treated. FIG. 13E is a graph depicting the results for serum autotaxin activity. n=4 for control, n=12 for WT treated, n=8 for KO treated. FIG. 13F is a graph depicting the results for serum met-enkephalin levels. n=4 for control, n=19 for WT treated, n=10 for cluster KO treated.

FIG. 16A is a graph depicting the results for mice injected subcutaneously at the nape of the neck with bilirubin in a vehicle containing 5% DMSO (pH 6.6-7.0).

FIG. 15A is a trace of fluorescence intensity where DRG neurons from WT mice were loaded with Fluo-4 AM calcium dye. Vehicle (0.5% DMSO) was added to neurons. After thirty seconds, a one-minute wash was applied. 50 μM bilirubin was added. 50 mM KCl was used as a positive control. Each trace represents a single neuron. FIG. 15B is a trace of fluorescence intensity where bilirubin was applied at 10 s. At 120 s, the bath solution was replaced with 3 mM EGTA bath solution. Bilirubin was reapplied in this period. FIG. 15C is a graph demonstrating where either vehicle or 50 μM bilirubin was applied to both WT and Cluster KO DRG neurons. A neuron was scored as "activated" if its peak fluorescence, during the imaging period, achieved at least a 50% increase over baseline—or a level of 50% of the KCl peak. Additionally, neurons were required to have elevated signal over baseline for at least 20 s. Motion artifacts were excluded from analysis. The total number of neurons across at least three mice were aggregated to calculate a percentage. FIG. 15D is a histogram depicting the diameter of neurons scored as "activated".

FIG. 16A-FIG. 16C is a series of graphs demonstrating that bilirubin mediated pruritus is non-histaminergic. FIG. 16A is a graph of histamine release (depicted as picogram per cell) when bilirubin is applied to mast cells was not different from controls. FIG. 16B is a trace of fluorescence intensity where bath application of bilirubin to peritoneal mast cells failed to elicit calcium influx. FIG. 16C is a bar graph of results when 1 mM bilirubin was injected into WT animals. The black bar is vehicle injected animals. The red bar is 30 mg/kg cetirizine, a H1R blocker.

FIG. 17A is a graph demonstrating the results when HEK cells stably expressing MrgprA1 were loaded with Fura-2 calcium dye. 50 μM bilirubin was added. After thirty seconds, a one minute wash was applied and the cells were allowed the return to baseline. 50 μM bilirubin was then added again. Each trace represents a single HEK cell. FIG. 17B is a graph demonstrating the results when U73122 the Gαq blocker was utilized. FIG. 17C is a graph demonstrating the results when U73343, a closely related analogue to U73122 that has no function against Gαq, was utilized. FIG. 17D is a graph demonstrating the results of the same experiment as FIG. 17A except with HEK cells stably expressing MrgprX4. 50 μM bilirubin was applied once. Each trace represents a single cell. FIG. 17E is a graph demonstrating the results of the same experiment as FIG. 17B but with X4. FIG. 17F is a graph demonstrating the results of the same experiment as FIG. 17C but with X4.

FIG. 18A is a graph depicting the EC50 of MrgprA1 for bilirubin is approximately 49 μM. FIG. 18B is a graph depicting the EC50 for MrgprX4 for bilirubin is approximately 3 μM. FIG. 18C is a graph demonstrating that the un-transfected HEK cells did not display an EC50 response.

FIG. 20A is a series of representative $Ca^{2+}$ traces showing activation of human MrgprX3 by hBD3. FIG. 20B is a graph of qPCR results showing effective knock down of MRGPRX3 from human primary keratinocytes by siRNA. MRGPRX4 was measured as control. FIG. 20C is a graph demonstrating that knocking down MRGPRX3 significantly reduced the percentage of human keratinocytes that produced a $Ca^{2+}$ response to hBD3.

FIG. 21A is an immunoblot demonstrating that RT-PCR revealed high expression of MrgprA6, A12 and B3 in purified mouse keratinocytes. FIG. 21B is a series of representative $Ca^{2+}$ traces showing activation of mouse MrgprA6 by mBD14. FIG. 21C is a representative trace demonstrating that MrgprB3 is not activated by mBD14 (data for other Mrgprs not shown). FIG. 21D is a schematic demonstrating the Mrgpr gene cluster in mouse and human genomes. Dashed lines indicate corresponding homologues.

FIG. 22 is a table depicting results of analyzing heme metabolites and Mrgprs. The heme metabolites are structurally related. Multiple heme metabolites activated MrgprA1, a mouse receptor, and MrgprX4, a human receptor. Dose of substance is listed above while approximate percentage of activation is depicted within the table.

FIG. 23A is a bar graph indicating scratching bouts were associated with injection of bilirubin. The indicated amount of bilirubin was injected in a 100 µL volume into the nape of the neck of mice. The blue bar (+HSA) represents animals that have been injected with 60 µg bilirubin (100 µL of 1 mM) pre-incubated with 1% human serum albumin. Veh n=8; 6 µg n=5, 18 µg n=11, 30 µg n=12, 60 µg n=7, +HSA n=12. FIG. 23B is a line graph depicting the time course of itch behavior associated with injection of bilirubin, histamine, or chloroquine. Scratching bouts were binned according to 5-minute intervals. Bilirubin n=16, Histamine n=13, Chloroquine n=11. FIG. 23C is a bar graph depicting results of 60 µg bilirubin injected into the nape of the neck of WT and Cluster−/− littermate mice. WT n=8, Cluster−/− n=13. FIG. 23D is a bar graph depicting results of 60 µg (100 µL of 1 mM) of the indicated metabolite injected to WT and Cluster−/− littermate mice. Haemin (WT n=10, Cluster−/− n=6), Biliverdin (WT n=7, Cluster−/− n=7), Urobilinogen (WT n=15, Cluster KO n=8), Stercobilin (WT n=7, Cluster−/− n=5). FIG. 23E is a schematic of the pathway of haem degradation. The skeletal formula of each metabolite is depicted above its optimal 3D geometry, as calculated by a B3LYP functional and 6-31G(d) basis set. Blue and orange represent orbital parity of each metabolite's HOMO obtained from DFT calculations. FIGS. 23A, 23C and 23D—Mean plus s.e.m. depicted. Each open circle represents an individual mouse. *, P<0.05; , P<0.01; *, P<0.001; two-tailed unpaired Student's t-test.

FIG. 24A-24N are data showing that bilirubin activated murine MRGPRA1 and human MRGPRX4. FIG. 24A-24E are data showing $Ca^{2+}$ imaging and transformed binding isotherms of HEK293 cells stably expressing MRGPRA1, or MRGPRX4 (FIG. 24F-24J). FIG. 24A-24C and FIG. 24F-24H are data showing 50 µM bilirubin added where indicated by black bars. After 15-seconds, a 1-minute wash was applied. Mean±95% confidence interval (CI) depicted. n=10. In FIG. 24A 30 µM FMRF was added after washing as indicated by the black bar. In FIG. 24B-24C and FIG. 24G-24H, cells were pre-incubated with either 10 µM of the PLC inhibitor U73122 or 10 µM of the $G_{\alpha q}$ inhibitor YM254890 for 30-minutes prior to imaging. Concentration-$Ca^{2+}$ response curves of bilirubin, conjugated bilirubin, and haemin towards (FIG. 24D) MRGPRA1, (FIG. 24I) MRGPRX4, and (FIG. 24M) MRGPRC11 and BAMS-22 towards MRGPRC11, an established peptide ligand. Data are a representative experiment of 2-3 independent replicates performed in triplicate, depicted as mean±s.e.m. Transformed binding isotherms for bilirubin, conjugated bilirubin, and haemin to (FIG. 24E) MRGPRA1, (FIG. 24J) MRGPRX4, and (FIG. 24N) MRGPRC11 and BAM8-22 to MRGPRC11. Data are an average of 3 independent experiments, depicted as mean±s.e.m.

FIG. 25A is an image that depicts GFP expression under the control of the endogenous Mrgpra1 locus (Mrgpra1$^{GFP}$). Red depicts anti-PLAP antibody staining where PLAP expression is controlled by the endogenous Mrgprd locus (Mrgprd$^{PLAP}$). Blue depicts antibody staining against calcitonin gene-related peptide (CGRP). Scale bar=50 µM. FIG. 25B is an image representative of whole-cell current-clamp recording of either WT or A1−/− DRG neurons. In WT DRG, bilirubin elicited action potentials in 5 out of 50 small-diameter neurons. In A1−/− DRG, bilirubin elicited action potentials in 0 out of 60 small-diameter neurons. Fisher's exact test P<0.05. FIG. 25C is an image representative of whole-cell current-clamp recording of a WT DRG neuron responsive to addition of both 50 µM bilirubin and 1 mM chloroquine (CQ). FIG. 25D is a graph showing $Ca^{2+}$ imaging of WT DRG neurons. After a 10 second baseline, 50 µM bilirubin was added. After 20 seconds, a 3 minute wash was applied before 1 mM chloroquine was added. After 15 seconds, 50 mM KCl was added. Mean plus 95% CI depicted. n=10 neurons. Compounds applied where indicated by black bars. FIG. 25E is a bar graph showing the percent activation of WT, A1−/−, and Cluster−/− DRG upon addition of either vehicle or 50 bilirubin. *, P<0.05; , P<0.01; *, P<0.001; Chi-squared test. FIG. 25F is a graph depicting the percent activation of Tg(Mrgpra3-Cre); lsl-tdTomato neurons as assessed by calcium imaging with vehicle, 1 mM Chloroquine, or 50 µM bilirubin. A neuron was considered to be activated if ΔF>0.2 for at a least 30 s. FIG. 25G-25H, $Ca^{2+}$ imaging of Cluster−/− DRG neurons (FIG. 25G) and (FIG. 25H) DRG neurons 48 hours after either mock infection with lentivirus (n=10) or infected with lentivirus encoding Mrgpra1 (n=6), MRGPRX4 (n=10), or MRGPRX3 (n=20). 50 µM bilirubin was added when indicated by the black bar. After 20 seconds, a 1 minute wash was applied before addition of 50 mM KCl. Compounds applied where indicated by black bars. Mean±95% CI depicted. n=10 neurons. FIG. 25I is a graph indicating the percent activation of uninfected, Mrgpra1-infected, MRGPRX4-infected, and MRGPRX3-infected Cluster−/− neurons by bilirubin. ***, P<0.001. Chi-squared test.

FIG. 26A is a bar graph depicting scratching bouts for vehicle and ANIT-treated mice among WT, Cluster−/−, and A1−/− groups. Bouts were assessed in a 30 minute period. For the vehicle cohort: WT n=15, Cluster−/− n=6, A1−/− n=6. For ANIT cohort: WT n=20, Cluster−/− n=14, A1−/− n=14. FIG. 26B is a bar graph depicting scratching bouts for vehicle and ANIT-treated animals among WT and BVR−/− groups. Bouts were assessed in a 30 minute period. For the vehicle cohort: WT n=5 and BVR−/− n=8. For ANIT cohort: WT n=21 and BVR−/− n=20. FIG. 26C is a bar graph depicting plasma bilirubin levels (mg/dL) from WT and Cluster−/− ANIT-treated and vehicle-treated animals. For the vehicle cohort: WT n=9, Cluster−/− n=5. For the ANIT cohort: WT n=10, Cluster−/− n=8. FIG. 26D is a bar graph depicting scratching bouts from WT ANIT-treated animals. Either vehicle or 1 mg/kg QWF was delivered i.p. Vehicle n=8, QWF n=9. FIG. 26E is a bar graph depicting scratching bouts from either WT mice injected with vehicle- or ANIT-treated plasma from WT and BVR−/− animals. For the vehicle plasma cohort: n=7. For cholestatic ANIT-treated plasma: WT n=10 and BVR−/− n=8. FIG. 26F is a table describing characteristics of patients from whom hyperbilirubinemic plasma was collected. FIG. 26G is a bar graph depicting scratching bouts from either WT or A1−/− mice injected with hyperbilirubinemic patient plasma. For Patient 1 plasma injection, WT n=7, A1−/− n=9. For Patient 2 plasma injection, WT n=8, A1−/− n=5. For Patient 3 plasma injection, WT n=7, A1−/− n=8. For Patient 4 plasma injection, WT n=6, A1−/− n=8. FIG. 26H is a bar graph depicting scratching bouts from mice injected with either untreated (NT) control human plasma, FeCl₃-treated control human plasma, NT cholestatic Patient 1 plasma (copy of Patient 1 WT data in (FIG. 26G)), or FeCl₃-treated Patient 1 plasma. For control plasma, NT n=6 and FeCl₃ n=5. For Patient 1 plasma, NT n=7 and FeCl₃ n=7. FIG. 26I is a bar graph depicting scratching bouts from mice injected with either normal rabbit IgG—treated Patient 1 plasma or anti-bilirubin IgG—treated Patient 1 plasma. Normal IgG n=5, Anti-bilirubin n=7. FIG. 26A-26I, Mean plus s.e.m. depicted. Open circles represent individual data points. *, P<0.05; , P<0.01; *, P<0.001 by unpaired two-tailed Student's t-test.

FIG. 27A depicts a bar graph showing scratching bouts associated with cheek injection of bilirubin. The indicated amount of bilirubin was injected in a 10 μl volume and the number of scratching bouts was assessed for thirty minutes. Vehicle n=6, 1.8 μg n=5, 3 μg n=4, 6 μg n=5, 6 μg (−/−) n=6. FIG. 27B depicts a bar graph showing wiping associated with injection of 6 μg bilirubin into the cheek. Wipes were assessed for 10 minutes post-injection, vehicle n=5, bilirubin n=7. FIG. 27C depicts a bar graph showing lick time associated with injection of 6 μg bilirubin into the paw. Licking was assessed for 10 minutes post-injection. n=3 per condition. FIG. 27D depicts a bar graph showing that H1 blocker did not inhibit bilirubin-induced pruritus. Either vehicle or 30 mg/kg Cetirizine was given i.p. thirty minutes prior to injection of bilirubin at the nape of the neck. Scratching bouts were assessed for 30 minutes post-injection. Vehicle n=10, Cetirizine n=5. FIG. 27E is a bar graph showing that mast cell histamine released in response to 100 μM bilirubin. Vehicle for Compound 48/80 n=4, Compound 48/80 (10 μg/mL) n=4, Vehicle n=6, Bilirubin n=8. FIG. 27F is a graph showing $Ca^{2+}$ imaging of murine peritoneal mast cells. After a 10 s baseline, 100 μM bilirubin was added. 15 s later, a 1 minute wash was applied before addition of 10 μg/mL compound 48/80. Drugs were applied when indicated by the black bars. Mean±95% CI depicted. n=26. FIGS. 27A-27C and 27D-27E, Mean plus s.e.m. depicted. Open circles represent independent data points. *, P<0.05; , P<0.01; *, P<0.001; two-tailed unpaired Student's t-test. n.s., not significant.

FIG. 28A is a graphical depiction of the mouse and human Mrpgr locus with previously published functionally homologous pairs highlighted in black. FIG. 28B-28F are graphs showing $Ca^{2+}$ imaging of HEK293 cells transiently expressing (FIG. 28B) MRGPRA3, (FIG. 28C) MRGPRC11, (FIG. 28D) MRGPRD, (FIG. 28E) MRGPRX1, or (FIG. 28F) MRGPRX2. 50 μM bilirubin was added where indicated by black bars. After fifteen seconds, a one minute wash was applied. After washing, either (FIG. 28b) 1 mM chloroquine, (FIG. 28c) 3 μM BAMS-22, (FIG. 28d) 1 mM β-alanine, (FIG. 28E) 3 μM BAMS-22, or (FIG. 28F) 10 μg/mL compound 48/80 was added as indicated by black bars. Mean±95% CI depicted. n=10.

FIG. 29A-29C depict data of CRISPR deletion of MRGPRA1. FIG. 29A is a schematic that depicts the comparison of WT (SEQ ID NO: 4) and A1−/− (SEQ ID NO: 5) genomic sequences. Location of 2 base pair (bp) deletion shown by dashes. Numbers correspond to MRGPRA1 open reading frame. FIG. 29B depicts sequencing data of the 2 bp deletion (SEQ ID NO: 9 shown on top and SEQ ID NO: 10 shown on bottom). FIG. 29C depicts a schematic of a translation (SEQ ID NO: 8) of the open reading frame of MRGPRA1−/− (sense sequence=SEQ ID NO: 6: antisense sequence=SEQ ID NO: 7) beginning with the start codon. The 2 bp deletion created a frameshift which resulted in early termination, marked by a red asterisk (far right).

FIG. 30A is a Venn diagram depicting total neurons activated by either bilirubin and/or chloroquine (Bilirubin alone=7, Chloroquine=40, Overlap=13). FIG. 30B is a histogram of bilirubin-activated neuronal soma diameter.

FIG. 31A is a graph depicting Plasma alkaline phosphatase (ALP) levels among vehicle and ANIT-treated animals. For vehicle cohort: WT n=10, Cluster−/− n=4, A1−/− n=4, BVR−/− n=6. For ANIT cohort: WT n=17, Cluster−/− n=6, A1−/− n=5, BVR−/− n=15. FIG. 31B is a graph depicting Plasma aspartate aminotransferase (AST) levels among vehicle and ANIT-treated animals. For vehicle cohort: WT n=10, Cluster−/− n=4, A1−/− n=4, BVR−/− n=9. For ANIT cohort: WT n=12, Cluster−/− n=6, A1−/− n=5, BVR−/− n=17. FIG. 31C is a graph depicting Alanine aminotransferase (ALT) levels among vehicle and ANIT-treated animals. For vehicle cohort: WT n=10, Cluster−/− n=4, A1−/− n=4, BVR−/− n=6. For ANIT cohort: WT n=15, Cluster−/− n=6, A1−/− n=5, BVR−/− n=17. FIG. 31D is a graph depicting Gamma-glutamyl transferase (GGT) levels among vehicle and ANIT-treated animals. For vehicle cohort: WT n=10, Cluster−/− n=4, BVR−/− n=6. For ANIT cohort: WT n=17, Cluster−/− n=6, BVR−/− n=15. FIG. 31E is a graph depicting Plasma bile acid levels (μM) from ANIT-treated and vehicle-treated animals. For the vehicle cohort: WT n=4, Cluster−/− n=5, BVR−/− n=5. For the ANIT cohort: WT n=10, Cluster−/− n=7, BVR−/− n=14. FIG. 31F is a graph depicting Met-enkephalin levels among plasma from vehicle and ANIT-treated animals For vehicle cohort: WT n=4, Cluster−/− and BVR−/− n=5. For ANIT cohort: WT n=19, Cluster−/− n=10, BVR−/− n=11. FIG. 31G is a graph depicting Autotaxin activity among plasma from vehicle and ANIT-treated animals. For vehicle cohort: WT and BVR−/− n=4, Cluster−/− n=5. For ANIT cohort: WT n=12, Cluster−/− n=8, BVR−/− n=10. FIG. 31H is a graph depicting scratching bouts in response to 10 μL of 1.3 mM deoxycholic acid (DCA) injected into cheek. WT n=9, Cluster−/− n=9. FIG. 31I is a graph depicting scratching bouts in response to 10 μL of 4 mM lysophosphatidic acid (LPA) injected into cheek. WT n=6, Cluster−/− n=6. FIG. 31J is a graph depicting WT n=7, Cluster−/− n=8. FIG. 31K is a graph depicting scratching bouts in response to 25 µg of DAMGO (50 µL volume) injected into back. WT n=5, Cluster−/− n=5. FIG. 31A-31J show Mean±s.e.m. depicted. Open circles represent independent data points. *, P<0.05; , P<0.01; *, P<0.001; two-tailed unpaired Student's t-test. n.s., not significant.

FIG. 32A is a bar graph showing quantitative PCR analysis of BLVRA transcript from whole brain of WT and BVR−/− mice. FIG. 32B is a representative chromatogram of HPLC analysis of plasma from WT and BVR−/− mice separated via a C18 column and analysed by absorbance at 450 nm. FIG. 32C depicts an HPLC chromatogram of plasma from a WT mouse spiked with excess bilirubin. FIG. 32D is a bar graph depicting total bilirubin levels from plasma of WT and BVR−/− animals. WT n=7, BVR−/− n=6. FIG. 32E is a bar graph depicting scratching bouts in response to 150 µg (50 µL of 10 mM) of chloroquine. After chloroquine injection, scratching bouts were assessed in a 30 minute period. WT n=9, BVR−/− n=5, A1−/− n=6. FIG. 32F is a bar graph depicting scratching bouts in response to 60 µg (100 µL of 1 mM) of bilirubin. After bilirubin injection, scratching bouts were assessed in a 30 minute period. WT n=8, BVR−/− n=9. FIG. 32D-32F show Mean plus S.E.M. depicted. Open circles represent independent data points. **, P<0.01 by student's t-test. n.s., not significant.

FIG. 33A is a bar graph showing scratching bouts for vehicle and Cyclosporin A-treated WT and A1−/− animals. For the vehicle cohort: n=5 for all. For Cyclosporin A cohort: WT n=10 and A1−/− n=8. FIG. 33B is a bar graph depicting scratching bouts from vehicle and Cyclosporin A treated WT and BVR−/− animals. Scratching bouts were assessed in a 30 minute period. For the vehicle cohort: n=5. For Cyclosporin A cohort: WT n=11 and BVR−/− n=7. FIGS. 33A and 33B show Mean plus s.e.m. depicted. Open circles represent individual data points. *, P<0.05; , P<0.01; *, P<0.001; two-tailed unpaired Student's t-test. n.s., not significant.

FIG. 34A is a graph of a concentration-response curve for bilirubin induced $Ca^{2+}$ signal in MRGPRA1-expressing HEK cells. 200 µM bilirubin was maintained in competition with indicated doses of QWF. Mean±s.e.m. depicted. n=3 replicates in duplicate. FIG. 34B-34C depict bar graphs of scratching bouts from (FIG. 34B) 60 µg (100 mL of 1 mM) bilirubin or (FIG. 34C) 150 µg chloroquine co-injected with either vehicle or 1 mg/kg QWF. After injection, the number of scratching bouts in 30 minutes was assessed. For bilirubin: Vehicle n=7, QWF n=8. For chloroquine: Vehicle n=4, QWF n=7. Mean plus s.e.m. depicted. *, P<0.05 by unpaired two-tailed Student's t-test. d-g, Plasma (FIG. 34D) bilirubin, (FIG. 34E) AST, (FIG. 34F) ALT, and (FIG. 34G) ALP levels from of vehicle and QWF-dosed WT animals that have undergone ANIT liver injury. FIG. 34D-34G show Mean±s.e.m. depicted. Open circles represent independent data points. n.s., not significant by two-tailed unpaired Student's t-test.

FIG. 35A show representative HPLC chromatograms of 100 µM biliverdin+100 µM bilirubin standards and treated plasma samples. Absorbance was measured at 405 nm. FIG. 35B shows a bar graph of the quantification of plasma bilirubin in untreated, $FeCl_3$, normal rabbit IgG, and bilirubin antibody-treated samples. Points represent technical replicates. Mean±s.e.m. depicted **, P<0.01; n.s., not significant by two-way ANOVA followed by post-hoc Tukey test.

DETAILED DESCRIPTION

Figure 1:
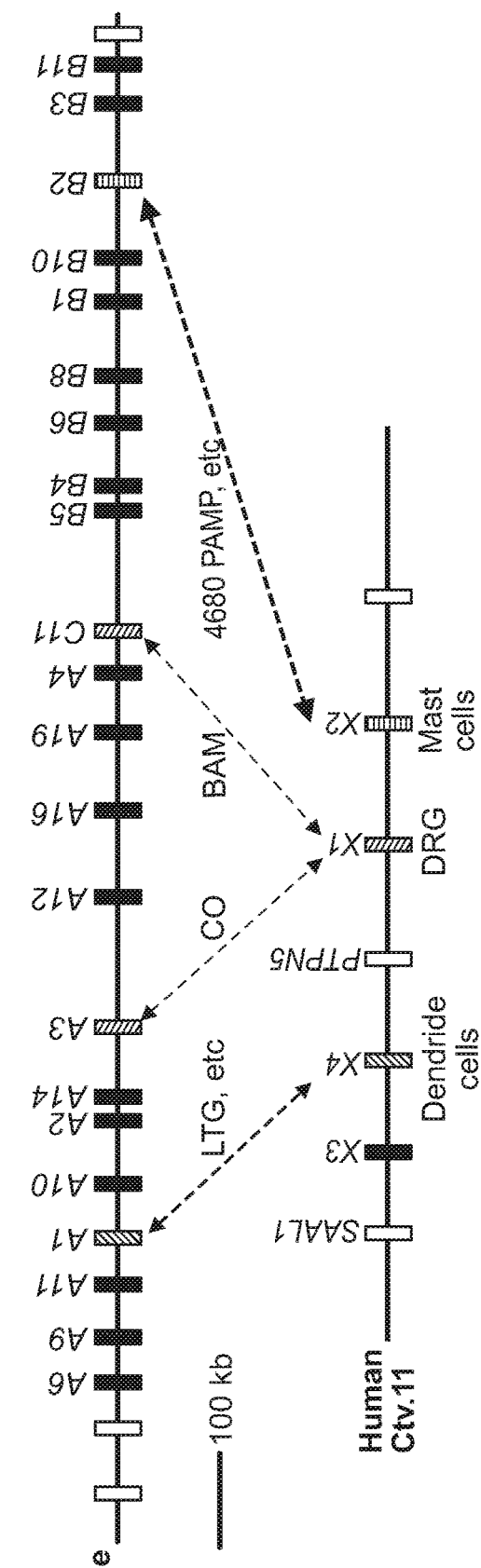
FIG. 1A-FIG. E is a series of illustrations, graphs, photographs and photomicrographs demonstrating that Lamotrigine directly binds mouse Mrgpra1 and its human orthologue MRGPRX4.
FIG. 1E shows that LTG induced internalization of Mrgpra1-GFP. LTG labeled with dye can create bright red-fluorescent (Texas Red). Serum-starved (>4 hs) Mrgpra1-GFP cells treated with medium, medium with dye, LTG, LTG with dye for 15 min at 37° C. Staining shown that LTG with dye internalized into the Mrgpra1-GFP cells.
FIG. 1B is a graph that shows elution profiles of LTG on the MRGPRX2/cell membrane chromatography (CMC) column and MRGPRX4/CMC column LTG cannot retain on the MRGPRX2/CMC column Retention time of lamotrigine on MRGPRX4/CMC column 16.7 min
FIG. 1C and FIG. 1D are graphs showing MRGPRX4/CMC breakthrough curves of LTG (FIG. 1C) and a regression curve achieved by plotting 1/[LR]s versus 1/[L]m (FIG. 1D). Each point with a bar represents the mean±SEM (n=5).
Figure 1:
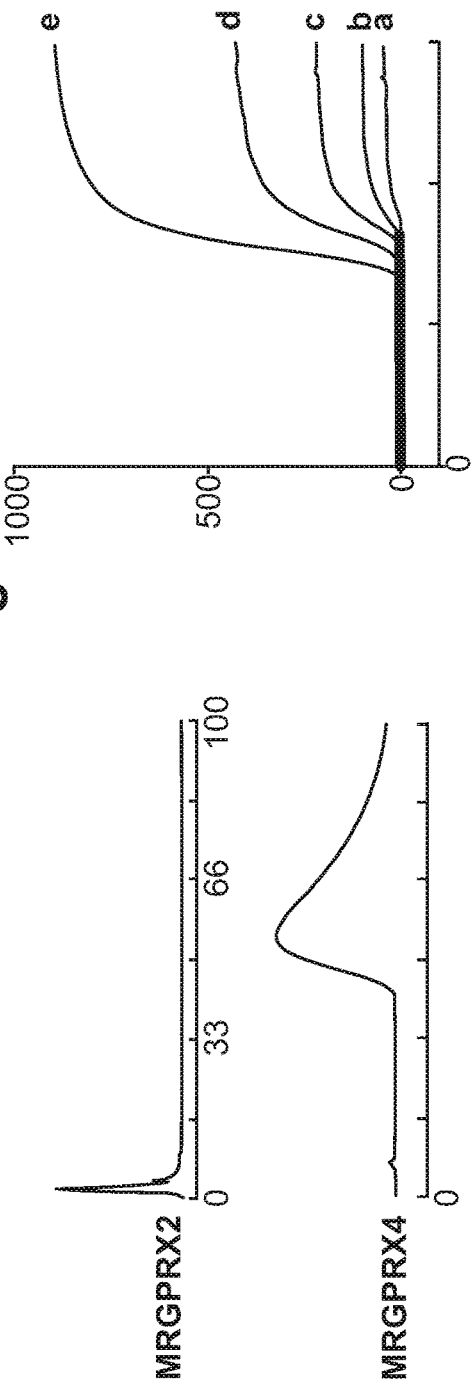
Figure 1:
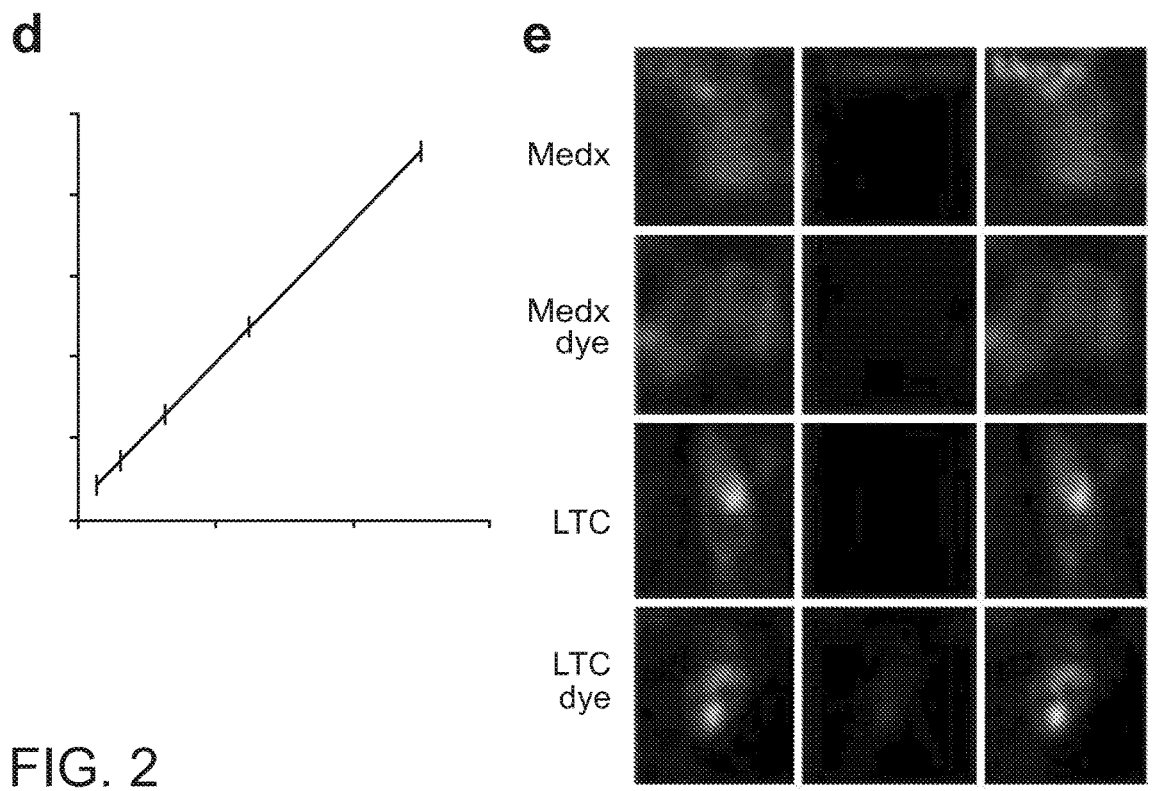

The invention is based, at least in part, on the identification of a novel G protein-coupled receptor: human MrgprX4 and mouse MrgprA1. MrgprX4 and MrgprA1 are expressed in a specific type of innate immune cell and mediate Stevens Johnson Syndromes (SJS) and are likely involved in autoimmune diseases. MrgprX4 and MrgprA1 are activated by many SJS causing drugs including lamotrigine and allopurinol. In addition, MrgprX4 and MrgprA1 are also expressed in sensory neurons and are important for itch sensation and cholestatic pruritus. In some embodiments, MrgprX4 and MrgprA1 are receptors for bilirubin. As described herein, prior to this discovery, no bilirubin receptor has been identified. In some embodiments, human MrgprX4 is a drug target for SJS, autoimmune diseases such as multiple sclerosis, cholestatic pruritus and other chronic itch conditions. As described herein, a role of MrgprX4 in any biological process and disease was completely unknown prior to this discovery. In some embodiments, MrgprX4 expressing cell-based assays (MrgprX4 cell line and cDNA, and MrgprA1 mutant mouse line) are used to screen and test drugs targeting these reactions. As described herein, MrgprX4-expressing cell lines are completely novel and used for high through-put screening for drug screening. In some embodiments, blocking MrgprX4 is a novel way to treat SJS; autoimmune diseases such as multiple sclerosis; and cholestatic pruritus and other chronic itch conditions.

The invention is also based, at least in part, on the discovery that human MrgprX3 and its mouse homologue MrgprA6 are expressed in keratinocytes, epithelial cells, and primary sensory neurons in dorsal root ganglion (DRG). It was also discovered that antimicrobial peptides defensin and cathelicidin are agonists of MrgprX3 and MrgprA6. Defensins and cathelicidin may play roles in multiple diseases and conditions including wound healing, chronic inflammation, malignant transformations, skin diseases such as psoriasis and dermatitis, airways and GI tract disorder, pain, and itch. In some embodiments, targeting MrgprX3 and MrgprA6 treats wound healing, chronic inflammation, malignant transformations, skin diseases such as psoriasis and dermatitis, airways and GI tract disorders, pain, and itch. As described herein, the role of MrgprX3 in any biological process and disease was previously unknown. In some embodiments, MrgprX3 expressing cell-based assays and MrgprA6 mutant mice are used to screen and test drugs targeting these reactions. As described herein, MrgprX3-expressing cell lines are novel and used for high through-put screening for drug screening. The invention features methods for determining whether a compound effects a G protein coupled receptor-mediated condition and methods for reducing the severity of a G protein coupled receptor-mediated condition in a subject. The present invention is based, at least in part, on the discovery of a G protein coupled receptor, i.e., MrgprX4 in humans and MrgprA1 in mice, exclusively expressed in a type of immune cell called dendritic cells, which is linked closely to adverse drug reactions and autoimmune disorders.

Prior to the invention described herein, the role of MrgprX4/MrgprA1 in adverse drug reactions and autoimmune disorders was completely unknown. Described herein is the use of MrgprX4/MrgprA1 expressing cell-based assays to screen for drugs that induce adverse drug reactions or autoimmune disorders, and to screen for antagonists of MrgprX4 that block or effect these reactions.

The isolated cells of the present invention express the human G-protein coupled receptor (GPCR) MrgprX4 or the mouse GPCR MrgprA1 which allows easy visualization of receptor activation in a calcium-based screening assay. These cell lines permit the screening of FDA-approved drugs and drugs in development for MrgprX4 agonist and antagonist activity.

Using these cells in a cell-based assay for drug screens, a positive result (i.e., activation of the cell line as measured by, e.g., calcium release) would indicate that the drug would normally activate dendritic cells and potentially cause an adverse reaction in a patient. Screens of drugs in development would predict their side effect profile; screens of drugs currently in use would identify a cause of the adverse effects of these drugs; screens of antagonists would lead to new therapeutic drugs that can be provided at the same time as drugs that induce adverse drug reactions, thus blocking activation of cells (e.g., dendritic cells and primary sensory neurons) while not interfering with their intended uses.

Described herein are cell lines that are used to screen for FDA-approved drugs and investigational compounds that activate or antagonize this receptor. These will be useful to determine whether a drug will induce allergic-type responses, and in screens to develop antagonists that block these responses.

Described in detail below is the introduction of a mouse model to study dendritic cells and primary sensory neuronactivation by adverse drug reactions and identification of MrgprX4 as a therapeutic target to reduce a adverse drug reactions.

As described herein, a novel G protein-coupled receptor is identified: human MrgprX4 and mouse MrgprA1. MrgprX4 and MrgprA1 are expressed in a specific type of innate immune cell, mediates Stevens Johnson Syndromes (SJS), and is likely involved in autoimmune diseases. MrgprX4 and MrgprA1 are activated by many SJS causing drugs including lamotrigine and allopurinol. In addition, MrgprX4 and MrgprA1 are also expressed in sensory neurons and important for itch sensation and cholestatic pruritus. MrgprX4 and MrgprA1 are the receptors of bilirubin. Prior to this discovery, no bilirubin receptor has been identified. Therefore, human MrgprX4 is an essential drug target. The role of MrgprX4 in any biological processes and diseases is completely unknown until this discovery, as described herein. Therefore, the use of MrgprX4 expressing cell-based assays (MrgprX4 cell line and cDNA, and MrgprA1 mutant mouse line) to screen and test drugs targeting these reactions are completely novel. A MrgprX4-expressing cell line is completely novel and essential for high through-put screening for drug screening. Blocking MrgprX4 may be a novel way to treat SJS, autoimmune diseases (such as multiple sclerosis), and cholestatic pruritus (and other chronic itch conditions).

As described herein,targeting MrgprX3 in humans and MrgprA6 in mice may treat wound healing, chronic inflammation, malignant transformations, skin diseases (e.g., psoriasis and dermatitis), airways and GI tract disorders, pain, and itch. The role of MrgprX3 in any biological processes and diseases were unknown prior to the present disclosure as described herein. Therefore, the use of MrgprX3 expressing cell-based assays and MrgprA6 mutant mice to screen and test drugs targeting these reactions is also novel. MrgprX3-expressing cell lines are novel and essential for high through-put screening for drug screening.

MrgprX4/MrgprA1

Mas-related G-protein coupled receptor member X4 is a protein that in humans is encoded by the MRGPRX4 gene. The MAS 1 oncogene is a G protein-coupled receptor which binds the angiotensin-II metabolite angiotensin-(1-7). The MAS1 receptor, when activated by binding angiotensin-(1-7), opposes many of the effects of angiotensin-II activated angiotensin receptor. MAS1 receptor agonists have similar therapeutic effects as angiotensin-II receptor antagonists including lowering blood pressure.

Adverse drug reactions (ADRs) are a serious unintentional and unwanted drug safety concern that account for around 6% of all hospital admissions and 9% of hospitalization costs, costing up to 30.1 billion dollars annually in the USA alone (Zalewska-Janowska, A., et al., *Immunol Allergy Clin North Am* 37, 165-181 (2017); Sultana, J., et al., J Pharmacol Pharmacother 4, S73-77 (2013)). One of the most serious ADRs, Stevens-Johnson syndrome (SJS) and toxic epidermal necrolysis (TEN) are life-threatening severe cutaneous ADR (cADR) characterized by blister lesions, mucosal breakdown and skin rash/detachment due to massive keratinocyte cell death with mortality rate up to 30% (Downey, A., et al., *J Am Acad Dermatol* 66, 995-1003 (2012); Lee, H. Y. & Chung, W. H., *Curr Opin Allergy Clin Immunol* 13, 330-336 (2013)). Though the involvement of inappropriate immune-mediated cytotoxicity has been shown (Downey, A., et al., *J Am Acad Dermatol* 66, 995-1003 (2012)), the molecular and cellular mechanisms of how drugs trigger SJS/TEN are largely unknown. As described herein, a novel drug-induced SJS mouse model with eye mucosal damage and paw blister bleeding has been established. In some embodiments, several SJS/TEN causative drugs can directly activate a G-protein-coupled receptor (GPCR) Mrgpra1 in mouse and its human functional orthologue MRGPRX4. Drug-induced SJS-like phenotypes are abolished in Mrgpra1 knockout animals. Furthermore, as described herein, both Mrgpra1 and MRGPRX4 are expressed on a subset of dendritic cells, professional antigen-presenting cells which are essential to initiate an adaptive immune response leading to cytotoxicity. Finally, a mutation in the MRGPRX4 gene has been identified in cADR patients resulting in increasing the sensitivity of the receptor to the drug. These discoveries reveal a new molecular mechanism of how these drugs may trigger the serious side effects and open new avenues of potential prevention and therapeutic treatment of ADRs.

SJS, which is a milder form of TEN, was first described by Albert M. Stevens and Frank C. Johnson in 1922 (Stevens, A. M. & Johnson, F. C., *Am J Dis Child* 24, 526-533 (1922)). Since then, the awareness of SJS/TEN has been increased in medical field due to its mortality and morbidity. Although several types of infection and malignances are implicated as the etiology of SJS/TEN, the main cause of SJS/TEN is adverse effects of medication (Heng, Y. K., et al., *Br J Dermatol* 173, 1250-1254 (2015)). More than 100 clinically used drugs including anti-epileptic drugs (e.g. lamotrigine, carbamazepine), anti-gout drugs (e.g. allopurinol), certain classes of antibiotics and nonsteroidal anti-inflammatory drugs have been associated with SJS/TEN, which is a major drug safety concern and closely monitored by Food Drug Administration (FDA) (Schotland, P., et al. *Eur J Pharm Sci* 94, 84-92, (2016)). The immunological reaction induced by the causative drugs has been considered as the underlying mechanisms of SJS/TEN pathogenesis. Although several models involving the interaction of causative drug, human leukocyte antigen (HLA) on antigen presenting cells, and T-cell receptor on T-cells have been proposed (Adam, J., et al. *Br J Clin Pharmacol* 71, 701-707 (2011); Chung, W. H., et al., *J Dermatol* 43, 758-766 (2016)), the molecular and cellular mechanisms of how drugs trigger SJS/TEN remain elusive at least partly due to the lack of good and simple animal model.

Stevens Johnson Syndrome

Stevens-Johnson syndrome (SJS) is a type of severe skin reaction. Together with toxic epidermal necrolysis (TEN) it forms a spectrum of disease, with SJS being less severe. Early symptoms include fever and flu-like symptoms. A few days later the skin begins to blister and peel forming painful raw areas. Mucous membranes, such as the mouth, are also typically involved. Complications include dehydration, sepsis, pneumonia, and multiple organ failure.

The most common cause is certain medications such as lamotrigine, carbamazepine, allopurinol, sulfonamide antibiotics, and nevirapine. Other causes can include infections such as Mycoplasma pneumoniae and cytomegalovirus or the cause may remain unknown. Risk factors include HIV/AIDS and systemic lupus erythematosus. The diagnosis is based on involvement of less than 10% of the skin. It is known as TEN when more than 30% of the skin is involved and an intermediate form with 10 to 30% involvement. Erythema multiforme (EM) is generally considered a separate condition.

Treatment typically takes place in hospital such as in a burn unit or intensive care unit. Efforts may include stopping the cause, pain medication, antihistamines, antibiotics, intravenous immunoglobulins, or corticosteroids. Together with TEN it affects 1 to 2 million people per year. It is twice as common in males as females. Typical onset is under the age of 30. Skin usually regrows over two to three weeks; however, complete recovery can take months.

Although SJS can be caused by viral infections and malignancies, the main cause is medications. A leading cause appears to be the use of antibiotics, particularly sulfa drugs. Between 100 and 200 different drugs may be associated with SJS. No reliable test exists to establish a link between a particular drug and SJS for an individual case. Determining what drug is the cause is based on the time interval between first use of the drug and the beginning of the skin reaction. A published algorithm (ALDEN) to assess drug causality gives structured assistance in identifying the responsible medication.

SJS may be caused by adverse effects of the drugs vancomycin, allopurinol, valproate, levofloxacin, diclofenac, etravirine, isotretinoin, fluconazole, valdecoxib, sitagliptin, oseltamivir, penicillins, barbiturates, sulfonamides, phenytoin, azithromycin, oxcarbazepine, zonisamide, modafinil, lamotrigine, nevirapine, pyrimethamine, ibuprofen, ethosuximide, carbamazepine, bupropion, telaprevir, and nystatin.

Medications that have traditionally been known to lead to SJS, erythema multiforme, and toxic epidermal necrolysis include sulfonamide antibiotics, penicillin antibiotics, cefixime (antibiotic), barbiturates (sedatives), lamotrigine, phenytoin (e.g., Dilantin) (anticonvulsants) and trimethoprim. Combining lamotrigine with sodium valproate increases the risk of SJS.

Nonsteroidal anti-inflammatory drugs (NSAIDs) are a rare cause of SJS in adults; the risk is higher for older patients, women, and those initiating treatment. Typically, the symptoms of drug-induced SJS arise within a week of starting the medication. Similar to NSAIDs, paracetamol (acetaminophen) has also caused rare cases of SJS. People with systemic lupus erythematosus or HIV infections are more susceptible to drug-induced SJS.

Autoimmune Disease

An autoimmune disease is a condition arising from an abnormal immune response to a normal body part. There are at least 80 types of autoimmune diseases. Nearly any body part can be involved. Common symptoms include low grade fever and feeling tired. Often symptoms come and go.

The cause is generally unknown. Some autoimmune diseases such as lupus run in families, and certain cases may be triggered by infections or other environmental factors. Some common autoimmune disease include celiac disease, diabetes mellitus type 1, Graves disease, inflammatory bowel disease, multiple sclerosis, psoriasis, rheumatoid arthritis, and systemic lupus erythematosus. The diagnosis can be difficult to determine.

Treatment depends on the type and severity of the condition. Nonsteroidal anti-inflammatory drugs (NSAIDs) and immunosuppressants are often used. Intravenous Immunoglobulin may also occasionally be used. While treatment usually improves symptoms they do not typically cure the disease.

About 24 million (7%) people in the United States are affected by an autoimmune disease. Women are more commonly affected than men. Often they start during adulthood. The first autoimmune diseases were described in the early 1900s.

The human immune system typically produces both T-cells and B-cells that are capable of being reactive with self-antigens, but these self-reactive cells are usually either killed prior to becoming active within the immune system, placed into a state of energy (silently removed from their role within the immune system due to over-activation), or removed from their role within the immune system by regulatory cells. When any one of these mechanisms fail, it is possible to have a reservoir of self-reactive cells that become functional within the immune system. The mechanisms of preventing self-reactive T-cells from being created takes place through the Negative selection process within the thymus as the T-cell is developing into a mature immune cell.

Some infections, such as *Campylobacter jejuni*, have antigens that are similar (but not identical) to the host's own self-molecules. In this case, a normal immune response to *C. jejuni* can result in the production of antibodies that also react to a lesser degree with receptors on skeletal muscle (i.e., myasthenia gravis). A major understanding of the underlying pathophysiology of autoimmune diseases has been the application of genome wide association scans that have identified a degree of genetic sharing among the autoimmune diseases.

Autoimmunity, on the other hand, is the presence of self-reactive immune response (e.g., auto-antibodies, self-reactive T-cells), with or without damage or pathology resulting from it. This may be restricted to certain organs (e.g. in autoimmune thyroiditis) or involve a particular tissue in different places (e.g. Goodpasture's disease which may affect the basement membrane in both the lung and the kidney).

Multiple Sclerosis

Multiple sclerosis (MS) is a demyelinating disease in which the insulating covers of nerve cells in the brain and spinal cord are damaged. This damage disrupts the ability of parts of the nervous system to communicate, resulting in a range of signs and symptoms, including physical, mental, and sometimes psychiatric problems. Specific symptoms can include double vision, blindness in one eye, muscle weakness, trouble with sensation, or trouble with coordination. MS takes several forms, with new symptoms either occurring in isolated attacks (relapsing forms) or building up over time (progressive forms). Between attacks, symptoms may disappear completely; however, permanent neurological problems often remain, especially as the disease advances.

While the cause is not clear, the underlying mechanism is thought to be either destruction by the immune system or failure of the myelin-producing cells. Proposed causes for this include genetics and environmental factors such as being triggered by a viral infection. MS is usually diagnosed based on the presenting signs and symptoms and the results of supporting medical tests.

There is no known cure for multiple sclerosis. Treatments attempt to improve function after an attack and prevent new attacks. Medications used to treat MS, while modestly effective, can have side effects and be poorly tolerated. Physical therapy can help with people's ability to function. Many people pursue alternative treatments, despite a lack of evidence. The long-term outcome is difficult to predict, with good outcomes more often seen in women, those who develop the disease early in life, those with a relapsing course, and those who initially experienced few attacks. Life expectancy is on average 5 to 10 years lower than that of an unaffected population.

Multiple sclerosis is the most common autoimmune disorder affecting the central nervous system. In 2015, about 2.3 million people were affected globally with rates varying widely in different regions and among different populations. That year about 18,900 people died from MS, up from 12,000 in 1990. The disease usually begins between the ages of 20 and 50 and is twice as common in women as in men. The name multiple sclerosis refers to the numerous scars (sclerae—better known as plaques or lesions) that develop on the white matter of the brain and spinal cord.

Cholestatic Pruritus

Itch (also known as pruritus) is a sensation that causes the desire or reflex to scratch. Itch has resisted many attempts to classify it as any one type of sensory experience. Modern science has shown that itch has many similarities to pain, and while both are unpleasant sensory experiences, their behavioral response patterns are different. Pain creates a withdrawal reflex, whereas itch leads to a scratch reflex. Unmyelinated nerve fibers of primary sensory neurons in dorsal root ganglion for itch and pain both originate in the skin; however, information for them is conveyed centrally in two distinct systems that both use the same nerve bundle and spinothalamic tract.

Cholestatic pruritus is the sensation of itch due to nearly any liver disease, but the most commonly associated entities are primary biliary cirrhosis, primary sclerosing cholangitis, obstructive choledocholithiasis, carcinoma of the bile duct, cholestasis (also see drug-induced pruritus), and chronic hepatitis C viral infection and other forms of viral hepatitis.

Cholestasis means "the slowing or stopping of bile flow" which can be caused by any number of diseases of the liver (which produces the bile), the gallbladder (which stores the bile), or biliary tract (also known as the biliary tree, the conduit that allows the bile to leave the liver and gallbladder and enter the small intestine). When this occurs, conjugated bilirubin and the waste products that usually would be cleared in bile reflux back into the bloodstream. This causes a primarily conjugated hyperbilirubinemia and jaundice; the liver conjugates the bile to make it water-soluble and because the bile has already been processed by the liver, when it gets backed up because of a blockage and is refluxed into the blood, the blood will have high levels of conjugated bilirubin. This is in contrast to primarily unconjugated hyperbilirubinemia which is the water-insoluble form that is bound to serum albumin; the liver has not had a chance to conjugate the bilirubin yet and can be caused either because too much unconjugated bilirubin is made (such as in massive hemolysis or ineffective erythropoiesis) or because too little is conjugated (Gilbert's disease or Crigler-Najjar syndrome). Unconjugated hyperbilirubinemia does not typically cause pruritus.

It is thought that bile salts that deposit into the skin are responsible for the pruritus (itching) but the levels of bilirubin in the bloodstream and the severity of the pruritus does not appear to be highly correlated. Patients that have been administered bile salt chelating agents do report some relief, however, and patients that have complete liver cell failure (and therefore cannot make these products to begin with) do not have pruritus. This suggests that products made by the liver must have some role in pruritus.

Chronic itch, or pruritus, causes much suffering (Halvorsen J A, et al. *Acta Derm Venereol* 92:543-6 (2012)). Clinically relevant chronic itch results from a wide range of pathologies (Ikoma A, et al. *Nat Rev Neurosci* 7:535-47 (2006)). One major cause is cholestasis. Cholestasis results from an impaired ability to secrete bile and can occur due to a multitude of pathologies including anatomical obstruction of the bile ducts and liver failure (Bergasa N V. Pruritus of Cholestasis. In Itch: Mechanisms and Treatment, ed. E Carstens, T Akiyama. Boca Raton (Fla.). Number of. (2014)). The pruritus that results from cholestasis is non-histaminergic and resolves with resolution of underlying disease pathology (Bergasa N V. Pruritus of Cholestasis. In Itch: Mechanisms and Treatment, ed. E Carstens, T Akiyama. Boca Raton (Fla.). Number of. (2014)). Cholestatic pruritus is hypothesized to result from pruritogens present in bile. Currently, endogenous opioids, bile acids (BA), and lysophosphatidic acid (LPA) are three leading candidates proposed to mediate cholestatic pruritus.

Endogenous opioids are upregulated in serum of both cholestatic animal models and patients (Swain M G, et al. 1992. *Gastroenterology* 103:630-5 (1992); Thornton J R, Losowsky M S. *BMJ* 297:1501-4-29 (1988); Thornton J R, Losowsky M S. *J Hepatol* 8:53-9 (1989); Thornton J R, Losowsky M S. *Gut* 30:1392-5 (1989)). In small clinical trials, the opioid antagonists naloxone and nalmefene were demonstrated to be effective in controlling cholestatic itch (Bergasa N V. *Am J Gastroenterol* 93:1209-10 (1998); Bergasa N V, et al. *Hepatology* 27:679-84 (1998); Bergasa N V, et al. *Gastroenterology* 102:544-9 (1992); Swain M G, et al. 1992. *Gastroenterology* 103:630-5 (1992)). BA, steroid metabolites of cholesterol, are also elevated in cholestatic patient sera, but their levels do not correlate with patient-reported pruritic intensity (Bergasa N V. Pruritus of Cholestasis. In Itch: Mechanisms and Treatment, ed. E Carstens, T Akiyama. Boca Raton (Fla.). Number of. (2014)). BA binding resins, in a series of human clinical trials, were validated as being efficacious in alleviating pruritus (Datta D V, Sherlock S. *Gastroenterology* 50:323-32 (1966); European Association for the Study of the L. EASL Clinical Practice Guidelines: management of cholestatic liver diseases. *J Hepatol* 51:237-67 (2009)). However, these conclusions have been challenged (Kremer A E, et al. *Gastroenterology* 139:1008-18, (2010); Kuiper E M, et al. *Hepatology* 52:1334-40 (2010)). In 2013, TGR5, a bile acid receptor, was identified in a subpopulation of itch coding sensory neurons (Alemi F, et al. *J Clin Invest* 123:1513-30 (2013)). Finally, autotaxin, the enzyme that converts lysophosphatidylcholine to LPA, is upregulated in cholestatic patient serum (Kremer A E, et al. *Gastroenterology* 139: 1008-18, (2010)). This elevation occurs exclusively in patients who report pruritus (Kremer A E, et al. *Hepatology* 56:1391-400 (2012)).

Endogenous opioids, BA, and LPA are all examples of non-histaminergic itch. Cholestatic patients do not exhibit classic signs of histamine release such as erythema or swelling (Bergasa N V. Pruritus of Cholestasis. In Itch: Mechanisms and Treatment, ed. E Carstens, T Akiyama. Boca Raton (Fla.). Number of. (2014)). Moreover, antihistamines are ineffective in treating cholestatic pruritus, with only a few patients reporting clinical improvement in their symptoms (Bergasa N V. *Clin Liver Dis* 12:385-406 (2008); Bergasa N V. Pruritus of Cholestasis. In Itch: Mechanisms and Treatment, ed. E Carstens, T Akiyama. Boca Raton (Fla.). Number of. (2014)).

Cholestasis and Bilirubin

Cholestasis will often result in jaundice, a yellowing of the skin and eyes. Jaundice occurs due to elevated levels of bilirubin that deposits in the skin. Bilirubin is a downstream metabolite of heme. In cells, heme is broken down by heme oxygenase 1 (HMOX1) to biliverdin, which is then reduced by biliverdin reductase (BVR) to bilirubin. Bilirubin is extremely lipophilic and is believed to be able to cross the cell membrane. In the blood, bilirubin is bound by albumin. In the liver, UGT1A*28 conjugates bilirubin to glucuronic acid to form a water-soluble compound. Both conjugated and unconjugated bilirubin are excreted in bile. In regards to human health, bilirubin is believed to be a physiological antioxidant with cardiovascular protective benefits (Bulmer A C, et al. *Prog Lipid Res* 52:193-205 (2013); Vitek L., et al. Atherosclerosis 160:449-56(2002)).

Mrgprs and Non-Histaminergic Itch

Mas-related G protein-coupled receptors (Mrgprs) have been implicated in non-histaminergic itch, both as receptors for pruritogenic ligands and as molecular markers for itch coding neurons (Liu Q, et al. *J Neurosci* 32:14532-7 (2012); Liu Q, et al. *Cell* 139:1353-65 (2009)). In mice, there are over 27 expressed Mrgprs, only a few of which have known physiologic ligands (McNeil B, Dong X. *Neurosci Bull* 28:100-10 (2012)). In humans, there are 4 expressed Mrgprs (MrgprX1-X4). MrgprX1, X3, and X4 have been identified as being specifically expressed in human DRG and trigeminal ganglia (TG), while MrgprX2 has been found in human mast cells (Flegel C, et al. *PLoS One* 10:e0128951 (2015); Goswami S C, et al. *Mol Pain* 10:44 (2014); Lembo P M, et al. *Nat Neurosci* 5:201-9 (2002); McNeil B D, et al. *Nature* 519:237-41 (2015)).

MrgprX3/MrgprA6

Mas-related G-protein coupled receptor member X3 is a protein that in humans is encoded by the MRGPRX3 gene. The MAS 1 oncogene is a G protein-coupled receptor which binds the angiotensin-II metabolite angiotensin-(1-7). The MAS1 receptor, when activated by binding angiotensin-(1-7), opposes many of the effects of angiotensin-II activated angiotensin receptor. MAS1 receptor agonists have similar therapeutic effects as angiotensin-II receptor antagonists including lowering blood pressure.

Human MrgprX3 and its mouse homologue MrgprA6 are expressed in keratinocytes and primary sensory neurons in dorsal root ganglion (DRG). More importantly, antimicrobial peptides defensin and Cathelicidin are the agonists of MrgprX3 and MrgprA6. Defensins and cathelicidin may play roles in multiple diseases and conditions including wound healing, chronic inflammation, malignant transformations, skin diseases such as psoriasis and dermatitis, airways and GI tract disorders, pain and itch. Targeting MrgprX3 and MrgprA6 may treat wound healing, chronic inflammation, malignant transformations, skin diseases such as psoriasis and dermatitis, airways and GI tract disorders, pain and itch. The role of MrgprX3 in any biological processes and diseases are unknown prior to the present disclosure as described herein. Therefore, the use of MrgprX3 expressing cell-based assays and MrgprA6 mutant mice to screen and test drugs targeting these reactions is also novel. MrgprX3-expressing cell lines are novel and essential for high through-put screening for drug screening.

Injury and pathogen invasion trigger a chain of inflammatory and repair responses that aim to restore the damaged tissue. It has also long been noted that repetitive irritation and chronic inflammation are strong risk factors for cancer. A thorough understanding of the wound healing process will thus provide important insights for the cause of various carcinomas, and accordingly for their prevention. Among the numerous host defense molecules released during the process are a large family of antimicrobial peptides (AMPs) named defensins. These AMPs are particularly interesting since, in addition to directly killing pathogens, they exert a myriad of immune modulatory effects on a range of cell types during multiple phases of the inflammatory response. In particular, human β-defensin hBD3 has been shown to assist wound healing by stimulating epithelial cell migration and proliferation. As described herein, a novel G protein coupled receptor (GPCR), MRGPRX3, is the defensin receptor in human keratinocytes and other epithelial cell types. As described herein, ligand homology and expression profiling point to mouse gene MrgprA6 as the murine homologue of human MRGPRX3 and the physiological and cell biological functions of these receptors are examined both in vitro and in vivo.

The skin is the largest immune organ and the first-line defender against infectious challenges. Upon injury and pathogen invasion, an inflammatory cascade is quickly triggered as a protective response (Pasparakis, M., et al. *Nat Rev Immunol* 14, 289-301 (2014); Singer, A. J. & Clark, R. A. F. *N. Engl. J. Med.* 341, 738-746 (1999)). Localized cutaneous inflammation is characterized by "redness and swelling with heat and pain", as documented by the ancient Romans (Owen, J. A., et al. *Immunology*. (W.H. Freeman, 2013)), and involves multiple cell types and numerous molecular mediators. This complex process involves coordinated actions of immune, neural, vascular and epithelial systems and is vital to our survival.

Human β-defensin hBD3 promote keratinocyte migration and wound healing. The defensins are a large family of anti-microbial peptides (AMPs). These cationic peptides are produced by epithelial and immune cells immediately following tissue damage and infection and can kill a broad spectrum of pathogens (Pazgier, M., et al. *Cell. Mol. Life Sci. C.* 63, 1294-1313 (2006); Amid, C. et al. *BMC Genomics* 10, 1-13 (2009)). Besides direct killing, defensins also exert many immune modulatory functions. Human β-defensin 3 (hBD3) exhibit a wide range of functions including chemotactic activities for various immune cells (Ganz, T. *Nat Rev Immunol* 3, 710-720 (2003); Röhrl, J., et al. *J. Immunol.* 184, 6688-6694 (2010)), mast cell degranulation (Befus, A. D. et al. *J. Immunol.* 163, 947-953 (1999); Subramanian, H. et al. *J. Immunol.* 191, 345-352 (2013)), and was shown to assist wound healing (Hirsch, T. et al. *J. Gene Med.* 11, 220-228 (2009); Sorensen, O. E. et al. *J. Immunol.* 170, 5583-5589 (2003); Aarbiou, J. et al. *Am. J. Respir. Cell Mol. Biol.* 30, 193-201 (2004); Otte, J.-M. et al. *J. Cell. Biochem.* 104, 2286-2297 (2008)). Experiments in cultured primary human keratinocytes showed that hBD3 can promote keratinocyte migration and proliferation (Niyonsaba, F. et al. *J. Invest. Dermatol.* 127, 594-604 (2016)). When applied on infected diabetic wounds, hBD3 significantly lowered bacteria load and promoted re-epithelialization and wound closure. The effect of hBD3 on keratinocytes can be blocked by pertussis toxin, indicating that the receptor is a GPCR (Niyonsaba, F. et al. *J. Invest. Dermatol.* 127, 594-604 (2016)).

MRGPRX3 as the primary receptor for hBD3 in human keratinocytes. MRGPRX3 belongs to the Mas-related G protein coupled receptors (Mrgprs) family of GPCRs. As described herein, research over the past decade has revealed diverse expression patterns and functions of these receptors in sensory neurons and immune cells (Liu, Q. et al. *Cell* 139, 1353-1365 (2009); Han, L. et al. *Nat Neurosci* 16, 174-182 (2013); McNeil, B. D. et al. *Nature* 519, 237-241 (2015)). Of the 4 human MRGPRXs, MRGPRX3 is highly expressed in epithelial cells, including in keratinocytes, while the others are specific for DRG neurons, mast cells or other immune cell types (Hruz, T. et al. *Adv. Bioinformatics* 2008, 420747 (2008); Kiatsurayanon, C. et al. *J. Dermatol. Sci.* doi:http://dx.doi.org/10.1016/j.jdermsci. (2016.05.006)). Overexpressing human MRGPRX3 using a universal promoter induced keratinocyte hyperproliferation in rats (Kaisho, Y. et al. *Biochem. Biophys. Res. Commun.* 330, 653-657 (2005)). As described herein, Ca2+imaging and knock down experiments in primary human keratinocytes demonstrate that MRGPRX3 is required for the cells to respond to hBD3. Expression analysis and ligand homology further pointed to the mouse gene MrgprA6 as the murine homologue of MRGPRX3, opening up the opportunity for in vivo investigation of these receptors.

Wound Healing

In undamaged skin, the epidermis (surface layer) and dermis (deeper layer) form a protective barrier against the external environment. When the barrier is broken, an orchestrated cascade of biochemical events is set into motion to repair the damage. This process is divided into predictable phases: blood clotting (hemostasis), inflammation, tissue growth (proliferation) and tissue remodeling (maturation). Blood clotting may be considered to be part of the inflammation stage instead of a separate stage.

Hemostasis (blood clotting) begins early in the wound healing process. Within the first few minutes of injury, platelets in the blood begin to stick to the injured site. This activates the platelets, causing a few things to happen. They change into an amorphous shape, more suitable for clotting, and they release chemical signals to promote clotting. This results in the activation of fibrin, which forms a mesh and acts as "glue" to bind platelets to each other. This makes a clot that serves to plug the break in the blood vessel, slowing/preventing further bleeding.

During the inflammation phase, damaged and dead cells are cleared out, along with bacteria and other pathogens or debris. This happens through the process of phagocytosis, where white blood cells "eat" debris by engulfing it. Platelet-derived growth factors are released into the wound that cause the migration and division of cells during the proliferative phase.

In the proliferation (growth of new tissue) phase, angiogenesis, collagen deposition, granulation tissue formation, epithelialization, and wound contraction occur. In angiogenesis, vascular endothelial cells form new blood vessels. In fibroplasia and granulation tissue formation, fibroblasts grow and form a new, provisional extracellular matrix (ECM) by excreting collagen and fibronectin. Concurrently, re-epithelialization of the epidermis occurs, in which epithelial cells proliferate and "crawl" atop the wound bed, providing cover for the new tissue. In wound contraction, myofibroblasts decrease the size of the wound by gripping the wound edges and contracting using a mechanism that resembles that in smooth muscle cells. When the cells' roles are close to complete, unneeded cells undergo apoptosis.

During maturation and remodeling, collagen is realigned along tension lines, and cells that are no longer needed are removed by programmed cell death, or apoptosis. The wound healing process is not only complex but also fragile, and it is susceptible to interruption or failure leading to the formation of non-healing chronic wounds. Factors that contribute to non-healing chronic wounds are diabetes, venous or arterial disease, infection, and metabolic deficiencies of old age.

Dendritic Cells

Dendritic cells (DCs) are antigen-presenting cells (also known as accessory cells) of the mammalian immune system. Their main function is to process antigen material and present it on the cell surface to the T cells of the immune system. They act as messengers between the innate and the adaptive immune systems. Dendritic cells are present in those tissues that are in contact with the external environment, such as the skin (where there is a specialized dendritic cell type called the Langerhans cell) and the inner lining of the nose, lungs, stomach and intestines. They can also be found in an immature state in the blood. Once activated, they migrate to the lymph nodes where they interact with T cells and B cells to initiate and shape the adaptive immune response. Immature dendritic cells are also called veiled cells, as they possess large cytoplasmic "veils" rather than dendrites.

Dorsal Root Ganglia

A dorsal root ganglion (or spinal ganglion) (also known as a posterior root ganglion), is a cluster of nerve cell bodies (a ganglion) in a dorsal root of a spinal nerve. The dorsal root ganglia contain the cell bodies of sensory neurons (afferent). Sensory neurons, also known as afferent neurons, are neurons that convert a specific type of stimulus, via their receptors, into action potentials or graded potentials. This process is called sensory transduction. The cell bodies of the sensory neurons are located in the dorsal ganglia of the spinal cord. A primary sensory neuron is the first in an afferent pathway, beginning at the receptor and ending at a synapse with a secondary sensory neuron, often within a nucleus of the central nervous system.

This sensory information travels along afferent nerve fibers in an afferent or sensory nerve, to the brain via the spinal cord. The stimulus can come from exteroceptors outside the body, for example light and sound, or from interoceptors inside the body, for example blood pressure or the sense of body position. Different types of sensory neurons have different sensory receptors that respond to different kinds of stimuli.

The axons of dorsal root ganglion neurons are known as afferents. In the peripheral nervous system, afferents refer to the axons that relay sensory information into the central nervous system (i.e. the brain and the spinal cord). The neuron consists of three parts: the dendrite, which receives information and relays it to the soma; the soma, the cell body of the neuron; and the axon, which relays information from the soma. In a neuron, the dendrite receives information from another neuron's axon at the synapse, and the axon sends information to the next neuron's dendrites, even though the dendrite may be covered with myelin.

Proton-sensing G protein-coupled receptors are expressed by dorsal root ganglion sensory neurons and might play a role in acid-induced nociception. In some embodiments, G protein-coupled receptors (e.g., MrgprX4 or MrpgrA1) in the primary sensory neurons of the dorsal root ganglion mediate sensations such as pain and itch.

The nerve endings of dorsal root ganglion neurons have a variety of sensory receptors that are activated by mechanical, thermal, chemical, and noxious stimuli. High-threshold channels have a possible role in nociception. The presynaptic regulation of the dorsal nerve ending discharge in the spinal cord can occur through certain types of GABAA receptors, which can control nociception and pain transmission.

HEK293 Cells

Human embryonic kidney 293 cells, also often referred to as HEK 293, HEK-293, 293 cells, or less precisely as HEK cells, are a specific cell line originally derived from human embryonic kidney cells (from an aborted human embryo) grown in tissue culture and from still born animals. HEK 293 cells are very easy to grow and transfect very readily and have been widely used in cell biology research for many years. They are also used by the biotechnology industry to produce therapeutic proteins and viruses for gene therapy. Described herein are HEK293 cells stably expressing either MrgprX3 or MrgprX4.

Pharmaceutical Compositions

In certain embodiments, the present invention provides for a pharmaceutical composition comprising an agent employed in the present invention. The agent can be suitably formulated and introduced into a subject or the environment of a cell by any means recognized for such delivery.

Such compositions typically include the agent and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in a selected solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The compositions of the invention could also be formulated as nanoparticle formulations. The compounds of the invention can be administered for immediate-release, delayed-release, modified-release, sustained-release, pulsed-release and/or controlled-release applications. The pharmaceutical compositions of the invention may contain from 0.01 to 99% weight—per volume of the active material. For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For a compound used in a method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of an agent (i.e., an effective dosage) depends on the agent selected. For instance, single dose amounts of an agent in the range of approximately 1 pg to 1000 mg may be administered; in some embodiments, 10, 30, 100, or 1000 pg, or 10, 30, 100, or 1000 ng, or 10, 30, 100, or 1000 µg, or 10, 30, 100, or 1000 mg may be administered. In some embodiments, 1-5 g of the compositions can be administered.

A therapeutically effective amount of the compound of the present invention can be determined by methods known in the art. In addition to depending on the agent and selected/pharmaceutical formulation used, the therapeutically effective quantities of a pharmaceutical composition of the invention will depend on the age and on the general physiological condition of the patient and the route of administration. In certain embodiments, the therapeutic doses will generally be between about 10 and 2000 mg/day and preferably between about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of an agent can include a single treatment or, optionally, can include a series of treatments.

It can be appreciated that the method of introducing an agent into the environment of a cell will depend on the type of cell and the makeup of its environment. Suitable amounts of an agent must be introduced and these amounts can be empirically determined using standard methods. Exemplary effective concentrations of an individual agent in the environment of a cell can be 500 millimolar or less, 50 millimolar or less, 10 millimolar or less, 1 millimolar or less, 500 nanomolar or less, 50 nanomolar or less, 10 nanomolar or less, or even compositions in which concentrations of 1 nanomolar or less can be used.

The pharmaceutical compositions can be included in a kit, container, pack, or dispenser together with instructions for administration.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Materials and Methods for Examples 2-11

The following materials and methods were used.
Animals

Wild-type 129S1/SvImJ, wild-type BALB/cJ and Rag1−/− in the BALB/c genetic background (C.129S7(B6)-Rag1$^{tm1Mom/J}$) were purchased from the Jackson Laboratory, bred and housed under specific-pathogen-free conditions at the Johns Hopkins School of Medicine. Animals were maintained on a 12-hour day-night cycle, and received autoclaved food and filtered water ad libitum Animals at 8- to 10-weeks of age were used for all other experiments. All animals were conducted under a protocol approved by the Institutional Animal Care and Use Committee of the Johns Hopkins University School of Medicine. All experiments involving equal treatments in WT and mutant samples and animals were conducted by experimenters blind to conditions.
Drug Preparation for Calcium Imaging Lamotrigine (LTG), allopurinol, carbamazepine and oxcarbazepine (all from Sigma) were prepared fresh on the day of the experiment. These drugs were dissolved into dimethyl sulfoxide (DMSO) first, and then were diluted at least 10000× into calcium imaging buffer before use. The final concentrations of drugs for each experiment were indicated in the corresponding figure legend.

HEK293 Cells Culture and Transfection

HEK293 human embryonic kidney cells (ATCC) were cultured in growth medium (DMEM supplemented with 10% heat-inactivated fetal bovine serum (FBS), 100 U ml$^{-1}$ penicillin and 100 mg ml$^{-1}$ streptomycin) at 37° C. To generate Mrgpr-expressing cells, HEK293 cells were transiently transfected with the pcDNA3.1 mammalian expression plasmid inserted with cDNA encoding the Mrgpr genes (except MRGPRX4 and mutated MRGPRX4 which were cloned and inserted into pLX304 vector) using Lipofectamine 3000 (Invitrogen). Stable cell lines expressing Mrgpra1-GFP, Mrgprc11-GFP and MRGPRX4-GFP were generated as previously described (24). Briefly, HEK293 cells were transfected with the cDNA encoding the GFP fused to the C-terminus of Mrgpr proteins in plasmid. The transfected cells were selected with zeocin or blasticidin in DMEM supplemented with 10% FBS. Each cloned cell was further selected as stable cell lines and confirmed the membrane localization of receptor-GFP fusion protein.

Calcium Imaging in HEK293 Cells

In initial experiments, HEK293 cells were plated on 100 μg/ml poly-D-lysine coated glass cover slips, and transiently transfected with vector containing Mrgprs gene, after 24-48 hours of culture, cells were loaded with Fura 2-acetomethoxy ester calcium indicator (0.5 μM, Molecular Probes) along with pluronic F-127 dispersing agent (0.1%, Molecular Probes) for 30 minutes in the dark at 37° C., then washed with calcium imaging buffer (CIB; NaCl 125 mM, KCl 3 mM, CaCl2 2.5 mM, MgCl2 0.6 mM, HEPES 10 mM, glucose 20 mM, NaHCO3 1.2 mM, sucrose 20 mM, brought to pH 7.4 with NaOH). Drugs were added to Fura 2-loaded cells and intracellular free calcium was measured using 340 nm and 380 nm excitation wavelengths with emission measured at 520 nm with a microscope based imaging system (Nikon Eclipse TE200). Changes in emission fluorescence ratios at 340/380 nm excitation were continuously monitored at 1 second intervals. Later, experiments were performed using Mrgpra1-GFP, Mrgprc11-GFP and MRGPRX4-GFP stable cell lines to confirm the findings obtained from the transiently expressing cells.

$EC_{50}$ Determination

Mrgpra1 or both wild-type and mutant MRGPRX4 stably expressed HEK cells were plated overnight in 100 μl culture media on 96-well plates. The next day, the media were replaced with dye-loading solution from the FLIPR® Calcium 5 assay kit (Molecular Devices), diluted in Hank's Balanced Salt Solution (HBSS) with 20 mM HEPES, pH 7.4. After 1 hour of incubation at 37° C., cells were allowed to recover for 10 minutes in the dark at room temperature prior to performing intracellular calcium mobilization assay in a FLEXSTATION® multi-mode plate reader (Molecular Devices). Tested drugs were prepared in HBSS/HEPES solution at 3× concentration. Wells were imaged according to manufacturer's specifications with simultaneous data collection for 180 seconds, and 50 μl of drugs were added at 20 seconds after imaging started. Substances were tested in at least three independent well and the signals were averaged. Responses were determined by subtracting the minimum signal (at the basal level before adding the drug) from the maximum signal (obtained after stimulating with the drug). Dose response curves were plotted as relative fluorescent signal (%) normalized to the highest response (100%) by SOFTMAX® Pro software (Molecular Devices). $EC_{50}$s (half maximal effective concentration) were determined as a concentration of the substances that gave 50% response of normalized peak response to that substance in that trial.

Drug Labeling and Internalization Assay

To label the drug with red-fluorescent dye, 1 μg of LTG was dissolved in 50 μl dimethyformamide (DMF) first, and further diluted with 450 μl reaction buffer (0.1M sodium bicarbonate buffer, pH9.0) to obtain LTG at a concentration of 7.8 mM. Then, 50 μl of Texas-red-conjugated sulfonyl chloride (Thermo Fisher Scientific, T1905) dissolved in DMF at 10 mg ml–1 was slowly added into LTG solution. The reaction was incubated at 4° C. for 1 hour with continuous stirring. The mixture was then diluted into cell culture medium for further use. LTG labeled with Texas Red dye can create bright red-fluorescence with excitation/emission maxima ~595/615 nm. HEK293 cells stably expressing Mrgpra1-GFP, Mrgprc11-GFP or MRGPRX4-GFP fusion protein were grown in DMEM with 10% FBS. After 4-6 hours of serum starvation, cells were treated with either medium, dye alone, unlabeled LTG or Texas-Red-labeled LTG at 37° C. for 15 or 60 min. Cells were washed with PBS and fixed with 4% paraformaldehyde in PBS. The subcellular localization of Mrgpr-GFP or drug was visualized under a confocal fluorescence microscope with a 400× magnification (Zeiss LSM 700).

LTG Binding Capacity

CMC analysis was performed with a Shimadzu LC-2010A apparatus that consisted of pumps, degasser, autosampler, column oven, and a diode-array detector (Shimadzu, Kyoto, Japan). The data were acquired by the Lab-solution program (Shimadzu). The mobile phase consisted of phosphate-buffered saline (PBS; 5 mM, pH 7.4) and was delivered at a flow rate of 0.2 ml/min. The stock solutions (100 μM) of lamotrigine were prepared by separately dissolving the standard drugs in methanol. Standard solutions at various concentrations were prepared by diluting the stock solutions with the mobile phase. The MRGPRX2/CMC and MRGPRX4/CMC column was prepared as follows. Briefly, MRGPRX4-expressed HEK293 cells (1×10$^8$) were harvested and centrifuged (1000 g, 10 min, at 4° C.). Cells were washed with physiological saline (pH=7.4) by centrifugation at 1000 g for 10 min at 4° C. Cells were lysed by ultrasonic in Tris-HCl (50 mM, pH=7.4) for 30 min and centrifuged twice at 1000 g for 10 min at 4° C. The collected supernatant was then centrifuged at 12000 g for 20 min at 4° C. and the pellet was resuspended in 5 ml ice-cold physiological saline solution. Silica (45 mg) was activated at 105° C. for 30 min. The cell membrane suspension was homogenized/adsorbed with the activated silica under vacuum with agitation at 4° C. overnight. The cell membrane stationary phase was then washed with distilled water and packed into a column using the wet packing procedure (10 Mpa, 5 min) to obtain the CMC column.

$K_D$ value of lamotrigine was determined by means of the MRGPRX4/CMC system as follows. Standard solutions of each compound were separately added to the mobile phase to obtain a set of new mobile phases with a concentration range of $2.0 \times 10^{-8}$, $4.0 \times 10^{-8}$, $8.0 \times 10^{-8}$, $1.6 \times 10^{-7}$, and $3.2 \times 10^{-7}$ Molar, respectively. This mobile phase with different concentrations of each compound was separately pumped through the MRGPRX4/CMC column at a flow rate of 0.2 ml min$^{-1}$ under the gradient program and the breakthrough curves of the compound with different concentrations were recorded. In accordance with Eq. 4, the corresponding graph of the reciprocal value of [LR]s versus [L]m was obtained.

Moreover, $K_D$ could be determined by calculating the ratio of the intercept to the slope, and [R]s was obtained from the inverse of the intercept.

Mrgpra1 Knockout-eGFP Knockin Mice Generation

SJS/TEN Mouse Model

Eight-to-ten week old male mice were orally gavaged with either causative drugs (LTG, allopurinol, oxcarbazepine) suspended in saline or saline once daily. The dosage was based on milligrams per kilogram of animal's body weight as indicated (for example, LTG 50 mg kg$^{-1}$ body weight). Skin, eyes, and mucosa, survival, body weight, physical and gross appearances (particularly on the eyes, mucosa and skins) were monitored every day.

Histological Analysis and Immunostaining

The animals were deeply anesthetized with pentobarbital and transcardially perfused with 20 ml 0.1 M cold PBS (pH 7.4) followed with 25 ml of cold 4% paraformaldehyde (PFA). Paw skin, eyelid, spleen, lymph nodes were dissected out. postfixed in 4% PFA for more than two hours, and cryoprotected in a 20% followed by 30% sucrose solution for 24 hours each at 4° C. Tissue samples were embedded in the optimal cutting temperature (OCT) and frozen before being serially cut into 20 µm sections and placed onto slides. Hematoxylin and eosin (H&E) staining was performed using standard procedures according to the manufacturer's instruction VITROVIEW™ H&E Stain Kit). To quantify amount of apoptotic cells, terminal deoxynucleotidyl transferase dUTP nick end labeling (TUNEL) assay, a method for detecting DNA fragmentation that results from apoptotic cells by labeling the terminal end of nucleic acids, was performed by following the protocol of Apo-BrdU DNA Fragmentation Assay Kit (Biovision). To estimate the total cell number in tissue, all nuclei were stained with propidium iodide. Digital photographs were captured under confocal fluorescent microscopy at x200 magnification (Zeiss LSM 700). The number of TUNEL-positive nuclei were counted and reported as a percentage over the number of total nuclei observed in the skin's epidermis layer.

For Granzyme B immunostaining, slides were washed with a 0.3% Triton X-100 PBS solution, incubated in blocking solution (10% normal goat serum) for one hour, then incubated 30 min at room temperature with 1:500 dilution of anti-Mouse Granzyme B Biotin (eBioscience, clone 16G6) in blocking solution, and developed color using ABC kit (Vector Laboratories) and TMB substrate kit (Vector Laboratories) as company's manual.

For immunofluorescent staining, slides were washed, blocked with 10% normal goat serum, and then incubated overnight at 4° C. with the following primary antibodies diluted in the blocking solution: chicken anti-GFP (1:500, Ayes Labs), Alexa Fluor 594 hamster anti-mouse CD11c (1:500, Biolegend, clone N418), Alexa Flour 647 rat anti-mouse CD3 (1:500, Biolegend, 17A2), Alexa Fluor 594 anti-mouse CD8a (1:500, Biolegend, 53-6.7). Slides were washed with the 0.3% Triton solution. For GFP staining, slides were subsequently incubated in Alexa Flour 488 goat anti-chicken IgY (1:1000 Thermo Fisher) for two hours at room temperature. Slides were next washed in PBS prior to mounting with an anti-fade solution for imaging.

Measurement of Mouse TNF-α and Granzyme B

The paw skins from SJS/TEN model mice were collected on day 9 after daily drug administration. The tissues were weighed and homogenized in cold PBS containing a protease inhibitor cocktail (Cell Signaling Technology) using the Bio-Gen Pro200 Homogenizer (Pro Scientific). Homogenates were then centrifuged at 10,000 g at 4° C. for 10 minutes. The supernatants were used to measure the levels of TNF-α and Granzyme B levels using Duoset® ELISA development system kits (R&D System). Each sample was assayed in minimum triplicate wells, and cytokine concentrations were reported as pg ml$^{-1}$ mg$^{-1}$ tissue.

Fluorescence-Activated Cell Sorting (FACS) of GFP+ Cells

To characterize GFP+ cells from Mrgpra1$^{GFP/GFP}$ mice, their spleens and lymph nodes were cut into small pieces and digested in RPMI 1640 medium containing 1 mg ml$^{-1}$ collagenase D (Sigma-Aldrich) and 30 µg ml$^{-1}$ DNase I (Worthington Biochemical) at 37° C. for 30 minutes. Digested tissues were then filtered through a 70-µm mesh nylon cell strainer (BD Falcon) to generate a single-cell suspension. Contaminating erythrocytes in splenocyte suspensions were lysed in ACK lysis buffer (Quality Biological) at room temperature for 5 minutes. The remaining cells were washed twice in PBS and stained with LIVE/DEAD Aqua (ThermoFisher, Molecular Probes) for 30 minutes on ice. Then, the cells were washed, resuspended in FACS staining buffer (1×PBS with 2% heated-inactivated FBS), and blocked non-specific binding with anti-mouse CD16/CD32 Fc Block (BD Biosciences) for 10 minutes prior to incubating for 30 minutes on ice with a variable panel of fluorochrome-conjugated surface marker staining antibodies including antibodies recognizing CD4 (clone RM4-5), CD8a (53-6.7), CD11b (M1/70), CD45 (30-F11), CD317 (927), CD370 (DNGR1, 7H11), F4/80 (BM8), I-A/I-E (M5/114.15.2), Ly6C (HK1.4), Ly6G (1A8), XCR1 (ZET; all from Biolegend), CD3 (145-2C11), and CD11c (N418; eBioscience). All stained samples were then washed twice in staining buffer and cell acquisition was performed on an LSR-II flow cytometer (BD Biosciences). All flow cytometry data were analyzed, gated as shown in FIG. 11A-11C and plotted with FlowJo software (FlowJo, LLC). Splenocytes and lymph node cells from Mrgpra1$^{+/+}$ wild-type (no GFP) mice were used to set a gate for GFP negative area. "Fluorescence minus one" controls were used for other surface staining when necessary.

Mouse Immune Cell Sorting for RNA Preparation and Calcium Imaging

Figure 12:
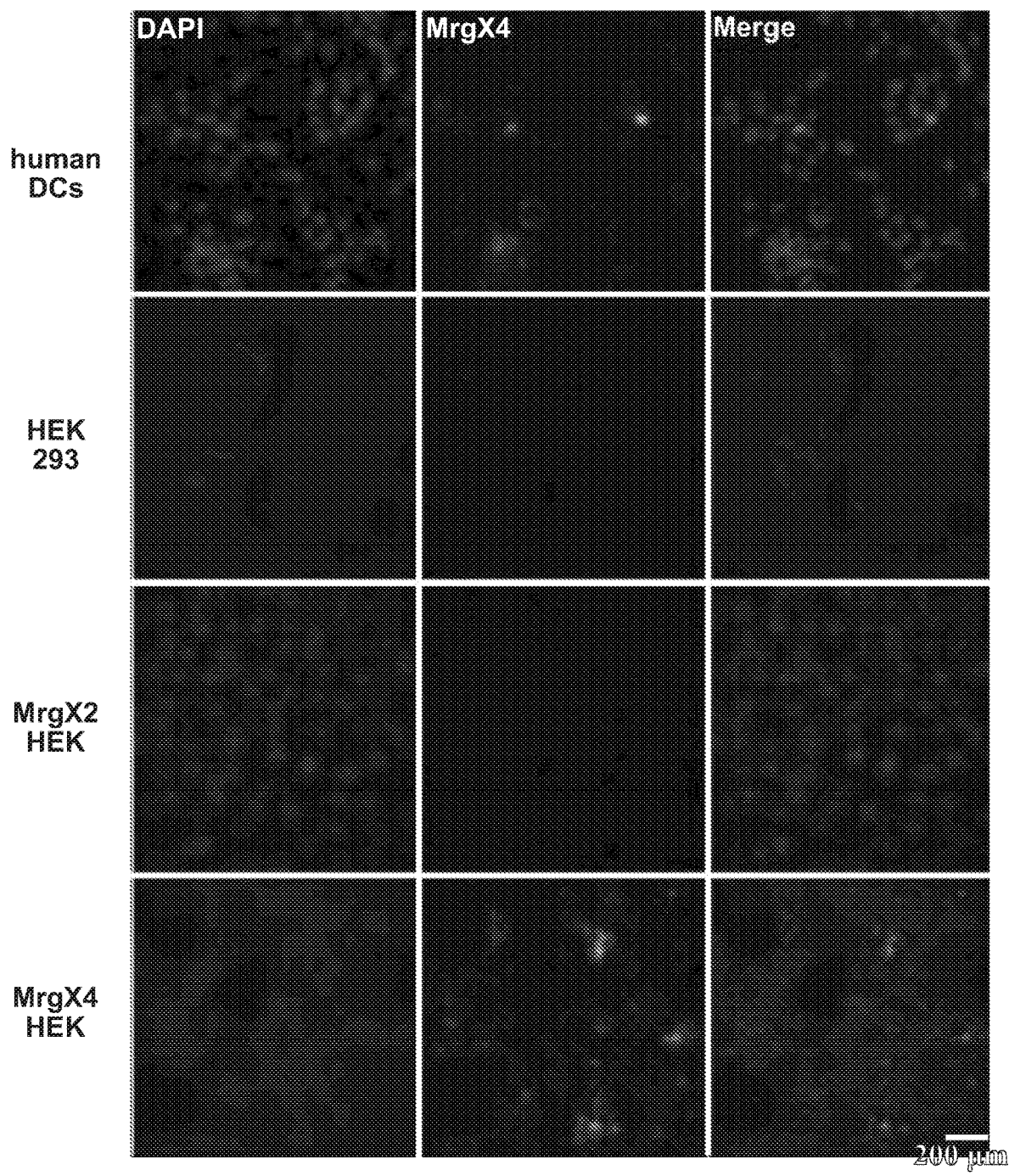
FIG. 12 is a series of photomicrographs demonstrating the expression of MRGPRX4 in human dendritic cells Immunofluorescence double staining of DAPI (blue) and MRGPRX4 (green) shows MRGPRX4 expressed in human dendritic cells. HEK293 and MRGPRX2-HEK cells were used as a negative control, while MRGPRX4-HEK cells are used as a positive control. Scale bar, 200 μm.

To sort different cell types of splenocytes based on CD11c and MHC-II expression, single cell suspension of mouse splenocytes was prepared as above described. Then. CD11c+ cells were enriched with EASYSEP™ Mouse CD11c Positive Selection Kit (StemCell Technologies) as suggested by manufacturer's protocol with some modification. Briefly. cell suspension was block for non-specific binding with mouse FcR blocker, then stained with phycoerythrin (PE)-conjugated antibody against CD11c and followed by incubating with tetrameric antibody complexes that recognized PE and magnetic nanoparticles. PE-labelled cells were then once recovered from immunomagnetic separation. Without repetitive magnetic separation. enriched CD11c+ cells were stained with APC-Cy7-conjugated anti-mouse I-A/I-E (clone M5/114.15.2) antibody (Biolegend). Cell populations were gated and sorted based on CD11c and MHC-II expression as shown in FIG. 12 on a FACSARIA™ IIu cell sorter (BD Bioscience) with FACSDIVA™ software. Sorted cells were then immediately used for either for RNA isolation to check Mrgpra1 expression or calcium imaging (as described on HEK cells).

RNA Isolation and Quantitative RT-PCR

Mouse tissue samples from different organs were homogenized and their RNA was extracted with either RNeasy Plus Mini Kit (Qiagen) or RNeasy Fibrous Tissue Mini Kit according to the manufacturer's manual. RNA was extracted from isolated mouse cells or cultured human dendritic cells using RNeasy Micro Kit (Qiagen). To minimize genomic DNA (gDNA) contamination, RNA was purified using gDNA Eliminator columns (Qiagen) and treated for 15 minutes with DNase I on the column Five hundred nanograms of total RNA from tissues or thirty nanograms from cells was reverse-transcribed into complementary DNA (cDNA) with oilgo-dT and random primers using an iScript cDNA synthesis kit (Bio-Rad) following the manufacturer's instruction. Negative control reactions without reverse transcriptase were performed to check for contamination of gDNA. Then quantitative PCR assays were carried out from 2 L of cDNA using 0.5 1 Taqman specific primer/probes (Thermo Fisher; Mm01703261 for Mrgpra1; Mm04394036 for Actb; Hs00607779 for MRGPRX4; Hs01060665 for ACTB), 7.5 L of Taqman Universal Master Mix (Thermo Fisher), and 5 L of DEPC-treated water. The PCR reaction was performed with the following thermal profile: 50° C. for 2 minutes, 95° C. for 10 minutes, and then 45 cycles of 95° C. (15 seconds), followed by 60° C. (1 minute). The PCR products were visualized by 2% agarose gel electrophoresis.

In Vivo Depletion of CD4 and CD8 T Cells

Figure 10:
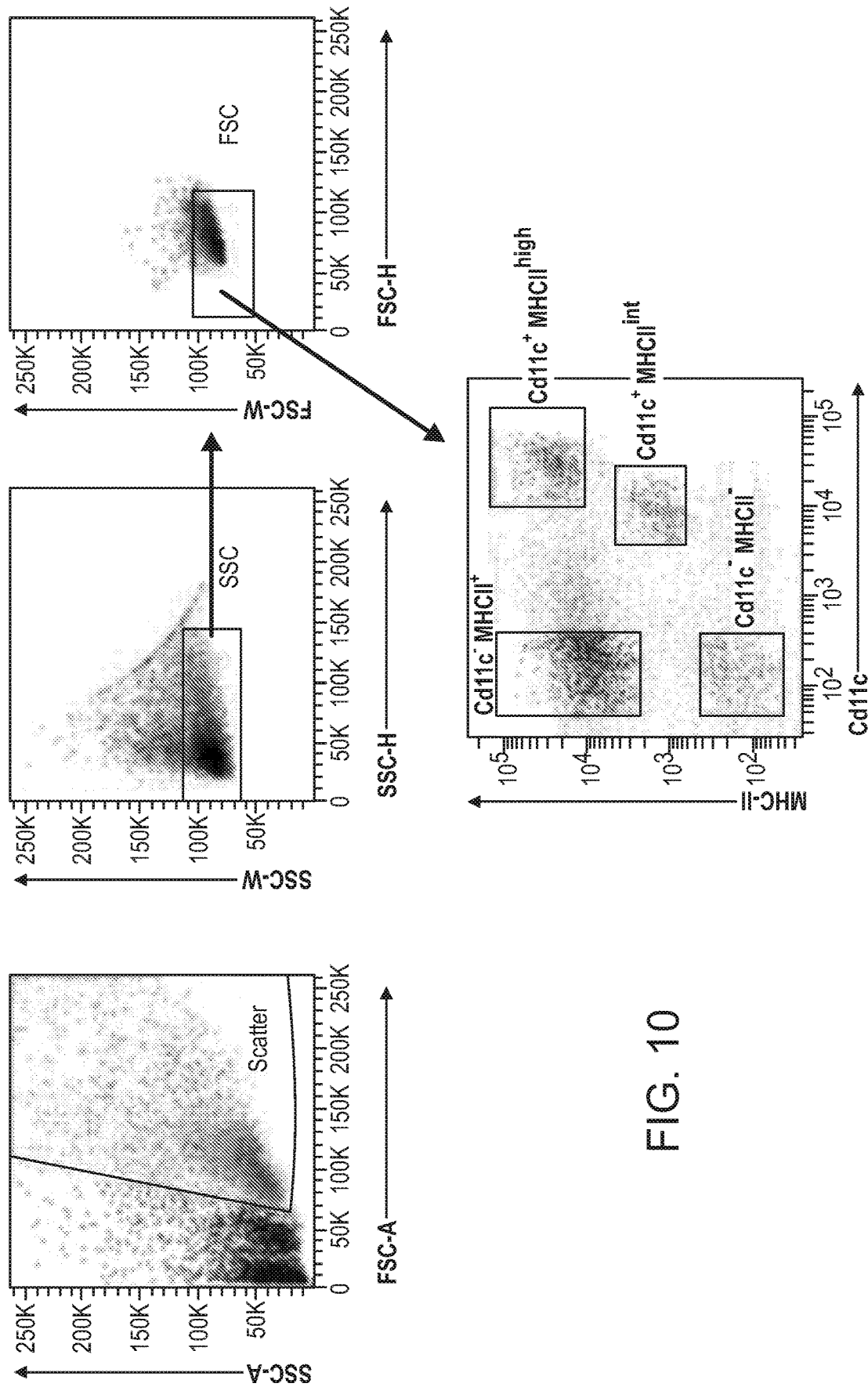
FIG. 10 is a series of FACS plots demonstrating the sorting of different types of splenocytes Immune cell populations were gated and sorted based on CD11c and MHC-II expression with FACS Diva software. Sorted cells were then immediately used for either for RNA isolation or calcium imaging.

Rat monoclonal antibodies against mouse CD4 (BioX-Cell, clone GK1.5) and CD8 (BioXCell, clone 2.43) were used for in vivo depletion of CD4/CD8 T lymphocytes. Male wild-type 129S1/SvImJ mice were given intraperitoneal injections of 200 µg of either CD4 or CD8 antibody at day −2, 0 and 3. The control group was treated with rat IgG2b isotype control antibody (BioXCell) with the similar protocol. All mice were gavaged with LTG (50 mg kg$^{-1}$ body weight) once a day starting from day 0. The efficacy of depletion was assessed on day 7 by flow cytometric analysis of spleen and peripheral blood. This depletion scheme resulted in approximately 98.4% and 89.9% reductions of CD4+ cells in spleen and peripheral blood of CD4-depleted mice vs 99.1% and 97.6% reductions of CD8+ cells in spleen and peripheral blood of CD8-depleted mice, respectively (FIG. 10).

Dendritic Cells Adoptive Transfer

Spleens from naïve 129S1 WT mice or Mrgpra1−/− mice were aseptically removed and DCs were isolated using mouse Pan Dendritic Cell isolation kit (Miltenyi Biotec) according to the manufacturer's manual. Briefly, single cell suspensions from spleen were generated by collagenase D/DNase I digestion as above mentioned. Then, cocktail of biotin-conjugated antibodies against non-dendritic cells followed by anti-biotin magnetic microbeads were added to the cell suspensions. Dendritic cells were separated from bead labelled non-dendritic cells using LS column. Dendritic cells freshly isolated either from WT mice or KO animals suspended in 200 µl Hanks' Balanced Salt Solution (HBSS) were injected intravenously (tail vein) into the naïve male Mrgpra1 knockout mice ($2 \times 10^6$ cells/mouse) one day before starting daily LTG (50 mg kg$^{-1}$ body weight) administration.

Human Peripheral Blood Dendritic Cells Culture

Human Peripheral Blood Dendritic Cells from four different donors were purchased from Lonza (cc-2701) and STEMCELL Technologies (70041). To maintain the cells as immature dendritic cells, cells were thawed and cultured in RPMI 1640 medium supplemented with 10% FBS, 50 ng ml-1 IL-4 and 50 ng ml$^{-1}$ GM-CSF in a humidified 37° C. 5% $CO_2$ incubator. All the experiments on these dendritic cells were completed within 7 days before the cells died.

siRNA Transfection of Human DCs

Expression of MRGPRX4 was down-regulated in dendritic cells using ON-TARGET plus SMARTpool siRNA against MRGPRX4 (Dharmacon). On day 3 after beginning of culture, human dendritic cells were washed with medium, collected and centrifuged at 200 g for 10 minutes at room temperature. Then cells were resuspended in Nucleofector® solution and transfected with either MRGPRX4 siRNA or non-targeting control siRNA using NUCLEOFACTOR™ 2b device (Lonza) according to Human Dendritic Cell NUCLEOFACTOR™ Kit's protocol. Following transfection, add 500 µl of supplemented culture medium into the sample gently and incubated for 48 hours. Then, cells were used for calcium imaging and internalization assays.

Internalization of Human DCs

Human dendritic cells were seeded on cover slips and cultured in RPMI 1640 medium with 10% FBS for 5 days. After 4-6 hours serum starvation, cells were treated with medium, dye alone, unconjugated LTG or Texas Red-conjugated LTG (Texas Red was conjugated to LTG as mentioned above) in the dark at 37° C. for 15 min Cells were fixed with 4% paraformaldehyde in PBS, and washed with PBS. Then fixed cells were blocked in blocking solution (10% normal goat serum) for one hour prior to incubation in rabbit anti-MRGPRX4 (10 ug ml$^{-1}$, Abcam, ab188740) at 4° C. overnight. Cells were subsequently washed with the 0.3% Triton solution and incubated in Alexa Flour 484-conjugated goat anti-rabbit IgG (1:1000, Thermo Fisher) for two hours at room temperature. The cover slips were washed with PBS and mounted with an antifade mounting medium with DAPI (Vector Laboratories).

Patients and Samples

The study was approved by the Research Ethics Committee of National Taiwan University Hospital (NTUH-REC No.: 2015121334RINC) and it was conducted according to the principles of the Declaration of Helsinki. The cases of severe adverse cutaneous reactions (cADR) to lamotrigine, including maculopapular eruption (MPE), drug reaction with eosinophilia and systemic symptoms (DRESS), and Stevens-Johnson syndrome (SJS), were evaluated and diagnosed by the dermatology specialist. The cases of lamotrigine tolerance were recruited from the neurology clinic with the history of usage for lamotrigine for more than 2 months and did not report any associated cutaneous adverse reactions. Peripheral blood mononuclear cells (PBMC) were separated from the peripheral blood as previously described (25). Blood samples were mixed with equal amount of Ficoll-Paque PLUS solution (GE Healthcare) and further centrifuged at 600 g for 40 minutes. The PBMC were preserved in −80° C.

Reverse Transcription and MRGPRX4 Sequencing

Total RNA from human PBMC was extracted with Trizol reagent (Invitrogen). Reverse transcription of the RNA was carried out with RevertAid RT Reverse Transcription Kit (ThermoFisher Scientific, K1691). PCR was carried out with the MRGPRX4 forward primer 5'-CAGAGATGATA-CAGCTGGTG-3' (SEQ ID NO: 1) and MRGPRX4 reverse primer 5'-GACTGGGATGAAATCTGACG-3' (SEQ ID NO: 2). PCR conditions: 94° C. 3 minutes and 30 cycles of 30 seconds at 94° C., 30 seconds at 52° C., and 30 seconds at 72° C. Sequencing was performed with both the forward and reverse primers.

Example 2: Identification of MRGPRX4 as a G Protein Coupled Receptor Involved in Adverse Drug Reactions (ADR)

As described herein, a mast cell specific receptor Mrgprb2/MRGPRX2 (a member of MAS-related G-protein coupled receptor (Mrgpr) subfamily) that is essential for drug-induced anaphylactoid reactions (FIG. 1A) was identified previously ((10), incorporated herein by reference). To determine whether Mrgprs are involved in other types of ADRs such as Stevens Johnson Syndromes (SJS), the SJS-causing drug lamotrigine was screened against Mrgprs individually expressed in HEK293 cells. Using a $Ca^{2+}$ imaging assay, it was determined that only mouse Mrgpra1 and human MRGPRX4 were specifically activated by several SJS-associated drugs such as lamotrigine (LTG) and oxcarbazepine The $EC_{50}$ of LTG on human MRGPRX4 is around 200 μM which within the dose range used in clinics (11,12). The EC50 of LTG on mouse MrgprA1 is around 30 μM.

To assess the physical interaction of ligand and receptor, cell membrane chromatography (CMC) experiments were performed in which an MRGPRX4-expressing HEK293 cell membrane was immobilized onto a column and the elution of LTG through the column was monitored. Using this affinity chromatography technique, it was determined that LTG could be retained on the MRGPRX4/CMC column with the binding $K_d$ of 417±24 nM (FIG. 1B-D), whereas it could not on MRGPRX2/CMC column (FIG. 1B). As most of GPCRs are internalized from the cell surface into intracellular compartment following to ligand-receptor interaction (13), it was then determined whether the drug can induce the internalization of Mrgpra1 and MRGPRX4. To assess this question, HEK293 cells overexpressing fusion protein of either Mrgpra1 or MRGPRX4 receptor with green fluorescent protein (GFP) were used and LTG with Texas Red fluorescent dye was conjugated. Stimulation of the cells with LTG can induce the internalization of Mrgpra1-GFP and MRGPRX4-GFP receptor, whereas the receptors remained mostly on the plasma membrane without agonist (FIG. 1E). Using Texas Red-labelled LTG, the uptake of drug into the cells along with the GFP-labelled receptor (FIG. 1E) was observed. LTG did not induce the internalization of Mrgprc11-GFP and was not absorbed into the cells expressing this receptor (data not shown). Taken together, these strongly suggested that LTG may specifically bind and activate Mrgpra1 and MRGPRX4.

Figure 2:
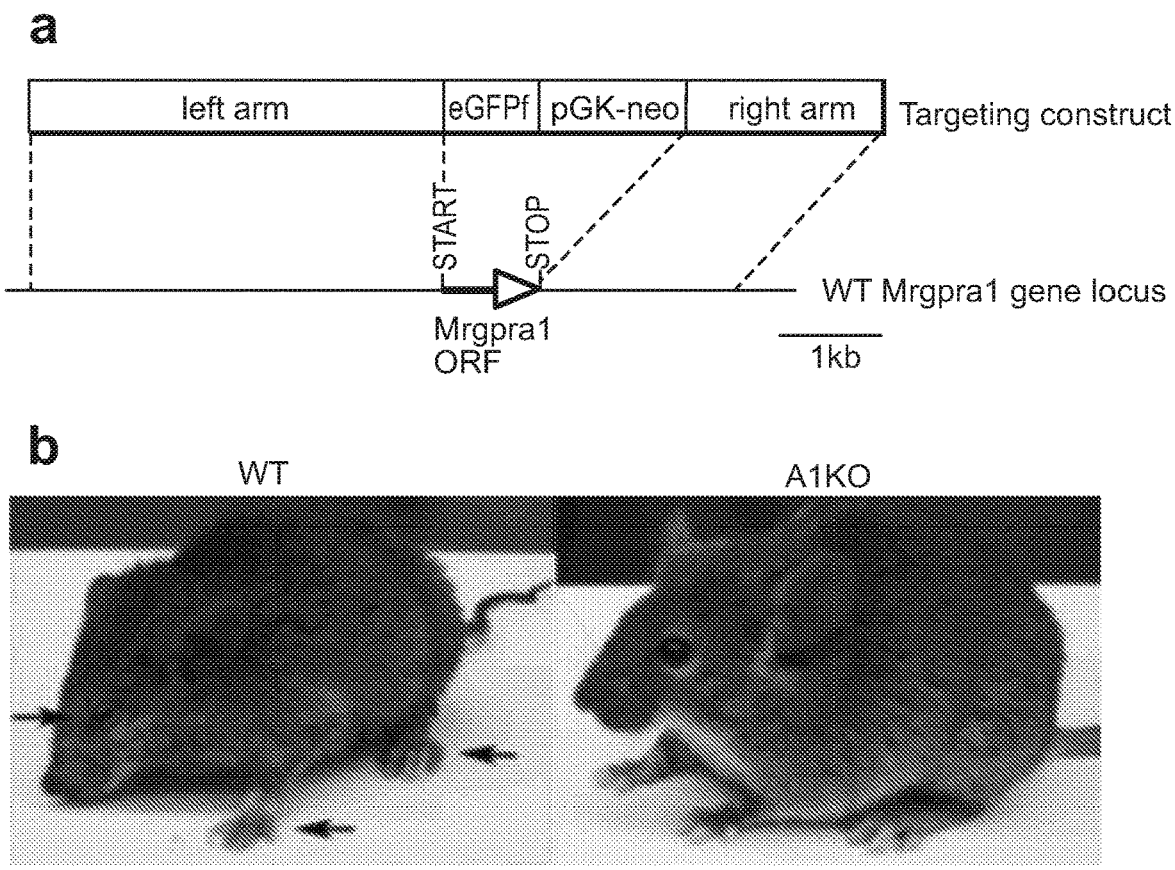
FIG. 2A-FIG. 2F is a series of illustrations, photographs, photomicrographs, and graphs demonstrating that LTG can induce SJS-like phenotypes in 129S1/SvImJ WT mice, but not in Mrgpra1 KO mice.
Figure 2:
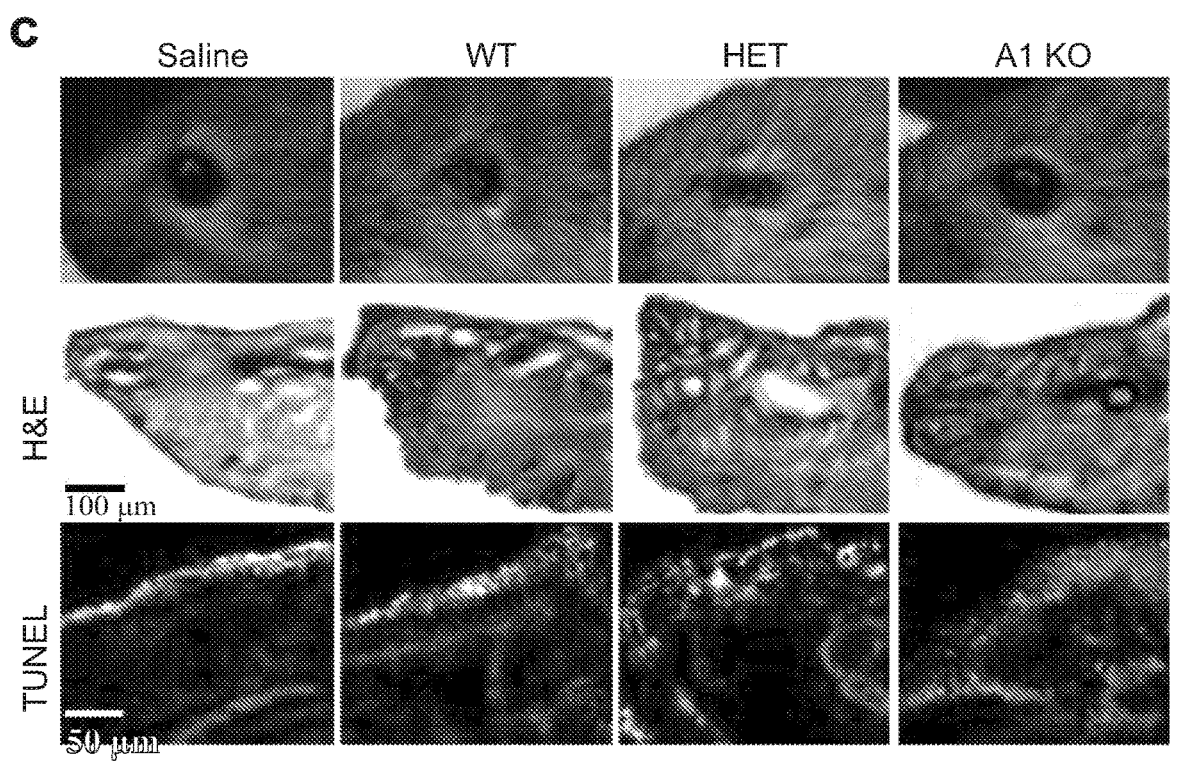
Figure 2:
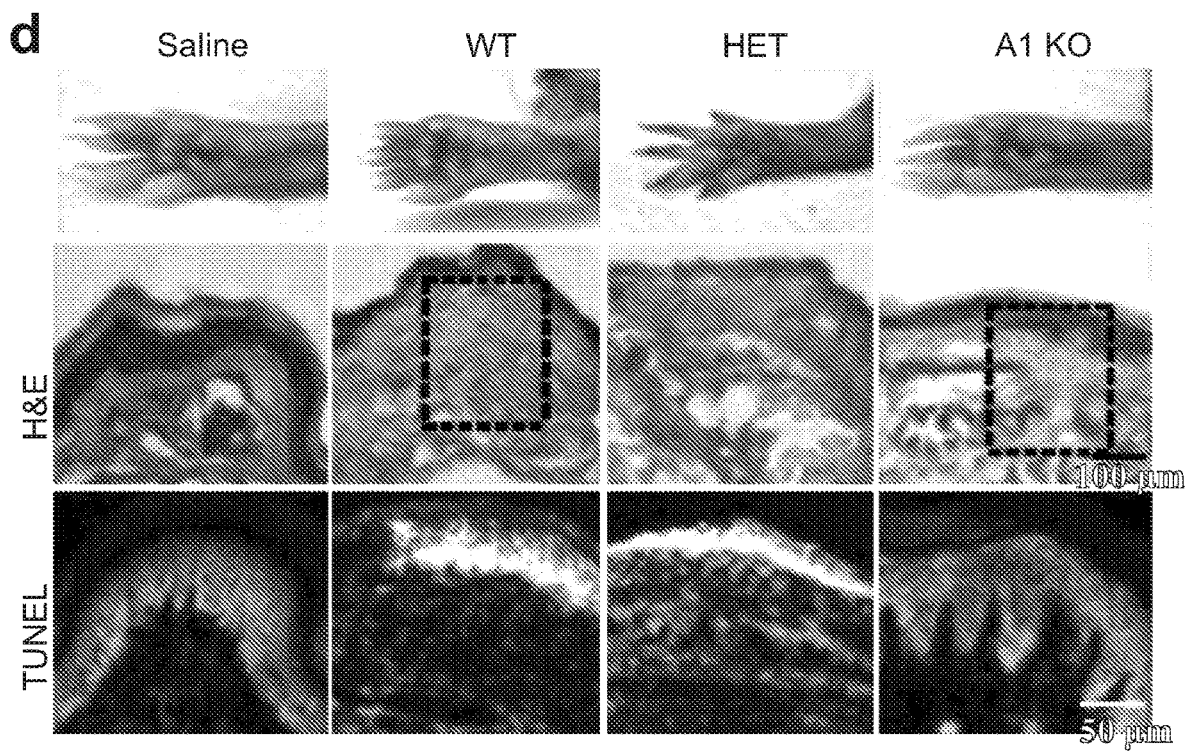
Figure 2:
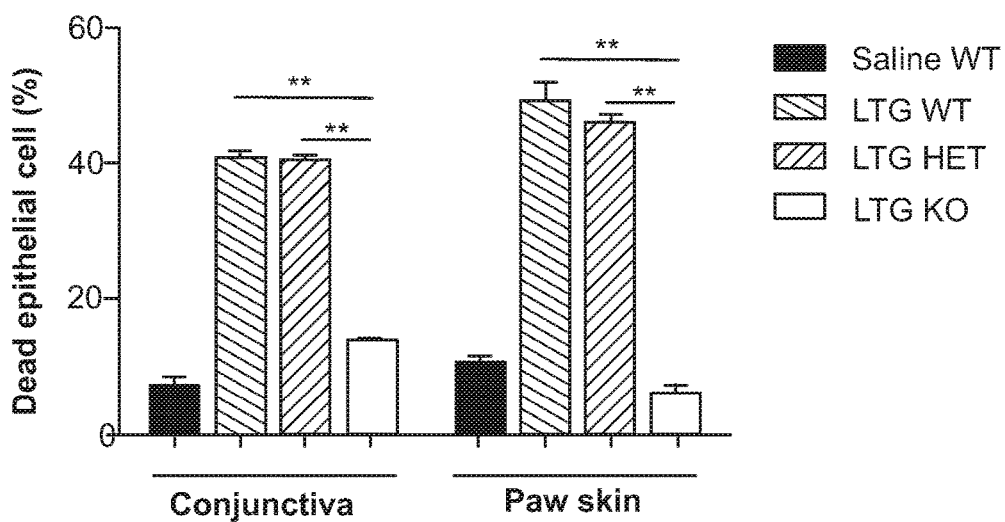
Figure 2:
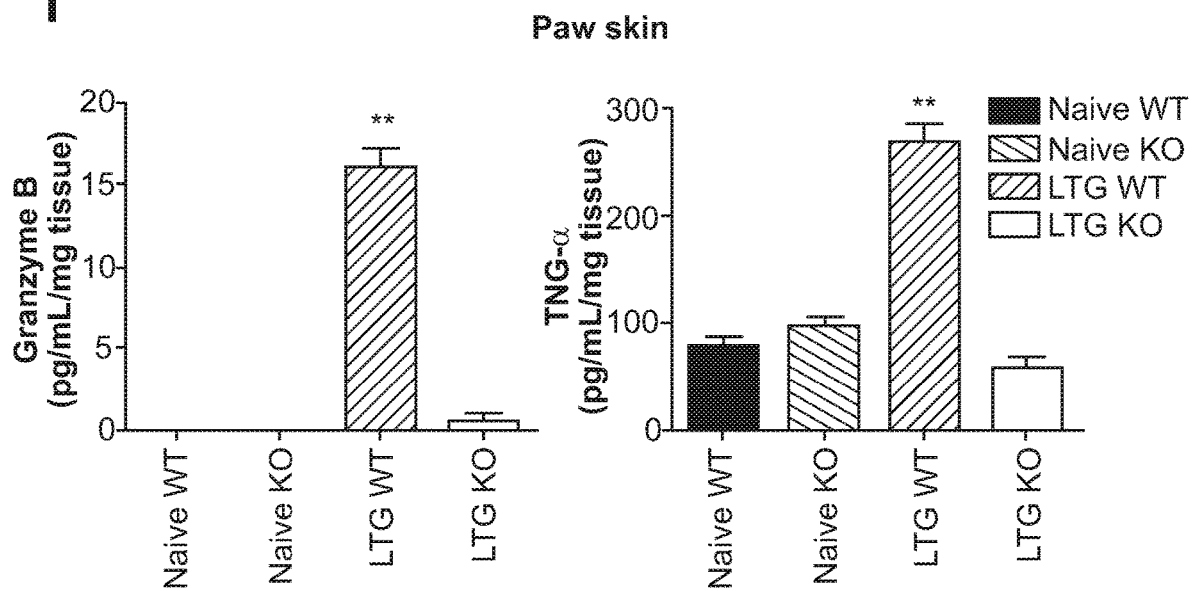
Figure 5:
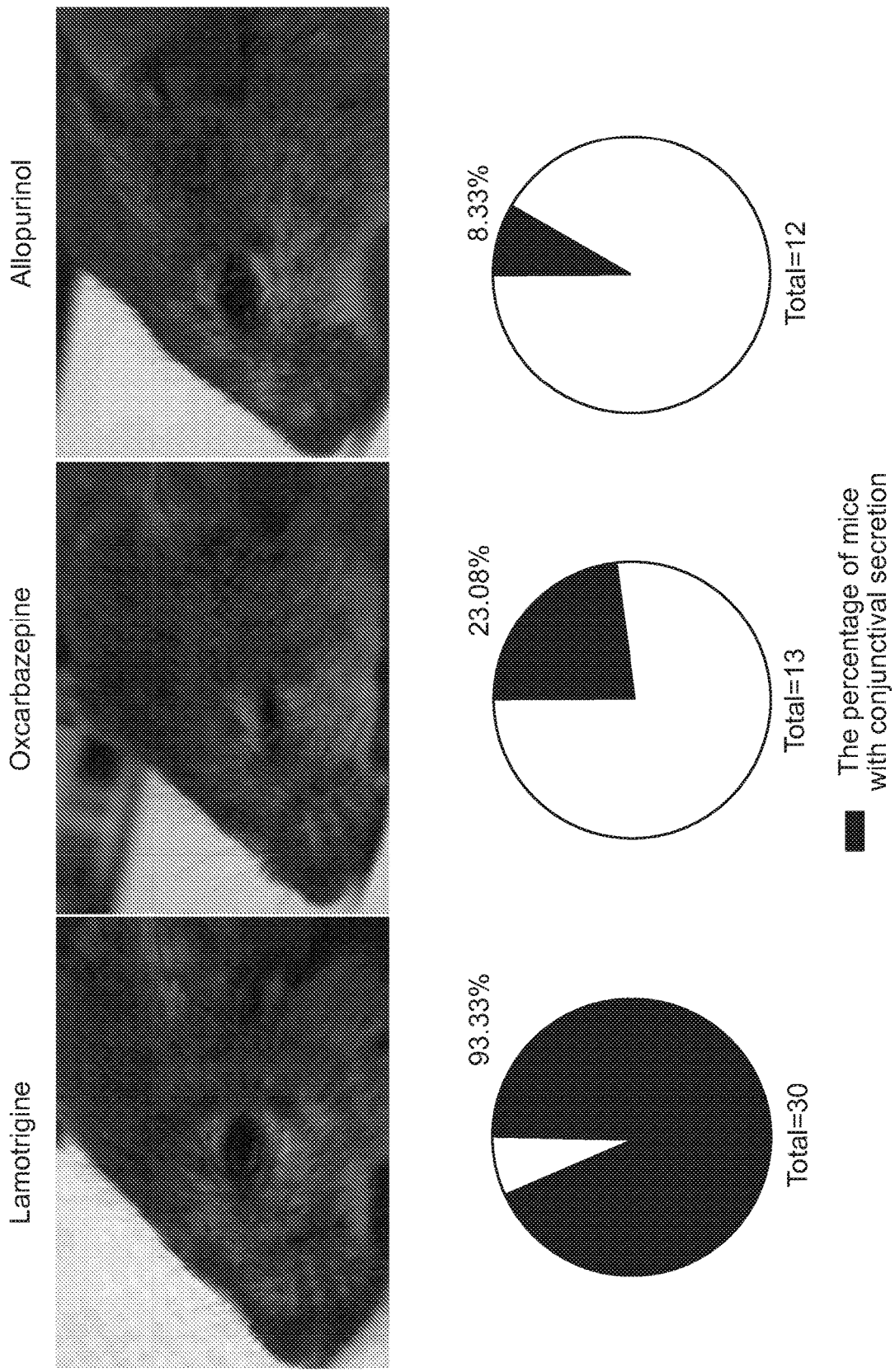
FIG. 5 is a series of photographs and graphs demonstrating the establishment of the SJS animal model. 129S1/SvImJ WT mice were gavaged with drugs that can induce SJS, such as lamotrigine (50 mg kg−1 body weight), oxcarbazepine (200 mg kg−1 body weight) and allopurinol (100 mg kg−1 body weight) daily for 20 days. At day 7, mice formed conjunctival secretion in their eyes in three groups. The highest incidence of mucosal secretion is induced by LTG (93.33%).
Figure 6:
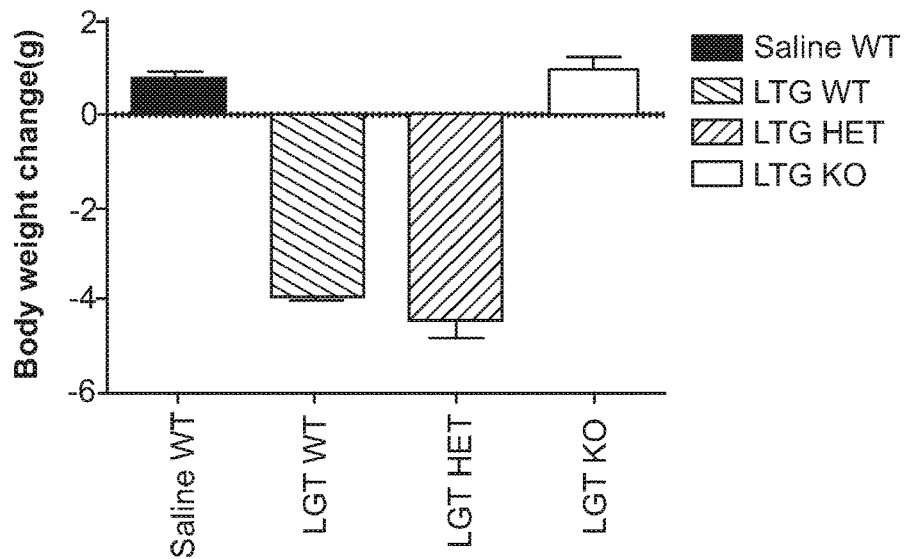
FIG. 6A-FIG. 6F is a series of graphs and photomicrographs demonstrating the injury induced by LTG.
Figure 6:
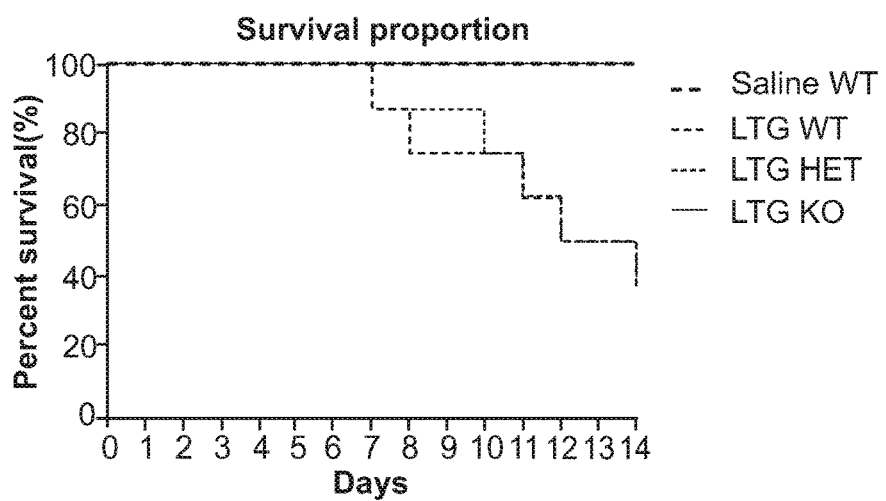
Figure 6:
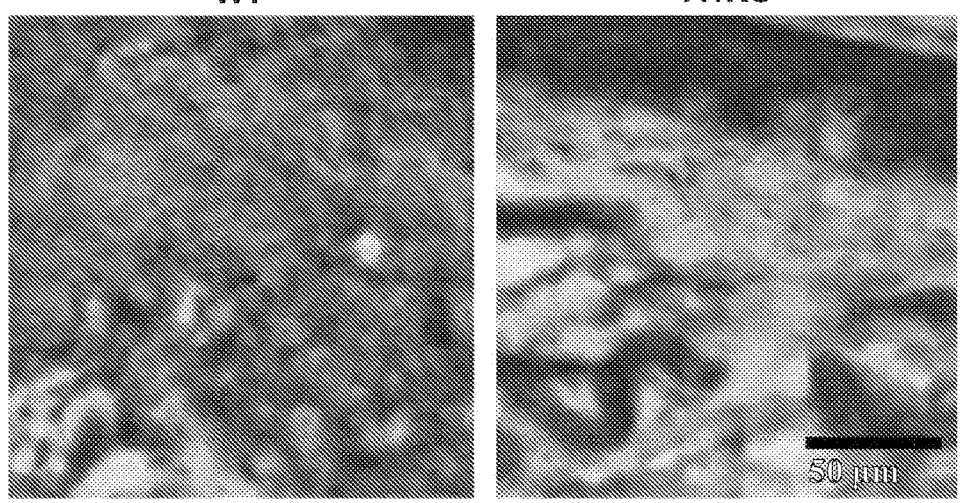
Figure 6:
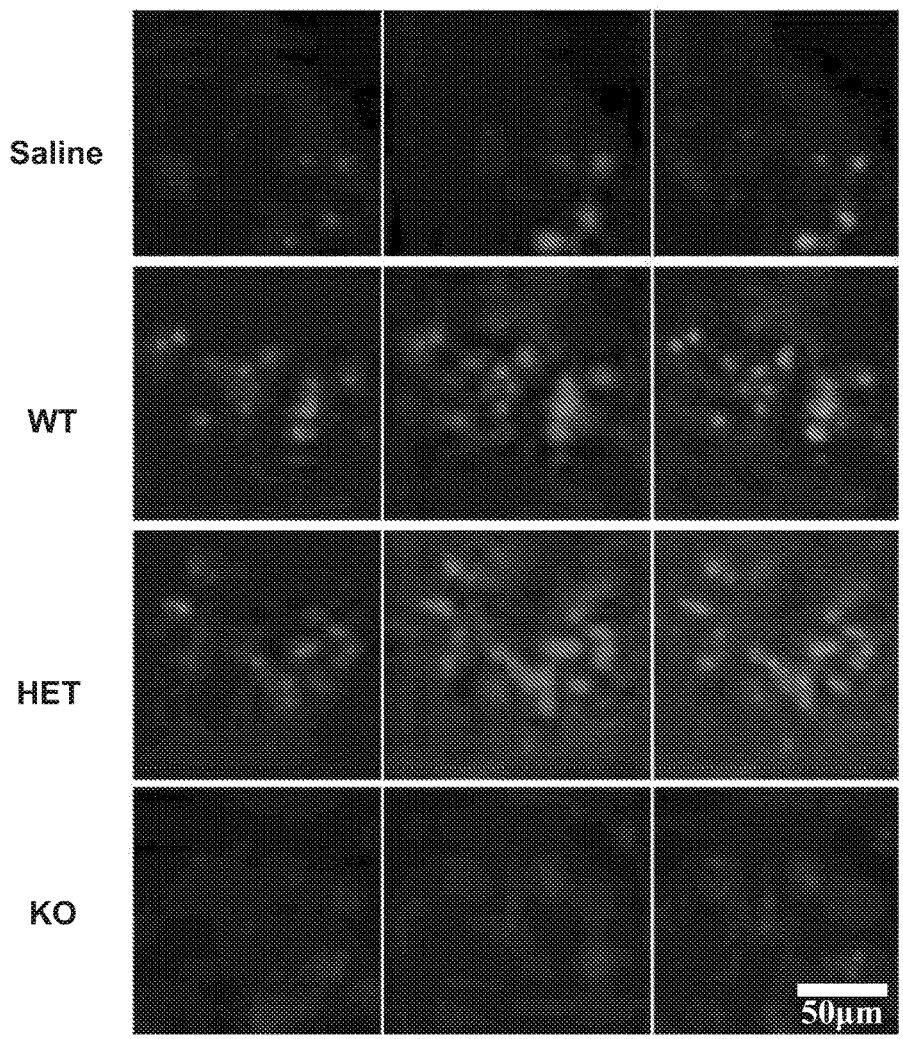
Figure 6:
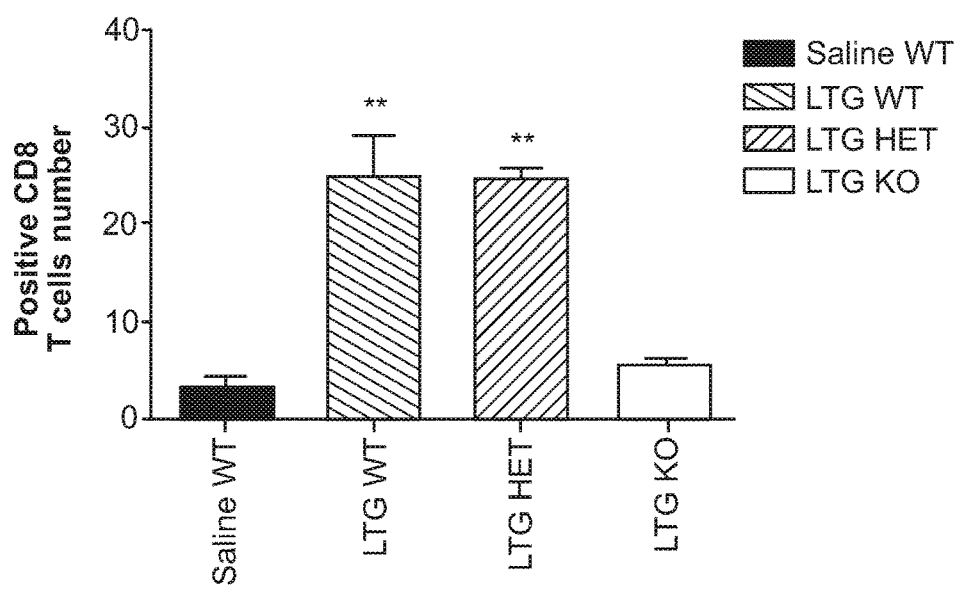
Figure 6:
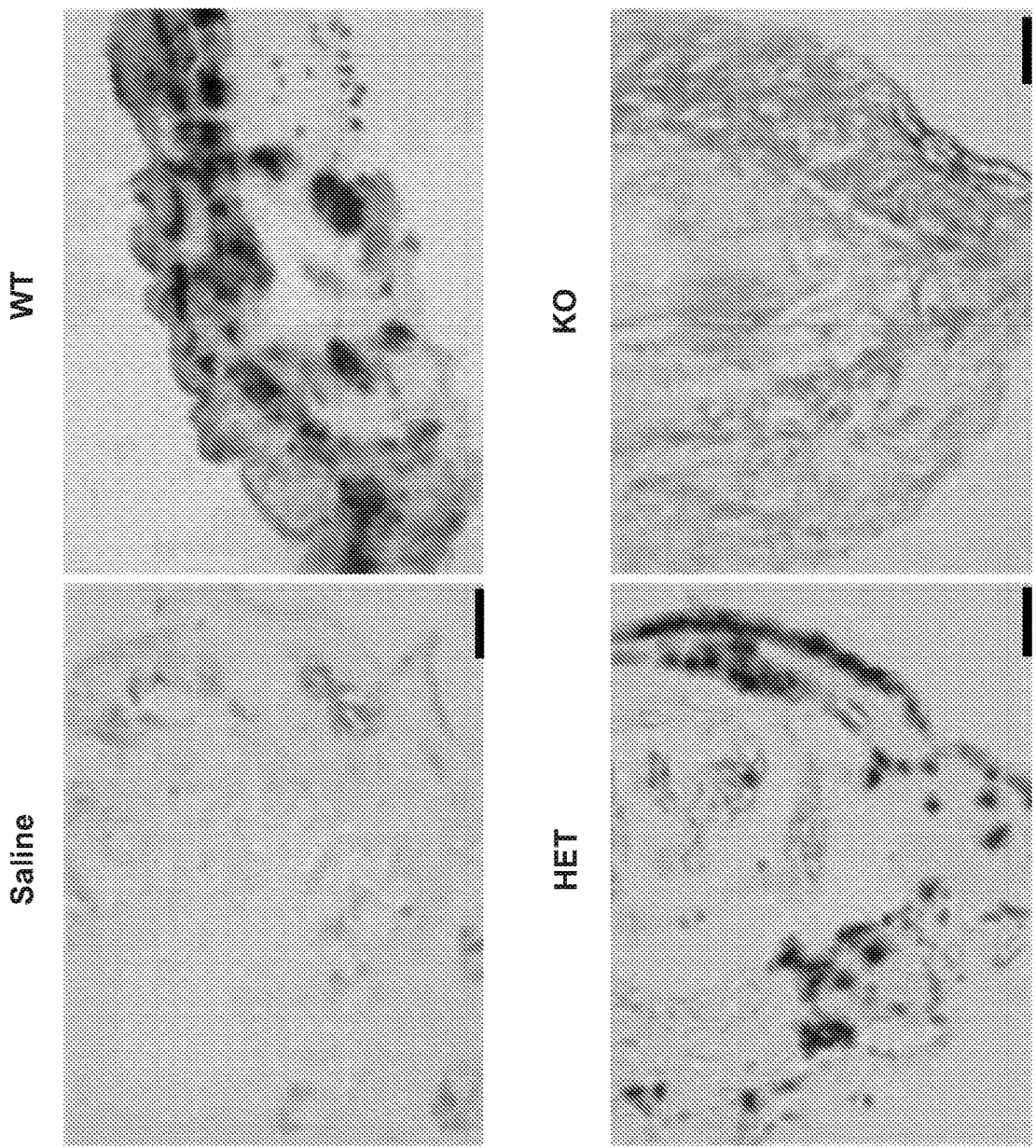

Example 3: Generation of a Mouse Model for MRGPRX4-Mediated Adverse Drug Reactions Knowing Mrgpra1 can bind the SJS-causing drug lamotrigine, its in vivo role was examined. To develop a mouse model of SJS/TEN, wild-type (WT) 129S1/SvImJ mice were orally gavaged with LTG at a dose of 50 mg $kg^{-1}$ body weight daily. Even though this LTG dose was higher than what it is recommended in clinic, it was still within the overdose range of LTG in human-developed SJS (14). After 7-10 days of the drug treatment, nearly every mouse lost their weight and exhibited SJS/TEN-like symptoms including eye mucosal secretion and blister bleeding in their paws with 60% mortality rate by day 14 (FIG. 2B, FIG. 6A, 6B). This phenotype onset resembles the drug-induced hypersensitivity in human patients which requires a few days to weeks after antigen exposure (15). Other SJS causative drugs including oxcarbazepine and allopurinol at a high dose can also induce eye manifestation in this strain of mice with lower incidence and without paw abnormality (FIG. 5). Notably, it was found that daily oral administration of high dose LTG can induce SJS-like features only in 129S1 and BALB/c strains (FIG. 8), but C57BL/6 mice seems to be resistant. This suggests considerable mouse strain variation in response to the drugs. Thus, an Mrgpra1 knockout mouse ($Mrgpra1^{GFP/GFP}$, KO mice) was generated in which Mrgpra1's open reading frame was replaced by GFP on 129S1/SvImJ background (FIG. 2A). Exposing to the same LTG treatment, while Mrgpra1 heterozygous mice ($Mrgpra1^{GFP/+}$, HET mice) developed similar phenotypes as WT mice, Mrgpra1 KO mice did not die, nor lose their weight and never developed any SJS-like symptoms (FIG. 2C, D and FIG. 6A, 6B). Histological staining of conjunctiva and hindpaw sections revealed obvious epidermal necrosis and inflammatory cell infiltration only in tissues of LTG-treated WT and HET mice, but not in LTG-treated KO mice or saline-treated control animals (FIG. 2C, 2D).

Example 4: Examination of the Pathophysiology in SJS Mouse Models

Figure 7:
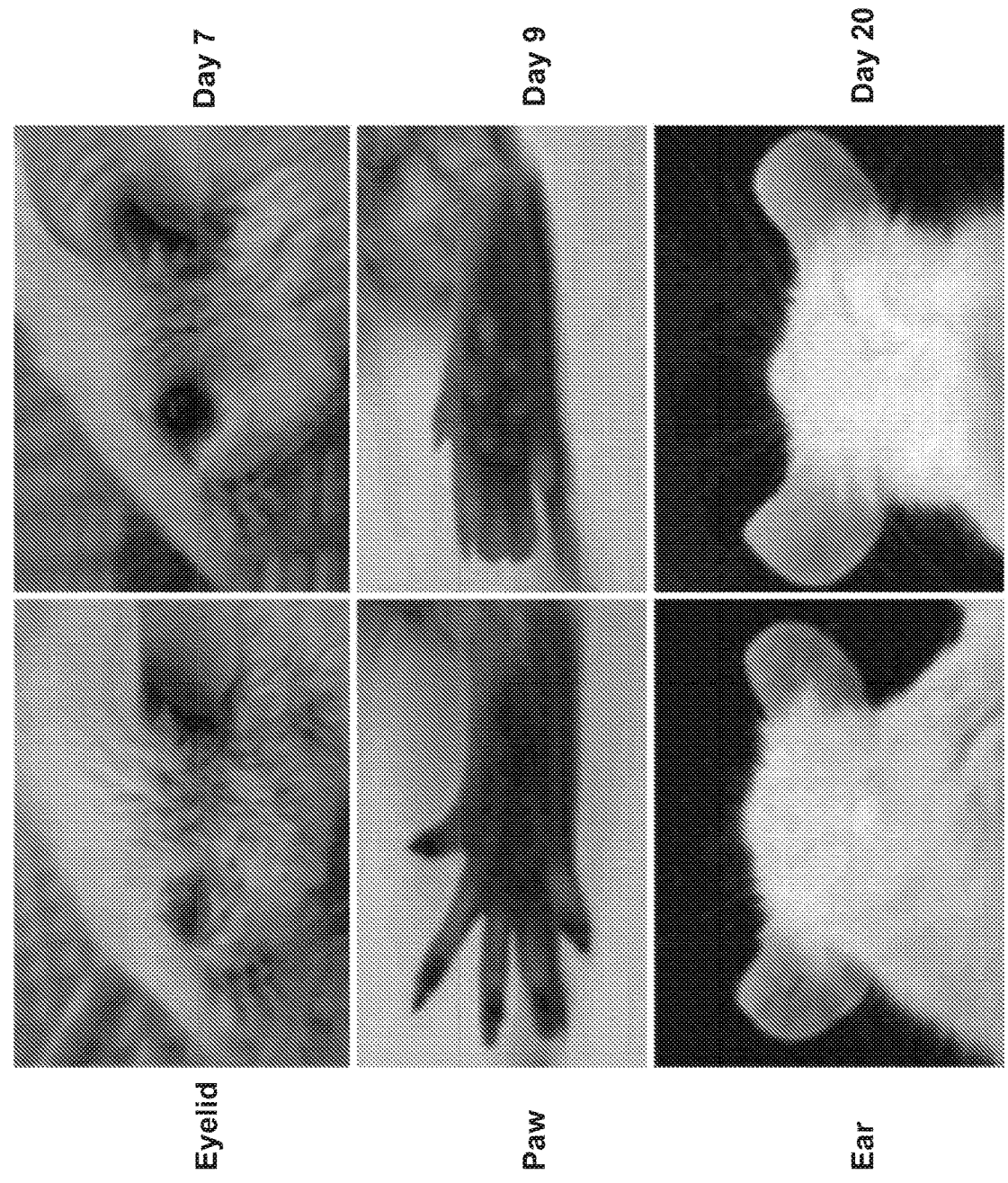
FIG. 7 is a series of photographs demonstrating Balb/c WT and Rag1 (−/−) mice received oral ingestion of LTG (50 mg kg−1 body weight) 20 days. The picture shows the phenotype of mice at day 7, 9, and 20. At day 7, Balb/c WT experienced formation of mucosal secretion in their eyes. At day 9, WT mice developed blister bleeding in their paw. At day 20, WT mice ears' skin appeared peeling with rough thickening.
Figure 8:
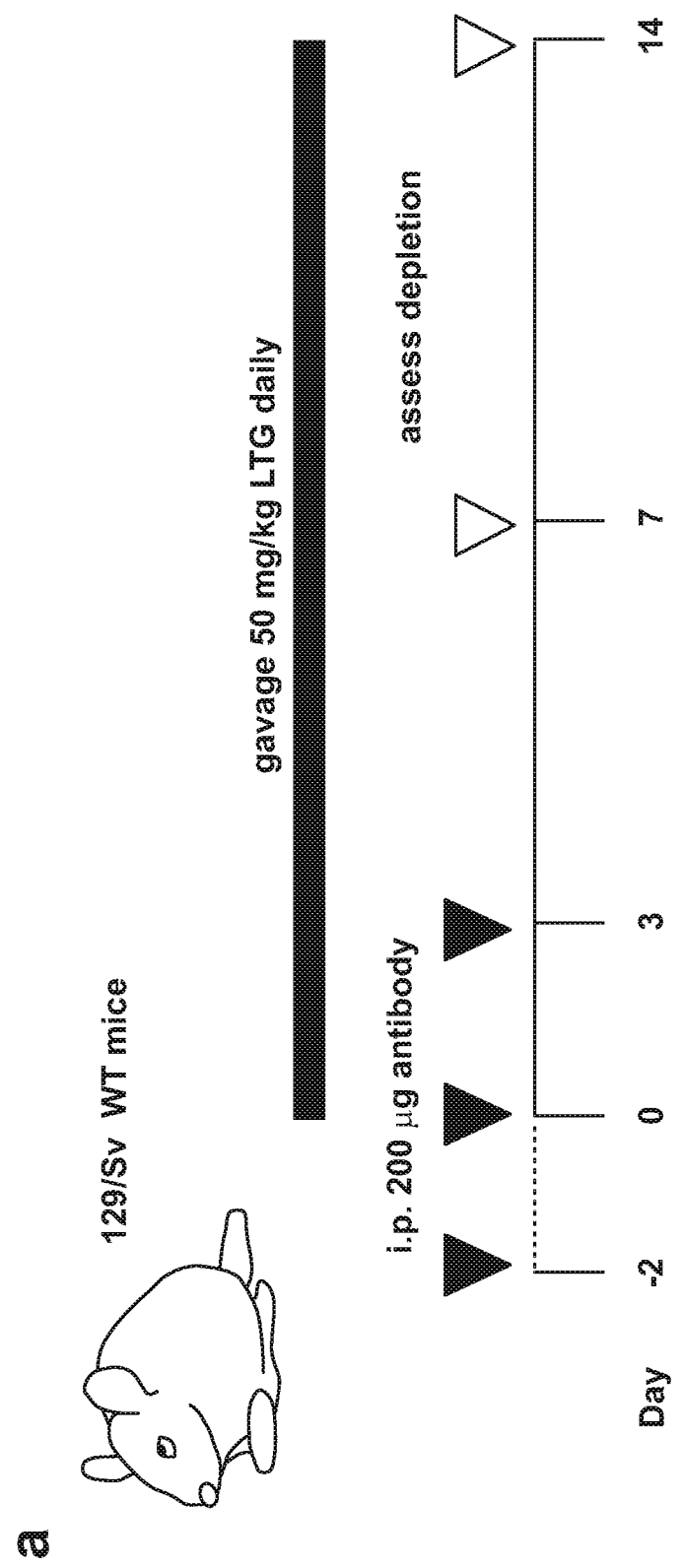
FIG. 8A-FIG. 8C is series of illustrations, FACS plots, and photographs demonstrating the role of CD4 and CD8 T cells during LTG treatment.
Figure 8B:
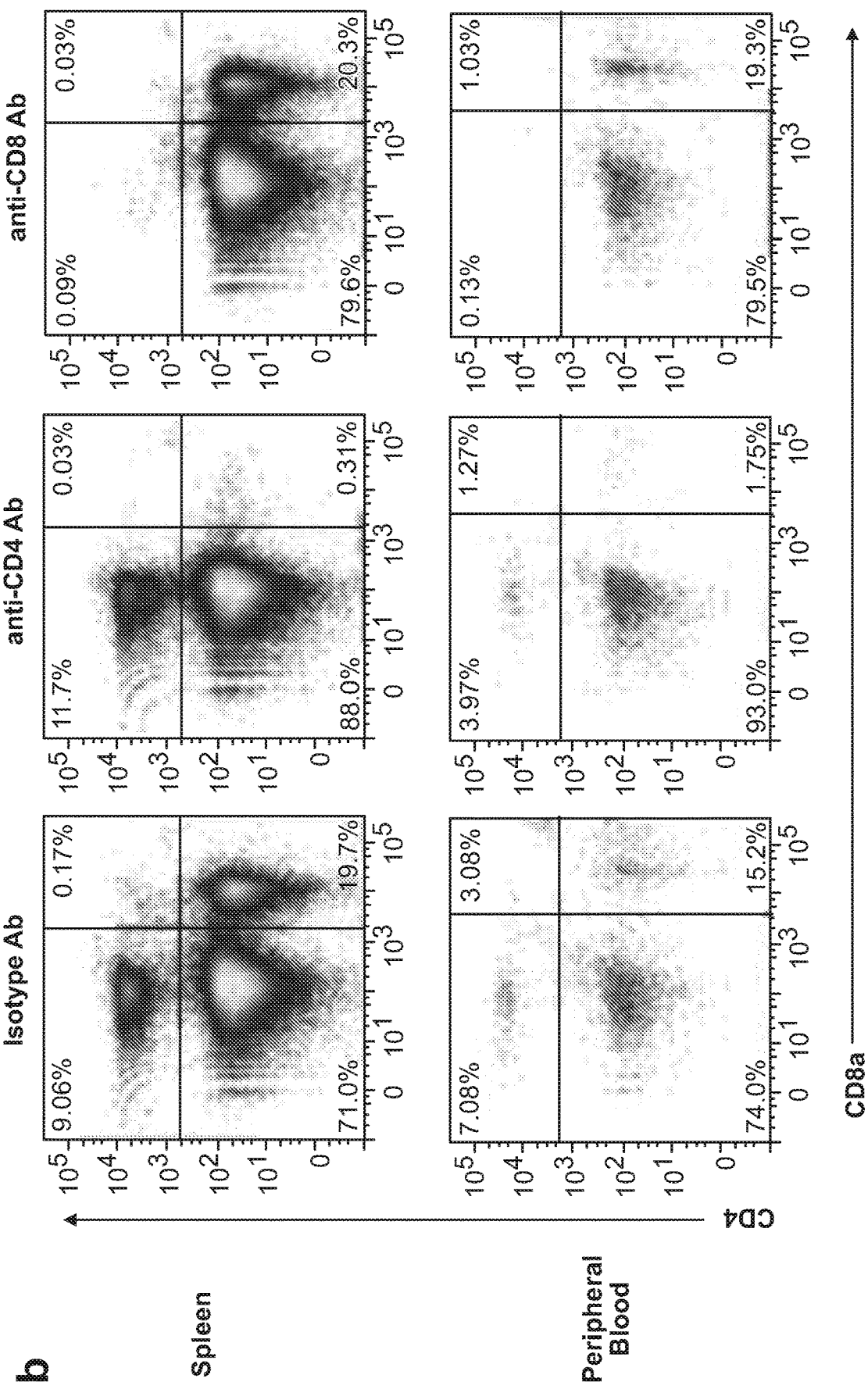
Figure 8:
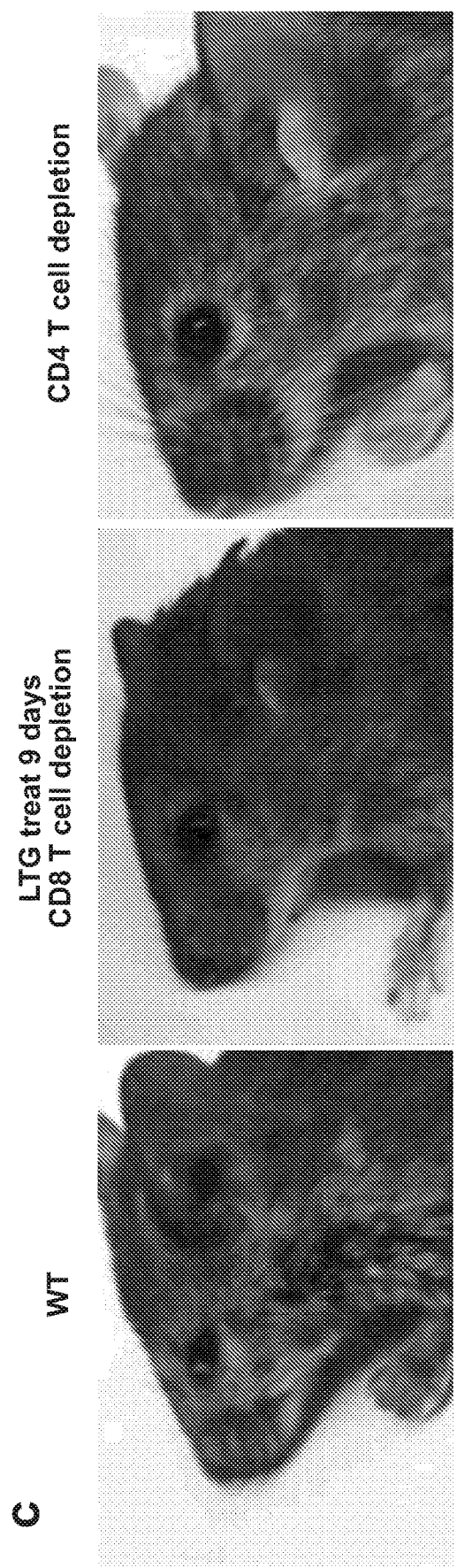

The histopathological examinations of SJS/TEN patients show an extensive keratinocyte apoptosis in epidermis (16, 17). This pathophysiology is proposed to be mediated by cytotoxic molecules (e.g. granzyme B, granulysin, Fas ligand) released from cytotoxic CD8+ T cells along with the elevation of several cytokines (including TNF-α, IFN-γ, IL-6, etc.) (17-21). These characteristics were next examined in the mouse model as described herein. Consistent to human SJS patients, there was a significant increase in the number of epithelial apoptotic cells and CD8+ T cells together with elevations of granzyme B and TNF-α in skins of LTG-gavaged Mrgpra1 WT and HET mice (FIG. 2C, FIG. 2D, FIG. 2E, FIG. 2F, FIG. 6D, FIG. 6E, and FIG. 6F). However, Mrgpra1 KO mice display no signs of cytotoxicity after drug exposure. To confirm if CD8+ T cell and its mediators is required for developing the SJS-like phenotypes in the mouse model as described herein, Rag1−/− mice (which contain no functional T and B lymphocytes) and CD8-depleted animal (which are depleted via antibody depletion) were utilized. No phenotypes were developed in these mice with null or low number of CD8+ T cells after exposing to LTG (FIG. 7, FIG. 8). All of these data suggest that 1) CD8+ T cells are required for the development of SJS in the animal model as described herein and 2) Mrgpra1 may be essential to initiate this immune responses.

Example 5: Dendritic Cell Expression of MRGPRA1

Figure 3:
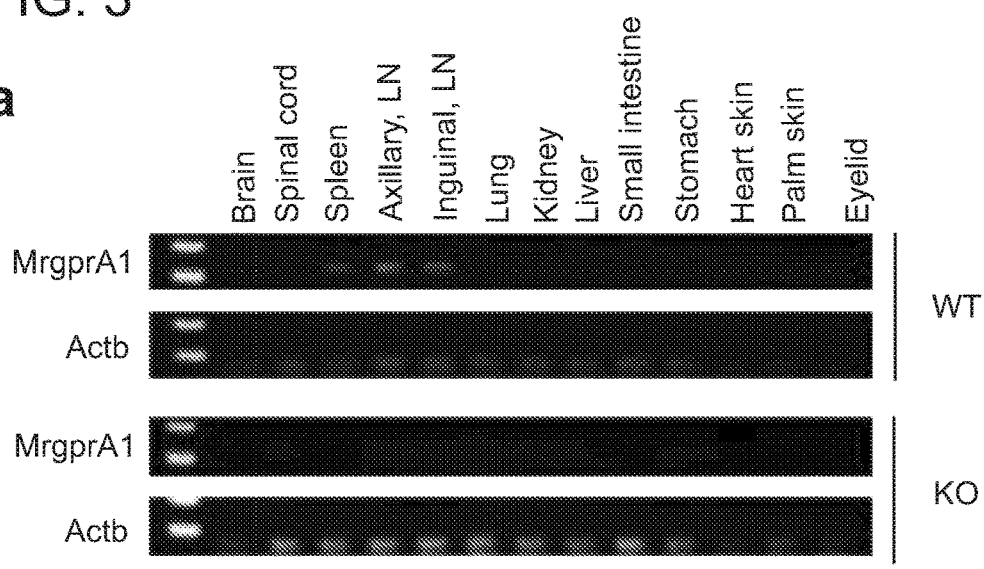
FIG. 3A-FIG. 3F is a series of graphs, photographs, photomicrographs, FACS plots, and immunoblots demonstrating that Mrgpra1 is expressed on a subset of dendritic cells (DCs) where these dendritic cells play a key role in the formation of the SJS phenotype.
Figure 3:
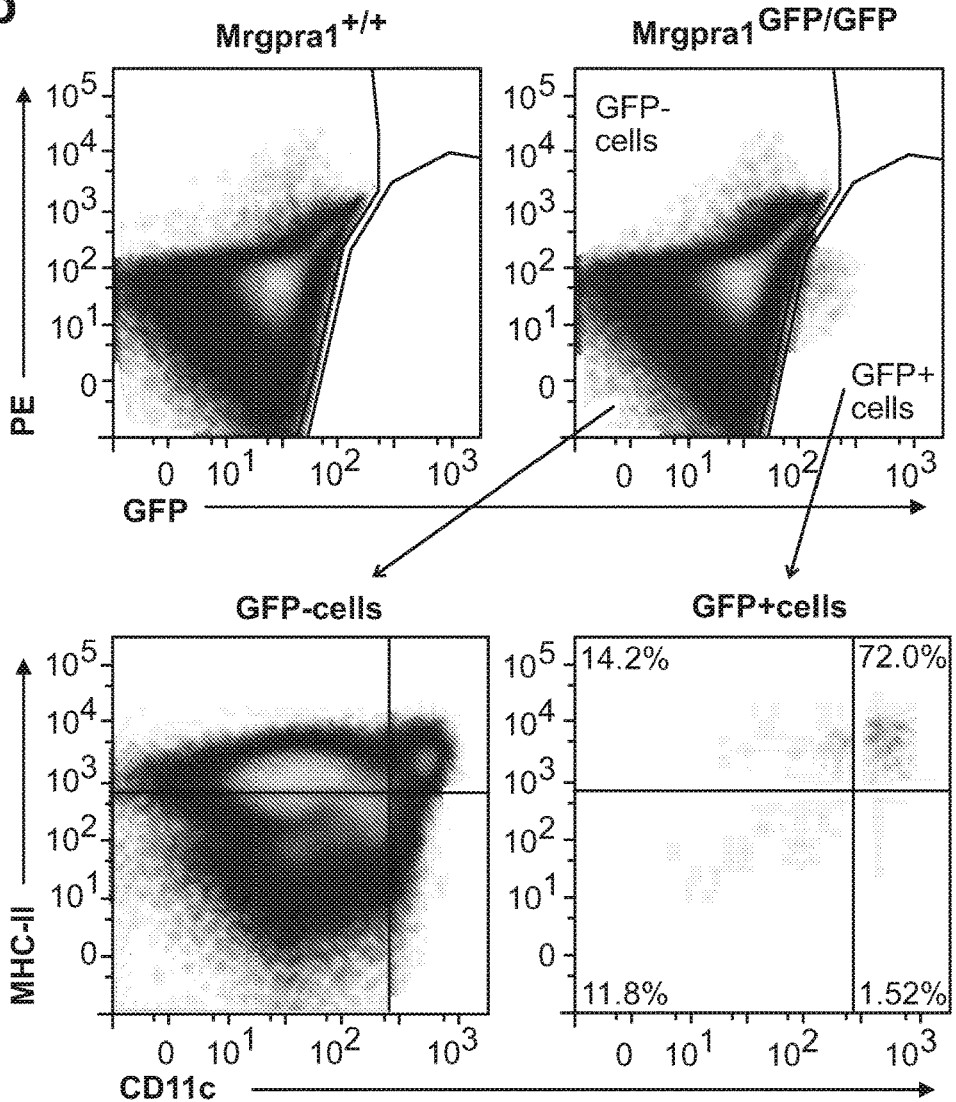
Figure 3:
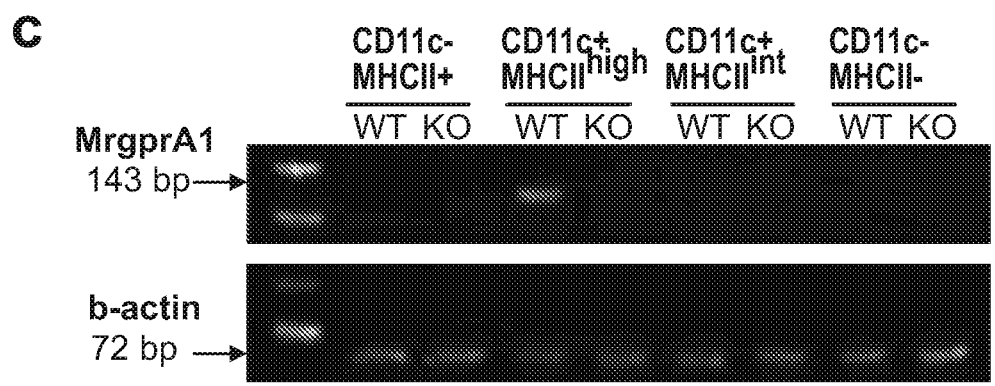
Figure 3:
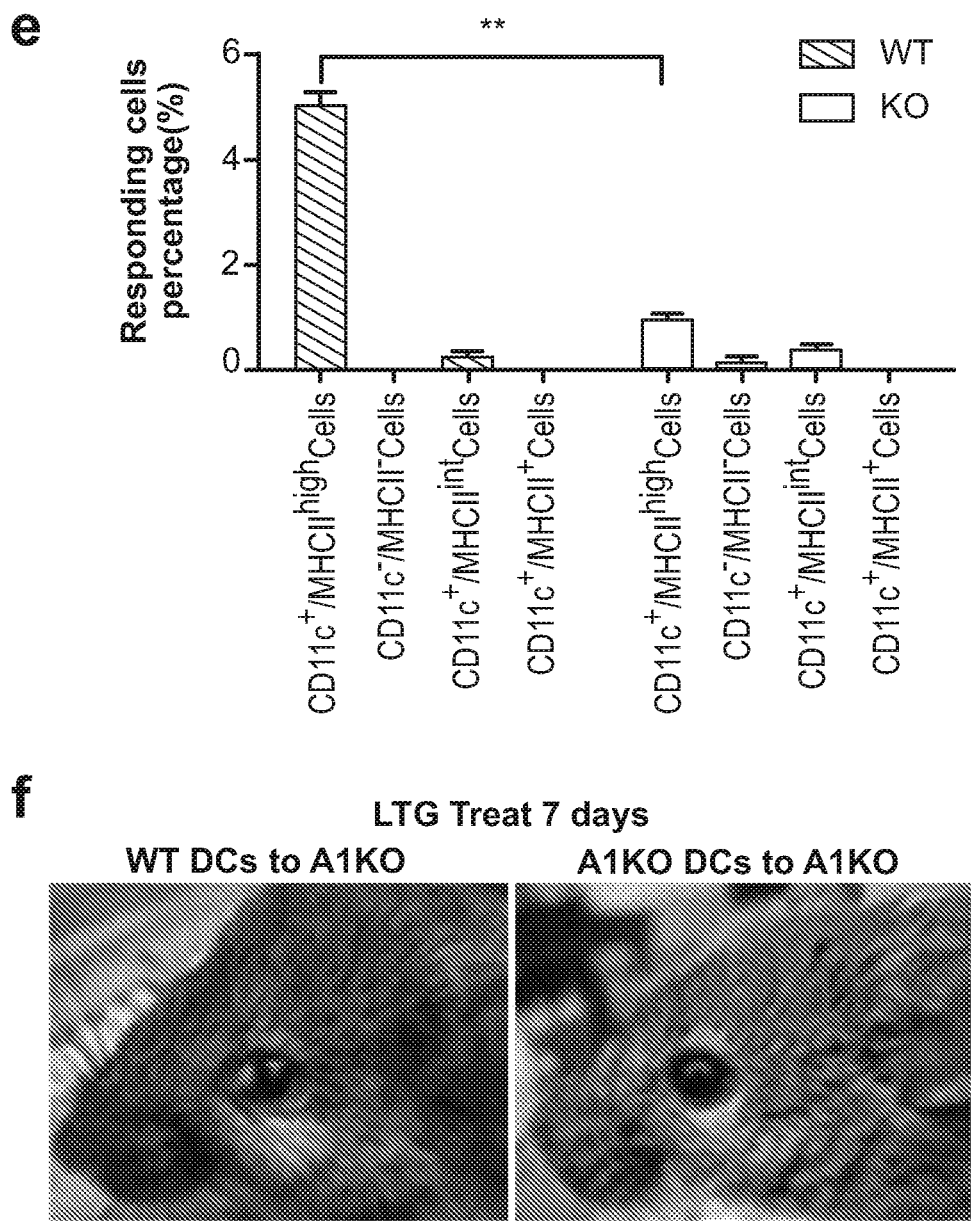
Figure 9A:
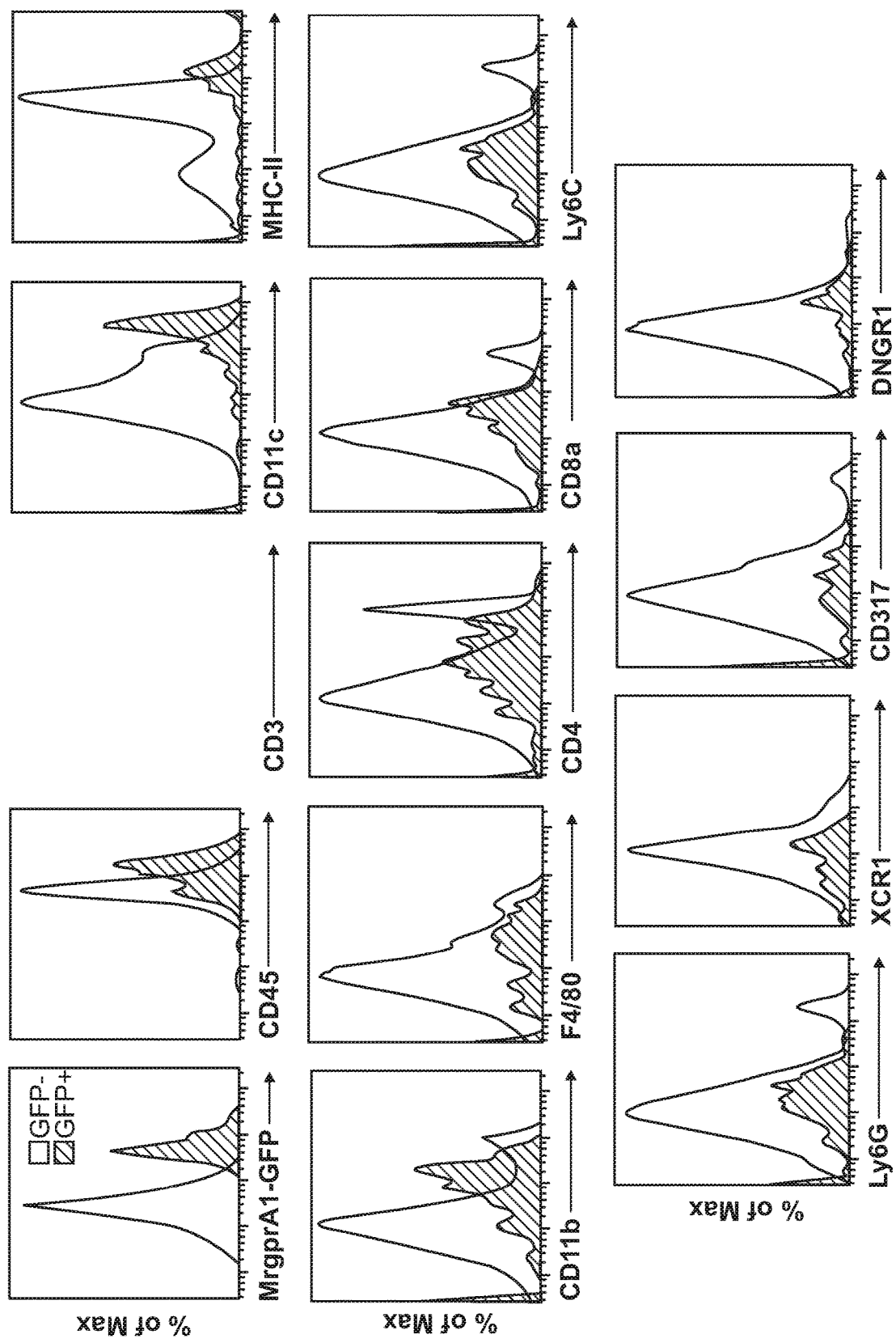
FIG. 9A-9C is a series of flow cytometry plots and photomicrographs demonstrating that Mrgpra1 cells were CD11c and MHC-II positive cells.
Figure 9:
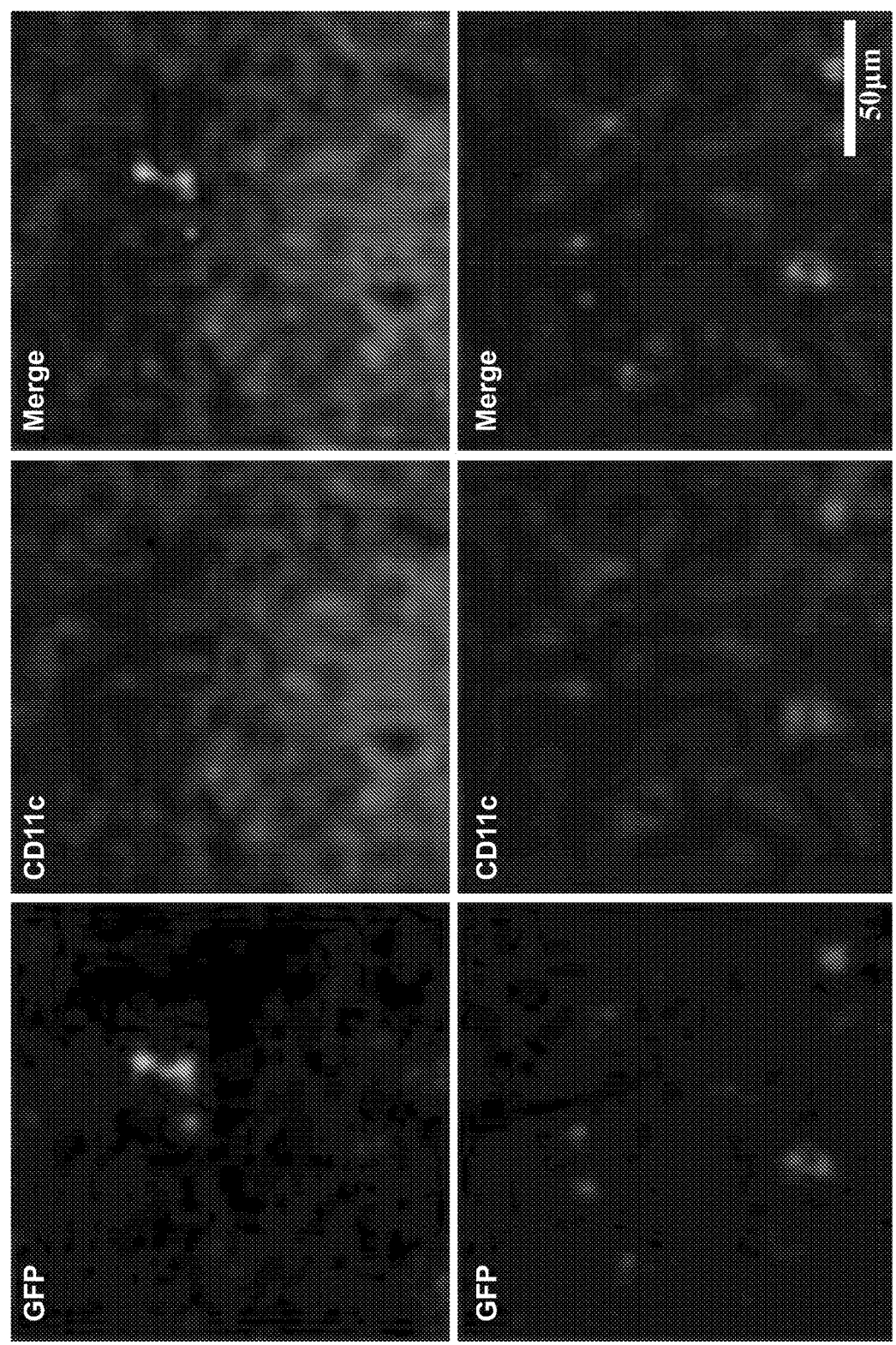
Figure 9:
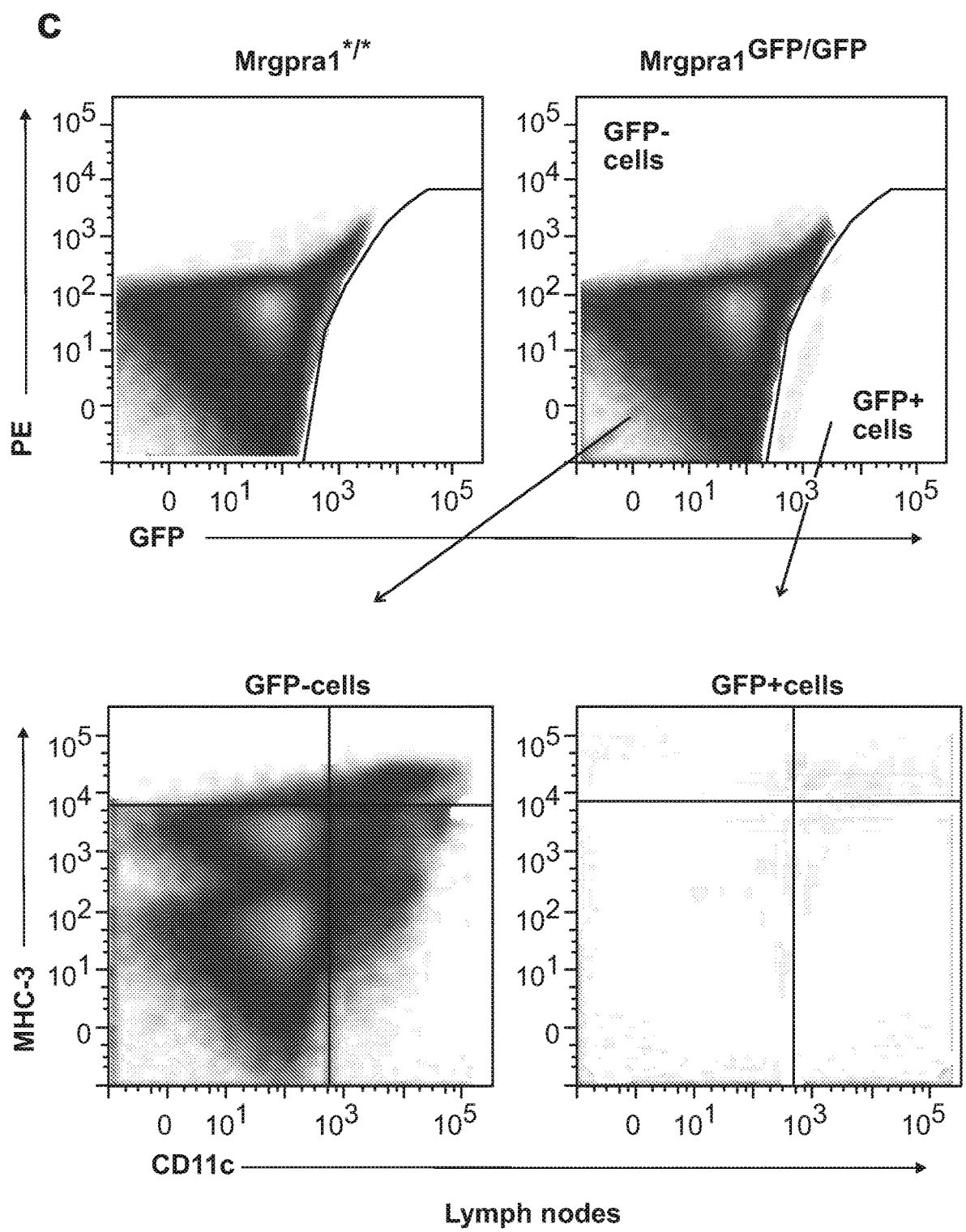
Figure 11:
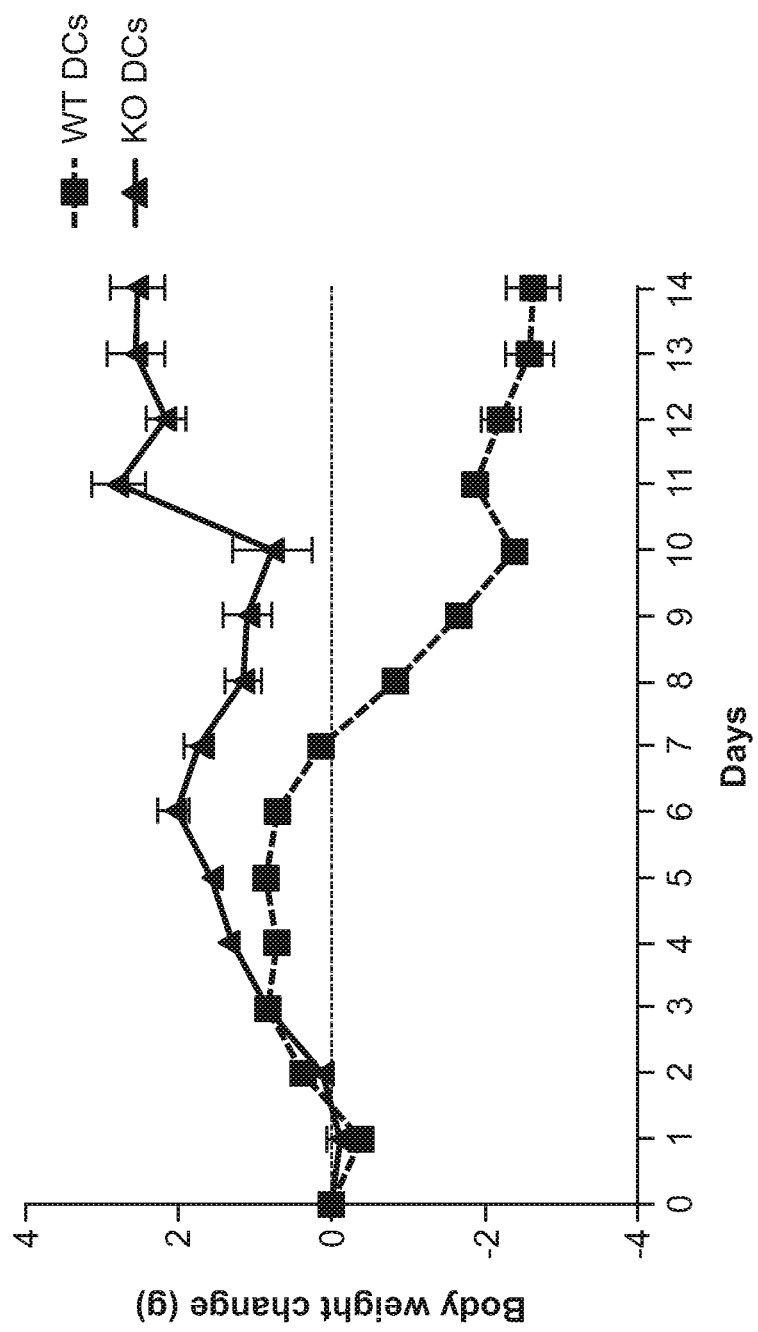
FIG. 11 is a graph demonstrating that body weight change of mice injected with WT and A1 KO mice's dendritic cells. A1 KO mice were treated with LTG daily, after which they received one injection of WT and A1 KO mice's dendritic cells (DCs). From the 7th day on, mice that received WT DCs experienced weight loss, while mice that received A1 KO DCs have experienced an increase in weight.

With the data suggesting Mrgpra1's role in development of SJS, the location of where this receptor is expressed was determined. Reverse transcription PCR (RT-PCR) showed Mrgpra1 was mainly expressed in lymph nodes and spleen (FIG. 3A). Then, Mrgpra1 KO mice generated by replacing Mrgpra1 gene with GFP ($Mrgpra1^{GFP/GFP}$) were used as reporter mice to identify Mrgpra1-expressing cells. Flow cytometric analysis of splenocytes and lymph node cells from Mrgpra1GFP/GFP mice revealed the presence of a small distinguished $GFP^+$ population (FIG. 3B and FIG. 9A). Further characterization showed that $GFP^+$ cells exhibited a characteristic of hematopoietic cells ($CD45^+$) with conventional dendritic cell markers (high expression of both integrin CD11c and class II major histocompatibility complex (MHC-II)), but not other cell types' markers (FIG. 3B and FIG. 9B). Immunostaining of spleen tissue section from these mice confirmed the identity of irregular shape and dendrite-like projected $GFP^+$ cells with $CD11c^+$, but not $CD3^+$ (a marker of T cell) (FIG. 9C). To further validate that Mrgpra1 is expressed and functional in dendritic cells, splenocytes from both $Mrgpra1^{+/+}$ and $Mrgpra1^{GFP/GFP}$ mice were sorted into 4 populations based on their expression of CD11c and MHC-II: $CD11c^+MHC-II^{high}$ (mostly dendritic cells), $CD11c^+MHC-II^{int}$ (mostly macrophages), $CD11c^-MHC-II^+$ (mostly B cells) and $CD11c^-$ $MHC-II^-$ (mostly T cells) (gating strategy as shown in FIG. 10). By RT-PCR analysis, the expression of Mrgpra1 was determined only in the CD11c⁺ MHC-II$^{high}$ population of WT animals (FIG. 3C). Mrgpra1 is absent in CD11c⁺ MHC⁻II$^{high}$ cells from Mrgpra1$^{GFP/GFP}$ knockout mice. Functionally, only a subset of WT CD11c⁺MHC-II$^{high}$ cells (approximately 5%) responded to LTG using Ca$^{2+}$ imaging assay and this LTG-induced activation was significantly reduced in KO cells (FIG. 3D, FIG. 3E). All these data suggest that Mrgpra1 is specifically expressed in a subset of dendritic cells and not in other immune cells. Subsequently, to examine whether these Mrgpra1-expressing dendritic cells are required for the development of drug-induced SJS/TEN symptoms in vivo, dendritic cells from Mrgpra1$^{+/+}$ mice were isolated and adoptive transferred into Mrgpra1 KO animals. After 7-10 days of drug exposure, Mrgpra1 KO animals who received WT dendritic cells lost their body weight and 64% of them developed the SJS-like eye manifestation, while no weight loss and no phenotypes were observed in the control animals who received KO dendritic cells (FIG. 3F and FIG. 11). However, these phenotypes found in WT dendritic cell-injected animals lasted only 3-4 days and disappeared after day 12. This is possibly due to a short lifespan of dendritic cells after their activation and interaction with lymphocytes (22). These finding strongly support the identification of Mrgpra1 in dendritic cells and its role in triggering and maintenance of SJS/TEN pathogenesis.

Example 6: Role of Human MRGPRX4 in SJS

Figure 4:
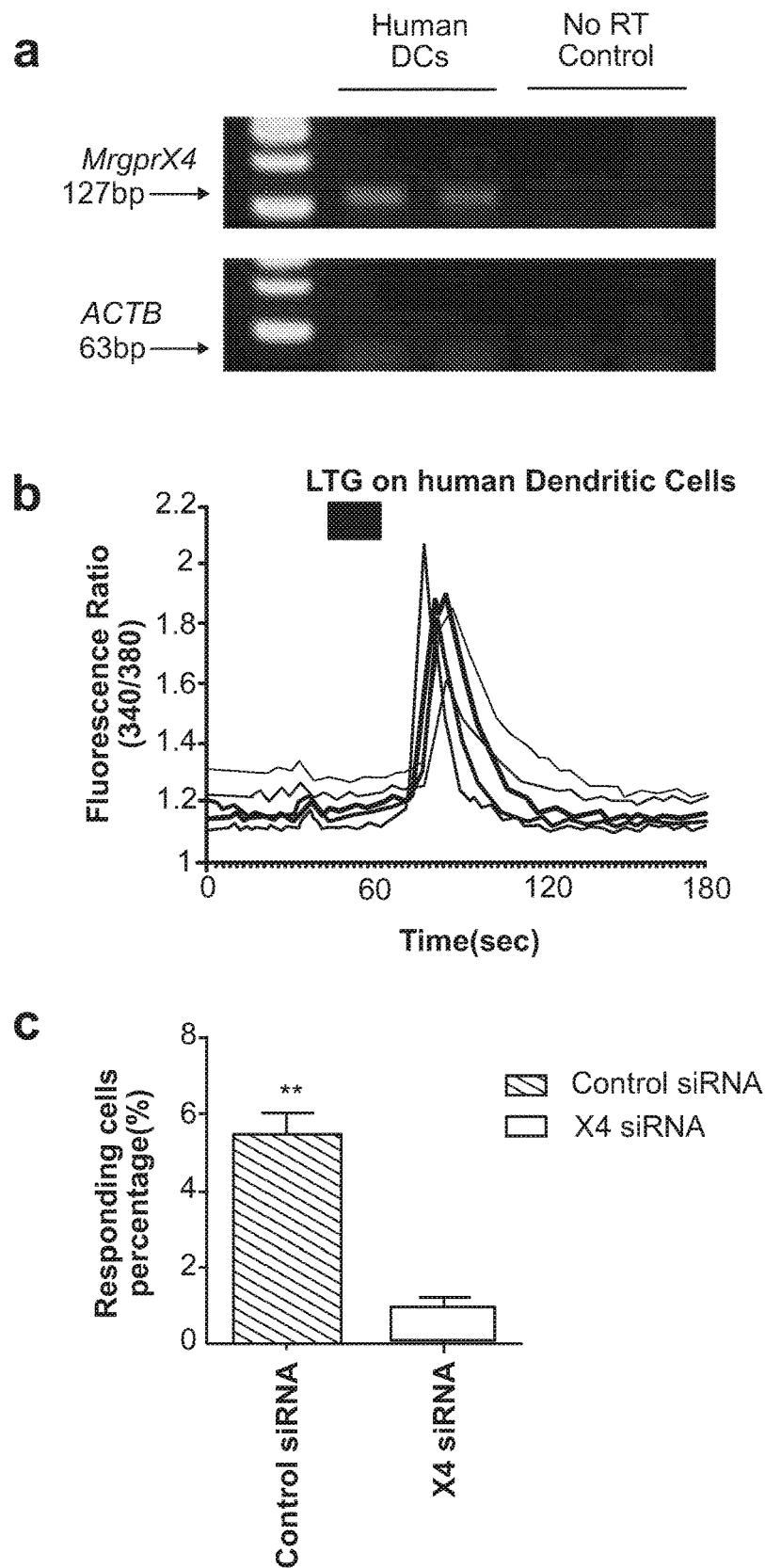
FIG. 4A-FIG. 4E is a series of graphs, photographs, photomicrographs, and immunoblots demonstrating that Human dendritic cells express MRGPRX4 and can be activated by LTG.
Figure 4:
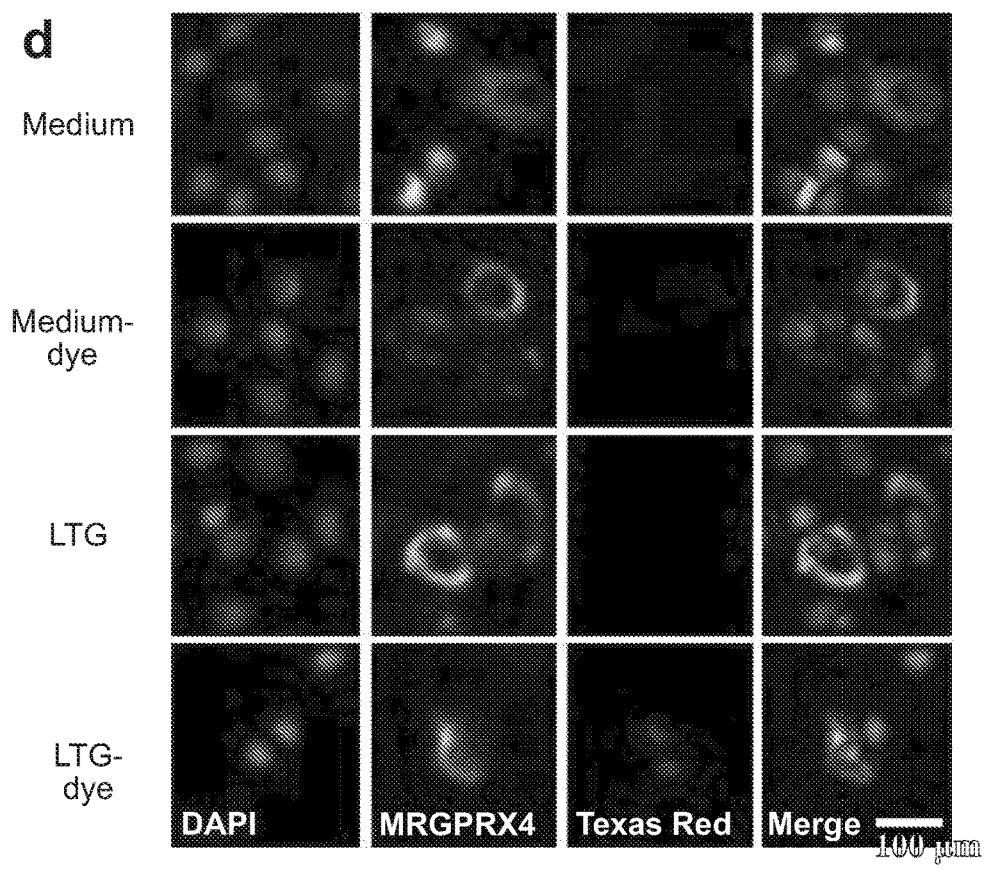
Figure 4:
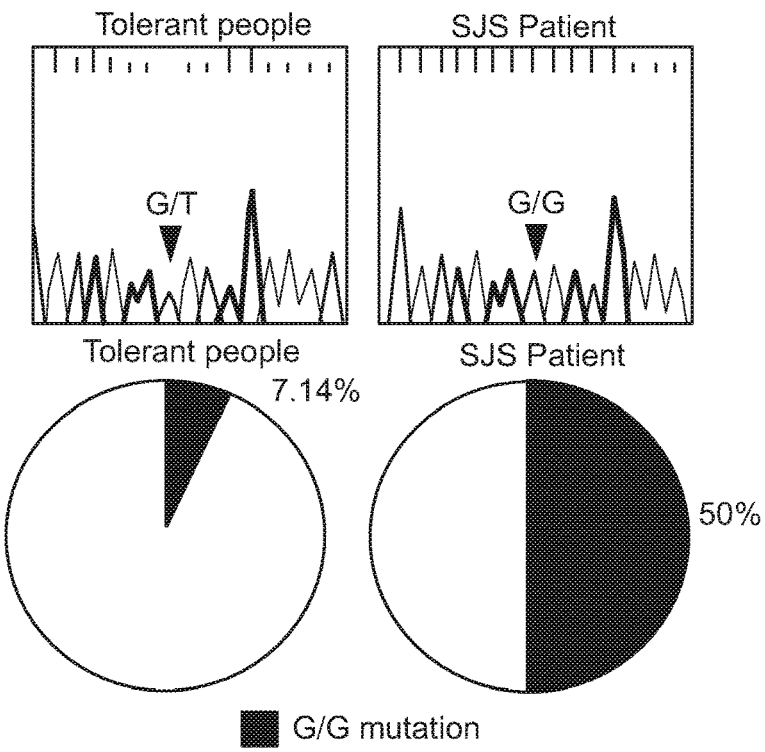

According to the Ca$^{2+}$ imaging data as described herein, human MRGPRX4 responded to the SJS causative drugs similar to mouse Mrgpra1 (FIG. 3C). Therefore, the possibility that MRGPRX4 is involved in the development of SJS/TEN in humans was investigated. First, both MRGPRX4 transcript by RT-PCR and MRGPRX4 protein by immunostaining were detected in human CD11c⁺ dendritic cells (FIG. 4A and FIG. 12). Second, LTG can activate human dendritic cells in MRGPRX4-dependent manner Similar to mouse dendritic cells, about 5% of human dendritic cells were activated by LTG in Ca$^{2+}$ imaging studies (FIG. 4B, FIG. 4C). MRGPRX4-knock down dendritic cells using short interfering RNA (siRNA) exhibited significantly less number of activated cells in response to LTG (FIG. 4C). Also, only MRGPRX4-expressing dendritic cells could internalize Texas Red-labelled LTG into their cytoplasmic compartment (FIG. 4D). A mutation in the MRGPRX4 gene associated with an incidence of cADR was identified. Six patients with cADR to LTG and 28 tolerant cases were recruited into the study. The cADR include SJS, DRESS, and MPE. Most of the LTG tolerant cases showed heterozygous G/T alleles at the 495th nucleotide of MRGPRX4 (accession NM_054032.3, rs2468774, position 495). There was a significantly higher prevalence of homozygous G/G alleles at the same locus leading to a missense variant of p.Asn25Lys in the protein level. Two out of 28 tolerant patients (7.1%) had homozygous G/G alleles whereas 3 out of 6 cADR patients had homozygous alleles (50%) (FIG. 4E). Together, these results suggest that MRGPRX4 is the human homologue of Mrgpra1 and mediates SJS in humans.

It has been puzzled for a long time how certain drugs can result in the cytotoxicity with drug-specific T cells. The findings, as described herein, is the first instance demonstrating that these drugs can interact with the MRGPRX4/Mrgpra1 receptor on dendritic cells which are the most efficient antigen presenting cells specialized in capturing, processing and presenting antigens for T cells activation (23). However, a mechanism of how internalized drugs are consequently processed in dendritic cells to generate the antigen presentation to T cells requires further investigation. Screening drugs that may react with the MRGPRX4 receptor, screening the receptor antagonists, and screening for the MRGPRX4 mutation in patients prior to drug intake may be beneficial in reducing the risk of cADRs.

References for Examples 1-6 are Listed Below

1. Zalewska-Janowska, A., Spiewak, R. & Kowalski, M. L. Cutaneous Manifestation of Drug Allergy and Hypersensitivity. *Immunol Allergy Clin North Am* 37, 165-181, doi:10.1016/j.iac.2016.08.006 (2017).
2. Sultana, J., Cutroneo, P. & Trifiro, G. Clinical and economic burden of adverse drug reactions. *J Pharmacol Pharmacother* 4, S73-77, doi:10.4103/0976-500X.120957 (2013).
3. Downey, A., Jackson, C., Harun, N. & Cooper, A. Toxic epidermal necrolysis: review of pathogenesis and management. *J Am Acad Dermatol* 66, 995-1003, doi: 10.1016/j.jaad.2011.09.029 (2012).
4. Lee, H. Y. & Chung, W. H. Toxic epidermal necrolysis: the year in review. *Curr Opin Allergy Clin Immunol* 13, 330-336, doi:10.1097/ACI.0b013e3283630cc2 (2013).
5. Stevens, A. M. & Johnson, F. C. A new eruptive fever associated with stomatitis and ophthalmia: Report of two cases in children. *Am J Dis Child* 24, 526-533 (1922).
6. Heng, Y. K., Lee, H. Y. & Roujeau, J. C. Epidermal necrolysis: 60 years of errors and advances. *Br J Dermatol* 173, 1250-1254, doi:10.1111/bjd.13989 (2015).
7. Schotland, P., Bojunga, N., Zien, A., Trame, M. N. & Lesko, L. J. Improving drug safety with a systems pharmacology approach. *Eur J Pharm Sci* 94, 84-92, doi: 10.1016/j.ejps.2016.06.009 (2016).
8. Adam, J., Pichler, W. J. & Yerly, D. Delayed drug hypersensitivity: models of T-cell stimulation. *Br J Clin Pharmacol* 71, 701-707, doi:10.1111/j.1365-2125.2010.03764.x (2011).
9. Chung, W. H., Wang, C. W. & Dao, R. L. Severe cutaneous adverse drug reactions. *J Dermatol* 43, 758-766, doi:10.1111/1346-8138.13430 (2016).
10. McNeil, B. D. et al. Identification of a mast-cell-specific receptor crucial for pseudo-allergic drug reactions. *Nature* 519, 237-241, doi:10.1038/nature14022 (2015).
11. Biton, V. Pharmacokinetics, toxicology and safety of lamotrigine in epilepsy. *Expert Opin Drug Metab Toxicol* 2, 1009-1018, doi:10.1517/17425255.2.6.1009 (2006).
12. Khanna, D. et al. 2012 American College of Rheumatology guidelines for management of gout. Part 1: systematic nonpharmacologic and pharmacologic therapeutic approaches to hyperuricemia. *Arthritis Care Res (Hoboken)* 64, 1431-1446, doi:10.1002/acr.21772 (2012).
13. Pavlos, N. J. & Friedman, P. A. GPCR Signaling and Trafficking: The Long and Short of It. *Trends Endocrinol Metab* 28, 213-226, doi:10.1016/j.tem.2016.10.007 (2017).
14. Alabi, A., Todd, A., Husband, A. & Reilly, J. Safety profile of lamotrigine in overdose. *Ther Adv Psychopharmacol* 6, 369-381, doi:10.1177/2045125316656707 (2016).
15. Pichler, W. J. Delayed drug hypersensitivity reactions. *Annals of internal medicine* 139, 683-693 (2003).
16. Paul, C. et al. Apoptosis as a mechanism of keratinocyte death in toxic epidermal necrolysis. *Br J Dermatol* 134, 710-714 (1996).
17. Chung, W. H. & Hung, S. I. Recent advances in the genetics and immunology of Stevens-Johnson syndrome and toxic epidermal necrosis. *J Dermatol Sci* 66, 190-196, doi:10.1016/j.jdermsci.2012.04.002 (2012).
18. Posadas, S. J. et al. Delayed reactions to drugs show levels of perforin, granzyme B, and Fas-L to be related to disease severity. *The Journal of allergy and clinical immunology* 109, 155-161 (2002).
19. Nassif, A. et al. Evaluation of the potential role of cytokines in toxic epidermal necrolysis. *J Invest Dermatol* 123, 850-855, doi:10.1111/j.0022-202X.2004.23439.x (2004).
20. Caproni, M. et al. Expression of cytokines and chemokine receptors in the cutaneous lesions of erythema multiforme and Stevens-Johnson syndrome/toxic epidermal necrolysis. *Br J Dermatol* 155, 722-728, doi:10.1111/j.1365-2133.2006.07398.x (2006).
21. Viard-Leveugle, I. et al. TNF-alpha and IFN-gamma are potential inducers of Fas-mediated keratinocyte apoptosis through activation of inducible nitric oxide synthase in toxic epidermal necrolysis. *J Invest Dermatol* 133, 489-498, doi:10.1038/jid.2012.330 (2013).
22. Chen, M., Huang, L., Shabier, Z. & Wang, J. Regulation of the lifespan in dendritic cell subsets. *Mol Immunol* 44, 2558-2565, doi:10.1016/j.molimm 2006.12.020 (2007).
23. Guermonprez, P., Valladeau, J., Zitvogel, L., Thery, C. & Amigorena, S. Antigen presentation and T cell stimulation by dendritic cells. *Annual review of immunology* 20, 621-667, doi:10.1146/annurev.immunol.20.100301.064828 (2002).
24. Han, S. K. et al. Orphan G protein-coupled receptors MrgA1 and MrgC11 are distinctively activated by RF-amide-related peptides through the Galpha q/11 pathway. *Proceedings of the National Academy of Sciences of the United States of America* 99, 14740-14745, doi:10.1073/pnas.192565799 (2002).
25. Chen, Y. C. et al. Human herpes virus reactivations and dynamic cytokine profiles in patients with cutaneous adverse drug reactions—a prospective comparative study. *Allergy* 70, 568-575, doi:10.1111/a11.12602 (2015).

Example 7: Mrgpr Cluster KO Mice Scratch Less in a Model of Cholestatic Pruritus The mouse Mrgpr locus contains twenty-seven intact Mrgpr open reading frames. Many Mrgprs expressed in mice have similar sequences (10; 20). To avoid possible compensation among Mrgpr members, a cluster deletion strategy whereby a group of Mrgprs are genetically deleted (Cluster KO) was pursued. Cluster KO mice are missing 845 kb of DNA that contains 12 intact Mrgpr ORFs(22).

Figure 13:
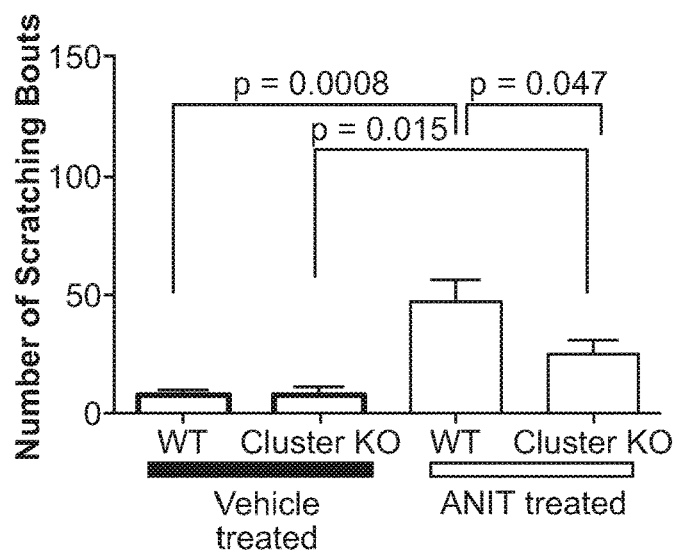
FIG. 13A-FIG. 13F is a series of graphs demonstrating that Mrgpr Cluster KO mice scratch less in a model of cholestatic pruritus.
Figure 13:
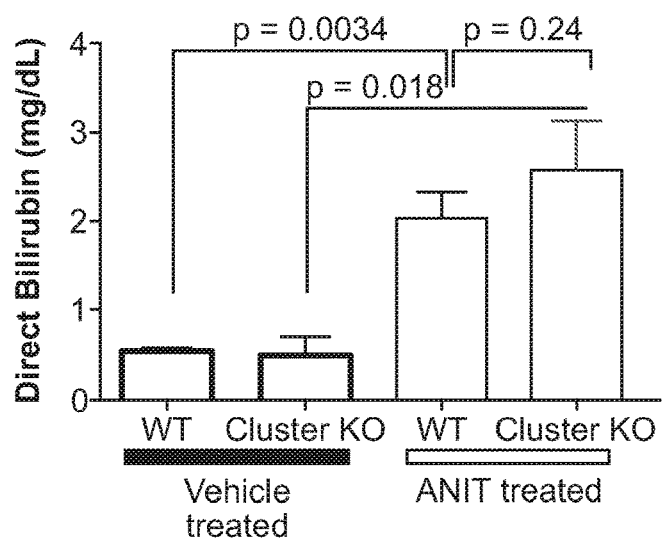
Figure 13:
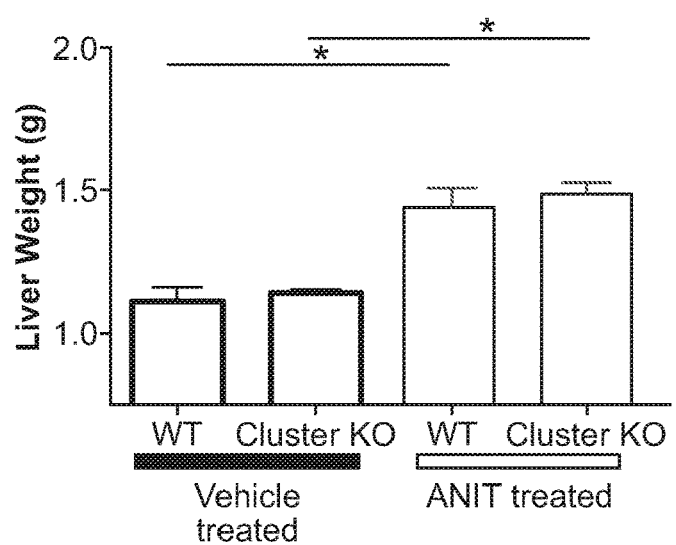
Figure 13:
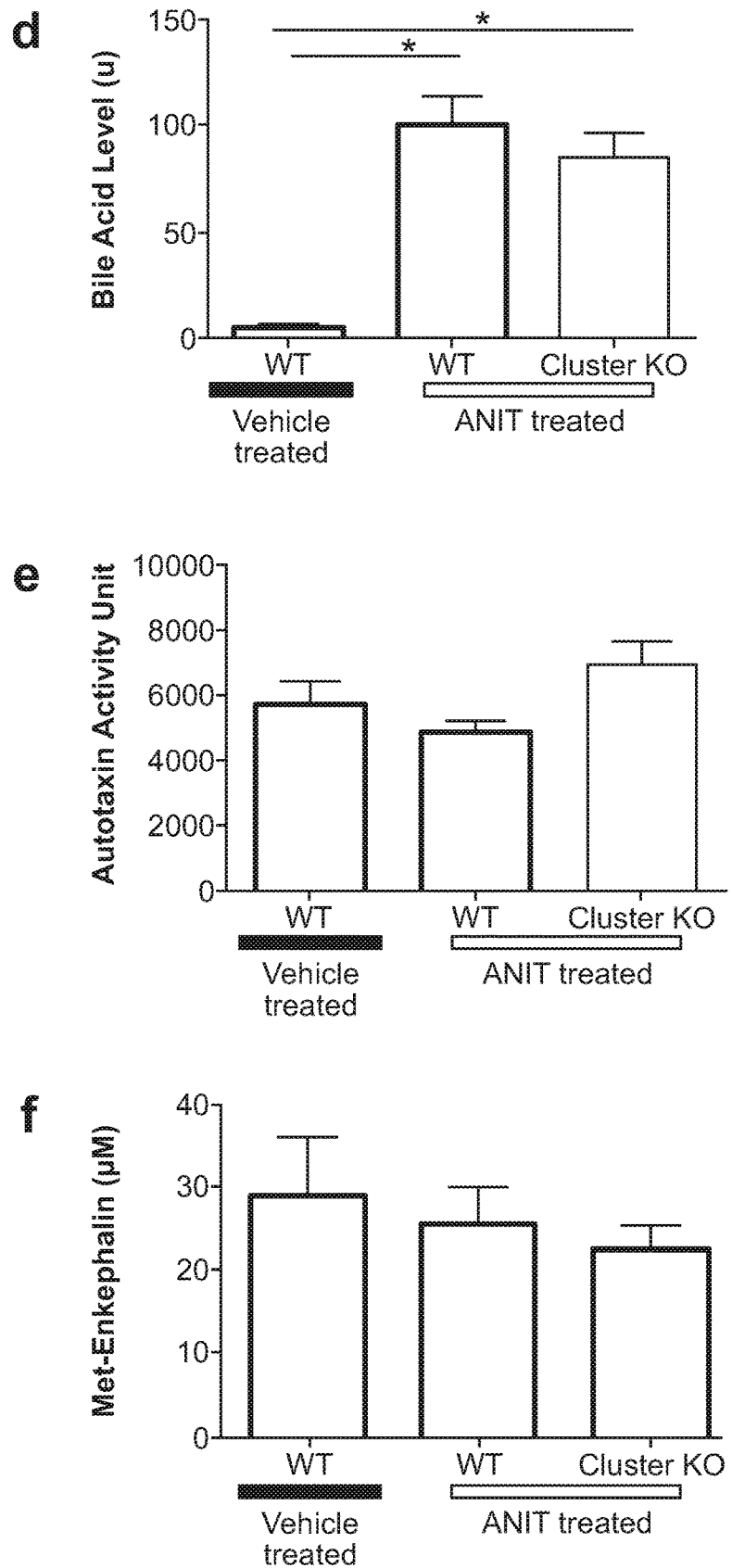

Dosing of α-naphthylisothiocyanate (ANIT) results in cholestatic injury and pruritus. ANIT causes intrahepatic cholestasis by selectively injuring biliary epithelial cells via an unknown mechanism (8). ANIT treatment resulted in an increase in spontaneous itch in both WT and Cluster KO animals (FIG. 13A). Cluster KO mice scratched significantly less than WT littermates, exhibiting an approximate 46% reduction in bouts (FIG. 13A). Vehicle-treated animals, both WT and Cluster KO, exhibited essentially no spontaneous itch (FIG. 13A). Indicators of cholestatic injury such as liver weight, direct bilirubin levels, total bilirubin levels, and liver enzymes all showed significant elevation in the treated condition compared to the control condition (FIG. 13B, FIG. 13C). Among these metrics, there was no difference between the WT treated and Cluster KO treated conditions indicating that the severity of cholestatic insult was comparable across WT and Cluster KO animals. Based on this, a difference in treatment does not account for the difference in itch. Additionally, among bile acids, met-enkephalin, and autotaxin (three substances hypothesized to play a role in cholestatic pruritus), only bile acids were elevated in ANIT-treated animals with no significant elevation of either met-enkephalin or autotaxin (FIG. 13D-FIG. 13F). Bile acid levels were no different between the WT and Cluster KO treated conditions (FIG. 13D).

Example 8: Bilirubin Causes Itch that is Dependent on MrgprA1

Figure 14:
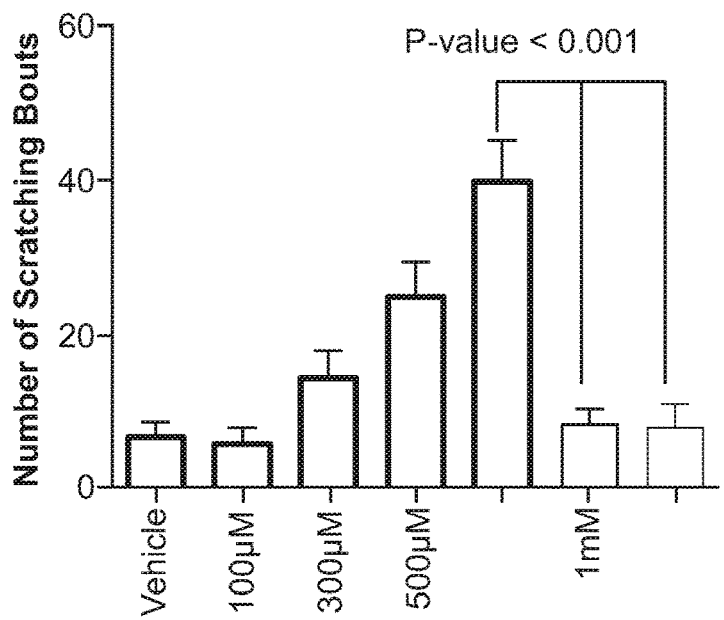
FIG. 14A is a series of graphs demonstrating that bilirubin causes itch in WT mice and not Cluster KO mice. Black bars are WT mice. Red bars are Cluster KO mice. Yellow bar is MrgprA1 single gene knockout. Animals were injected with pruritogen. In the thirty minutes following injection, the number of scratching bouts were assessed. Mice used in the study were 8-12 week old male littermates. A blind study was conducted regarding treatment during scoring. Mean with SEM was depicted.
FIG. 14B is a graph depicting the results for mice injected at the nape of the neck with 1 mg/kg morphine in 50 μl saline.
FIG. 14C is a graph depicting the results for mice injected at the nape of the neck with 1 mg/kg DAMGO in 50 μl saline.
FIG. 14D is a graph depicting the results for mice injected at the cheek with the indicated doses of bilirubin.
FIG. 14E is a graph depicting the results for mice injected with 1.3 mM DCA in the cheek.
FIG. 14F is a graph depicting the results for mice injected with 4 mM LPA in the cheek.
Figure 14:
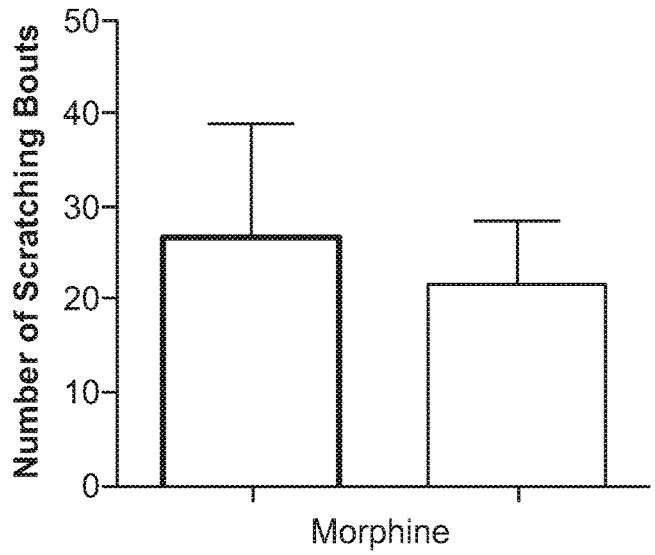
Figure 14:
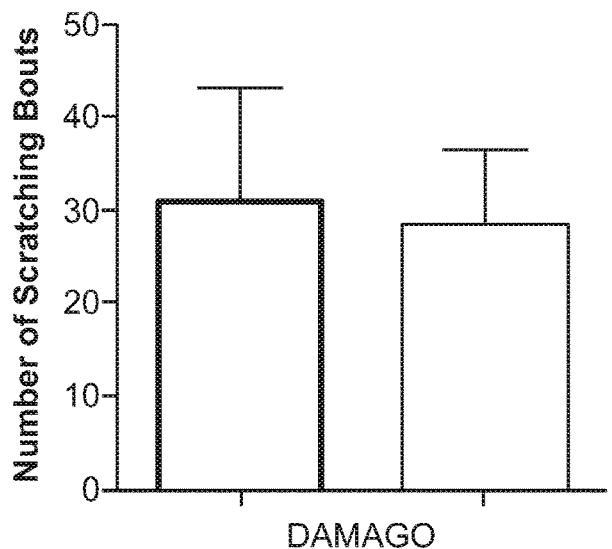
Figure 14:
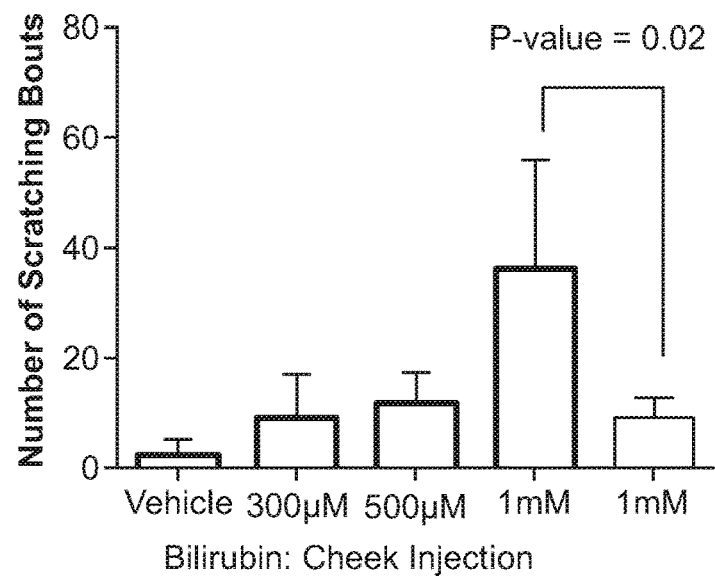
Figure 14:
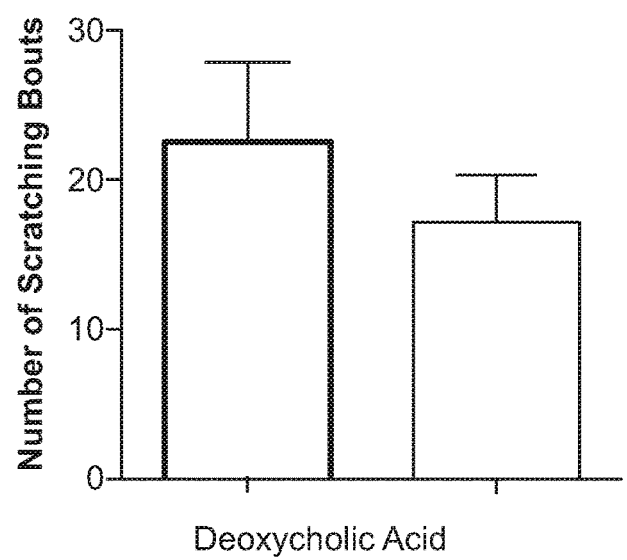
Figure 14:
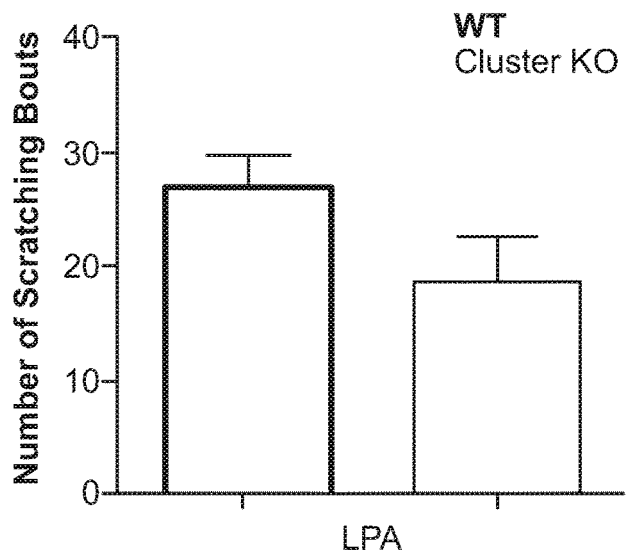
Figure 15:
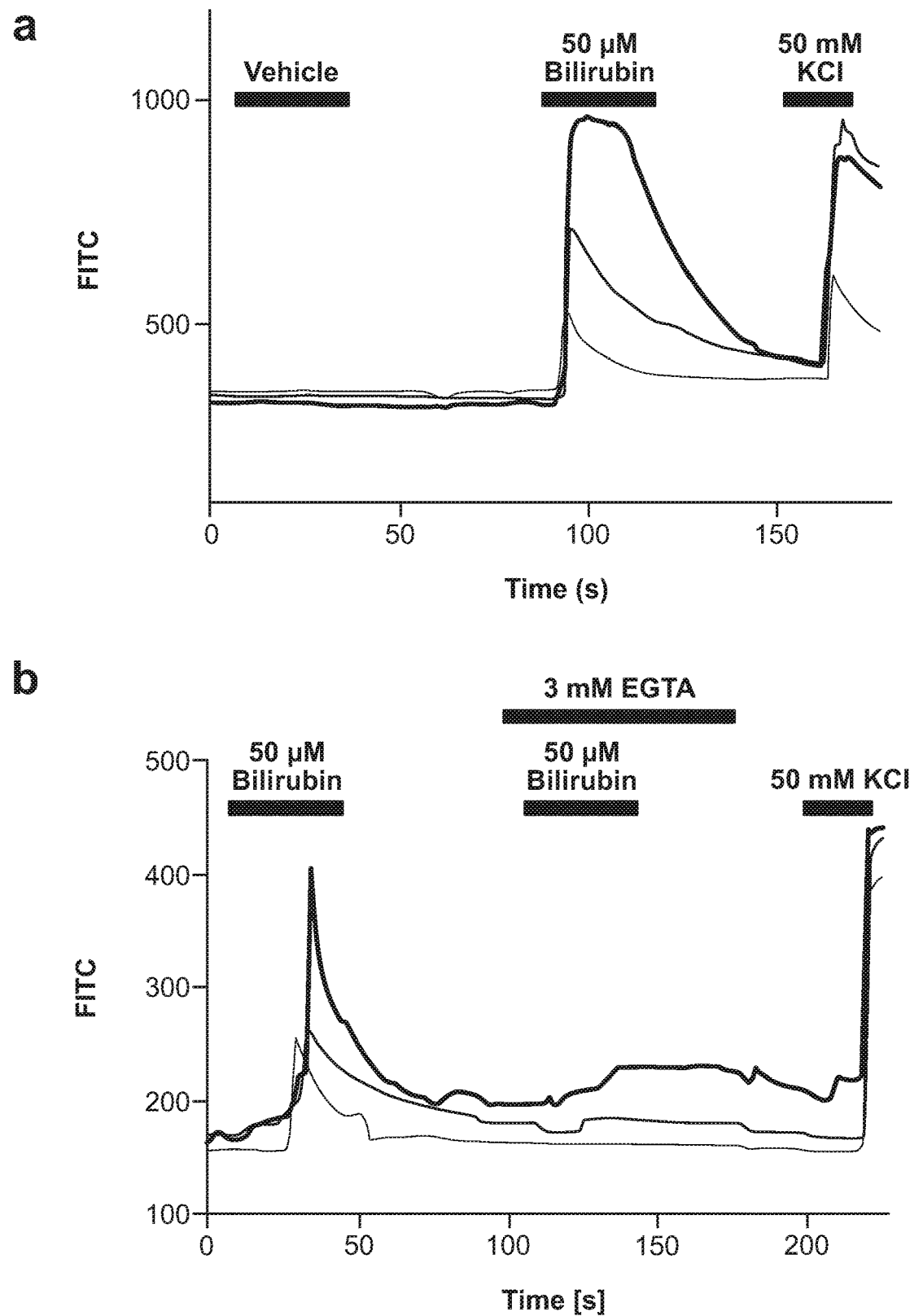
FIG. 15A-FIG. 15D is a series of graphs demonstrating that bilirubin activates a population of dorsal root ganglia neurons in a Mrgpr-dependent manner
Figure 15:
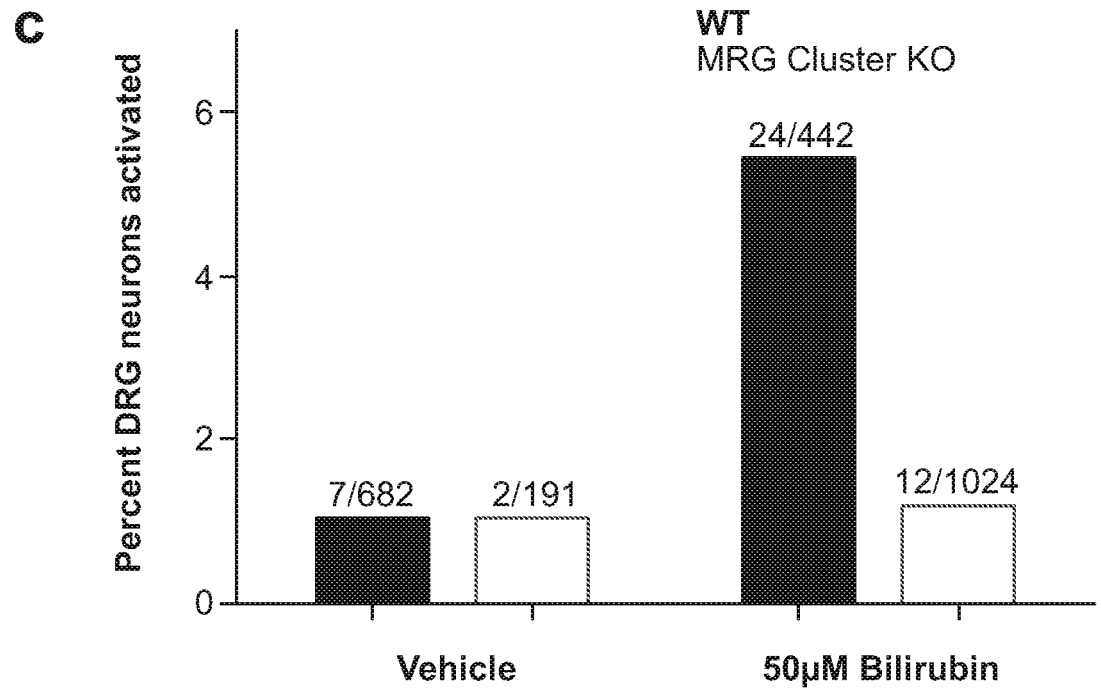
Figure 15:
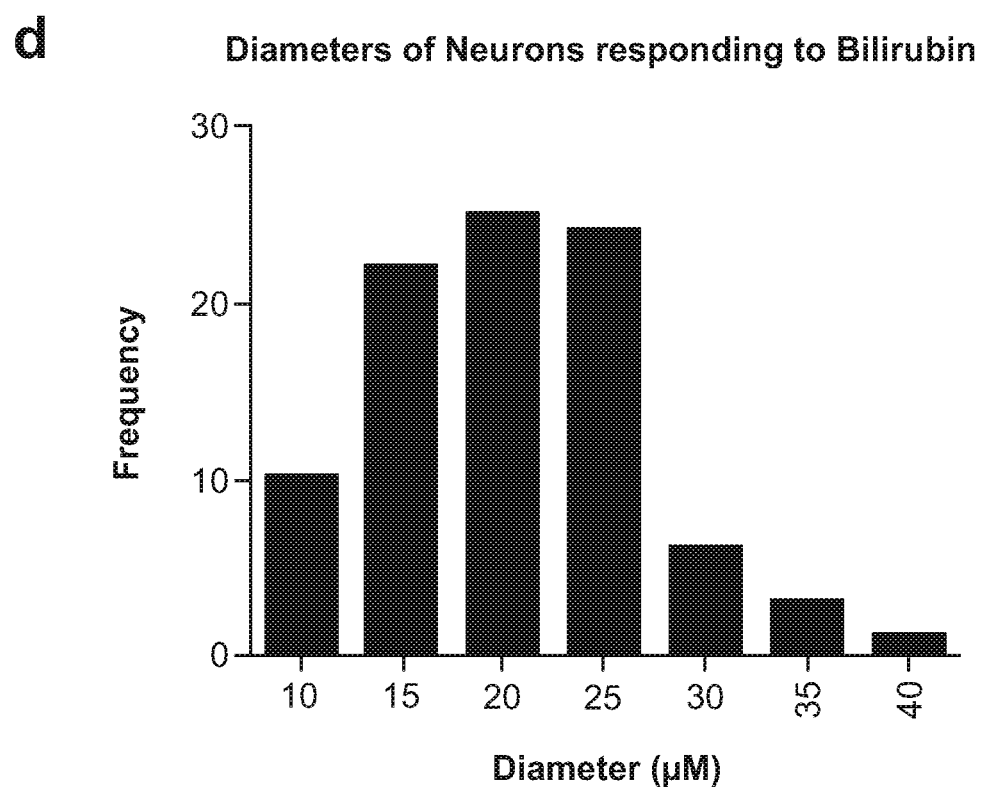

ANIT treatment results in many pathological changes. Bile constituents, normally present in trace amounts in serum, are upregulated. In addition, ANIT causes hepatocyte injury which results in further perturbations of biological homeostasis. Due to these changes, there are many hypotheses that could explain the reduced cholestatic itch seen in Cluster KO animals. To address this, numerous bile components hypothesized to be involved in cholestatic pruritus were injected in both WT and Cluster KO littermates. After injection, acute itch was assessed. From these injections, bilirubin was identified as a pruritogen, a previously unpublished phenomenon. WT mice scratch in response to injection of bilirubin at either the cheek or the back (FIG. 14A, FIG. 14D). This scratch response is dose-dependent, and animals do not scratch at lower doses (FIG. 14A). Of note, injection of bilirubin failed to elicit itch in Cluster KO animals (FIG. 14A). Bilirubin mediated pruritus was not believed to be histaminergic in nature as bilirubin failed to activate mast cells both in a histamine release assay and by calcium imaging (FIG. 15A, FIG. 15B). Additionally, an H1 receptor blocker did not inhibit behavior (FIG. 15C). Injection of other pruritogens, DAMGO, morphine, LPA, and DCA, representative members of three proposed mediators of cholestatic pruritus, all elicited comparable itch responses in both WT and Cluster KO animals (FIG. 14B, FIG. 14C, FIG. 14E, FIG. 14F). Based on this, the mechanism of reduced cholestatic pruritus in Cluster KO animals was due to a decreased activity of bilirubin against an Mrgpr within the cluster.

Figure 16:
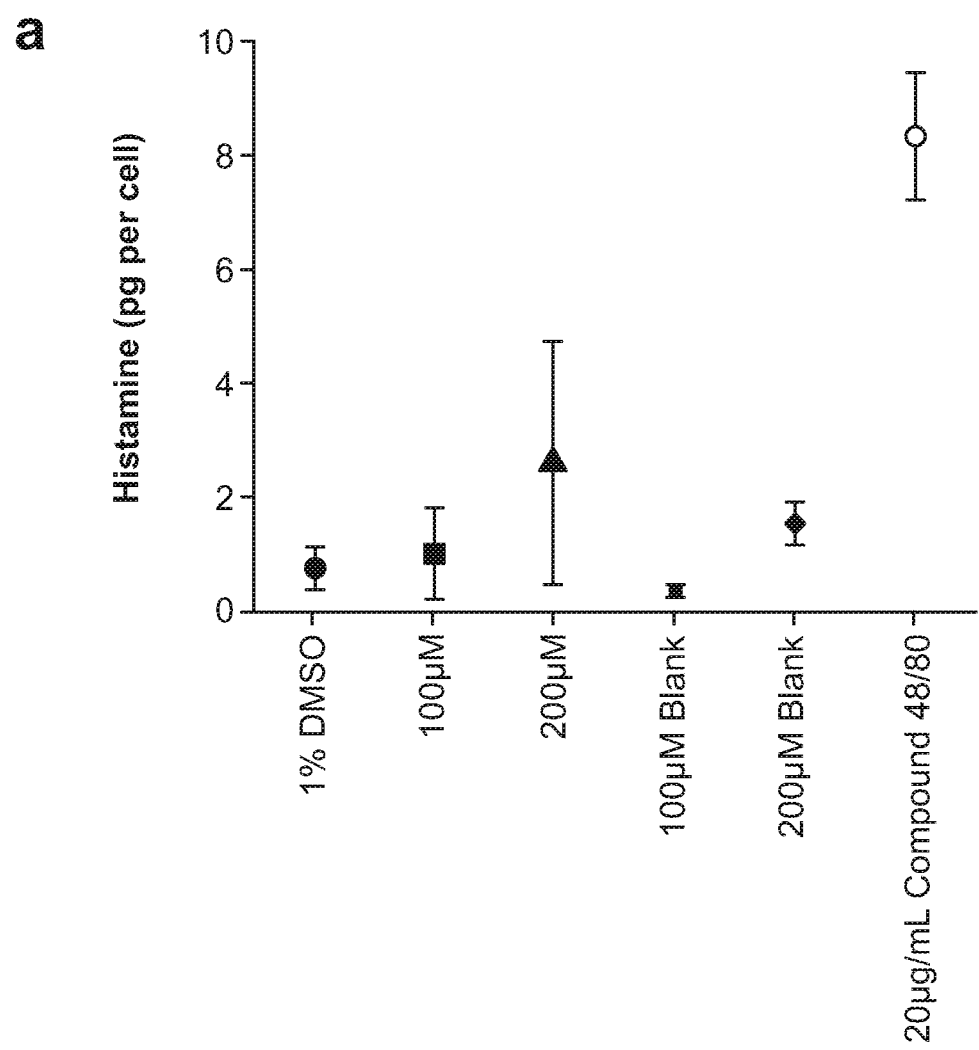
Figure 16:
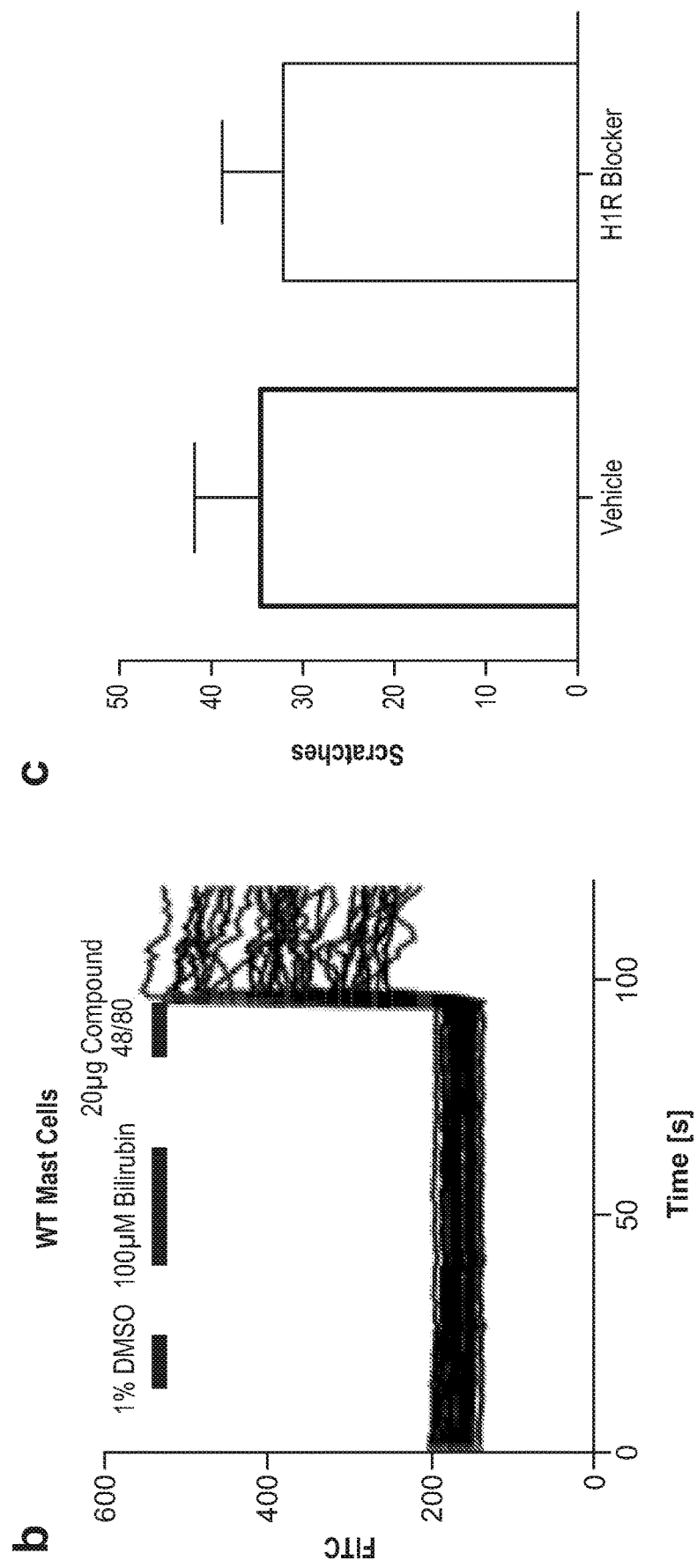

In support of this behavior data, bath application of bilirubin to dissociated DRG neurons evoked transient increases in calcium (FIG. 16A). Bilirubin evoked calcium flux was dependent on the presence of extracellular calcium (FIG. 16B). 50 µM bilirubin activated 4 to 6 percent of total DRGs (FIG. 16C). Importantly, compared to vehicle control, Cluster KO DRGs did not exhibit an increase in the number of neurons activated in response to bilirubin (FIG. 15C). The mean diameter of an activated neuron was 20.6 µm [19.2, 21.7] (FIG. 16D). Based on size, these neurons were classified as small-diameter nociceptive neurons (FIG. 16D) (19; 25).

Figure 17:
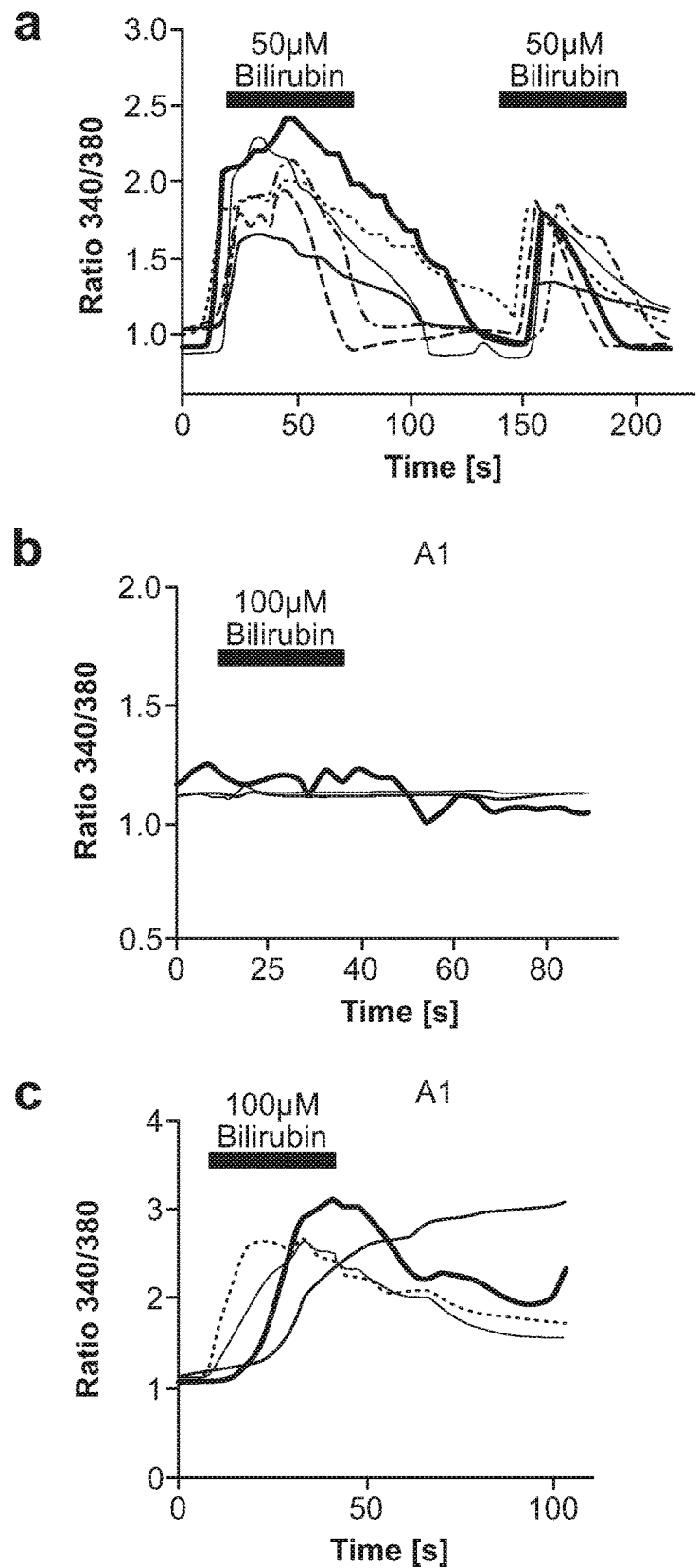
FIG. 17A-FIG. 17F is a series of graphs demonstrating that MrgprA1 and MrgprX4 are activated by bilirubin in a Gαq-dependent manner
Figure 17:
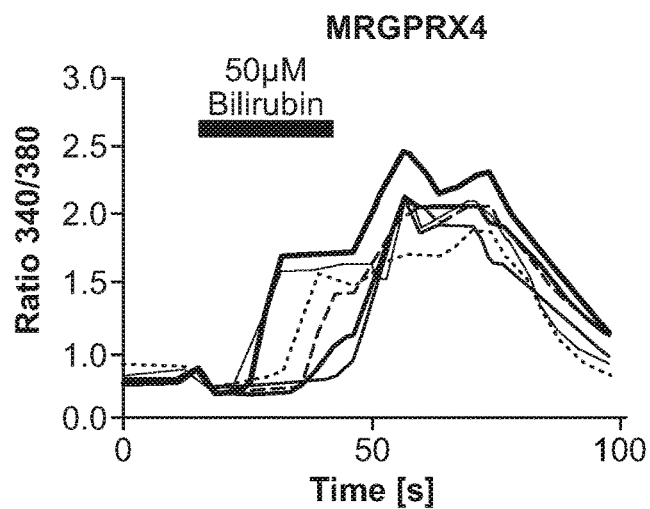
Figure 17:
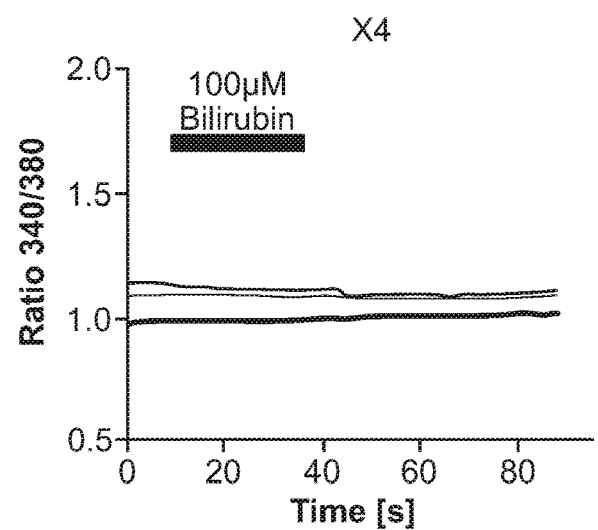
Figure 17:
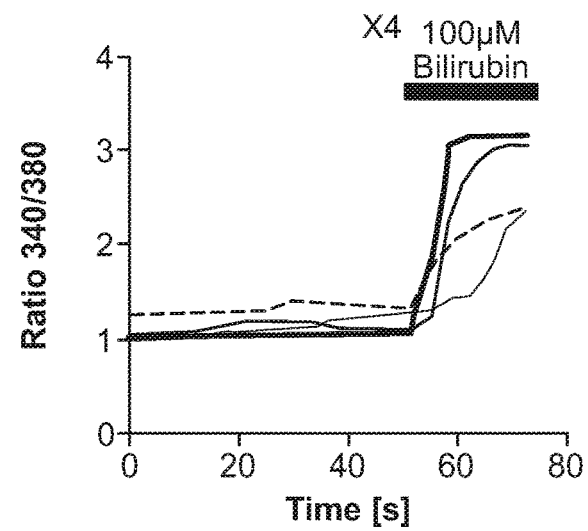
Figure 18:
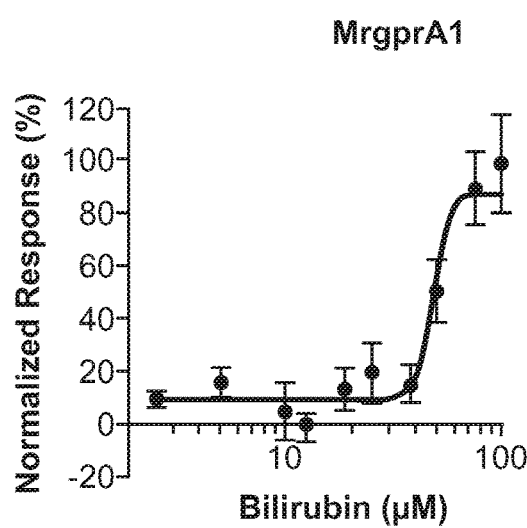
FIG. 18A-18C is a series of graphs demonstrating that MrgprA1 and MrgprX4 have EC50s for bilirubin at pathophysiological concentrations. EC50s were calculated using HEK cells stably expressing either MrgprA1 or MrgprX4. Cells were loaded with FLIPR calcium imaging dye, and a Flexstation3 machine (Molecular Devices) was used for reading changes in fluorescence. Wells were run in triplicate, and all values from each plate were normalized to the highest responding well. Vehicle only addition did not cause a change in fluorescence in either cell line. Un-transfected cells exhibited some changes in fluorescence but no dose response curve (not shown). The x-axis depicts a modified logarithmic scale.
Figure 18:
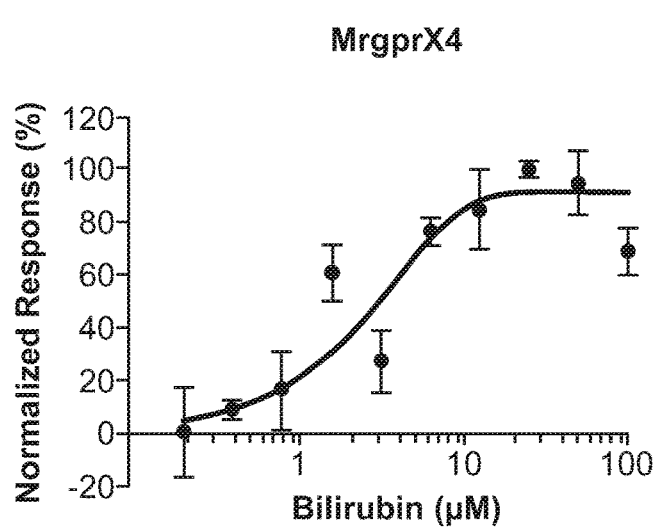
Figure 18:
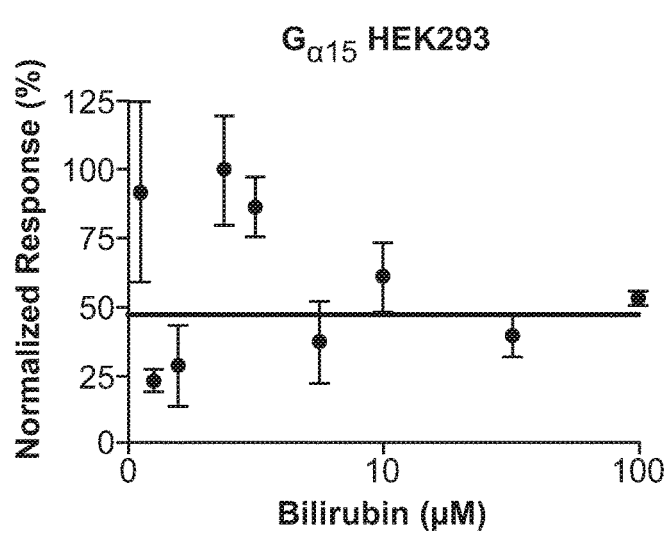
Figure 19:
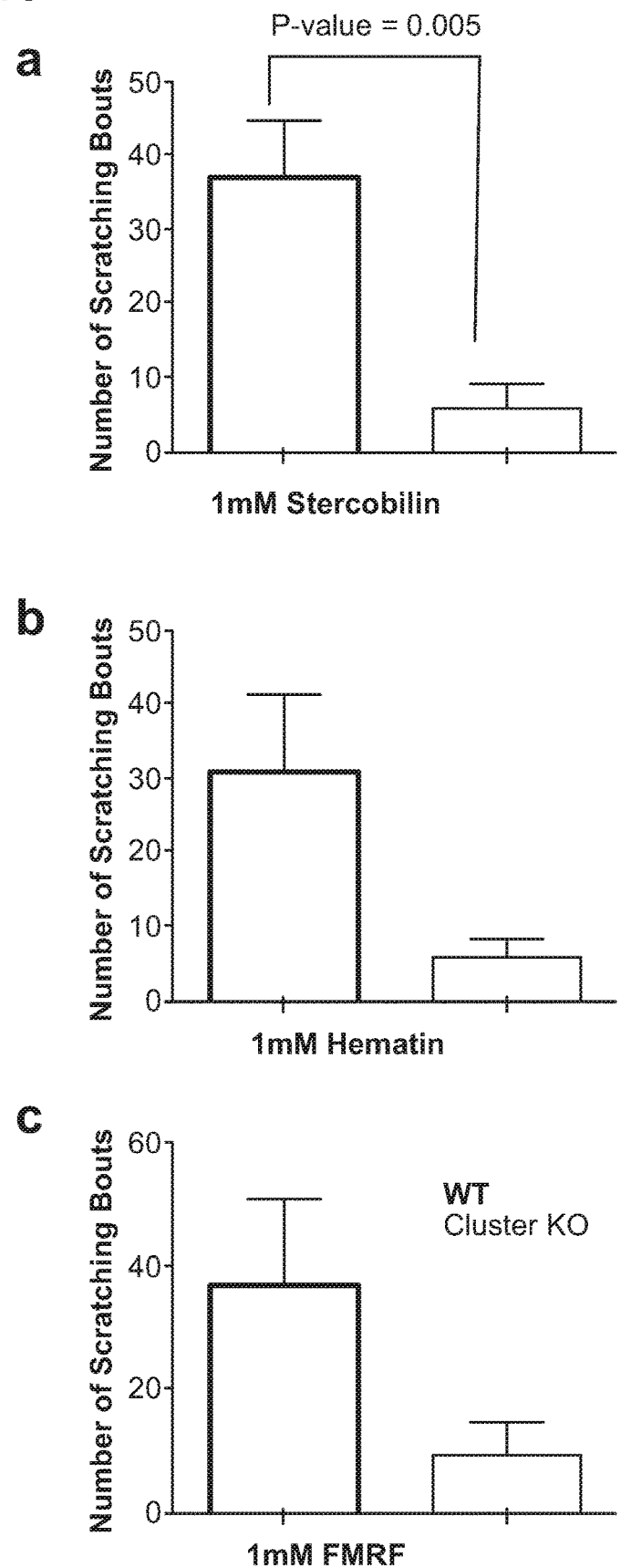
FIG. 19A-FIG. 19C is a series of graphs demonstrating that the activation of MrgprA1 results in itch. The injection of 1 mM Stercobilin, 1 mM Hematin, or 1 mM FMRF were elicited in WT animals and not in Cluster KO animals. All three compounds are agonists for MrgprA1 and not other Mrgprs.

There are 12 intact Mrgpr ORFs deleted in the Cluster KO animals. To determine which one(s) were involved in mediating bilirubin-associated pruritus, each Mrgpr in the cluster was serially transfected into human embryonic kidney (HEK) cells. Using calcium imaging, bilirubin was tested against these transfected cells to identify which cell populations fluxed calcium in the presence of bilirubin. Untransfected HEK cells did not respond to bilirubin, and out of all the Mrgprs in the cluster, only cells expressing MrgprA1 displayed positive signal in response to bilirubin with an EC50 of approximately 49 µM (FIG. 17A, FIG. 18A). U73122 blocked the calcium influx, suggesting that increases in transient calcium were Gαq-mediated (FIG. 17B, FIG. 17C). Behavior confirmed the calcium imaging analysis as an MrgprA1 single-gene KO animal did not scratch upon bilirubin injection (FIG. 14A). Members of the murine MrgprA family of receptors are most closely related to members of the human MrgprX family. To determine if any human receptor responded to bilirubin, HEK cell lines stably expressing each of the four human Mrgprs X1-X4 was screened. Of these four, only MrgprX4 exhibited a positive response to bilirubin with an EC50 of 2 μM (FIG. 17D, FIG. 18B). Once again, the calcium signal was Gαq-mediated (FIG. 17E, FIG. 17F).

Example 9: Additional Heme Metabolites Activate MrgprA1 and X4

Structurally, heme metabolites are very similar. Based on this, additional heme metabolites may be expected to have activity against MrgprA1 and X4. Indeed, as assessed by calcium imaging, multiple heme metabolites activated these receptors and not related receptors A3 and X1 (Table 1, FIG. 22). The heme metabolites are structurally related. Multiple heme metabolites activated MrgprA1, a mouse receptor, and MrgprX4 human receptor. Dose of substance is listed above while approximate percentage of activation is depicted within the table. This calcium imaging was validated by injecting a few identified MrgprA1 agonists into WT mice. Other heme metabolites with activity against MrgprA1 like hematin and stercobilin all elicited itch in WT animals that was absent in cluster KO animals. Additionally, activation of MrgprA1 with a structurally different agonist, FMRF, caused itch. Based on this, activation of MrgprA1 was sufficient to induce itch. Based on calcium imaging established functional homology, activation of MrgprX4 in humans leads to itch.

References for Examples 7-9 are Listed Below

1. Alemi F, Kwon E, Poole D P, Lieu T, Lyo V, et al. 2013. The TGR5 receptor mediates bile acid-induced itch and analgesia. *J Clin Invest* 123:1513-30
2. Bergasa N V. 1998. Hypothesis: taste disorders in patients with liver disease may be mediated in the brain: potential mechanisms for a central phenomenon. *Am J Gastroenterol* 93:1209-10.
3. Bergasa N V. 2008. Pruritus in primary biliary cirrhosis: pathogenesis and therapy. *Clin Liver Dis* 12:385-406; x.
4. Bergasa N V. 2014. Pruritus of Cholestasis. *In Itch: Mechanisms and Treatment*, ed. E Carstens, T Akiyama. Boca Raton (Fla.). Number of.
5. Bergasa N V, Schmitt J M, Talbot T L, Ailing D W, Swain M G, et al. 1998. Open-label trial of oral nalmefene therapy for the pruritus of cholestasis. *Hepatology* 27:679-84.
6. Bergasa N V, Talbot T L, Ailing D W, Schmitt J M, Walker E C, et al. 1992. A controlled trial of naloxone infusions for the pruritus of chronic cholestasis. *Gastroenterology* 102:544-9.
7. Bulmer A C, Verkade H J, Wagner K H. 2013. Bilirubin and beyond: a review of lipid status in Gilbert's syndrome and its relevance to cardiovascular disease protection. *Prog Lipid Res* 52:193-205.
8. Chisholm J W, Dolphin P J. 1996. Abnormal lipoproteins in the ANIT-treated rat: a transient and reversible animal model of intrahepatic cholestasis. *J Lipid Res* 37:1086-98.
9. Datta D V, Sherlock S. 1966. Cholestyramine for long term relief of the pruritus complicating intrahepatic cholestasis. *Gastroenterology* 50:323-32.
10. Dong X, Han S, Zylka M J, Simon M I, Anderson D J. 2001. A diverse family of GPCRs expressed in specific subsets of nociceptive sensory neurons. *Cell* 106:619-32.
11. European Association for the Study of the L. 2009. EASL Clinical Practice Guidelines: management of cholestatic liver diseases. *J Hepatol* 51:237-67.
12. Flegel C, Schobel N, Altmuller J, Becker C, Tannapfel A, et al. 2015. RNA-Seq Analysis of Human Trigeminal and Dorsal Root Ganglia with a Focus on Chemoreceptors. *PLoS One* 10:e0128951.
13. Goswami S C, Thierry-Mieg D, Thierry-Mieg J, Mishra S, Hoon M A, et al. 2014. Itch-associated peptides: RNA-Seq and bioinformatic analysis of natriuretic precursor peptide B and gastrin releasing peptide in dorsal root and trigeminal ganglia, and the spinal cord. *Mol Pain* 10:44.
14. Halvorsen J A, Dalgard F, Thoresen M, Bjertness E, Lien L. 2012. Itch and pain in adolescents are associated with suicidal ideation: a population-based cross-sectional study. *Acta Derm Venereol* 92:543-6.
15. Ikoma A, Steinhoff M, Stander S, Yosipovitch G, Schmelz M. 2006. The neurobiology of itch. *Nat Rev Neurosci* 7:535-47.
16. Kremer A E, Martens J J, Kulik W, Rueff F, Kuiper E M, et al. 2010. Lysophosphatidic acid is a potential mediator of cholestatic pruritus. *Gastroenterology* 139:1008-18, 18 e1.
17. Kremer A E, van Dijk R, Leckie P, Schaap F G, Kuiper E M, et al. 2012. Serum autotaxin is increased in pruritus of cholestasis, but not of other origin, and responds to therapeutic interventions. *Hepatology* 56:1391-400.
18. Kuiper E M, van Erpecum K J, Beuers U, Hansen B E, Thio H B, et al. 2010. The potent bile acid sequestrant colesevelam is not effective in cholestatic pruritus: results of a double-blind, randomized, placebo-controlled trial. *Hepatology* 52:1334-40.
19. LaMotte R H, Dong X, Ringkamp M. 2014. Sensory neurons and circuits mediating itch. *Nat Rev Neurosci* 15:19-31.
20. Lembo P M, Grazzini E, Groblewski T, O'Donnell D, Roy M O, et al. 2002. Proenkephalin A gene products activate a new family of sensory neuron—specific GPCRs. *Nat Neurosci* 5:201-9.
21. Liu Q, Sikand P, Ma C, Tang Z, Han L, et al. 2012. Mechanisms of itch evoked by beta-alanine. *J Neurosci* 32:14532-7.
22. Liu Q, Tang Z, Surdenikova L, Kim S, Patel K N, et al. 2009. Sensory neuron-specific GPCR Mrgprs are itch receptors mediating chloroquine-induced pruritus. *Cell* 139:1353-65.
23. McNeil B, Dong X. 2012. Peripheral mechanisms of itch. *Neurosci Bull* 28:100-10.
24. McNeil B D, Pundir P, Meeker S, Han L, Undem B J, et al. 2015. Identification of a mast-cell-specific receptor crucial for pseudo-allergic drug reactions. *Nature* 519: 237-41.
25. Ross S E. 2011. Pain and itch: insights into the neural circuits of aversive somatosensation in health and disease. *Curr Opin Neurobiol* 21:880-7.
26. Swain M G, Rothman R B, Xu H, Vergalla J, Bergasa N V, Jones E A. 1992. Endogenous opioids accumulate in plasma in a rat model of acute cholestasis. *Gastroenterology* 103:630-5.
27. Thornton J R, Losowsky M S. 1988. Opioid peptides and primary biliary cirrhosis. *BMJ* 297:1501-4.

28. Thornton J R, Losowsky M S. 1989. Methionine enkephalin is increased in plasma in acute liver disease and is present in bile and urine. *J Hepatol* 8:53-9.
29. Thornton J R, Losowsky M S. 1989. Plasma leucine enkephalin is increased in liver disease. *Gut* 30:1392-5.
30. Vitek L, Jirsa M, Brodanova M, Kalab M, Marecek Z, et al. 2002. Gilbert syndrome and ischemic heart disease: a protective effect of elevated bilirubin levels. *Atherosclerosis* 160:449-56.

Example 10: MRGPRX3 is Expressed in Human Keratinocytes and is Required for their Response to hBD3

Figure 20A:
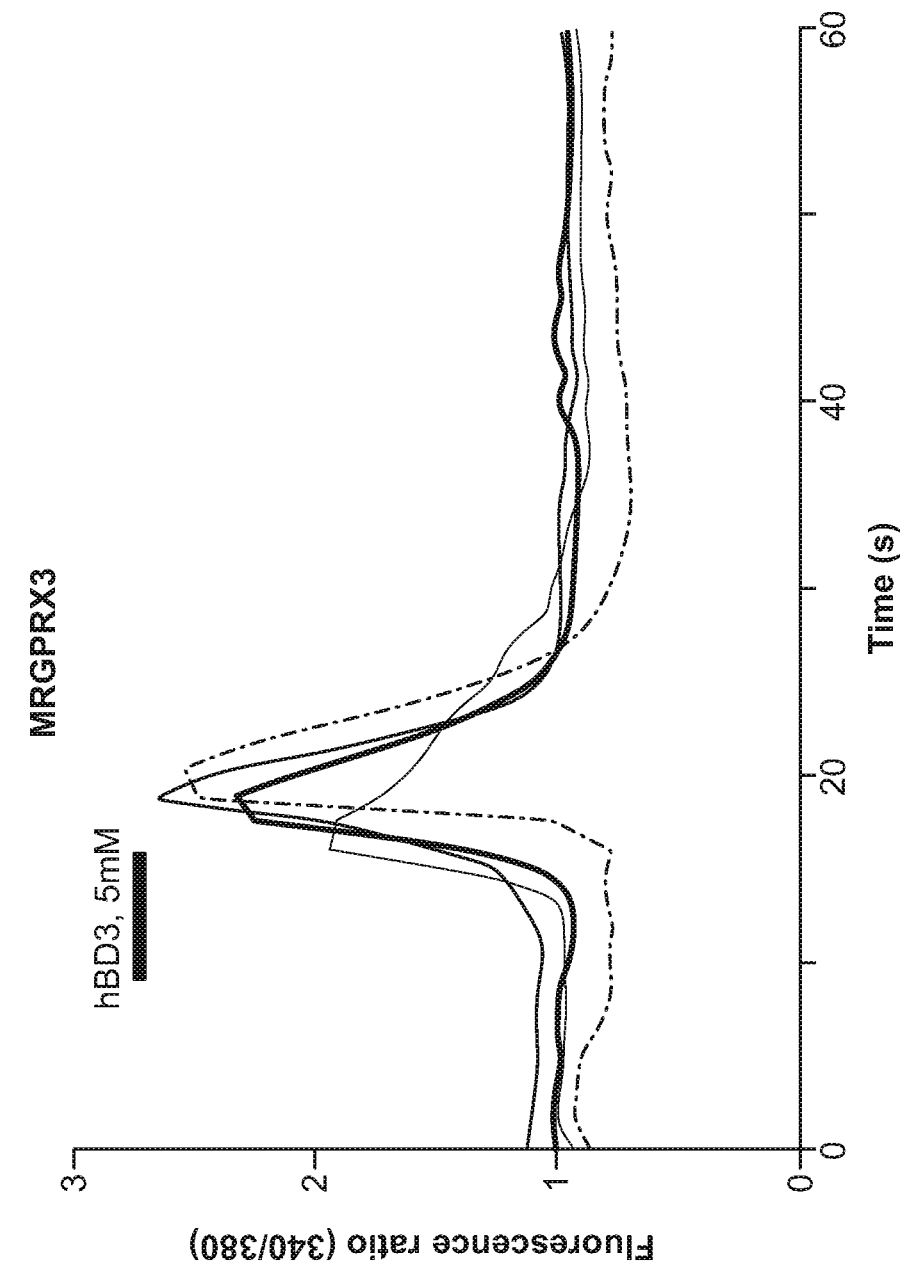
FIG. 20A-FIG. 20C is a series of graphs demonstrating that MRGPRX3 is a novel keratinocyte receptor for hBD3.
Figure 20:
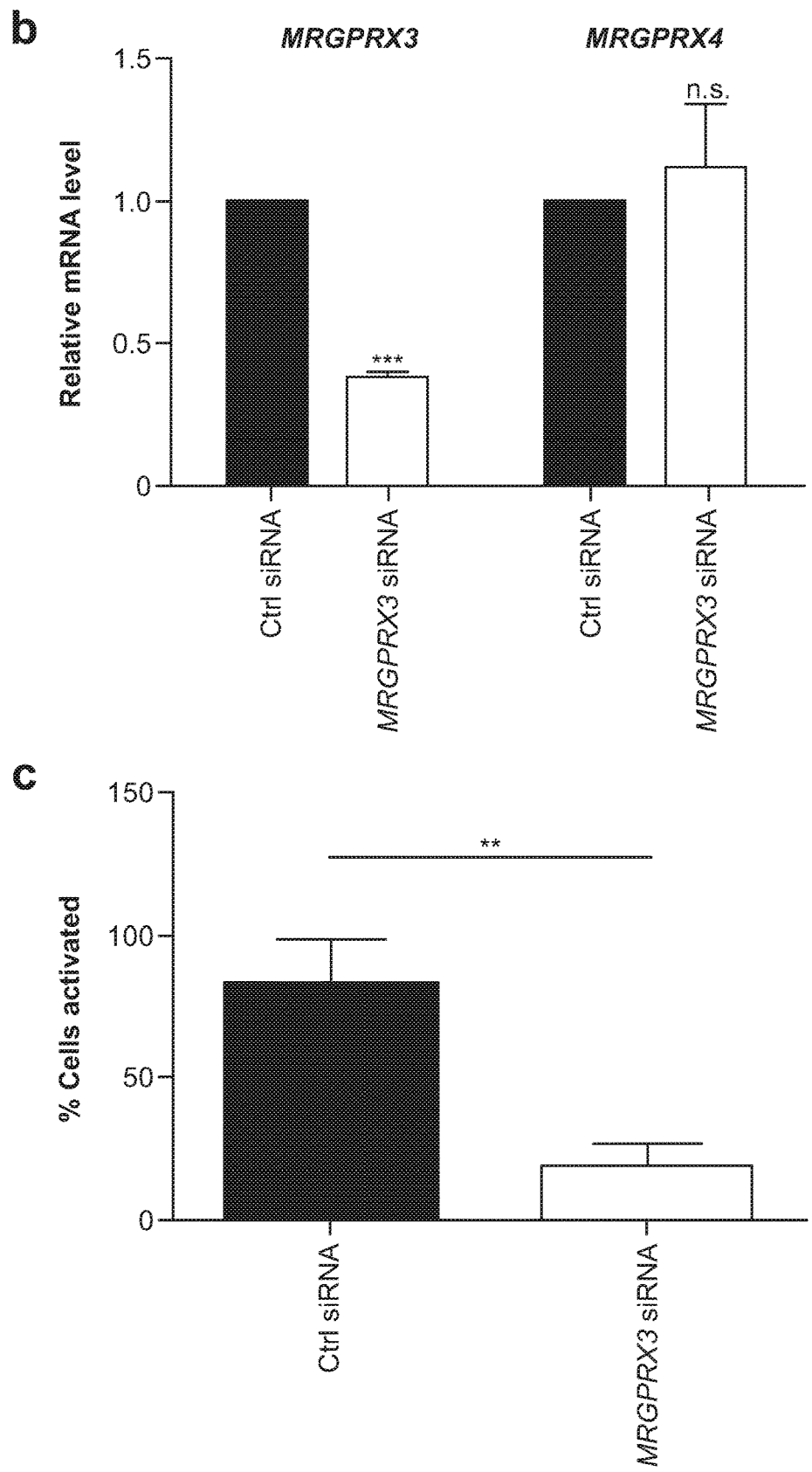

As shown in FIG. 20A, HEK cells expressing MRGPRX3 produced a robust $Ca^{2+}$ response to synthetic human Beta-defensin 3 (hBD3). RT-PCR was used to analyze the expression of MRGPRX3 in primary human keratinocytes and confirm that the gene is expressed at intermediate levels. siRNA against MRGPRX3 effectively reduced the expression of this receptor without affecting another family member MRGPRX4 (FIG. 20B). Knocking down MRGPRX3 significantly reduced the percentage of keratinocytes that responded to hBD3 from >80% to <20%, demonstrating that MRGPRX3 is necessary for the cells to sense and respond to the ligand.

Figure 21A:
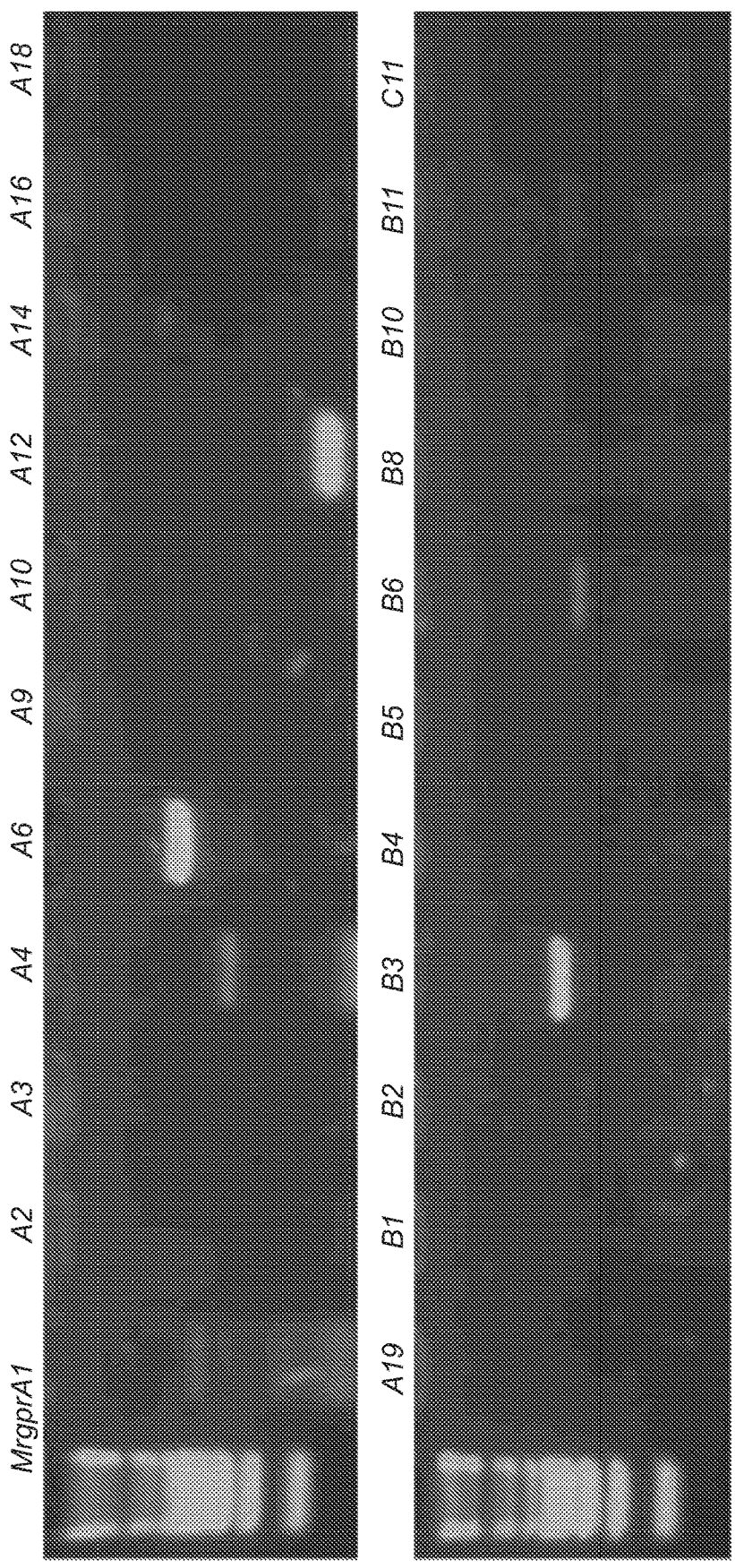
FIG. 21A-FIG. 21D is a series of immunoblots, graphs and illustrations that demonstrate the mouse MrgprA6 is the putative homologue of human MrgprX3.
Figure 21:
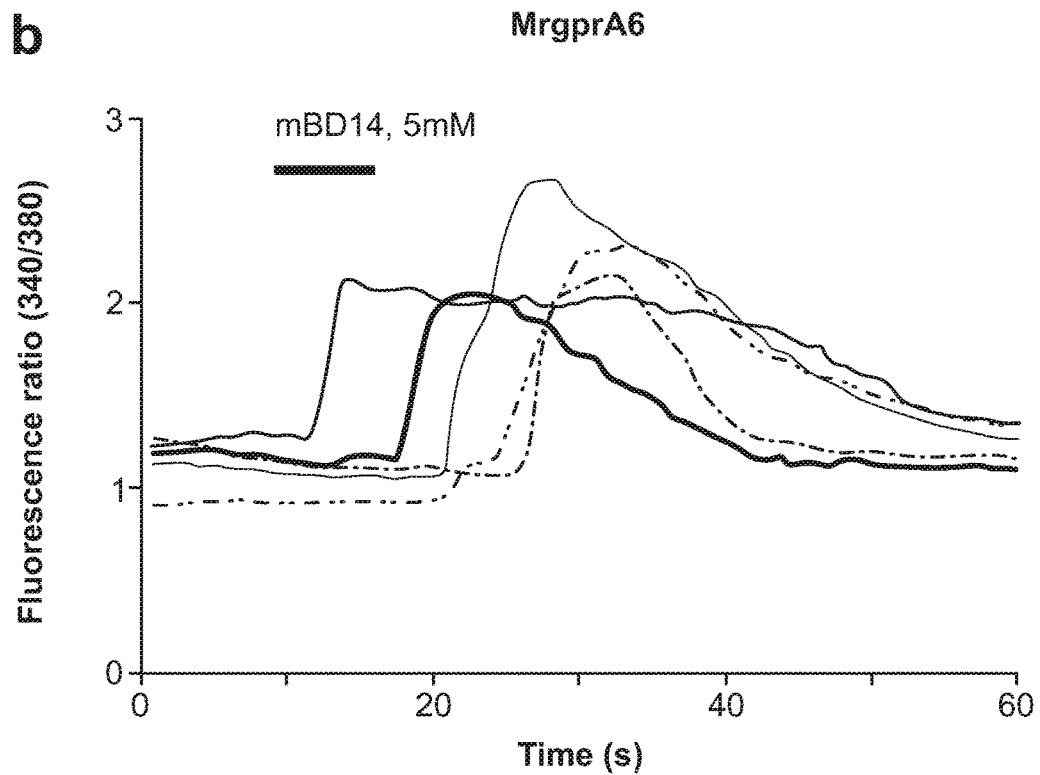
Figure 21:
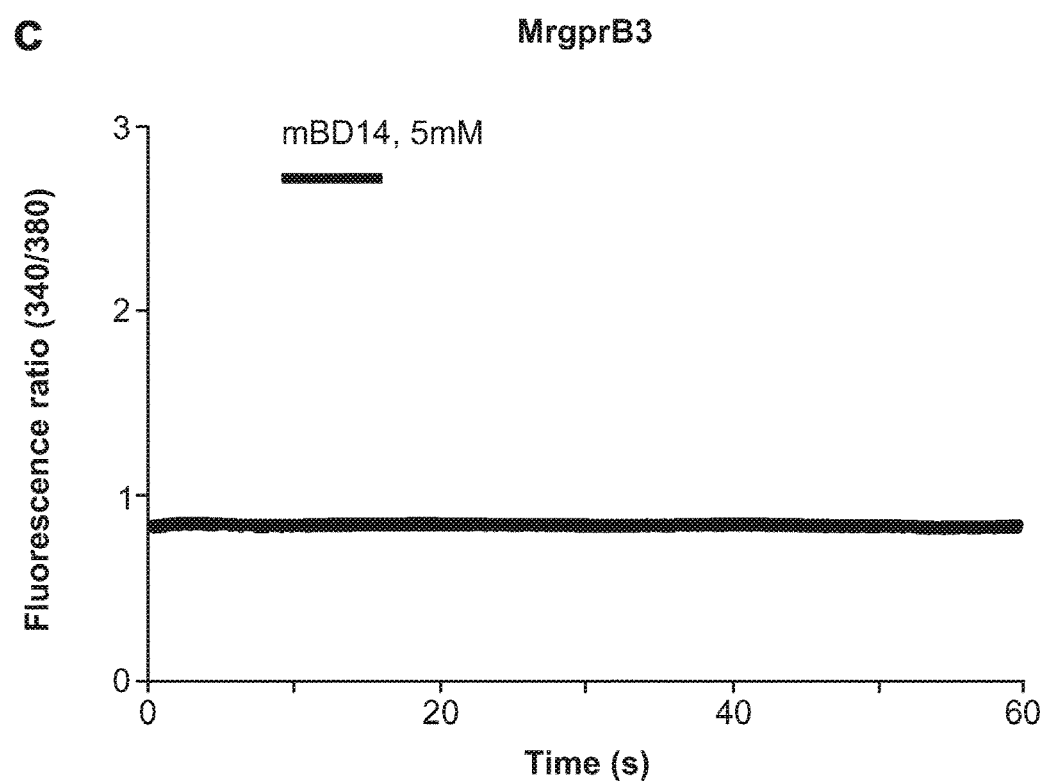
Figure 21:
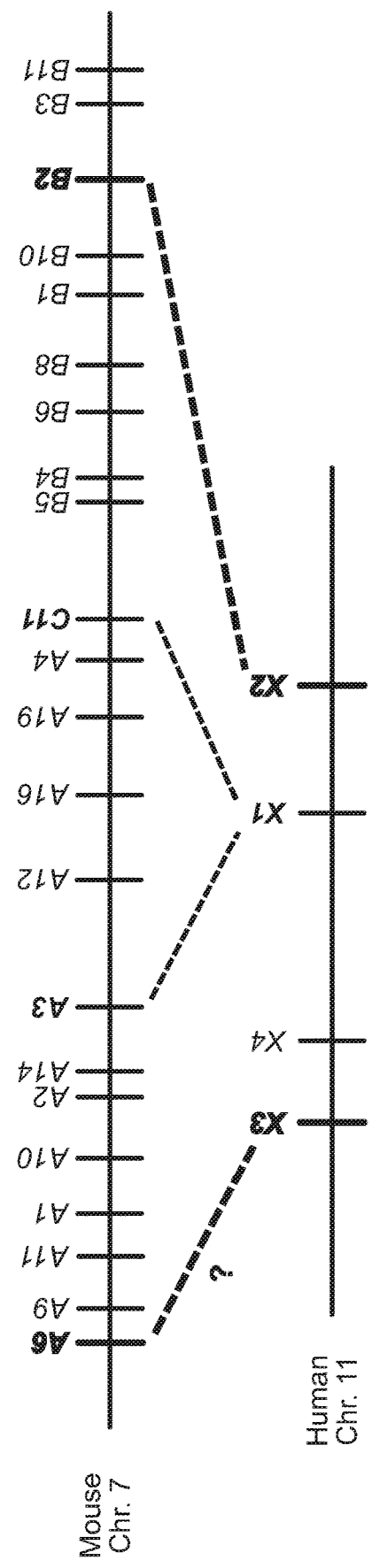

Example 11: Murine MrgprA6 is the Putative Homologue of Human MRGPRX3 MrgprA6 is Expressed in Keratinocytes The identity of the mouse homologue of human MRGPRX3 was determined. The Mrgpr gene cluster was largely expanded during evolution, with >20 receptors encoded relative to 4 MRGPRXs in humans (FIG. 21C). The first step was to isolate keratinocytes from the mouse epithelium and determine which of the Mrgpr genes were robustly expressed. RT-PCR revealed that only 3 genes, MrgprA6, A12 and B3 were strongly expressed in mouse keratinocytes. MrgprA1, A4 and B6 showed weak expression (FIG. 21A).

MrgprA6 Responds to mBD14, the Sole Mouse Homologue of hBD3.

MrgprX3 is an orphan receptor, and hBD3 is its first identified agonist. A well-conserved mouse homologue of hBD3, mouse Beta-Defensin-14 (mBD14), was used to further probe for the mouse homologue of hMrgprX3. Among the receptors that showed expression in mouse keratinocytes (FIG. 21A), MrgprA6 was the only one strongly activated by mBD14 while MrgprA1, A4, A12, B3, and B6 did not show any response (FIG. 21B).

MrgprA6 KO mice and MrgprA6-cre BAC mice were generated. These mouse lines are unique and important for in vivo wound closure assays and other skin disease models. Keratinocytes isolated from wild type and mutant animals are important cell based assays for their responses to mBD14 and to further examine the intracellular signaling pathways downstream of the MrgprA6 receptor. Similarly, human keratinocytes with MrgprX3 knockdown or mutant expression are essential for human cell-based assay testing MrgprX3 in skin disease models. Other potential skin diseases involving MrgprX3 function include: psoriasis, dermatitis, chronic skin ulcer and carcinomas. Furthermore, the disease indication of MrgprX3 can be expanded from the cutaneous system to the mucosal system since hBD3 and other defensins also provide defense to the airway and intestines. Therefore, targeting MrgprX3 and MrgprA6 has the potential to treat wound healing, chronic inflammation, malignant transformations, skin diseases such as psoriasis and dermatitis, airways and GI tract disorders, pain and itch.

References for Examples 10-11 are Listed Below

1. Pasparakis, M., Haase, I. & Nestle, F. O. Mechanisms regulating skin immunity and inflammation. *Nat Rev Immunol* 14, 289-301 (2014).
2. Singer, A. J. & Clark, R. A. F. Cutaneous Wound Healing. *N Engl. J. Med.* 341, 738-746 (1999).
3. Owen, J. A., Punt, J., Kuby, J. & Stranford, S. A. Kuby Immunology. (W.H. Freeman, 2013).
4. Pazgier, M., Hoover, D. M., Yang, D., Lu, W. & Lubkowski, J. Human β-defensins. *Cell. Mol. Life Sci. C.* 63, 1294-1313 (2006).
5. Amid, C. et al. Manual annotation and analysis of the defensin gene cluster in the C57BL/6J mouse reference genome. *BMC Genomics* 10, 1-13 (2009).
6. Ganz, T. Defensins: antimicrobial peptides of innate immunity. *Nat Rev Immunol* 3, 710-720 (2003).
7. Röhrl, J., Yang, D., Oppenheim, J. J. & Hehlgans, T. Human β-Defensin 2 and 3 and Their Mouse Orthologs Induce Chemotaxis through Interaction with CCR2. *J. Immunol.* 184, 6688-6694 (2010).
8. Befus, A. D. et al. Neutrophil Defensins Induce Histamine Secretion from Mast Cells: Mechanisms of Action. *J. Immunol.* 163, 947-953 (1999).
9. Subramanian, H. et al. β-Defensins Activate Human Mast Cells via Mas-Related Gene X2. *J. Immunol.* 191, 345-352 (2013).
10. Hirsch, T. et al. Human beta-defensin-3 promotes wound healing in infected diabetic wounds. *J. Gene Med.* 11, 220-228 (2009).
11. Sørensen, O. E. et al. Wound Healing and Expression of Antimicrobial Peptides/Polypeptides in Human Keratinocytes, a Consequence of Common Growth Factors. *J. Immunol.* 170, 5583-5589 (2003).
12. Aarbiou, J. et al. Neutrophil Defensins Enhance Lung Epithelial Wound Closure and Mucin Gene Expression In Vitro. *Am. J. Respir. Cell Mol. Biol.* 30, 193-201 (2004).
13. Otte, J.-M. et al. Human beta defensin 2 promotes intestinal wound healing in vitro. *J. Cell. Biochem.* 104, 2286-2297 (2008).
14. Niyonsaba, F. et al. Antimicrobial Peptides Human Beta-Defensins Stimulate Epidermal Keratinocyte Migration, Proliferation and Production of Proinflammatory Cytokines and Chemokines. *J. Invest. Dermatol.* 127, 594-604 (2016).
15. Liu, Q. et al. Sensory neuron-specific GPCRs Mrgprs are itch receptors mediating chloroquine-induced pruritus. *Cell* 139, 1353-1365 (2009).
16. Han, L. et al. A subpopulation of nociceptors specifically linked to itch. *Nat Neurosci* 16, 174-182 (2013).
17. McNeil, B. D. et al. Identification of a mast-cell-specific receptor crucial for pseudo-allergic drug reactions. *Nature* 519, 237-241 (2015).
18. Hruz, T. et al. Genevestigator V3: A Reference Expression Database for the Meta-Analysis of Transcriptomes. *Adv. Bioinformatics* 2008, 420747 (2008).
19. Kiatsurayanon, C. et al. Angiogenic peptide (AG)-30/5C activates human keratinocytes to produce cytokines/chemokines and to migrate and proliferate via MrgX receptors. *J. Dermatol. Sci.* doi:http://dx.doi.org/10.1016/j.jdermsci.2016.05.006

20. Kaisho, Y. et al. Transgenic rats overexpressing the human MrgX3 gene show cataracts and an abnormal skin phenotype. *Biochem. Biophys. Res. Commun.* 330, 653-657 (2005).

Example 12: Materials and Methods for Examples 12-17

The following materials and methods were used.
Animal Care and Use

All experiments were performed in accordance with protocols approved by the Animal Care and Use Committee at the Johns Hopkins University School of Medicine.
Isolation of Human Plasma Plasma from patients suffering from hyperbilirubinemia, specifically cholestasis, was isolated under a protocol approved by the Institutional Review Board at the Johns Hopkins University School of Medicine (Study number: IRB00154650). Whole blood was collected into PAXgene tubes (PreAnalytiX 761115) and centrifuged for 5 minutes at 300 g. Plasma was then collected, aliquoted, and stored at −20° C. until experimentation. Normal control human plasma was purchased from Sigma (P9523).
Molecules and Preparation The following molecules were used: bilirubin IXα (Frontier Scientific). α-naphthyl isothiocyanate (ANIT, Sigma), biliverdin (Sigma), chloroquine (Sigma), compound 48/80 (Sigma), cyclosporin A (Sigma), haemin (Sigma), human serum albumin (HSA, Sigma), BAMS-22 (Sigma), BOC-GLN-D-(FORMYL)TRP-PHE-BENZYLESTER (QWF, Sigma), bilirubin ditaurate (Lee Biosciences). cetirizine (Tocris Biosciences), stercobilin (Santa Cruz Biotechnology), urobilinogen (Santa Cruz Biotechnology), cholera toxin (Santa Cruz Biotechnology), U73122 (Santa Cruz Biotechnology), YM-254890 (Wako Chemicals), pertussis toxin (Fisher Scientific), fibronectin (Sigma), Fluo 4-AM (Molecular Probes), and Fura 2-AM (Molecular Probes).

Bilirubin is highly susceptible to oxidation and photolysis. Accordingly, bilirubin was freshly prepared just prior to each experiment in either DMSO or 0.1 M NaOH and then maintained in the dark. For calcium imaging analyses, bilirubin was diluted into calcium imaging buffer a few seconds before use. Final concentration of DMSO in all applicable tested solutions was <0.5%. ANIT and cyclosporin A were dissolved in olive oil and prepared freshly as needed. Urobilinogen and stercobilin were dissolved in phosphate buffered saline and adjusted to a pH of 7.4 before being stored at −20° C. in 100 µl aliquots until needed. All other drugs were prepared as 100 µl-1,000 µl aliquots and stored at −20° C. before thawing at 4° C. Freeze/thaw cycles were avoided whenever possible.
Behavioral Studies All applicable behavioral tests were performed and analyzed with the experimenter blind to genotype. All mice used were 8-12 week old males (20 to 30 g) that had either been generated on a C57BL/6J background or backcrossed to C57BL/6J mice for at least 10 generations. All itch behavior experiments were performed between 8 a.m. and 12 p.m. On the day before the experiment, animals were placed in the test chamber for 30 minutes before being subjected to a series of three mock injections with 5-minute break periods in between. On the day of the experiment, animals were first allowed to acclimatize to the test chamber for 10 minutes before injection. Pruritic compounds were subcutaneously injected into the nape of the neck or cheek, and scratching behavior was observed for 30 minutes. A bout of scratching was defined as a continuous scratching movement with either hindpaw directed at the area of the injection site. In the cheek injection model, a wipe was defined as a single forepaw stroking the site of the injection. Use of both forepaws on the face or cheek was considered as grooming behavior. Scratching behavior was quantified by counting the number of scratching bouts at 5 min intervals over the 30-min observation period. Wiping was quantified at 2 min intervals over a ten-minute observation period. For H1R block, 30 mg/kg of cetirizine HCl (pH 7.4) was given intraperitoneally thirty minutes prior to injection of bilirubin. Licking behavior was quantified in seconds and identified as the licking of the toes or footpad of the hind paw site of injection that was neither preceded nor followed by licking of any other portion of the body.
Generation of Knock-In and Knock-Out Mice Mrgpr-clusterΔ$_{-/-}$ mice, Mrgpra1$^{GRP}$ mice, and Mrgprd$^{PLAP}$ were generated as previously described[4,21,44]. Tg(Mrgpra3-Cre) mice were generated as previously described[24]. Lsl-tdTomato mice (Ai9, 007909) were purchased from Jackson Labs. Mrgpra1$^{-/-}$ mice were generated using CRISPR-Cas9 on the C57BL/6 background using the following guide RNA sequence: TTCCCAGCAGCACCTGTGCAGGG (SEQ ID NO: 3). Blvra$^{-/-}$ mice were generated at Ozgene (Australia) on a C57BL/6J background.
Calcium Imaging and Analysis Cells were imaged in calcium imaging buffer (CIB; 10 mM HEPES, 1.2 mM NaHCO$_3$, 130 mM NaCl, 3 mM KCl, 2.5 mM CaCl$_2$, 0.6 mM MgCl$_2$, 20 mM glucose, and 20 mM sucrose at pH 7.4 and 290-300 mOsm). To monitor changes in intracellular [Ca$^{2+}$] ([Ca$^{2+}$]$_i$), cells were loaded with either Fura 2-AM (HEK293 cells) or Fluo 4-AM (DRG neurons and mast cells) for 30 min in the dark at 37° C. in CIB just prior to imaging. With Fura 2-AM, emission at 510 nm was monitored from excitation at both 340 nm and 380 nm. With Fluo 4-AM, emission at 520 nm was monitored from excitation at 488 nm. Cells were identified as responding if the intracellular [Ca$^{2+}$] rose by either 50% compared to baseline or 50% compared to the [Ca$^{2+}$]$_i$ change assayed during addition of 50 mM KCl (neurons only). Damaged, detached, high-baseline, and motion-activated cells were excluded from analysis.
HEK293 Cells In initial screens, HEK293 cells stably expressing the murine G-protein alpha-subunit G$_{\alpha 15}$, a unique G$_\alpha$ protein that non-selectively couples a large variety of GPCRs to phospholipase C[30], were plated on poly-D-lysine-coated coverslips and transiently transfected with constructs encoding the MRGPR of interest. 12-24 h later, cells were loaded with the Fura 2-AM. Unless otherwise specified, compounds were perfused into the imaging chamber for approximately thirty seconds after a baseline period was established. Response was then monitored at 5 s intervals for an additional 60 s.
DRG Neurons DRGs were incubated with Fluo-4 AM 24 hour after dissociation (native genotype) or 48 hour after dissociation (virally transduced). Unless otherwise noted, cells were imaged for 20 seconds to establish a baseline before compounds were added. After 30 seconds, a 2 minute wash was applied before addition of another substances. At the end of every imaging trial, 50 mM KCl was added as a positive control. Cells included in calculating percentages all displayed at least a 50% increase in [Ca$^{2+}$]$_i$ compared to baseline upon addition of KCl.

Mast Cells

Mast cells were purified as described and plated onto glass coverslips coated with 30 mg/mL fibronectin and allowed to recover for 2 h at 37° C. Cells were then loaded with Fluo-4 AM.

$EC_{50}$ and $IC_{50}$ Determinations

HEK293 cells stably expressing either MRGPRA1, MRGPRX4, and MRGRPC11 were seeded in poly-D-lysine-coated 96-well plates at 10,000 cells/well. Cells were loaded with Fura 2-AM, washed twice, and maintained in CIB. Haem metabolites were freshly dissolved in DMSO in dim light and then diluted into a buffer comprised of 20 mM Tris and 150 mM NaCl at pH 8.8. Potential changes in pH were evaluated prior to each experiment. $EC_{50}$ values were determined from dose-responses performed in triplicate, repeated 2-4 times. To determine potential antagonism by QWF against bilirubin, cells were treated with varying doses of QWF for 1 min in CIB prior to application of agonist.

Murine Peritoneal Mast Cell Purification and Calcium Imaging.

Adult male mice 8-12 weeks of age were sacrificed through $CO_2$ inhalation. A total of 25 mL of mast cell dissociation media (MCDM; HBSS with 3% fetal bovine serum and 10 mM HEPES, pH 7.2) was chilled on ice before being used to make two sequential peritoneal lavages. Lavages were combined and spun at 200 g. The pellet was re-suspended in 2 mL MCDM, layered over 4 ml of an isotonic 70% Percoll suspension (2.8 ml Percoll, 320 ml 10% HBSS, 40 ml 1 M HEPES, 830 ml MCDM), and spun for 20 min at 500 g at 4° C. Mast cells were recovered in the pellet. Mast cells were re-suspended in DMEM with 10% fetal bovine serum (FBS) and 25 ng/mL recombinant mouse stem cell factor (Sigma).

Mouse Peritoneal Mast Cell Histamine Release Assay

Mast cells were purified as described and allowed to recover for 2 h at 37° C. Cells were then seeded in 96-well plates coated with 20 mg/mL fibronectin at 300 cells/well. Plates were incubated at 37° C. for 45 min before assay. For the assay, all compounds tested were diluted in CIB. Five minutes after compound addition, supernatant was aspirated and frozen at −80° C. until histamine levels were determined with an HTRF histamine assay kit (Cisbio Assays) according to the manufacturer's instructions.

DRG Dissociation and Culture

DRG neurons from all spinal levels were collected in cold DH10 media (90% Dulbecco's modified Eagle's medium (DMEM)/F-12, 10% FBS, penicillin (100 U/mL), and streptomycin (100 μg/mL)). DRGs were digested with a dispase (5 mg/ml)/collagenase type I (1 mg/ml) enzyme mixture at 37° C. for 45 minutes. After trituration, cells were spun at 300 g and re-suspended in DH10 before being plated on glass coverslips coated with poly-D-lysine (0.5 mg/ml) and laminin (10 μg/ml, Invitrogen). DRGs were cultured with DH10 supplemented with 50 ng/mL NGF at 37° C.

DRG Viral Transduction

Lentiviruses encoding various cDNA for MRGPRs were generated using psPAX2 and pMD2.G. Virus was pelleted by centrifugation at 100,000 g for 4 h, gently washed with twice with DH10 media, and suspended in DH10. One day after DRG isolation and culture, DRGs were infected with lentivirus 24 h overnight. The following morning, media was completely replaced with fresh DH10 supplemented with 50 ng/mL NGF. 24 h after infection, cells were processed for calcium imaging.

DRG Electrophysiology

DRG neurons from 3-5 week old mice were collected as described. After culture for 1-3 days, DRG neurons were transferred into a chamber with extracellular solution containing (in mM) 144 NaCl, 2.5 KCl, 2 CaCl2, 0.5 $MgCl_2$, 5 HEPES, and 10 glucose, adjusted to pH 7.4 with NaOH. Whole-cell current-clamp recordings were performed at ~23° C. using borosilicate capillary glass electrodes (Sutter Instrument) with a tip resistance of 3-5 Ma Internal solution contained (in mM) 80 K-acetate, 30 KCl, 40 HEPES, and 1 CaCl2, adjusted to pH 7.4 with potassium hydroxide (KOH). Small-diameter neurons with diameter 15-25 μm were chosen for patch-clamp. Data were acquired using an Axopatch 700B Amplifier and Digidata 1322A Digitizer with pClamp9.2 software package (Axon Instrument). Chloroquine (CQ) in 1 mM was added by perfusion for 20 seconds, and bilirubin freshly made in 50 μM was added by pipette. Solutions containing 50 mM KCl were applied at the end of each cellular recording. Only neurons that could fire action potentials after adding KCl were regarded as healthy and appropriate for inclusion in data analysis.

Microscale Thermophoresis Binding Assay

Binding isotherms for MRGPRA1, MRGPRX4, and MRGRPC11 towards various ligands were determined by microscale thermophoresis with the NanoTemper monolith NT.115 instrument[27]. Ligands were pre-incubated with 10 μM of the GFP-tagged receptor of interest for 5 minutes at room temperature in binding buffer (20 mM Tris and 150 mM NaCl at pH 8.8). Receptors were crudely purified as a membrane fraction from cells stably expressing the receptor[45]. Haem metabolites were freshly dissolved in 0.1 M NaOH in dim light and then diluted into assay buffer. Lyophilized BAMS-22 was dissolved in binding buffer. The pH of each ligand was evaluated prior to incubation with a receptor. Samples were loaded into NT.115 Hydrophobic-Treated Capillaries from NanoTemper. Microscale thermophoretic experiments were executed using 20% LED power and 15% MST power. $K_D$s were calculated using the law of mass action with data from three independent experiments. Binding between bilirubin and receptors was evaluated purely thermophoretically, whereas binding between BAMS-22 and MRGPRC11 was evaluated by T-Jump. Samples with dramatic deviations in initial fluorescence were excluded.

[$^{35}$S]GTPγS Binding

MRGPR activation was determined by measuring binding of a radiolabelled and non-hydrolyzable form of GTP, [$^{35}$S] guanosine-5'-(γ-thio)triphosphate ([$^{35}$S]GTPγS) as previously described[45]. Briefly, 10 μg of crude membrane fractions were diluted into 175 μL assay buffer (50 mM HEPES, 5 mM $MgCl_2$, 100 mM NaCl, 1 mM EDTA, 0.1% Triton 80) supplemented with 10 μM GDP and incubated at room temperature for 5 min. Membranes were then incubated an additional 1 min in a final volume of 199 μL assay buffer supplemented with 50 μM bilirubin. Samples were then brought to 200 μL with the addition of 10 nM [$^{35}$S]GTPγS. Samples were incubated for 2 h at 4° C. with gentle agitation. The experiment was terminated by rapid filtration onto GF/B filters and washed three times with wash buffer (50 mM Tris-HCl, 5 mM $MgCl_2$, and 50 mM NaCl at pH 7.4). Filters were then immersed in scintillation cocktail and counted. Nonspecific binding was determined by competition with 10 μM unlabeled GTPγS. GTPγS binding assays were performed as two independent experiments, in triplicate.

Immunohistochemistry

Adult mice (5-6 weeks old) were anesthetized with pentobarbital and perfused with 20 mL cold 0.1 M PBS (pH 7.4) followed with 2.5 mL of cold fixative (4% formaldehyde (v/v) and 14% sat. picric acid (v/v) in 0.1 M PBS). DRG were dissected from perfused mice and post-fixed in 4% paraformaldehyde at 4° C. for 1 h. Tissues were cryoprotected in 20% sucrose (w/v) for more than 24 h before being embedded in Optimal Cutting Temperature compound (OCT) and sectioned with a cryostat. The sections were dried at 37° C. on slides for 1 h and fixed with 4% paraformaldehyde at 21-23° C. for 10 min. The slides were pre-incubated in blocking solution (10% normal goat serum (v/v), 0.2% Triton X-100 (v/v) in PBS, pH 7.4) for 1 h at 21-23° C., then incubated overnight at 4° C. with primary antibodies. Secondary antibody incubation was performed at 21-23° C. for 2 h. For primary antibodies, rabbit antibody was to CGRP (T-4239, Peninsula, 1:1,000) and rabbit antibody to GFP (A-11122, Molecular Probes, 1:1,000). For secondary antibodies, goat antibody to rabbit (A11011, Alexa 568 conjugated; A11008, Alexa 488 conjugated; Molecular Probes) diluted was used 1:500 in blocking solution.

Generation of Cells Stably Expressing GFP-Tagged MRGPRs

HEK293 stable cell lines expressing GFP-tagged MRGPRA3, MRGPRC11, MRGPRD, MRGPRX1, and MRGPRX2 were generated in previously described reports[21,23,46]. Briefly, plasmids containing the receptor of interest were transfected into HEK cells using Lipofectamine 3000. After 3 days, cells were then selected using 0.5 mg/mL G418. After 3 weeks, monoclonal colonies were established and each the highest expressing clones were identified. For this study, Mrgpra1 and MRGPRX4 were inserted into pEGFP-N1 and transfected into HEK293 cells. MRGPR-positive cells were selected using 0.5 mg/mL G418 for three weeks, after which GFP-positive cells were sorted by FACS and monoclonally expanded. Two lines expressing similar levels of MRGPRA1 and MRGPRX4, as measured by GFP fluorescence, were selected for study.

High Pressure Liquid Chromatography (HPLC)

Plasma bilirubin was detected by HPLC using an analytical LC-18 column, 25 cm×4.6 mm (Xterra, Waters Corporation). Bilirubin was eluted with gradients of mobile phases: 0.1 M ammonium acetate in 60% methanol/40% water (v/v) (pH 5.2) (Solvent A) and 100% methanol (Solvent B). Bilirubin was eluted as follows: 0 to 14 min: linear gradient from 100% A to 100% B; 14 to 19 min: linear gradient from 100% A to 100% B; 19-24 min: isocratic elution at 100% A. Bilirubin exhibited a retention time of approximately 14-15 min and was detected by measuring absorbance at 450 nm. The peak corresponding to plasma bilirubin was confirmed with the addition of 10 µM bilirubin to the sample as an internal standard.

Mouse Models of Cholestasis and Sample Collection 1-naphthyl isothiocyanate (ANIT; Sigma) was solubilized in olive oil (Sigma). Animals were dosed with 25 mg/kg ANIT per os daily for five days. On day five, animals were acclimatized for itch behavior. On day six, animals were placed in test chambers and videotaped for one hour. The number of scratching bouts, defined as a continuous scratching movement with either hindpaw, was counted and binned in five minute intervals during the one hour period. After itch behavior was assessed, animals were administered pentobarbital (50 mg/kg, i.p.). Blood was collected by cardiac puncture and placed into heparinized tubes (BD Biosciences). After centrifugation, plasma was collected, aliquoted, and stored at −20° C. until analysis. Bile acid levels were assessed by a fluorometric kit from Cell Biolabs. When applicable, mice were then proceeded for histology.

Histology

For histologic assessment of ANIT-induced cholestasis, animals were transcardially perfused with cold PBS, followed by 4% PFA (w/v). Livers were dissected, post-fixed in 4% PFA overnight, and cryopreserved through gradients of 10 to 30% sucrose (w/v). Livers were embedded OCT and sectioned with a cryostat. Sections were dried at for 1 h at room temperature and then stained with haematoxylin, counterstained with eosin, rinsed, and then dehydrated.

Quantum Mechanical Calculations

DFT calculations were performed with Spartan 16 and modelled with wxMacMolPlt. Geometry optimizations and single point energy calculations were carried out with DFT-Hartree Fock hybrid B3LYP theory with the 6-31G(d) basis set. Energies were calculated at ground state in the gas phase 298 K.

Plasma Bilirubin Depletion

Plasma bilirubin was depleted either by selective oxidation by $FeCl_3$ to biliverdin IXα/biliverdin XIIIα or by immunoprecipitation. $FeCl_3$ was prepared as solution of 20% $FeCl_3$ in 0.1N HCl/methanol. $FeCl_3$ was fluxed with plasma at a final concentration of 1.5% $FeCl_3$ at 37° C. for 10 min. $FeCl_3$ is a mild oxidant but exhibits a redox potential that the oxidation of bilirubin to biliverdin[47]. Bilirubin was also immunoprecipated by incubating plasma with 5 µg of either normal rabbit IgG or anti-bilirubin antibody (generated as previously described[10]) coupled to protein A/G beads for 1 h at 25° C. To quantify bilirubin depletion, bilirubin was extracted from samples with 100% methanol and subjected to HPLC and UV-visible spectroscopic analysis. Absorbance was adjusted to a baseline of 0 OD, and bilirubin was quantified by integrating the area under the chromatographic peak.

Data Analysis

Group data were expressed as mean±SEM unless otherwise noted. Two-tailed unpaired Student's t-tests, Fisher's exact test, and Chi-squared tests were used to determine significance in statistical comparisons, and differences were considered significant at $P<0.05$. Statistical power analysis was used to justify sample size, and variance was determined to be similar among all treatment groups as determined by F test. No samples or animals subjected to successful procedures and/or treatments were excluded from analysis. All behavior experiments were designed in a blocked manner with consideration for both genotype and treatment.

Example 13: Bilirubin Elicited Non-Histaminergic, Mrgpr-Dependent Pruritus

Itch, clinically known as pruritus, is perceived by primary sensory neurons in the dorsal root ganglia that innervate the skin and mucosal surfaces[5-8]. While effective therapeutic options exist for histamine-mediated itch, non-histaminergic conditions such as jaundice-associated pruritus are more difficult to treat[2]. Jaundice, or the yellowing of the skin, sclera, and mucosa, is the result of an abnormal accumulation of the yellow metabolite bilirubin.

Bilirubin possesses complex physiologic and pathophysiologic properties. At physiologic and mildly elevated concentrations (0.2-2.7 mg/dL, 3.4-46.2 µM), bilirubin can act as an antioxidant 9 and is both neuroprotective[10] and cardioprotective[11]. At elevated levels however, such as in cutaneous jaundice (>5 mg/dL, >85.5 µM bilirubin), it is associated with pruritus, a correlation first noted by physicians as early as the second century B.C.E. 1.

Figure 23:
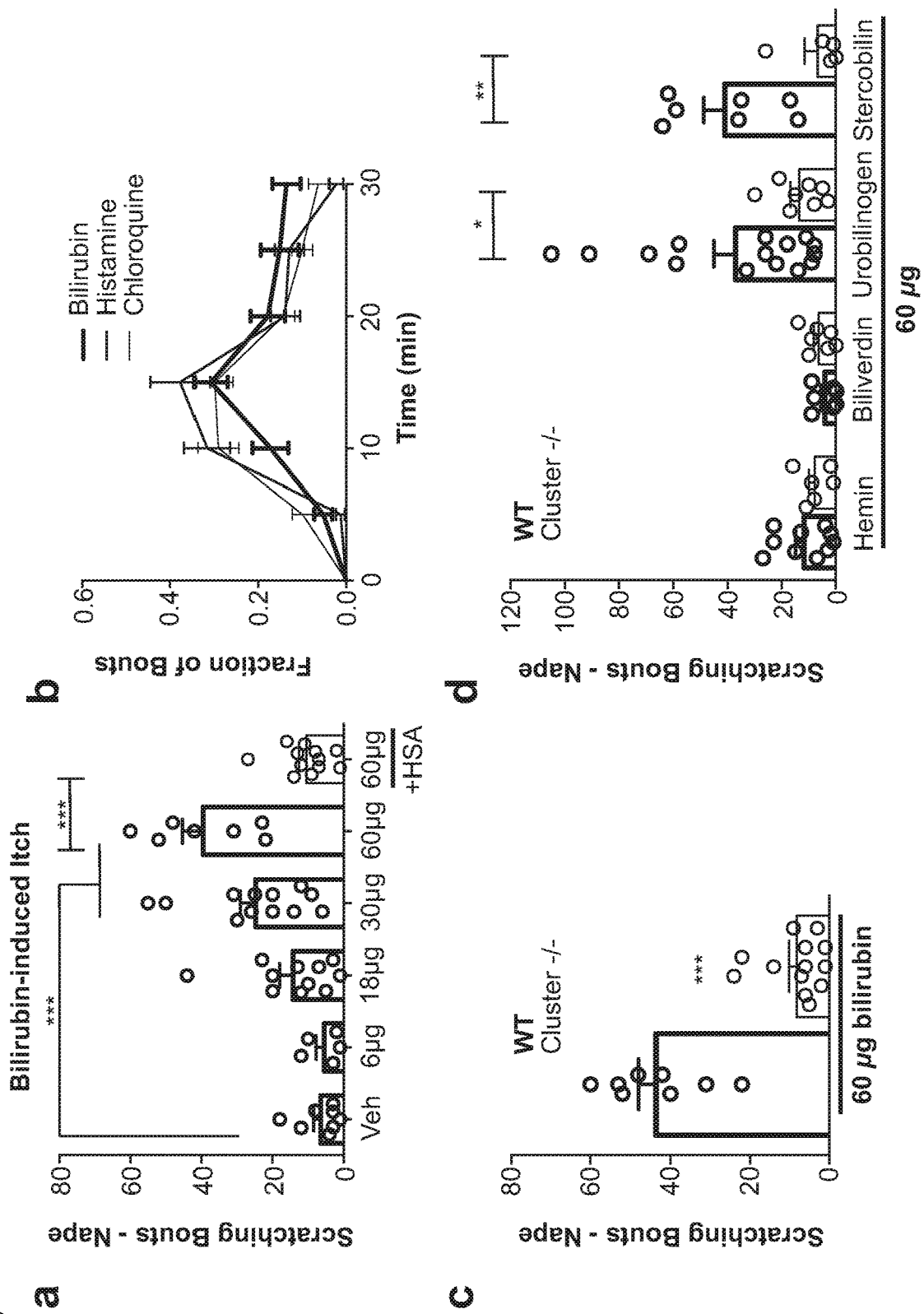
FIG. 23A-23E are images depicting that Bilirubin elicited non-histaminergic, Mrgpr-dependent pruritus.
Figure 23:
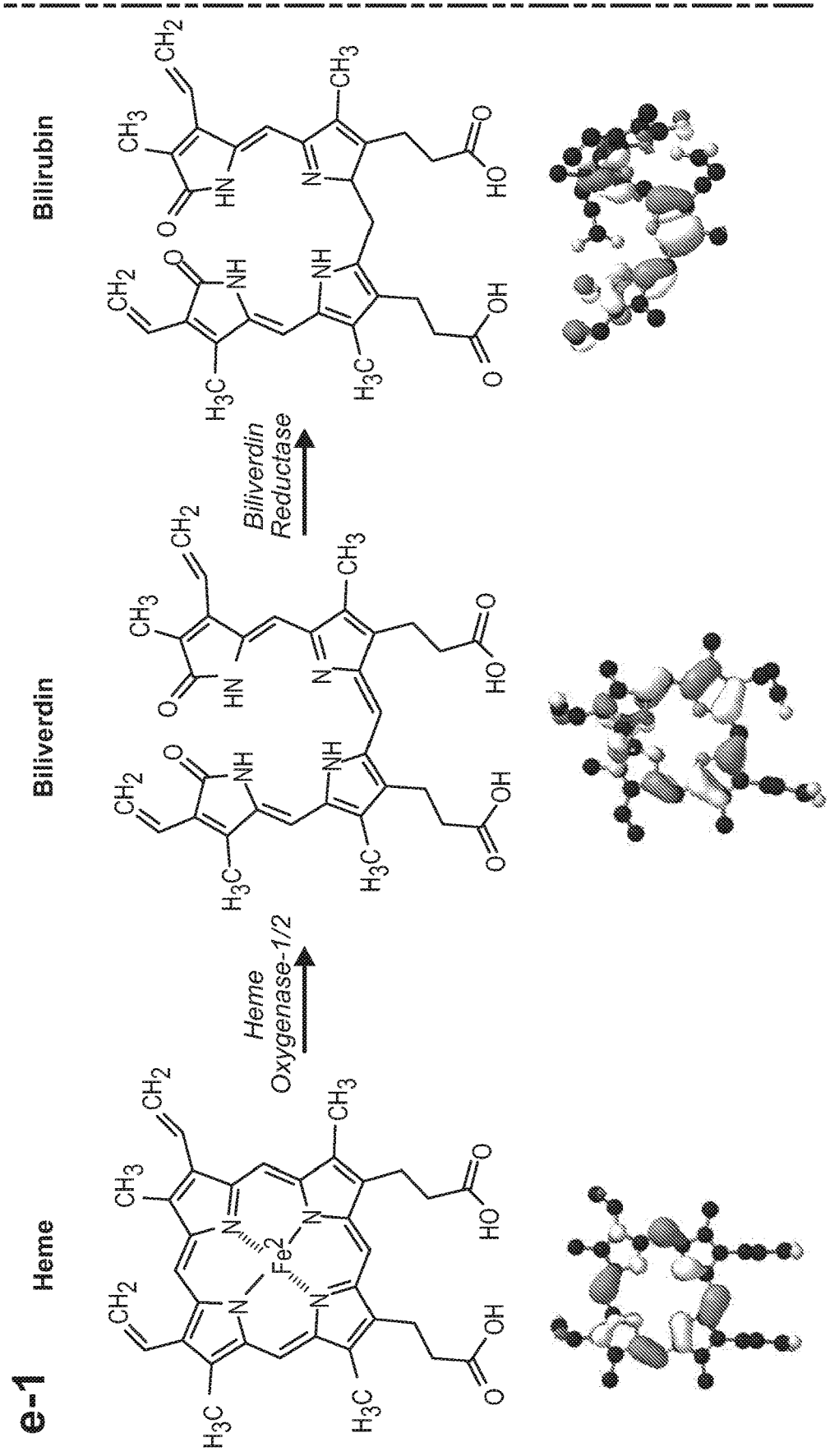
Figure 23:
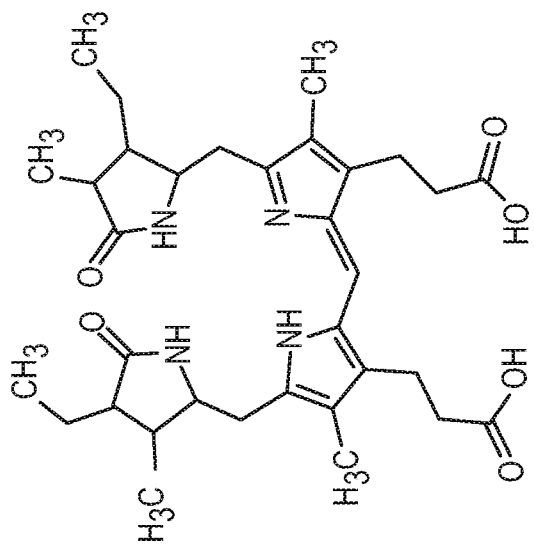
Figure 23:
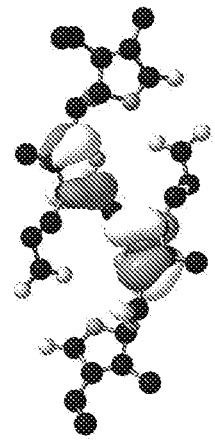
Figure 23:
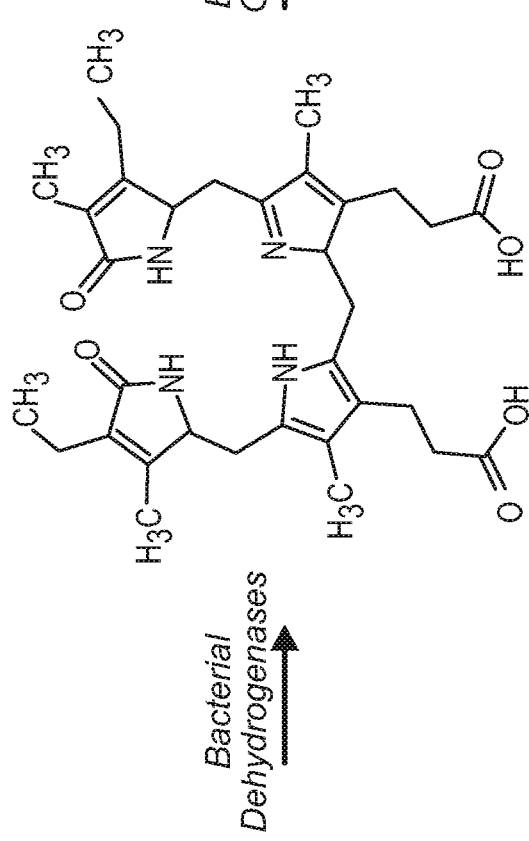
Figure 23:
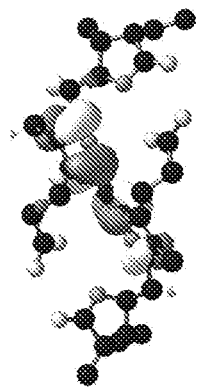

Despite the long-standing association between jaundice and pruritus[12], bilirubin itself has not been previously investigated as a pruritogen. To determine whether bilirubin directly elicits pruritus, bilirubin was injected intradermally into the nape of the neck of mice. Pathophysiologic concentrations of bilirubin stimulated scratching in a dose-dependent manner at the site of injection (FIG. 23A). Pre-incubating bilirubin with human serum albumin, which binds bilirubin with high affinity[13-15], elicited fewer scratches (FIG. 23A). The time course of bilirubin-induced scratching mirrored that of two well-characterized pruritogens, histamine and chloroquine (FIG. 23B).

Figures 27A, 27B, 27C:
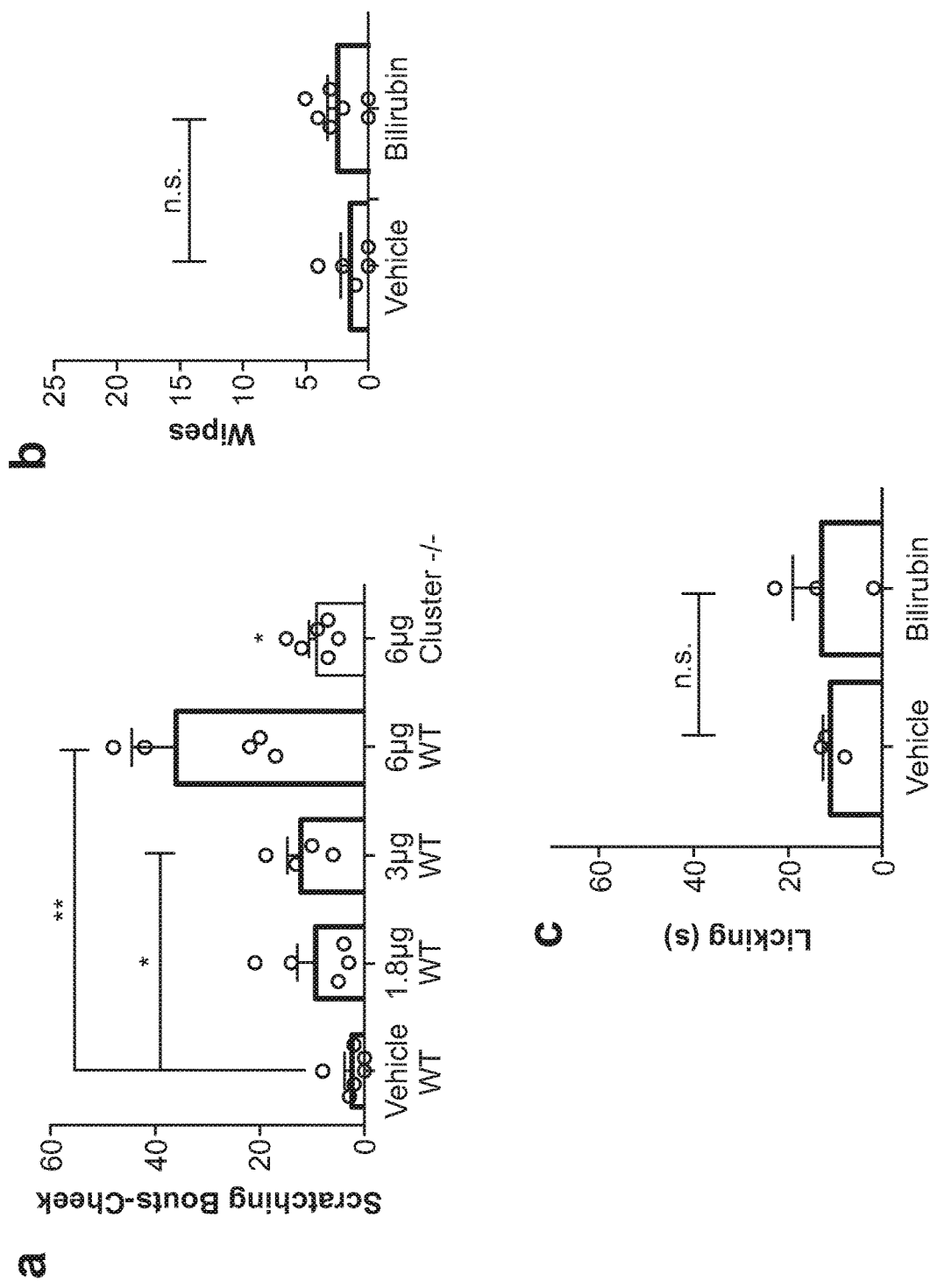
FIG. 27A-27F depict data showing that bilirubin elicited non-histaminergic pruritus, but not pain.

To confirm that bilirubin elicited itch and not pain, bilirubin was injected into the cheek of mice, an injection site that allows behavioral differentiation between itchy and painful stimuli[16]. Injecting bilirubin in the cheek, just as in the nape, prompted dose-dependent scratching (FIG. 27A). Bilirubin elicited neither wiping nor licking, indicating that it selectively stimulated itch and not pain (FIG. 27B-27C).

Mice were injected with similarly structured metabolites to determine the specificity of bilirubin's pruritic activity (FIG. 23D). The two metabolites directly epistatic to bilirubin, haemin and biliverdin, did not induce scratching despite also being tetrapyrroles (FIG. 23D). While haemin, biliverdin, and bilirubin displayed only minor atomic and electronic differences between them, they varied substantially in their physiochemical properties and structures (FIG. 23E).

To better understand these differences, density functional theory (DFT) calculations were performed[17-20] followed by single point energy calculations to ascertain the optimal geometry of each metabolite. Unlike in haem and biliverdin, bilirubin's four pyrroles are extended and not all in the same plane (FIG. 23E). DFT calculations revealed that urobilinogen and stercobilin, two bacterial metabolites downstream of bilirubin, adopted similar extended conformation. Both urobilinogen and stercobilin were able to stimulate scratching behavior (FIG. 23D), indicating that the extended conformation of bilirubin's pyrroles may be important for its pruritic activity.

Figures 27D, 27E, 27F:
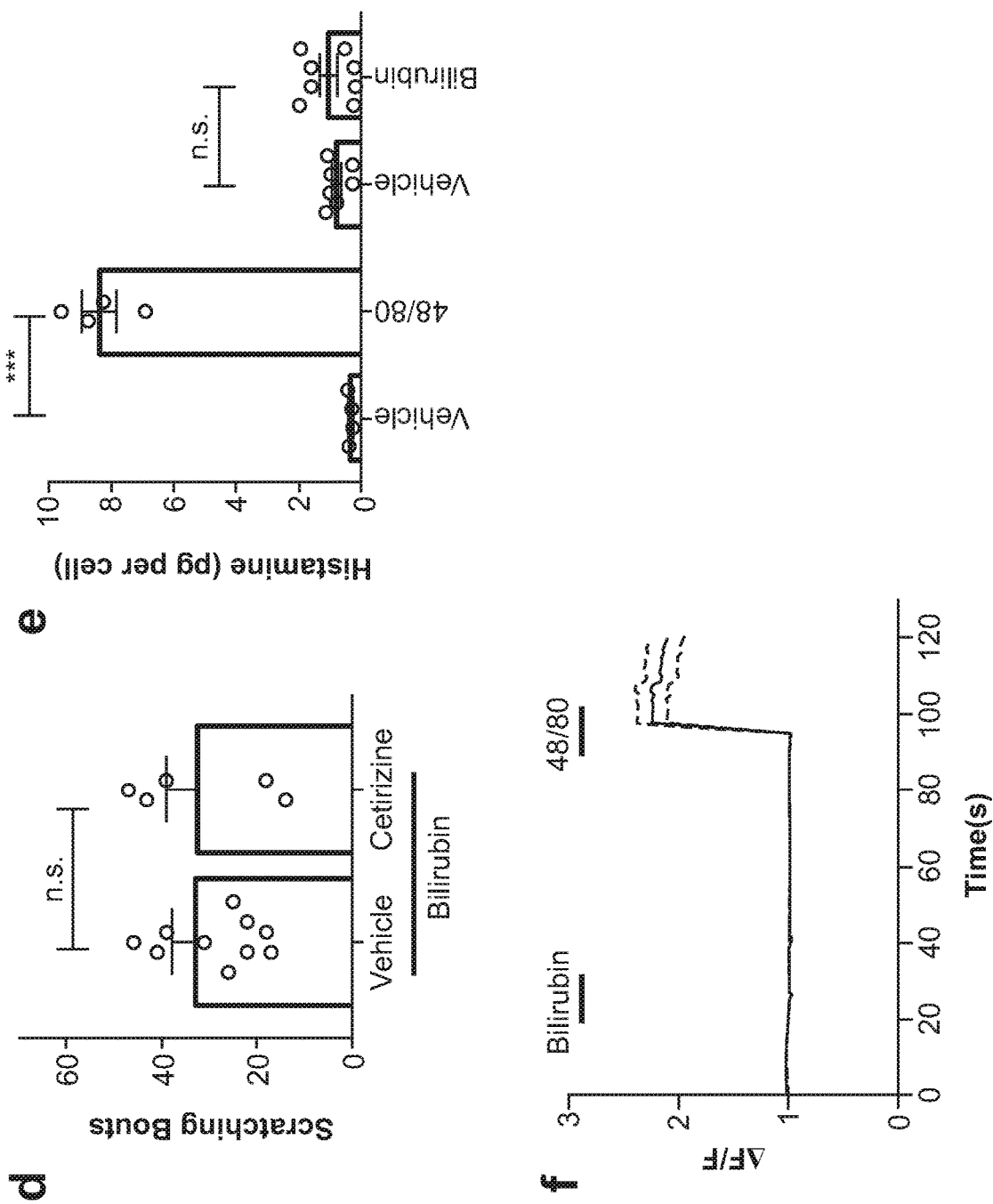

Patients with jaundice-associated pruritus receive little benefit from antihistamines[3]. Consistent with these clinical findings, the histamine receptor 1 blocker cetirizine (30 mg/kg, i.p.) failed to temper scratching behavior in mice injected with bilirubin (FIG. 27D). Furthermore, bilirubin did not elicit a calcium response or induce appreciable histamine release from peritoneal mast cells (FIG. 27E-27F).

Figure 28A:
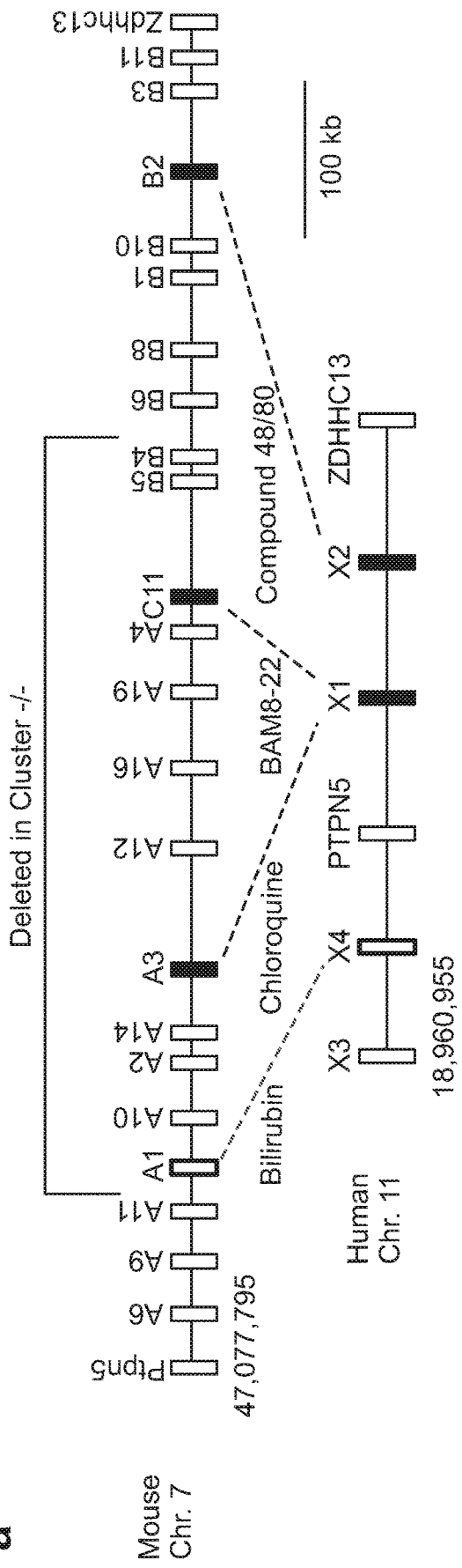
FIG. 28A-28F are data showing that bilirubin did not activate other MRGPRs.
Figures 28B, 28C, 28D, 28E, 28F:
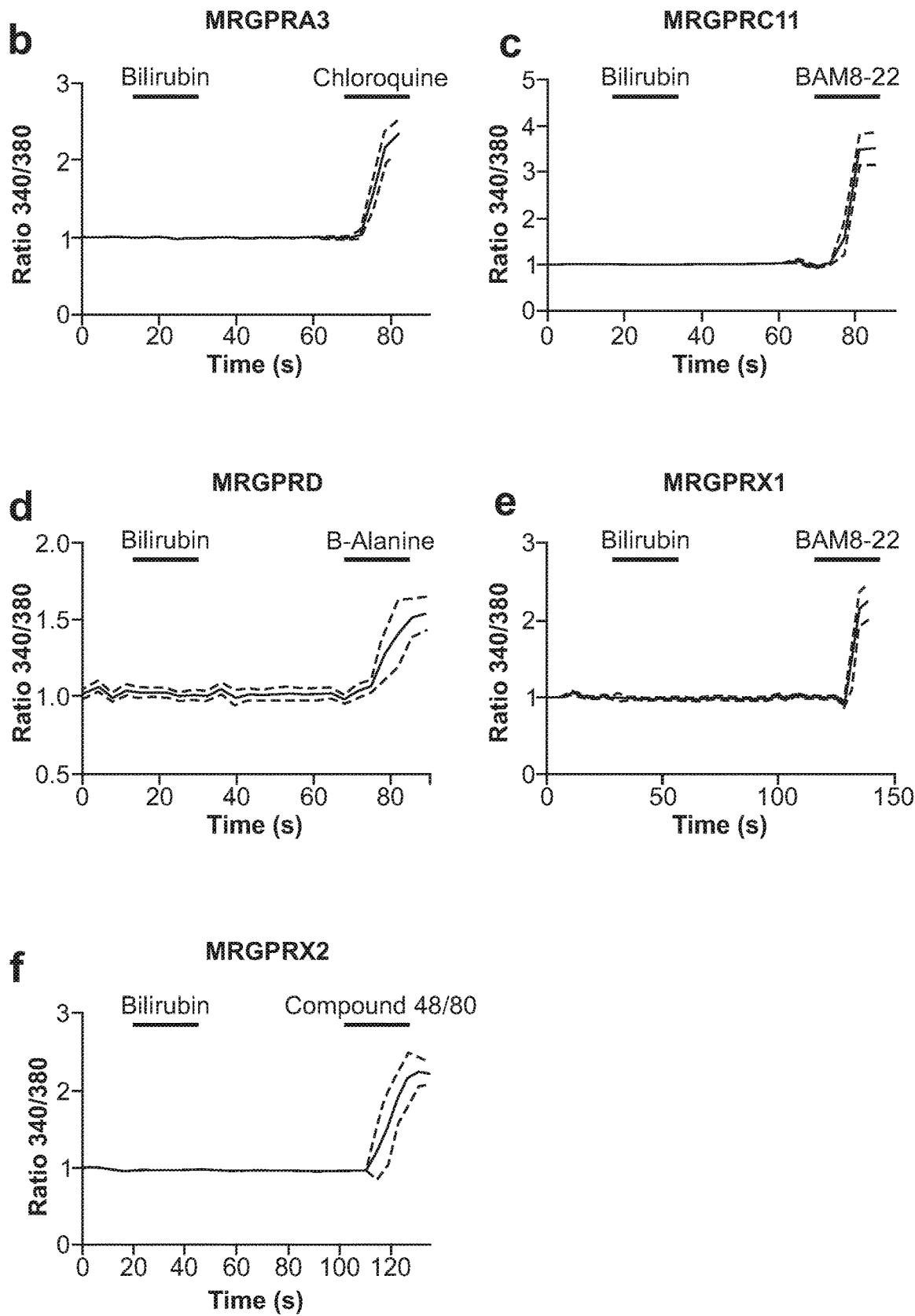

The Mas-related G-protein coupled receptor (Mrgpr) family of receptors is a major mediator of non-histaminergic pruritus[21-24]. To test whether Mrgprs mediate bilirubin-induced pruritus, mice lacking a cluster of 12 Mrgpr genes (Cluster−/−) were injected with bilirubin[21] (FIG. 28A). Cluster−/− animals scratched approximately 75% less than wild type (WT) mice, indicating that one or more of the 12 Mrgprs within the cluster mediates bilirubin-induced pruritus (FIG. 23A).

Example 14: Bilirubin Activated Murine MRGPRA1 and Human MRGPRX4

To identify the Mrgpr responsible, each of the 12 Mrgprs deleted in the Cluster−/− mouse in human embryonic kidney (HEK) 293 cells were individually expressed, and changes were monitored in intracellular calcium upon application of bilirubin. To ensure a calcium response was observed upon a positive ligand-receptor interaction, HEK293 cells stably expressing the murine G-protein alpha-subunit $G_{\alpha 15}$, a $G_\alpha$ protein that couples GPCRs to calcium signaling via phospholipase C (PLC) was used.

Figures 24A, 24B, 24C, 24D, 24E:
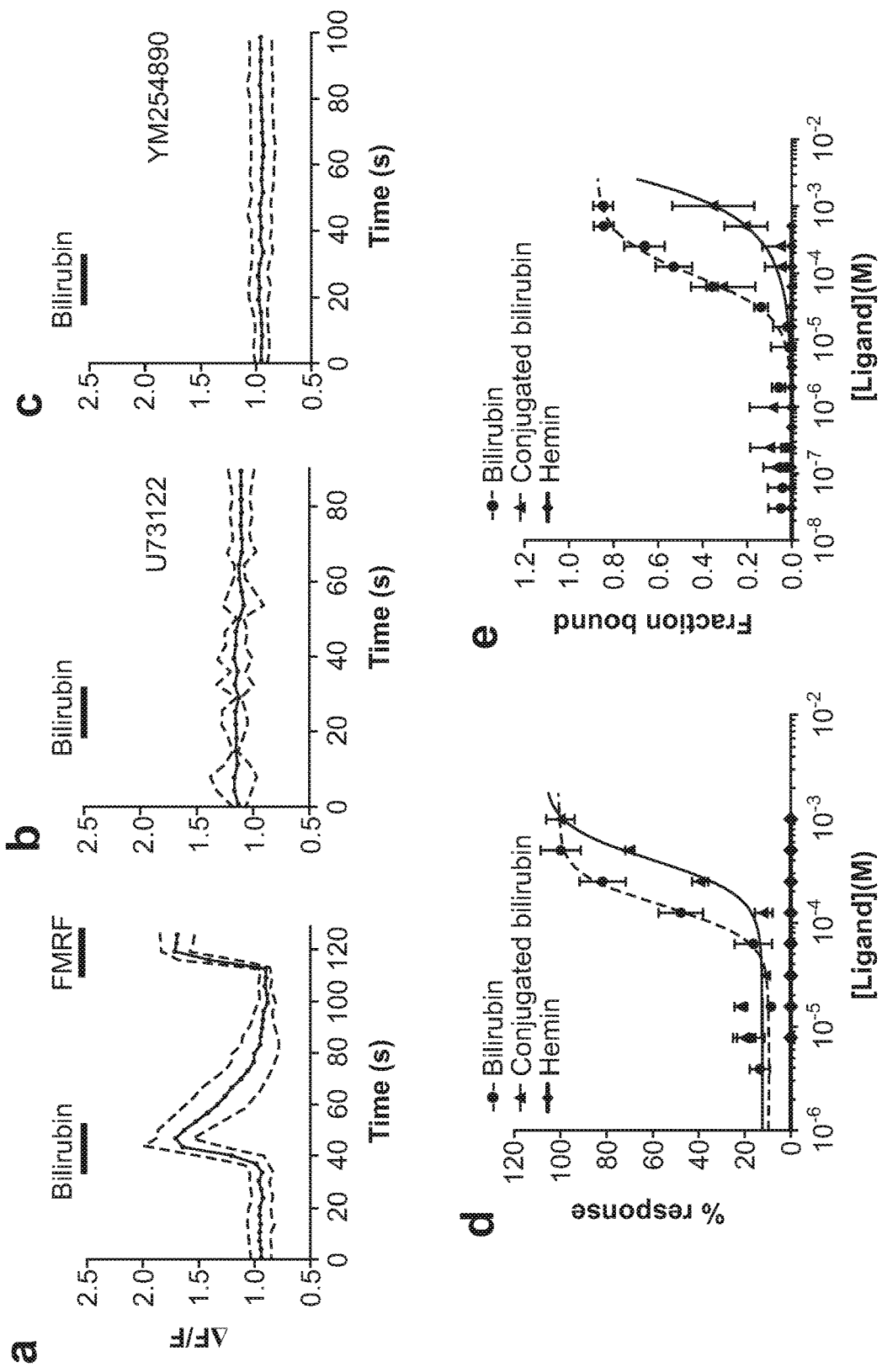

Among the twelve mouse receptors, only MRGPRA1-expressing HEK cells exhibited a calcium response upon application of bilirubin ($EC_{50}$ of 145.9 μM[96, 220]) (FIGS. 24A and 24C). The same cells that were responsive to bilirubin also responded to FMRF, an MRGPRA1 agonist[4]. To ensure that bilirubin initiated cell signaling at MRGPRA1, MRGPRA1-expressing cells were pre-treated with inhibitors of GPCR signaling: the PLC inhibitor U73122 or the $G_{\alpha q}$ inhibitor YM-254890. Both compounds abolished bilirubin-induced calcium responses (FIG. 24B-24C).

In addition to bilirubin itself, glucuronidated bilirubin is often upregulated in jaundice-associated itch. It was assessed whether a similar bilirubin derivative could activate MRGPRA1. Indeed, ditaurate bilirubin (conjugated bilirubin) activated MRGPRA1-expressing cells (FIG. 24D). In agreement with the initial behavioral findings, haemin failed to activate MRGPRA1 (FIG. 24D). No other Mrgpr among the 12 that were screened responded to bilirubin (FIG. 24M, FIG. 28B-28F).

Figures 24F, 24G, 24H, 24I, 24J:
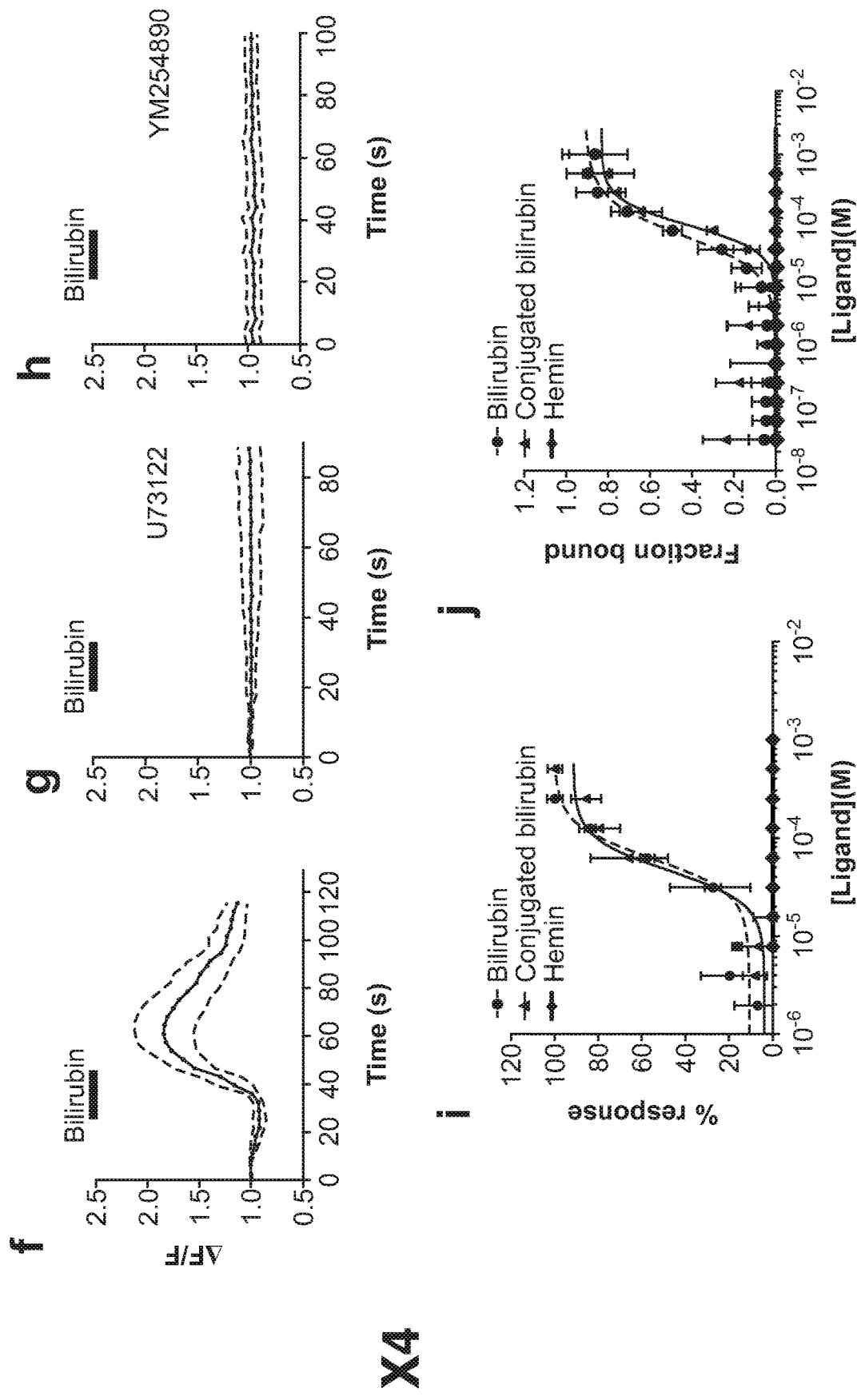

The mouse Mrgpra family is closest in sequence homology to the human MRGPRX family (FIG. 28A-28F)[4,25,26]. Of the four human MRGPRX receptors, only MRGPRX4-expressing cells responded to bilirubin ($EC_{50}$ of 61.9 μM[44, 87]) (FIGS. 24F and 24I). U73122 and YM-254890 inhibited bilirubin-induced calcium responses in MRGPRX4-expressing cells just as with MRGPRA1 (FIG. 24G-24H). Conjugated bilirubin also activated MRGPRX4, whereas haemin had no effect (FIG. 24I).

Figures 24K, 24L:
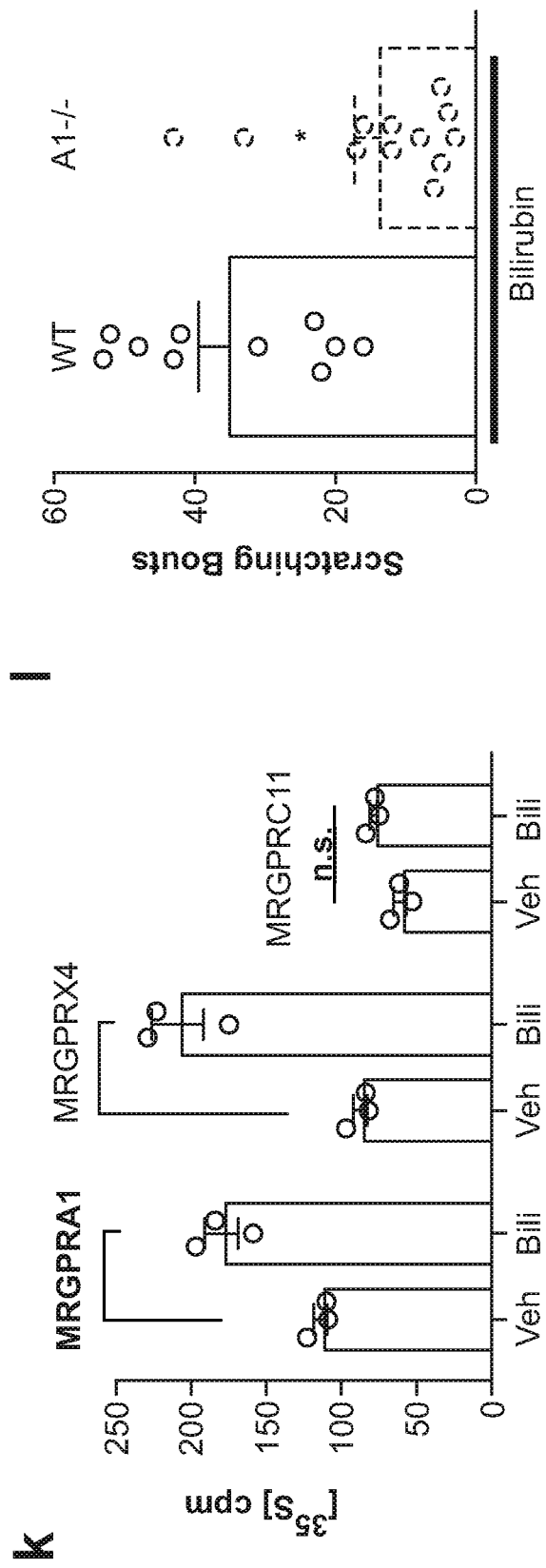
FIG. 24K depicts a bar graph of Bilirubin-stimulated G-protein activity of partially-purified MRGPRA1, MRGPRX4, and MRGPRC11 membrane complexes. [$^{35}$S]GTPγS binding was measured in the presence of 0.5% DMSO or 50 µM bilirubin. Mean±s.e.m. depicted. **, P<0.01; two-tailed unpaired Student's t-test.
FIG. 24L is a bar graph depicting scratching bouts from injection of 60 µg (100 µL of 1 mM) of bilirubin in WT and A1−/− animals. Mean plus s.e.m. depicted. Open circles represent individual mice. WT n=10, A1−/− n=12*, P<0.05 by two-tailed unpaired Student's t-test.
Figures 24M, 24N:
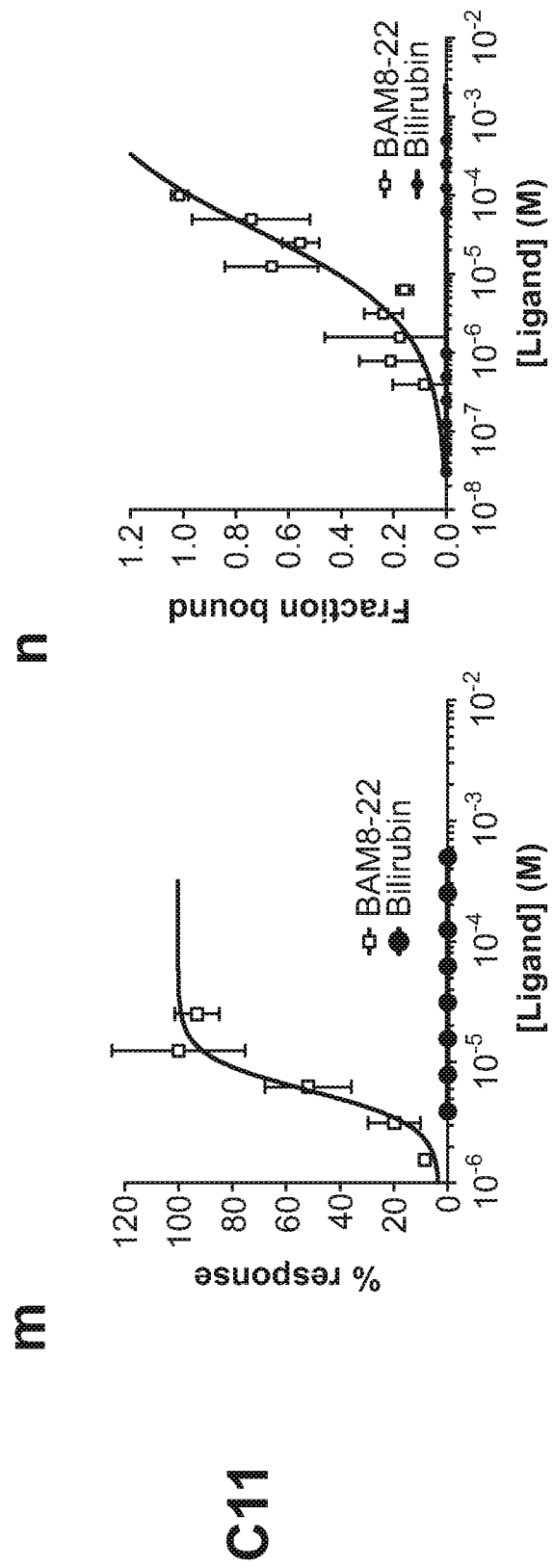

To confirm that bilirubin directly binds the identified receptors, thermophoresis of receptors were assayed in the presence and absence of bilirubin. Thermophoresis of a molecule is affected by physical parameters such as size, charge, and solvation, and can therefore be used to assess interactions between molecules[27]. Using this approach, it was determined that bilirubin bound MRGPRA1 with a $K_D$ of 92.9±15 μM and MRGPRX4 with a $K_D$ of 54.4±13 μM (FIGS. 24E and 24J). Bilirubin exhibited little to no affinity for the BAMS-22 receptor MRGPRC11 (FIG. 24N). Haemin, which did not activate MRGPRA1 or MRGPRX4 by calcium imaging (FIGS. 24D and 24I), also did not bind MRGPRA1 or MRGPRX4 (FIGS. 24E and 24J). Conjugated bilirubin bound both MRGPRA1 and MRGPRX4, although with lower affinities compared to bilirubin (FIGS. 24E and 24J). To make certain that bilirubin activates MRGPRA1 and MRGPRX4 upon binding, the exchange of guanosine diphosphate (GDP) for guanosine triphosphate (GTP) was measured, one of the first events in GPCR signaling. Bilirubin increased GTP binding to MRGPRA1- and MRGPRX4 membrane complexes, but not to MRGPRC11 (FIG. 24K). To confirm that bilirubin activated MRGPRA1 in vivo to elicit itch, an Mrgpra1 (A1−/−) knockout mice line was generated using CRISPR-Cas9[28] (FIG. 29A-29C). A1−/− animals scratched significantly less than WT mice upon bilirubin injection (FIG. 24L).

Example 15: Bilirubin Activated Sensory Neurons in an MRGPR-Dependent Manner

Figure 25A:
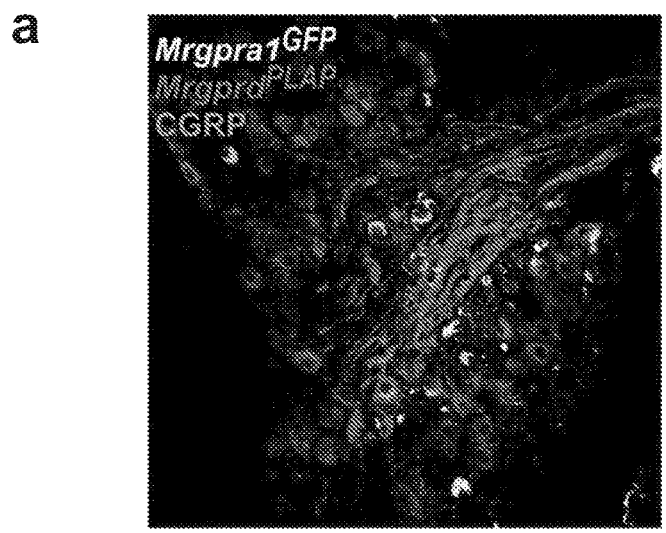
FIG. 25A-25I depict data indicating that bilirubin activated sensory neurons in an MRGPR-dependent manner.

Previous studies have demonstrated that both MRGPRA1 and MRGPRX4 are expressed in a subset of sensory neurons within the dorsal root ganglia (DRG)[4,25,29]. Six-week-old adult mice express MRGPRA1 in a small percentage of sensory neurons. (FIG. 25A). Application of 50 μM bilirubin elicited robust action potentials in small-diameter (<30 μm) WT DRG sensory neurons (5 of 50). However, bilirubin failed to induce action potentials in A1−/− neurons (0 of 60)

Figure 25B:
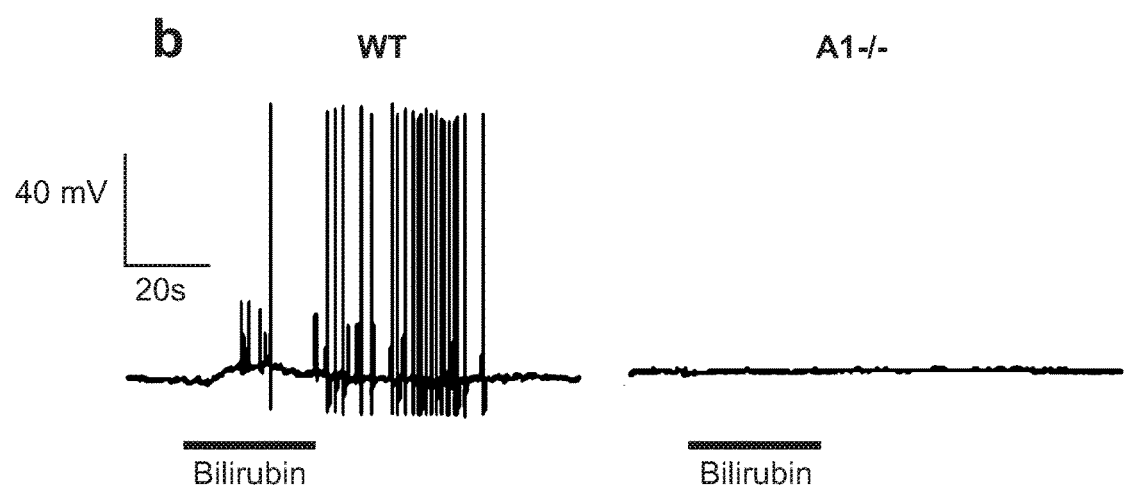
Figure 25C:
Figures 25D, 25E, 25F:
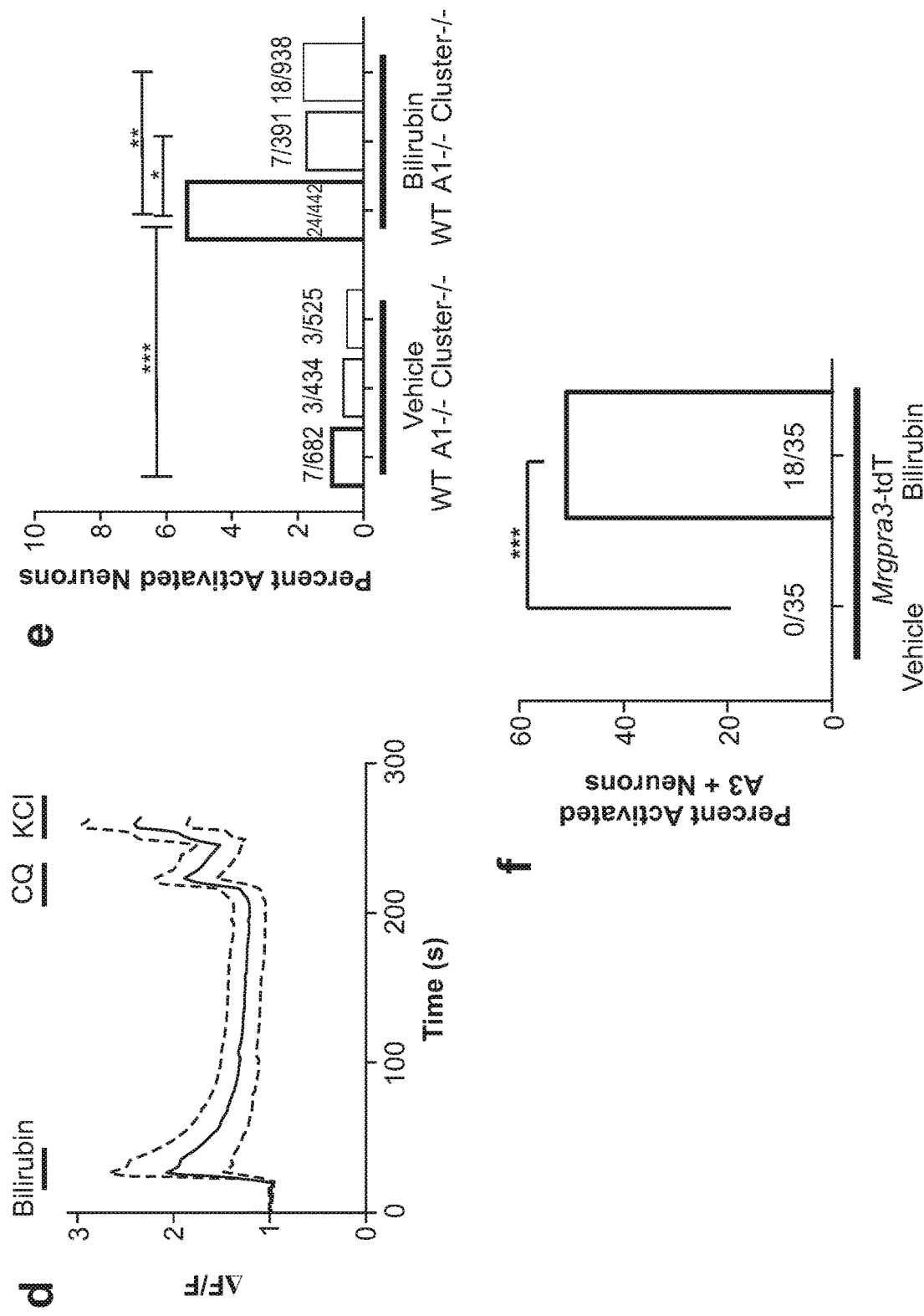
Figure 30A:
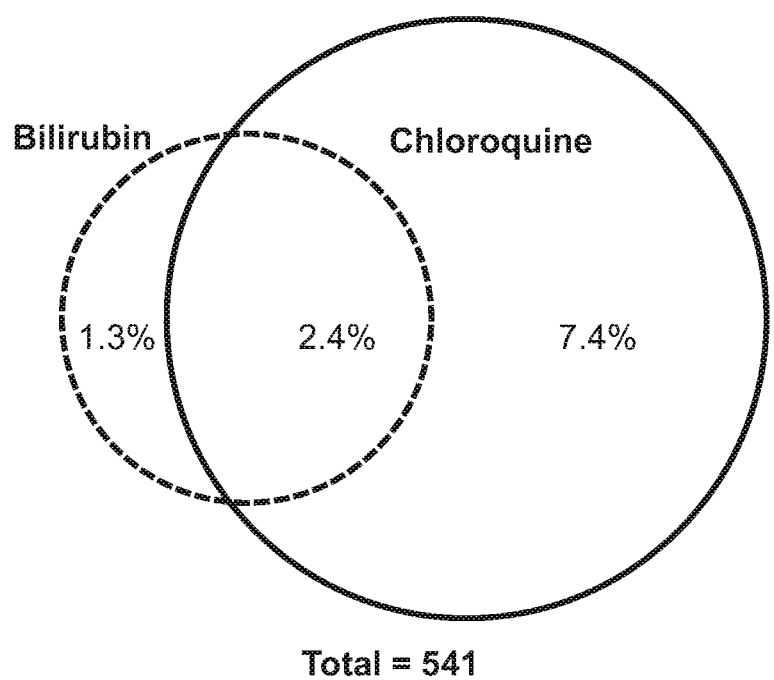
FIGS. 30A and 30B depict images showing that bilirubin activated a similar population of diameter sensory as chloroquine.
Figure 30B:
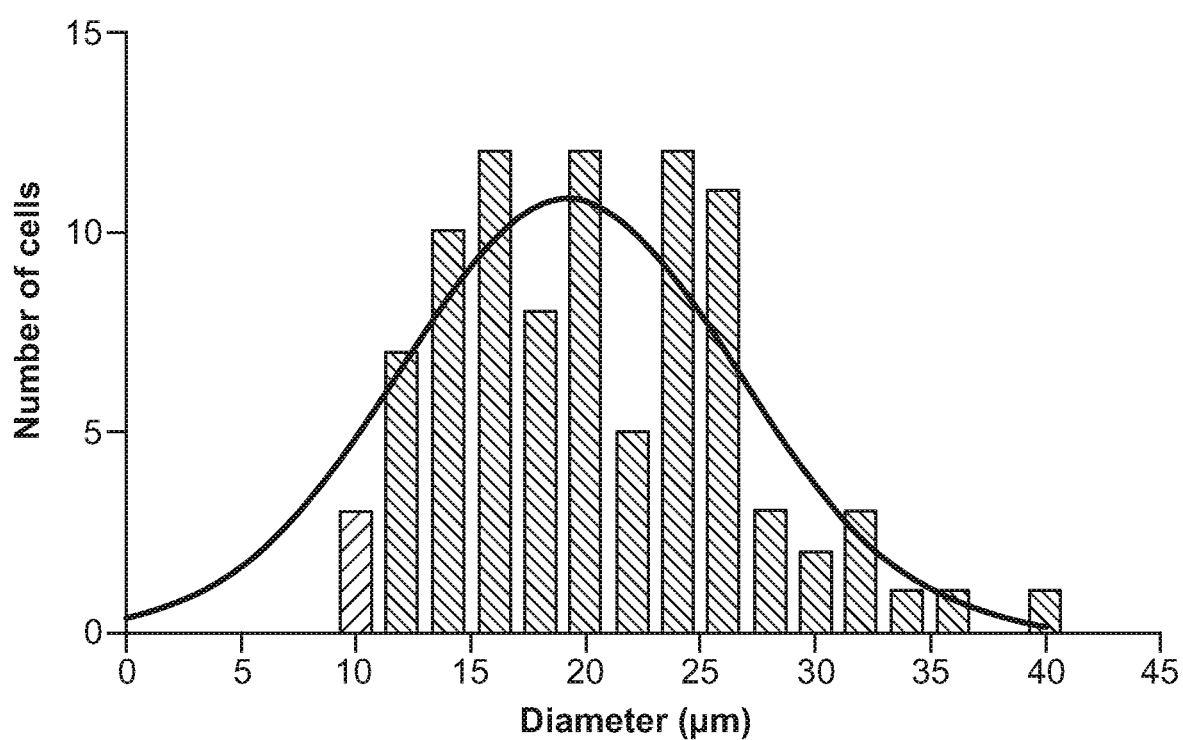

(FIG. 25B). MRGPRA1 expression in sensory neurons overlaps with MRGPRA3 expression, which typifies itch sensory neurons (Dong et al., 2001; Han et al., 2012). As determined by both electrophysiology and $Ca^{2+}$ imaging, bilirubin-responsive neurons partially overlapped with neurons that also responded to 1 mM chloroquine, a ligand for MRGPRA3 (Qin Liu, Dong, Cell 2009) (FIG. 25C, FIG. 30A). Bilirubin-sensitive neurons had an average somal diameter of 20.4±1.3 μm, a diameter characteristic of itch sensory neurons (FIG. 30B). Approximately 5% of WT DRG neurons responded to application of 50 μM bilirubin, whereas significantly fewer sensory neurons from either Cluster−/− or A1−/− DRG responded (FIG. 25D-25E).

To confirm that bilirubin activates putative MRGPRA3-positive itch neurons, calcium imaging was performed on DRG neurons isolated from Tg(Mrgpra3-Cre); lsl-tdTomato mice, which express the fluorescent protein tdTomato in MRGPRA3-positive neurons. Fifty μM bilirubin activated a substantial percentage of tdTomato-positive neurons (FIG. 25F).

Figures 25G, 25H, 25I:
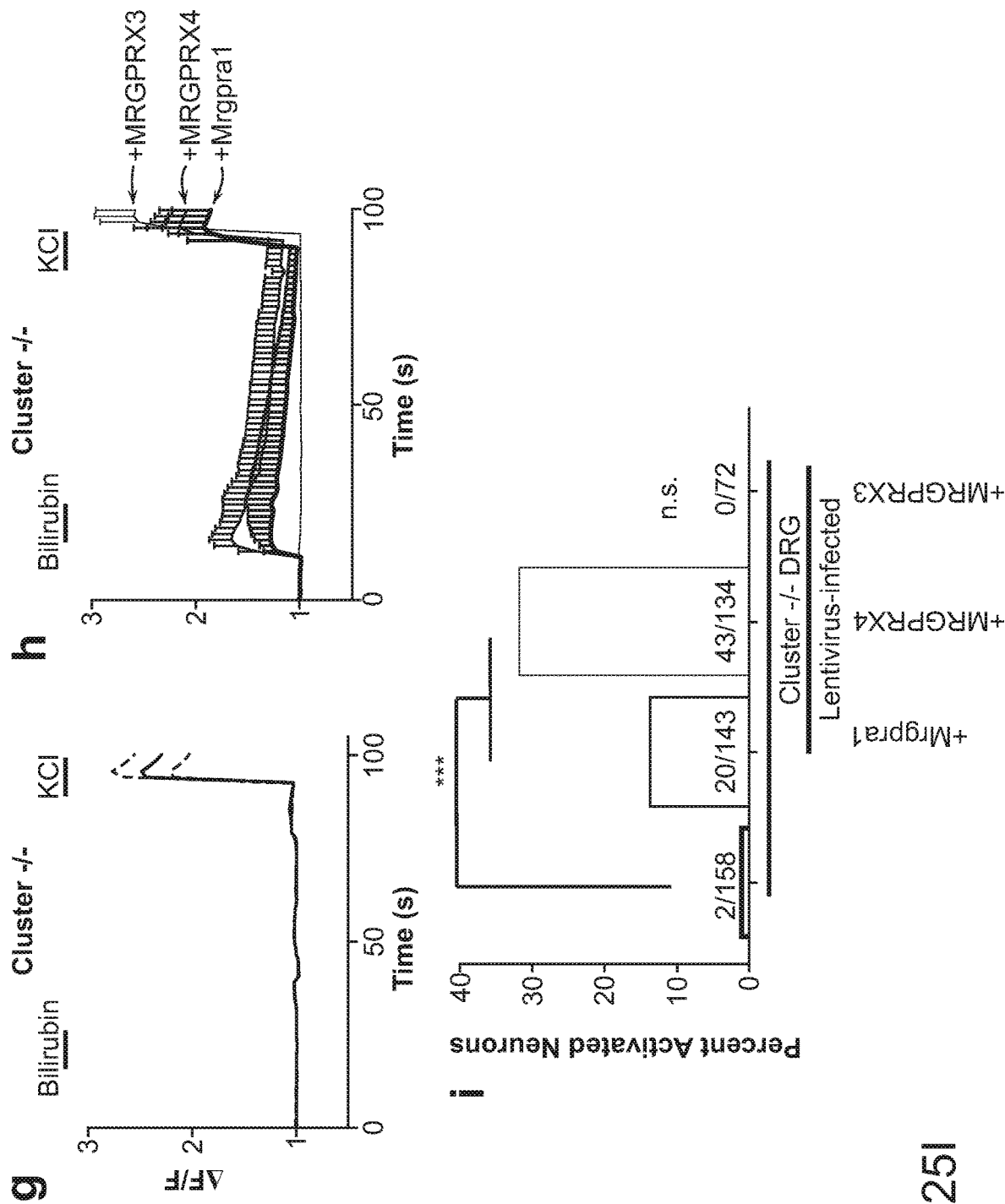

It was next determined whether expression of either MRGPRA1 or MRGPRX4 was sufficient to render neurons sensitive to bilirubin. To address this question, Cluster−/− DRGs were infected with lentivirus carrying either Mrgpra1, MRGPRX4, or MRGPRX3. Bilirubin activated 14% of Mrgpra1- and 32% of MRGPRX4-transduced Cluster−/− DRGs (FIG. 25G-25I). Cluster−/− DRGs infected with the control gene MRGPRX3 failed to respond to bilirubin.

It was next addressed whether chronic elevation of bilirubin in vivo could stimulate Mrgpr-dependent pruritus. To address this question, α-napthyl isothiocyanate (ANIT) was administered to mice to induce intrahepatic cholestasis, or the slowing or stoppage of bile flow[30]. Bile is the primary means by which bilirubin is excreted, and patients with cholestasis exhibit elevated levels of bilirubin and other pruritogenic substances in their blood. WT, Cluster−/−, and A1−/− animals were treated with 25 mg/kg ANIT for five days before assessing spontaneous itch. WT, Cluster−/−, and A1−/− animals exhibited equivalent severity of cholestatic injury, as determined by liver histology and relative increases in plasma bilirubin, bile acids, alkaline phosphatase (ALP), aspartate aminotransferase (AST), alanine aminotransferase (ALT), and gamma-glutamyl transferase (GGT) (FIG. 31A-31D).

Figures 31A, 31B, 31C, 31D:
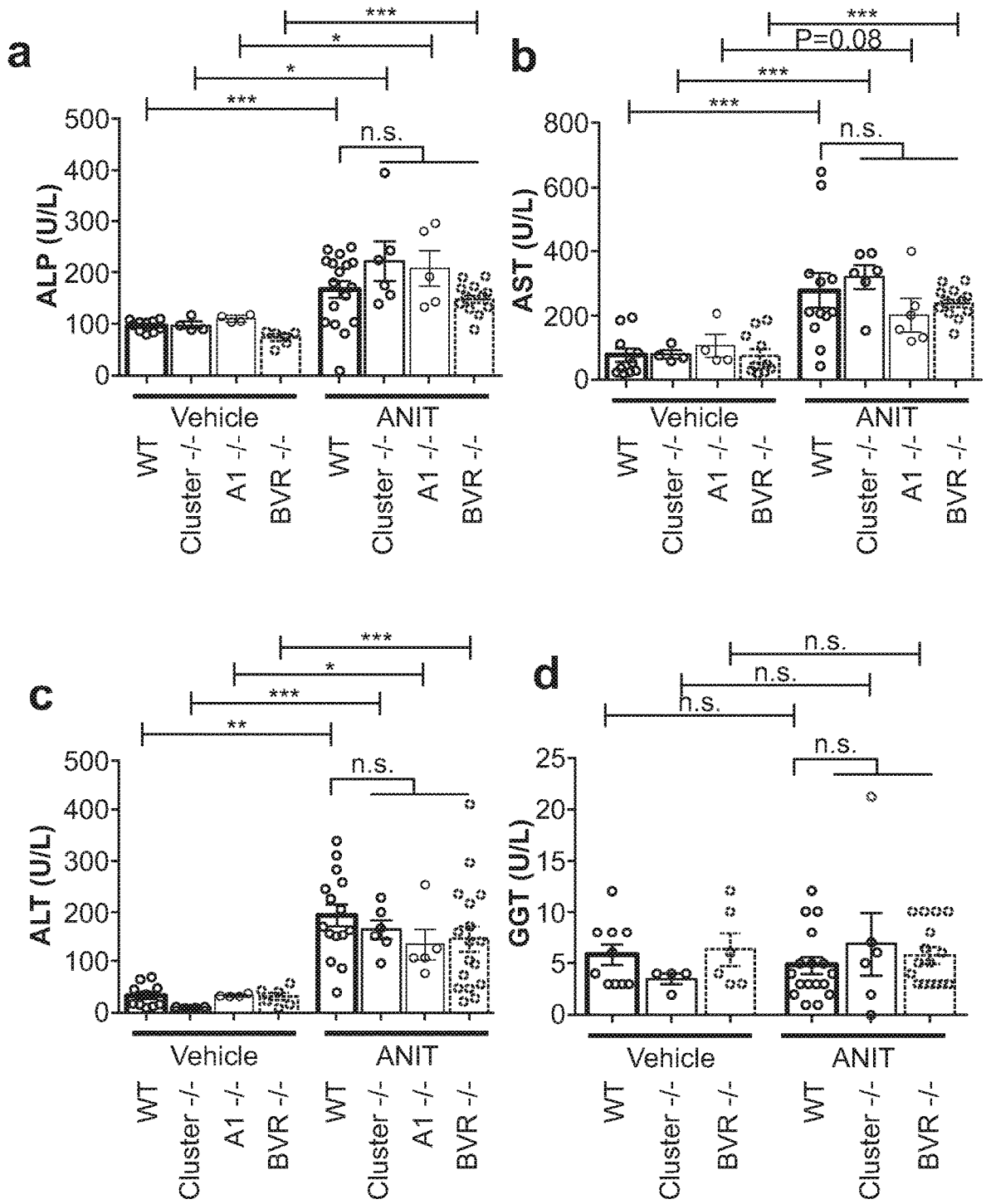
FIG. 31A-31K are graphs depicting that the plasma levels of pathological markers of liver injury are no different among WT, Cluster−/−, A1−/−, and BVR−/− animals.
Figures 31E, 31F, 31G:
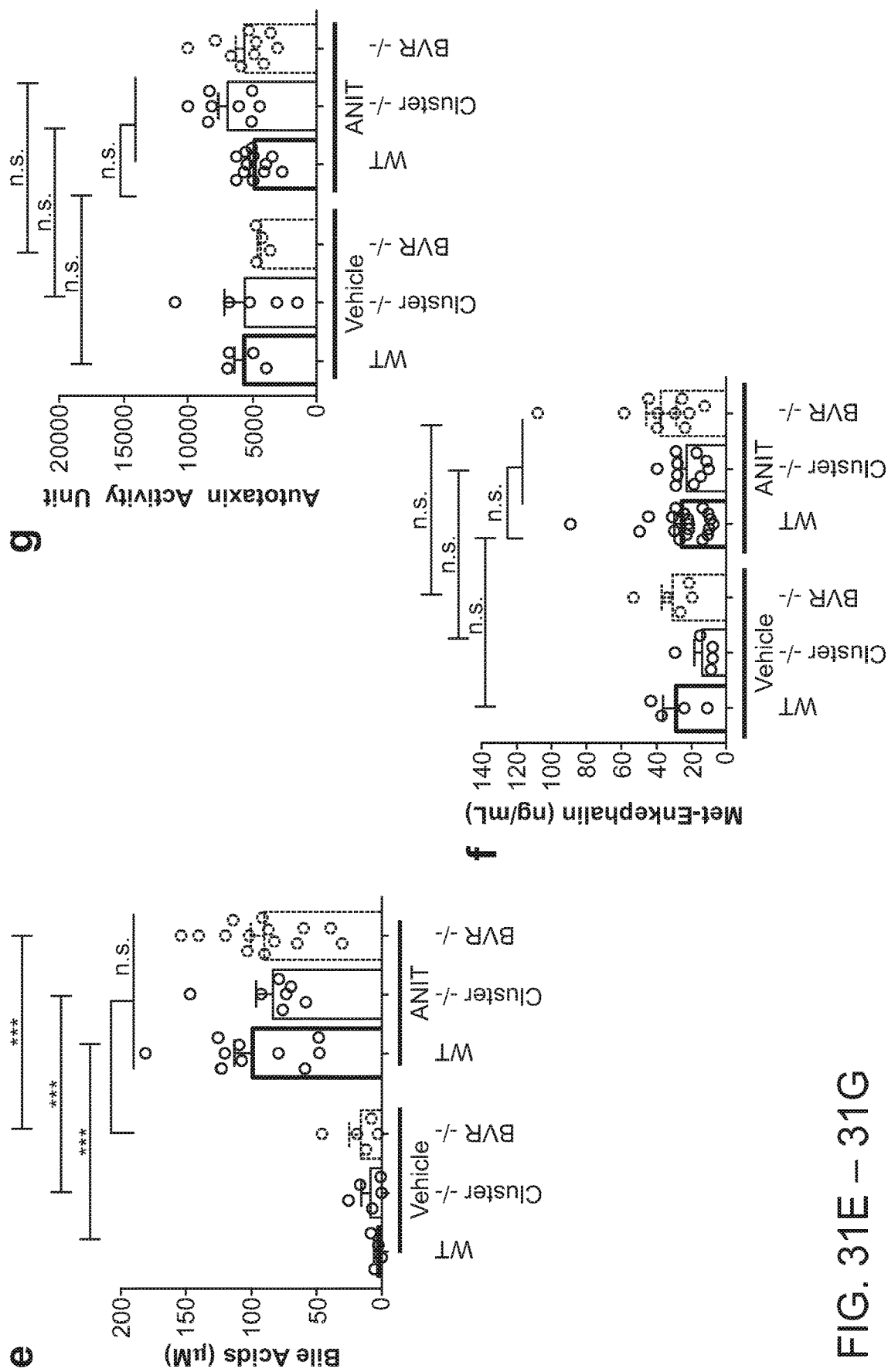

Example 16: Mrgpra1−/−, Cluster−/−, and BVR−/− Animals Exhibited Decreased Cholestatic Pruritus Compared to vehicle treatment, ANIT treatment resulted in significantly increased pruritus in all animals (FIG. A). However, Cluster−/− and A1−/− mice scratched markedly less than WT mice (FIG. 26A), suggesting that MRGPRA1 mediated a component of cholestatic pruritus. In humans, bile acids, endogenous opioids, and LPA are often increased in cholestatic sera and have been shown to mediate pruritus[31-34]. The serum of ANIT-treated animals exhibited elevated bile acids (FIG. 31E), whereas neither the endogenous opioid peptide met-enkephalin[35,36] nor the LPA-producing enzyme autotaxin were elevated (FIG. 31F-31G).

To confirm that Cluster−/− and A1−/− mice scratched less with ANIT because bilirubin, and not some other cholestatic pruritogen, is no longer able to stimulate MRGPRA1-dependent itch, WT and Cluster−/− were injected with bile acids, opiates, and LPA. None of the other cholestatic pruritogens are Mrgpr-dependent, as they all elicited equivalent degrees of itch in WT and Cluster−/− animals (FIG. 31H-31K). Therefore, Cluster−/− and A1−/− mice scratched less with ANIT because MRGPRA1 specifically mediates jaundiced pruritus.

Figures 26A, 26B, 26C:
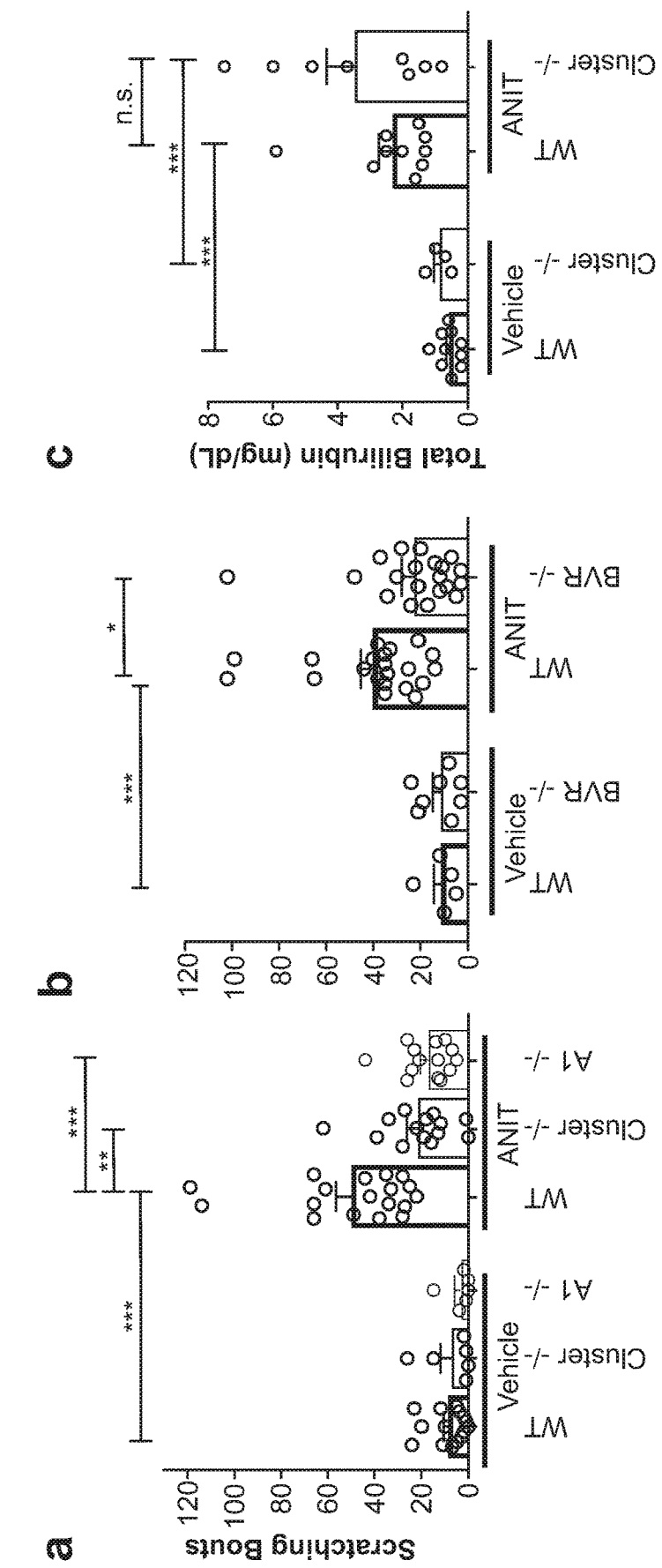
FIG. 26A-26I are images depicting that Mrgpra1−/−, Cluster−/−, and BVR−/− animals all exhibited decreased cholestatic pruritus.
Figure 32A:
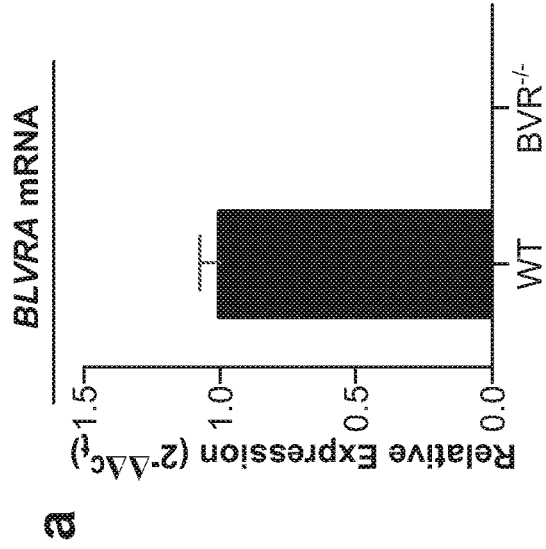
FIG. 32A-32F are data showing that BVR−/− and A1−/− animals have intact itch circuits.
Figure 32B:
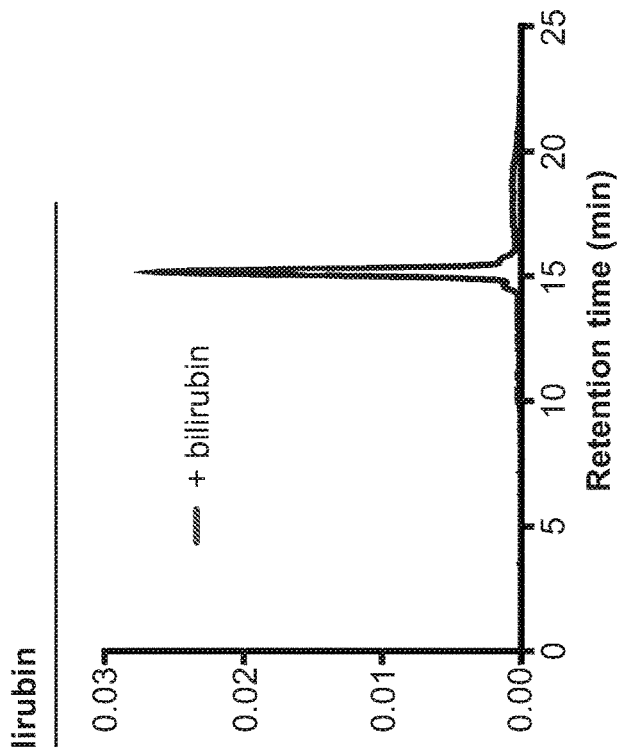
Figure 32C:
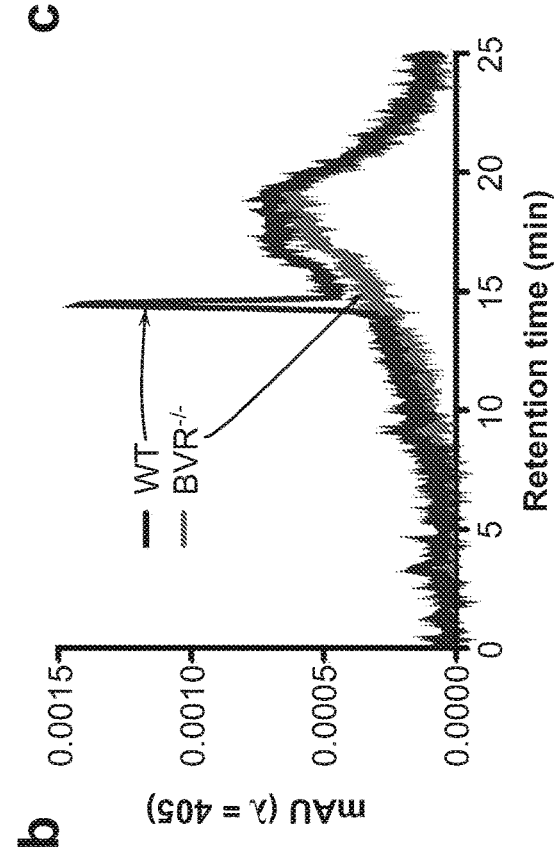
Figure 32D:
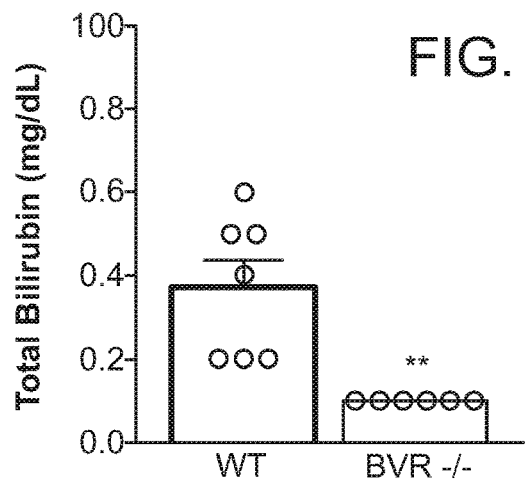
Figure 32E:
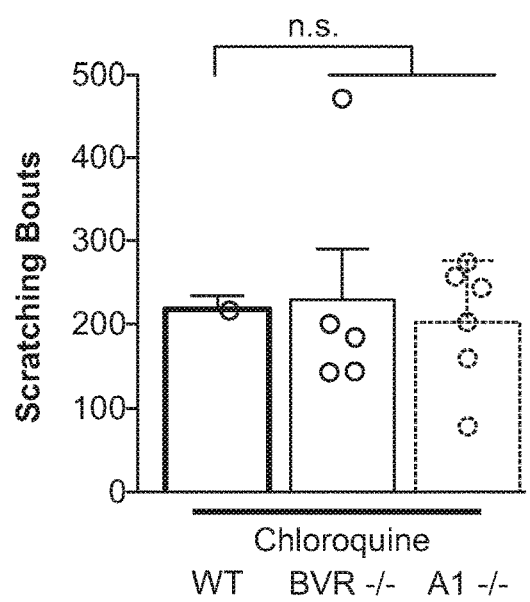
Figure 32F:
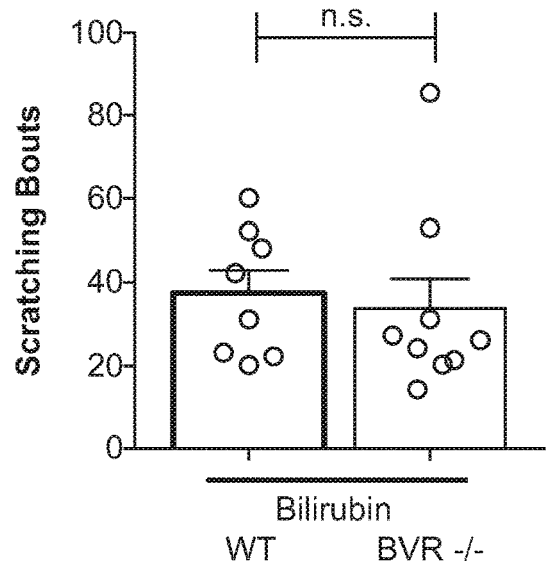

To further demonstrate that bilirubin interacted with MRGPRA1 to stimulate itch in cholestasis, a mouse was generated that lacked the biosynthetic enzyme for bilirubin, biliverdin reductase (BVR−/−)[37] (FIG. 23E, FIG. 32A). Mice lacking BVR did not have detectable levels of bilirubin in plasma (FIG. 32B-32D). When treated with ANIT, BVR−/− mice scratched significantly less than WT mice (FIG. 26B). Plasma levels of bile acids, ALP, AST, ALT, and GGT were indistinguishable between treated BVR−/− animals and WT controls (FIG. 31A-31D). The diminished response to ANIT is not due to aberrant itch circuits, as BVR−/− mice scratched normally when injected with either chloroquine or exogenous bilirubin (FIG. 32E-32F).

Figure 33A:
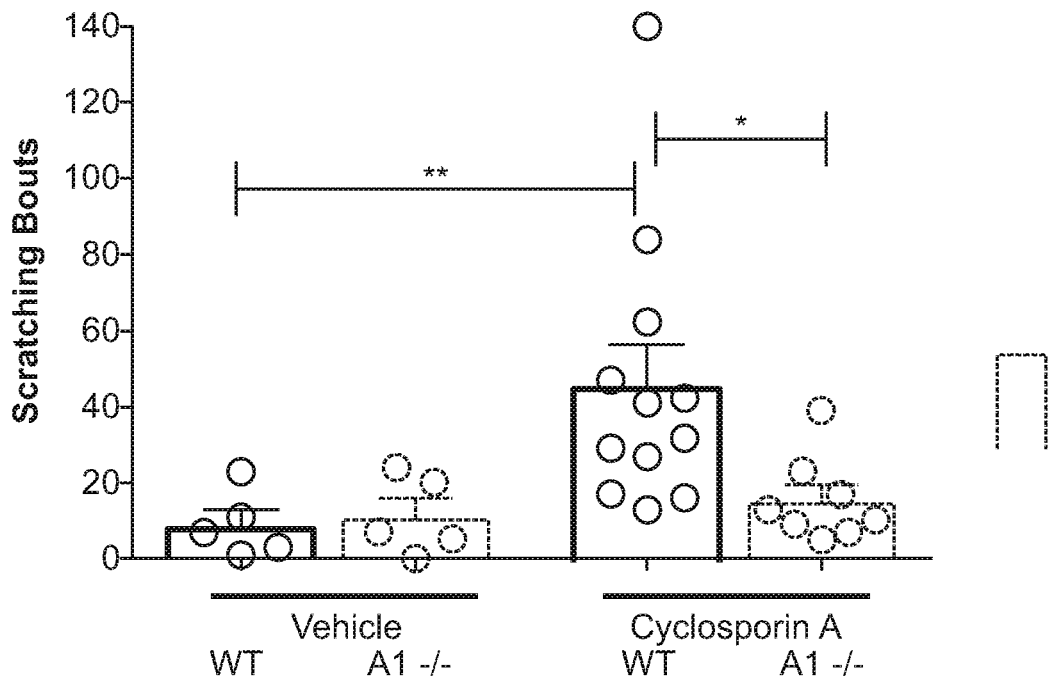
FIGS. 33A and 33B depict graphs showing that A1−/− and BVR−/− animals have decreased itch associated with Cyclosporin A treatment.
Figure 33B:
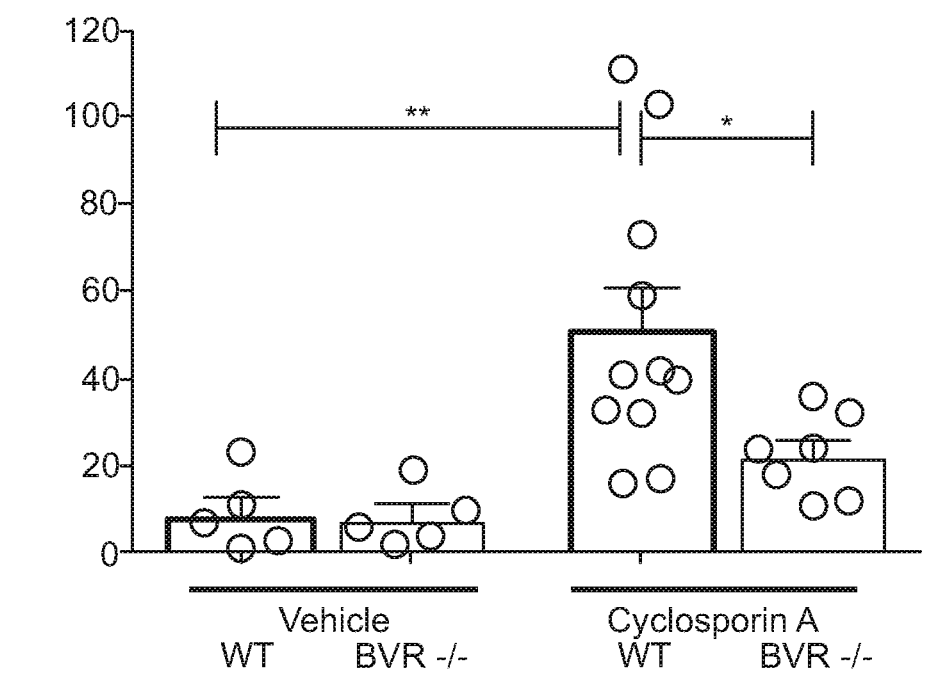

To confirm that the observed differences in cholestatic pruritus were not just specific to ANIT, the hepatotoxin cyclosporin A were administered to WT, A1−/−, and BVR−/− mice[38]. Mice were treated with either 50 mg/kg cyclosporin A or vehicle for eight days before assessing spontaneous itch (FIGS. 33A and 33B). Cyclosporin A induced spontaneous itch in WT animals, whereas A1−/− and BVR−/− mice again scratched significantly less than WT mice (FIGS. 33A and 33B).

Figure 34A:
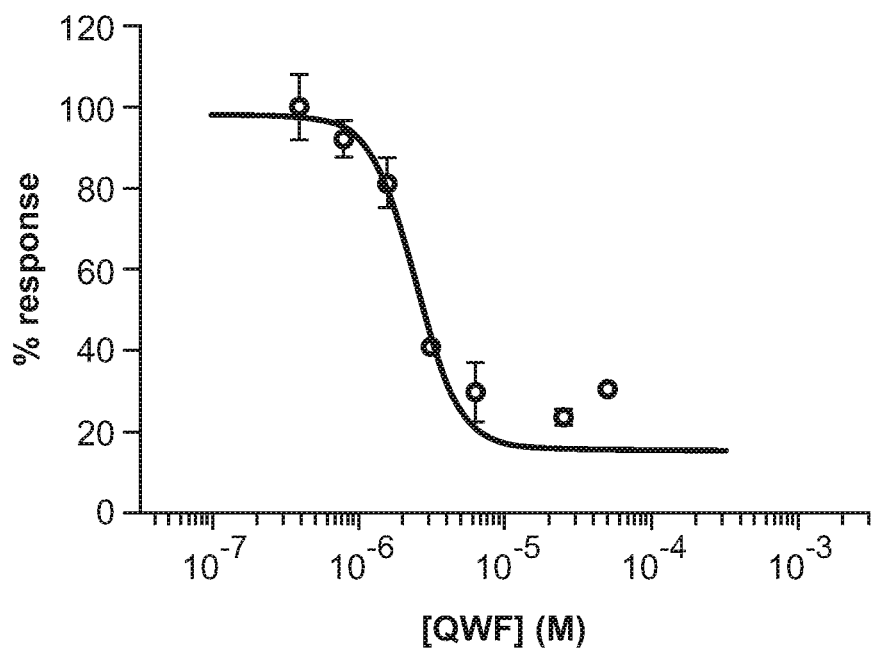
FIG. 34A-34G depict graphs showing that QWF treatment does not affect severity of cholestatic liver injury.
Figure 34B:
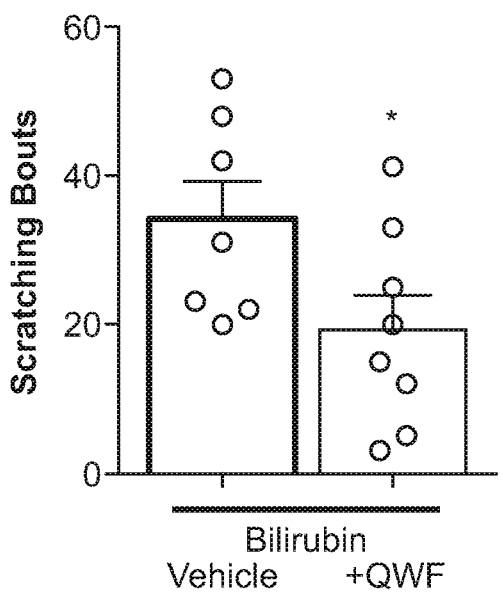
Figure 34C:
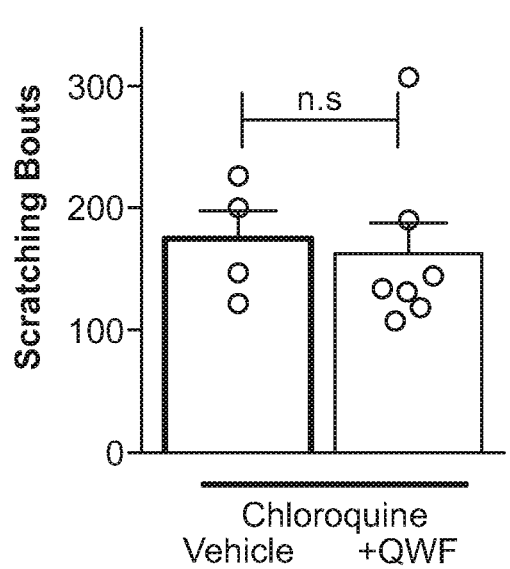
Figure 34D:
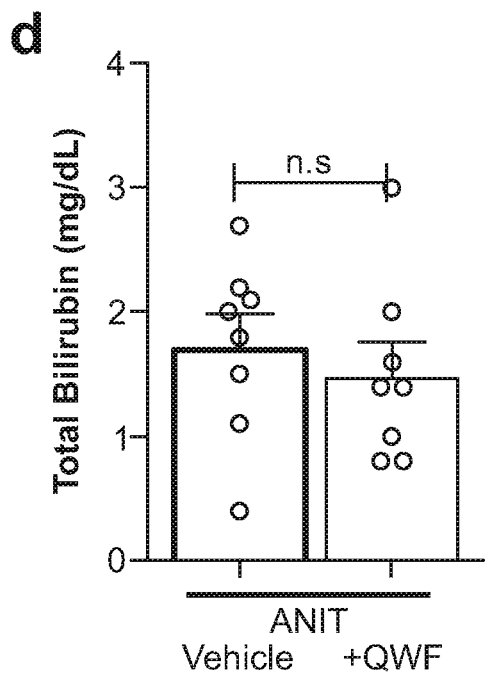
Figure 34E:
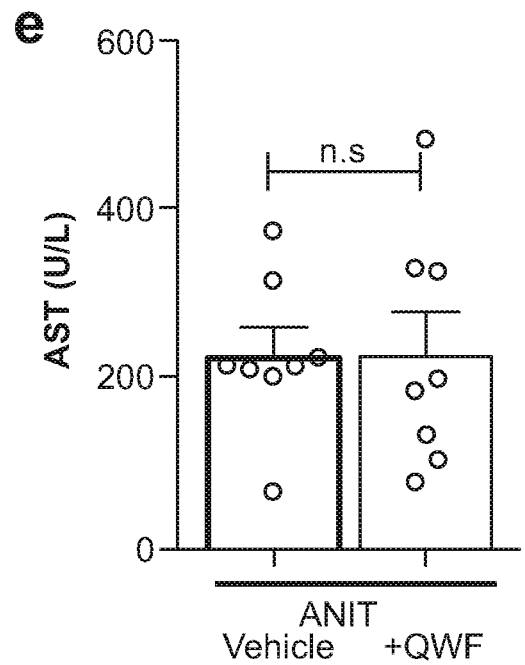
Figure 34F:
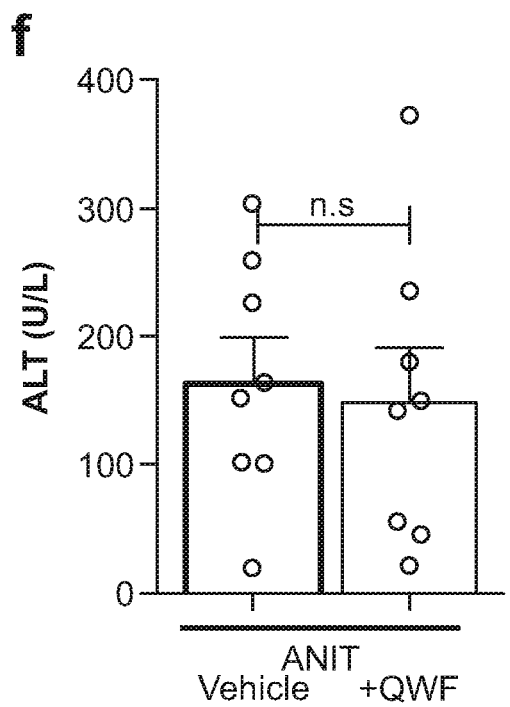
Figure 34G:
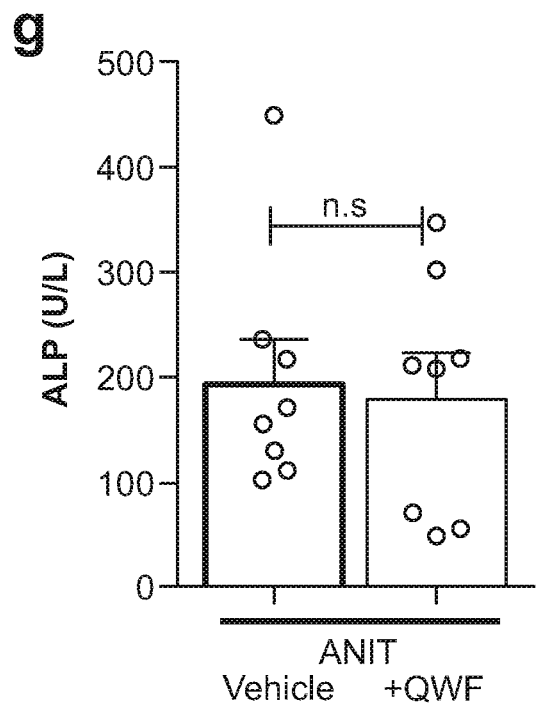

It was assessed whether pharmacological antagonism of MRGPRs could alleviate cholestatic itch. Recently, a 3-amino acid peptide, QWF, was identified as an MRGPRA1 antagonist[39]. QWF abolished bilirubin-associated calcium signaling in MRGPRA1-expressing cells with an $IC_{50}$ of 2.9 $\mu M^{[1,5]}$ (FIG. 34A). Mirroring its pharmacology in vitro, 0.25 mg/kg QWF was co-injected with bilirubin significantly alleviated pruritus associated with bilirubin (FIG. 34B). Antagonism by QWF was specific to bilirubin, as it did not attenuate chloroquine-MRGPRA3 associated itch (FIG. 34C).

Figures 26D, 26E, 26F:
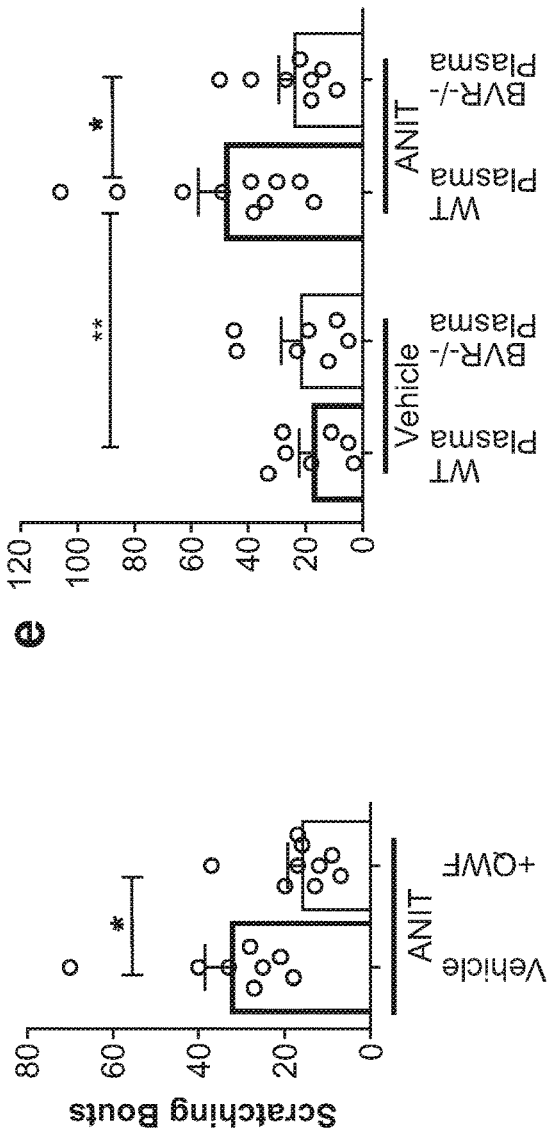

It was evaluated whether the MRGPRA1 antagonist QWF could alleviate cholestatic pruritus in vivo. WT animals were dosed with ANIT as previously described, but intraperitoneally injected mice with either vehicle or 1 mg/kg QWF thirty minutes prior to behavioral analysis. Mice treated with QWF scratched significantly less than vehicle-treated animals (FIG. 26D). QWF treatment did not change plasma levels of total bilirubin, AST, ALT, or ALP, suggesting that QWF treatment did not alter the underlying liver pathology (FIG. 34D-34G).

Nasobiliary drainage is the most effective treatment for cholestatic pruritus[40]. Based on this observation, it was predicted that plasma isolated from cholestatic animals would elicit pruritus. Indeed, plasma from WT animals with cholestasis elicited itch when injected into naïve WT animals (FIG. 26E). Cholestatic plasma isolated from BVR−/− mice, which lacks bilirubin (FIG. 32B-32D), elicited significantly fewer scratches than WT cholestatic plasma (FIG. 26E). The levels of ALP, AST, and ALT were indistinguishable between WT and BVR−/− cholestatic plasma (FIG. 31A-31D), suggesting equivalent liver damage from the original WT and BVR−/− mice. Instead, BVR−/− plasma likely results in less pruritus because it lacks bilirubin.

Figures 26G, 26H, 26I:
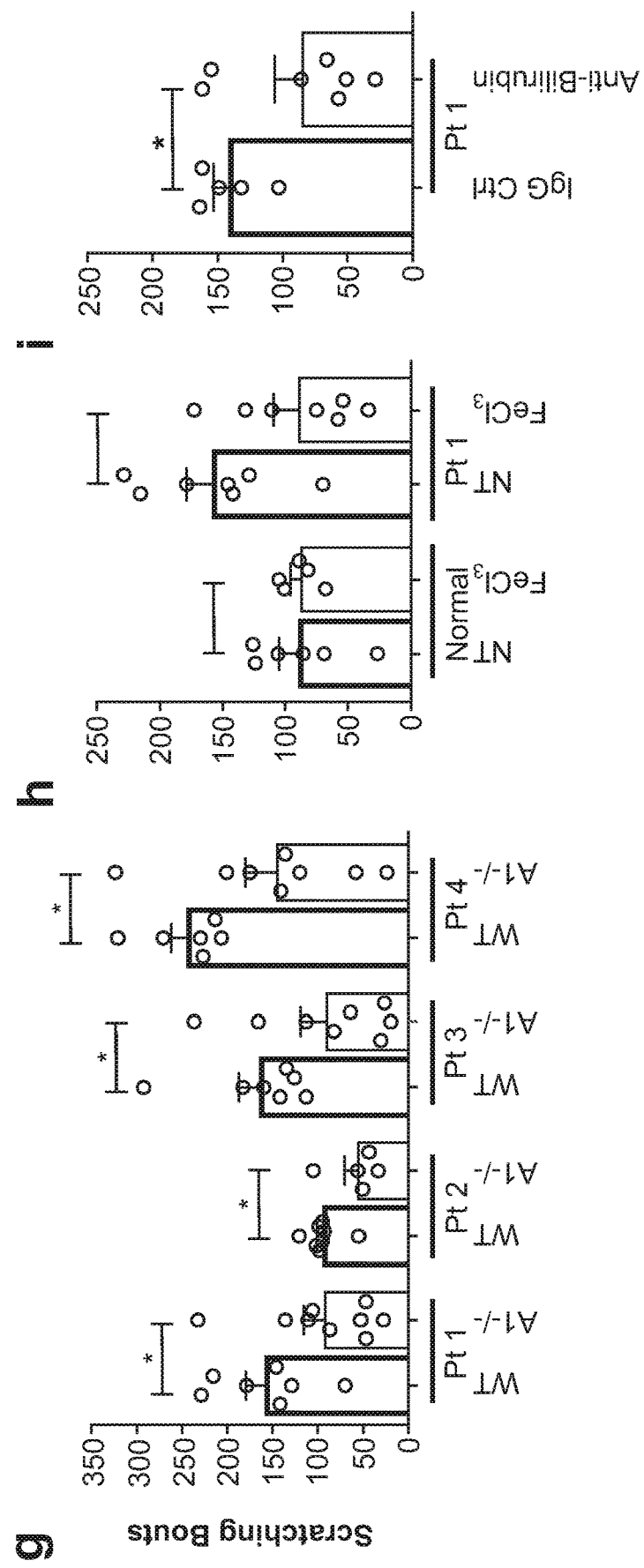
Figure 35A:
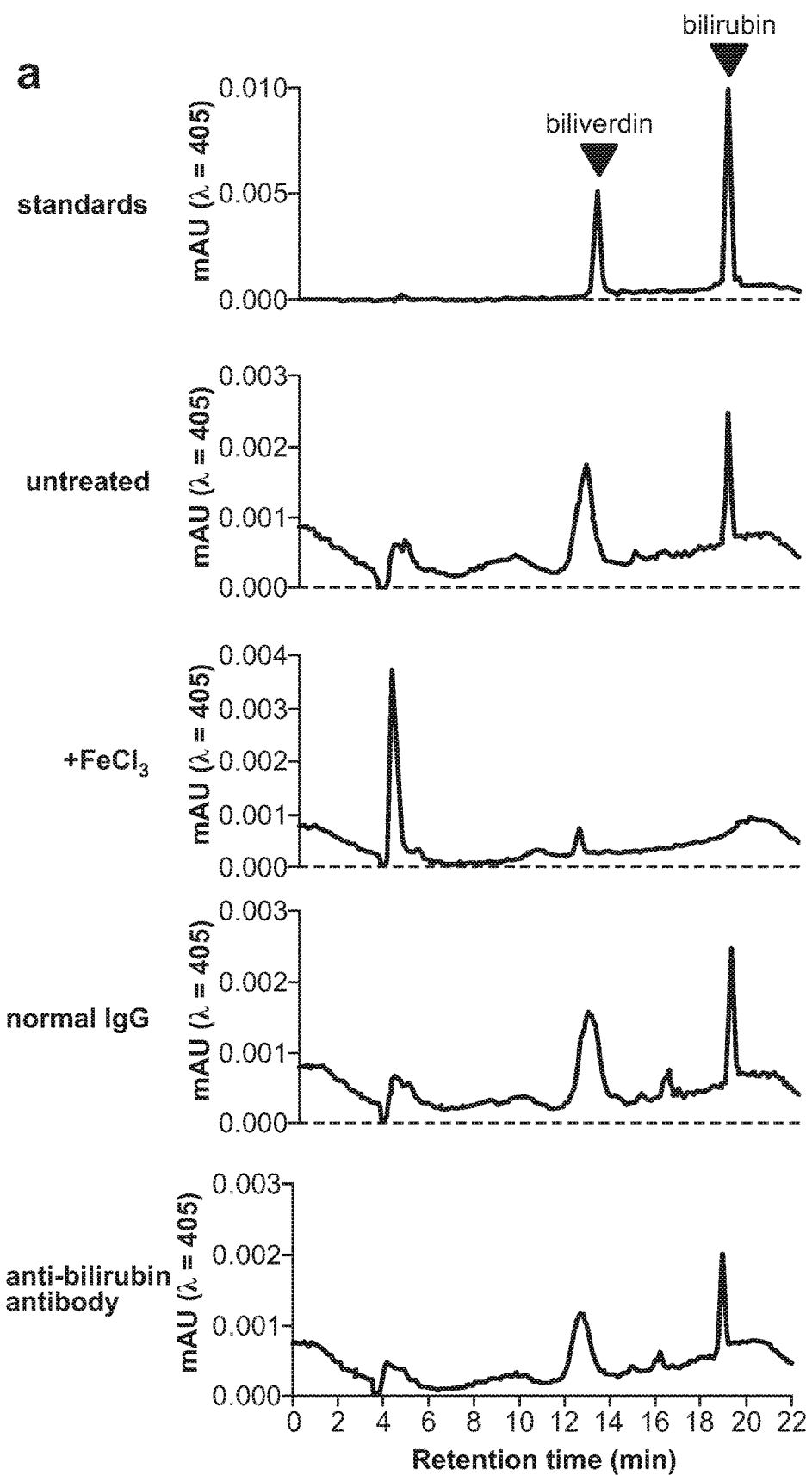
FIGS. 35A and 35B depict data showing $FeCl_3$ and anti-bilirubin antibody depletion of plasma bilirubin.
Figure 35B:
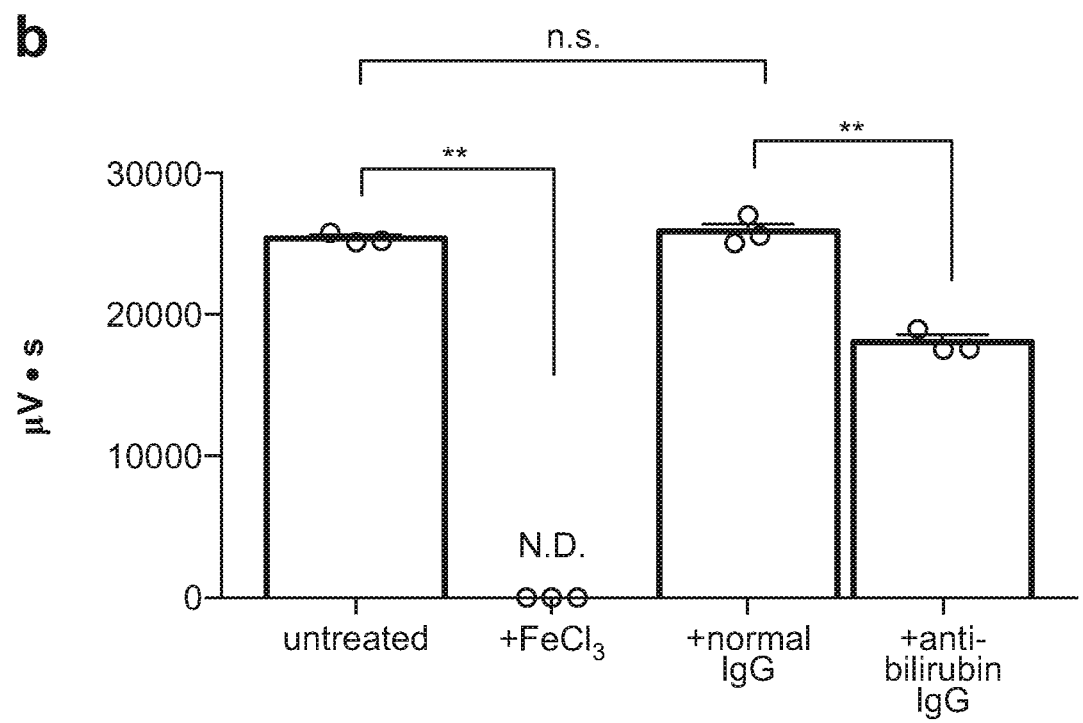

Plasma from four patients suffering from various conditions that result in hyperbilirubinemia (FIG. 26F) was isolated. All four patients' plasma evoked itch in WT animals (FIG. 26G). When injected into A1−/− animals, each patient's plasma elicited less pruritus (FIG. 26G). To assess whether removing bilirubin from cholestatic plasma may be therapeutic, bilirubin was depleted by selective oxidation or an anti-bilirubin antibody and then re-evaluated its pruritic capacity. Removal of bilirubin was verified by both HPLC and UV-visible derivative spectroscopy (FIG. 35A-35B). Injecting WT mice with plasma from Patient #1 after treating with $FeCl_3$ or a bilirubin antibody resulted in less pruritus compared to untreated plasma and normal IgG-treated patient plasma (FIG. 26H-26I).

Example 17

Various pathologic conditions result in jaundice, a yellowing of the skin due to a buildup of bilirubin. Patients with jaundice commonly report experiencing an intense non-histaminergic itch[1-3]. Despite this association, the pruritogenic capacity of bilirubin itself has not been explored, and no bilirubin receptor has been identified. Herein it was demonstrated that pathophysiologic levels of bilirubin excite peripheral itch sensory neurons and elicit pruritus through Mrgprs, a family of G-protein coupled receptors expressed in primary sensory neurons[4]. Bilirubin binds and activates two previously uncharacterized Mrgprs, mouse MRGPRA1 and human MRGPRX4. In two mouse models of pathologic hyperbilirubinemias, it was shown that genetic deletion of either Mrgpra1 or BVR, the bilirubin-producing enzyme, attenuates itch. Similarly, plasma isolated from hyperbilirubinemic patients evoked itch in wild-type animals but not Mrgpra1−/− animals. Removing bilirubin decreased the pruritogenic capacity of patient plasma. Based on these data, targeting MRGPRs is a promising strategy for alleviating jaundice-associated itch To date, there are no known cell surface receptors for bilirubin. The results herein demonstrated that bilirubin might be inappropriately overlooked as an inert biomarker in disease, as it likely evokes pruritus by binding and activating MRGPRs.

Figure 31H:
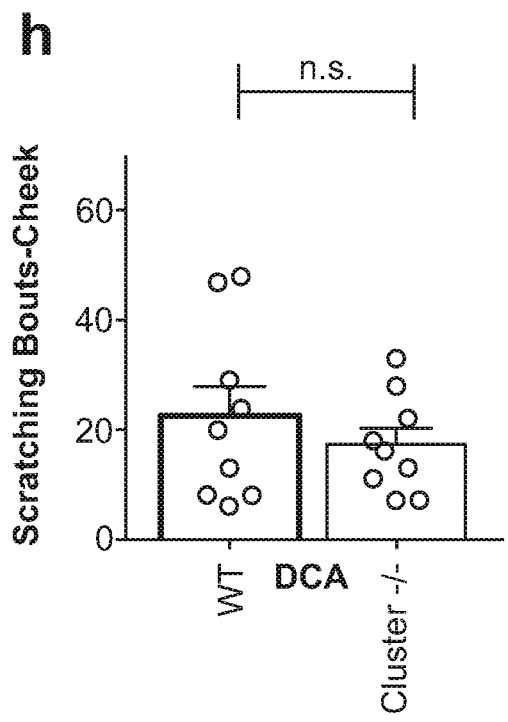
Figure 31I:
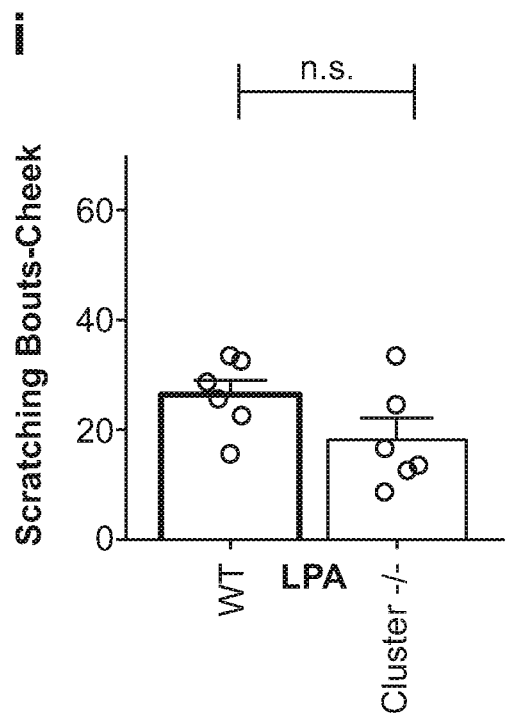
Figure 31J:
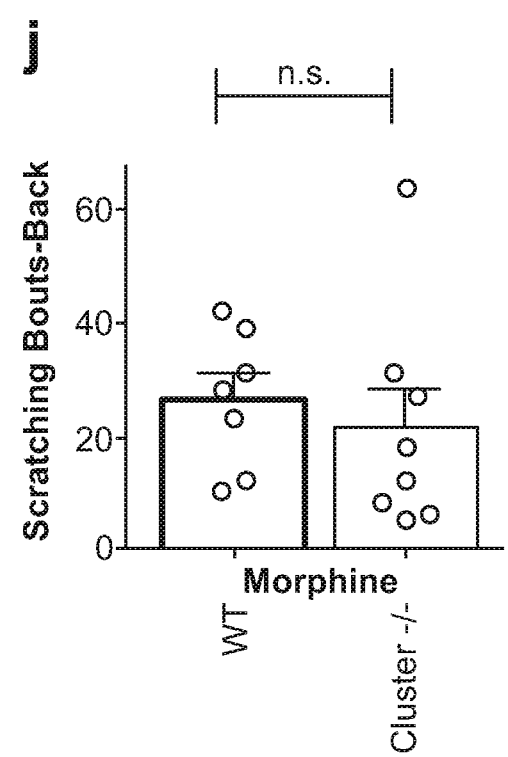
Figure 31K:
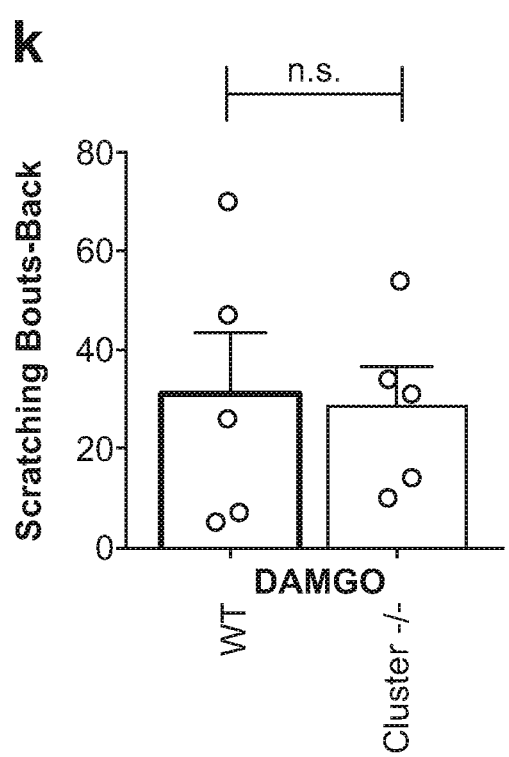

Not every patient who suffers from cholestatic pruritus is jaundiced, suggesting that bilirubin is likely one of several pruritogens present in these patients suffering from cholestatic pruritus. Other responsible pruritogens likely include bile acids, endogenous opioids, and LPA, which may act through non-Mrgpr mechanisms (FIG. 31H-3K). Additionally, not every patient with jaundice experiences itch. For example, patients with Dubin-Johnson syndrome, an autosomal recessive disorder involving mutations in the bilirubin transporter ABCC2, have increased serum conjugated bilirubin yet rarely complain of pruritus[41]. There are several reasons why these patients and other patients with jaundice may not experience pruritus. Because bilirubin is a lipophilic molecule that is strongly bound by serum albumin, incongruences between total bilirubin levels in serum versus levels in tissue likely exist. Notably, one of the best predictive metrics for cholestatic pruritus is the Mayo risk score, which employs both serum bilirubin and albumin levels[12]. Additionally, serum bilirubin in these non-pruritic jaundice disorders is significantly lower than serum bilirubin levels in pruritic jaundice[41]. In patients with primary biliary cholangitis, typical serum values of total bilirubin are roughly 2-3 fold higher than in patients with Dubin-Johnson syndrome, suggesting that patients with non-pruritic jaundice likely do not have sufficient levels of bilirubin to induce pruritus[41]. Moreover, most bilirubin is likely bound to albumin and other serum proteins in patients with isolated hyperbilirubinemia, thereby precluding bilirubin from entering the skin or interacting with receptors present on sensory nerves[13,42,43]. Notwithstanding these questions, the results suggested that blocking MRGPRX4 may offer relief to those suffering from jaundice-associated pruritus.

References for Examples 12-17 are Listed Below

1. Bassari, R. Jaundice associated pruritus: A review of pathophysiology and treatment. *World J. Gastroenterol.* 21, 1404-11 (2015).
2. Kremer, A. E., Elferink, R. P. J. O. & Beuers, U. Pathophysiology and current management of pruritus in liver disease. *Clin Res Hepatol Gastroenterol* 35, 89-97 (2011).
3. Carstens, E., Akiyama, T. & Bergasa, N. V. Pruritus of Cholestasis. (2014).
4. Dong, X., Han, S.-K., Zylka, M. J., Simon, M. I. & Anderson, D. J. A Diverse Family of GPCRs Expressed in Specific Subsets of Nociceptive Sensory Neurons. *Cell* 106, 619-632 (2001).
5. LaMotte, R. H., Dong, X. & Ringkamp, M. Sensory neurons and circuits mediating itch. *Nature Publishing Group* 15, 19-31 (2014).
6. Bautista, D. M., Wilson, S. R. & Hoon, M. A. Why we scratch an itch: the molecules, cells and circuits of itch. *Nat. Neurosci.* 17, 175-182 (2014).
7. Yosipovitch, G. & Bernhard, J. D. Clinical practice. Chronic pruritus. *N. Engl. J. Med.* 368, 1625-1634 (2013).
8. Ikoma, A., Steinhoff, M., Ständer, S., Yosipovitch, G. & Schmelz, M. The neurobiology of itch. *Nat. Rev. Neurosci.* 7, 535-547 (2006).
9. Baranano, D. E., Rao, M., Ferris, C. D. & Snyder, S. H. Biliverdin reductase: A major physiologic cytoprotectant. *Proc. Natl. Acad. Sci. U.S.A.* 99, 16093-16098 (2002).
10. Dore, S. et al. Bilirubin, formed by activation of heme oxygenase-2, protects neurons against oxidative stress injury. *Proc. Natl. Acad. Sci. U.S.A.* 96, 2445-2450 (1999).
11. Clark, J. E. et al. Heme oxygenase-1-derived bilirubin ameliorates postischemic myocardial dysfunction. *Am. J. Physiol. Heart Circ. Physiol.* 278, H643-H651 (2000).
12. Talwalkar, J. A., Souto, E., Jorgensen, R. A. & Lindor, K. D. Natural history of pruritus in primary biliary cirrhosis. *Clin. Gastroenterol. Hepatol.* 1, 297-302 (2003).
13. Jacobsen, J. & Broderson, R. Albumin-bilirubin binding mechanism. *J Biol Chem* 258, 6319-6326 (1983).
14. Breaven, G. H., D'Albis, A. & Gratzer, W. B. The interaction of bilirubin with human serum albumin. *Eur. J. Biochem.* 33, 500-509 (1973).
15. Griffiths, W. C., Diamond, I. & Dextraze, P. The albumin binding of unconjugated bilirubin in serum. *Clin. Biochem.* 8, 254-260 (1975).
16. Shimada, S. G. & LaMotte, R. H. Behavioral differentiation between itch and pain in mouse. *Pain* 139, 681-687 (2008).
17. Hohenberg, P. & Kohn, W. Inhomogeneous Electron Gas. *Physical Review B* 136, B864-+ (1964).
18. Kohn, W. & Sham, L. J. Self-Consistent Equations Including Exchange and Correlation Effects. *Physical Review* 140, 1133-& (1965).
19. Becke, A. D. Density-Functional Thermochemistry. 3. the Role of Exact Exchange. *Journal of Chemical Physics* 98, 5648-5652 (1993).
20. Stephens, P. J., Devlin, F. J., Chabalowski, C. F. & Frisch, M. J. Ab-Initio Calculation of Vibrational Absorption and Circular-Dichroism Spectra Using Density-Functional Force-Fields. *Journal of Physical Chemistry* 98, 11623-11627 (1994).

21. Liu, Q. et al. Sensory Neuron-Specific GPCR Mrgprs Are Itch Receptors Mediating Chloroquine-Induced Pruritus. *Cell* 139, 1353-1365 (2009).
22. Sikand, P., Dong, X. & LaMotte, R. H. BAMS-22 peptide produces itch and nociceptive sensations in humans independent of histamine release. *Journal of Neuroscience* 31, 7563-7567 (2011).
23. Liu, Q. et al. Mechanisms of itch evoked by β-alanine. *Journal of Neuroscience* 32, 14532-14537 (2012).
24. Han, L. et al. A subpopulation of nociceptors specifically linked to itch. *Nat. Neurosci.* 16, 174-182 (2012).
25. Lembo, P. M. C. et al. Proenkephalin A gene products activate a new family of sensory neuron—specific GPCRs. *Nat. Neurosci.* 5, 201-209 (2002).
26. Zhang, L. et al. Cloning and expression of MRG receptors in macaque, mouse, and human. *Brain Res. Mol. Brain Res.* 133, 187-197 (2005).
27. Duhr, S. & Braun, D. Why molecules move along a temperature gradient. *Proc. Natl. Acad. Sci. U.S.A.* 103, 19678-19682 (2006).
28. Jinek, M. et al. A Programmable Dual-RNA-Guided DNA Endonuclease in Adaptive Bacterial Immunity. *Science* 337, 816-821 (2012).
29. Flegel, C. et al. RNA-Seq Analysis of Human Trigeminal and Dorsal Root Ganglia with a Focus on Chemoreceptors. *PLoS ONE* 10, e0128951 (2015).
30. Eliakim, M., Eisner, M. & Ungar, H. Experimental intrahepatic obstructive jaundice following ingestion of alphanaphthyl-iso-thiocyanate. *Bull Res Counc Isr Sect E Exp Med* 8E, 7-17 (1959).
31. Kremer, A. E., Martens, J., Kulik, W. & Rueff, F. Lysophosphatidic acid is a potential mediator of cholestatic pruritus. *Gastroenterology* (2010). doi:10.1053/j.gastro.2010.05.009
32. Alemi, F. et al. The TGR5 receptor mediates bile acid-induced itch and analgesia. *J. Clin. Invest.* 123, 1513-1530 (2013).
33. Bergasa, N. V. et al. A controlled trial of naloxone infusions for the pruritus of chronic cholestasis. *YGAST* 102, 544-549 (1992).
34. Bergasa, N. V. et al. Open-label trial of oral nalmefene therapy for the pruritus of cholestasis. *Hepatology* 27, 679-684 (1998).
35. Thornton, J. R. & Losowsky, M. S. Methionine enkephalin is increased in plasma in acute liver disease and is present in bile and urine. *J. Hepatol.* 8, 53-59 (1989).
36. Thornton, J. R. & Losowsky, M. S. Plasma leucine enkephalin is increased in liver disease. *Gut* 30, 1392-1395 (1989).
37. Kutty, R. K. & Maines, M. D. Purification and characterization of biliverdin reductase from rat liver. *J. Biol. Chem.* 256, 3956-3962 (1981).
38. Laupacis, A., Keown, P. A., Ulan, R. A., Sinclair, N. R. & Stiller, C. R. Hyperbilirubinaemia and cyclosporin A levels. *Lancet* 2, 1426-1427 (1981).
39. Azimi, E. et al. Dual action of neurokinin-1 antagonists on Mas-related GPCRs. *JCI Insight* 1, e89362 (2016).
40. Hegade, V. S. et al. The safety and efficacy of nasobiliary drainage in the treatment of refractory cholestatic pruritus: a multicentre European study. *Aliment. Pharmacol. Ther.* 43, 294-302 (2016).
41. Levitt, D. G. & Levitt, M. D. Quantitative assessment of the multiple processes responsible for bilirubin homeostasis in health and disease. *Clin Exp Gastroenterol* 7, 307-328 (2014).
42. Kozaki, N. et al. Significance of serum delta-bilirubin in patients with obstructive jaundice. *J. Surg. Res.* 79, 61-65 (1998).
43. Kalir, T., Catanese, G. S. & Clejan, S. Clinical Diagnostic Utility of Delta Bilirubin. *Lab Med* 21, 159-162 (1990).
44. Liu, Q. et al. Molecular genetic visualization of a rare subset of unmyelinated sensory neurons that may detect gentle touch. *Nat. Neurosci.* 10, 946-948 (2007).
45. Vasavda, C., Zaccor, N. W., Scherer, P. C., Sumner, C. J. & Snyder, S. H. Measuring G-protein-coupled Receptor Signaling via Radio-labeled GTP Binding. *J Vis Exp* (2017). doi:10.3791/55561
46. McNeil, B. D. et al. Identification of a mast-cell-specific receptor crucial for pseudo-allergic drug reactions. *Nature* 519, 237-241 (2015).
47. Dolphin, D. *The Porphyrins: Biochemistry, part A-B.* (Academic Pr, 1978).

Example 18: MrgprX4 Inverse Agonists and Antagonists

Intracellular inositol phosphate levels were determined using a 384-well homogenous time-resolved fluorescence assay (HTRF IP-One®, CisBio International, Bagnols/Ceze, France, Cat #62IPAPEJ) as described by the manufacturer's one-step protocol. Briefly, HEK293 cells stably expressing recombinant human MrgprX4 were harvested and suspended in phenol-red free OptiMEM (ThermoFisher) and plated into 384-well assay plates (Perkin Elmer, Proxiplate-Plus® Cat #6008280) at 15,000 cells/well in a volume of 10 µL/well. These cell plates were then incubated overnight at 37° C. in a humidified $CO_2$ incubator. Test compounds were dissolved in DMSO and were further diluted in Assay Buffer (Tris.HCl 40 mM, NaCl 300 mM, LiCl 350 mM, pH 8) and added to the cells (2 µL addition, final assay concentration typically 10 µM). In this configuration, the assay can detect agonists and inverse agonists. For detection of antagonists, test compound addition was followed by addition of bilirubin (2 µL addition, final assay concentration 100 µM). Regardless of the assay format (agonist/inverse agonist vs. antagonist) plates were then incubated for 1 h, at 37° C., followed by 30 minutes at room temperature. Lysis/detection reagents (6 uL/well) were then added and plates incubated for 1 h at room temperature before reading on an HTRF compatible reader such as a Perkin Elmer EnVision® or BMG Pherastar®.

The Inverse Agonist and Antagonist Activity of representative compounds against the MrgprX4 receptor are provided in Table 1 below. The compounds of Table 1 were identified by screening a commercially available small molecule library by the techniques disclosed above. With respect to MrgprX4 inverse agonist activity: "++++" denotes an activity of at least 3 standard deviations below baseline; and "+++" denotes an activity of from 2 standard deviations to less than 3 standard deviations below baseline. With respect to MrgprX4 antagonist activity: "++++" denotes a blockade of bilirubin induced signal of at least 85%; and "+++" denotes a blockade of bilirubin induced signal of from 70% to less than 85%.

TABLE 1

| Cmpd. No. | Structure | Calculated m/z | Inverse Agonist Activity | Antagonist Activity |
|---|---|---|---|---|
| | MrgprX4 Modulators | | | |
| 1 | 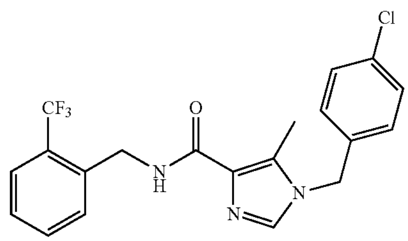 [SMILES: Cc1c(C(=O)NCc2ccccc2C(F)(F)F)ncn1Cc1ccc(Cl)cc1] | 407.10 | ++++ | ++++ |
| 2 | 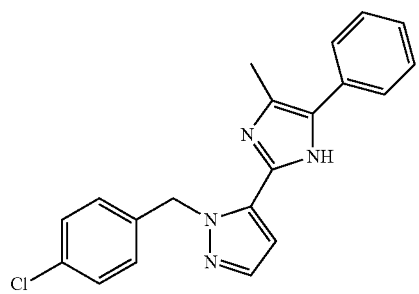 [SMILES: Cc1nc(-c2ccnn2Cc2ccc(Cl)cc2)[nH]c1-c1ccccc1] | 348.11 | ++++ | ++++ |
| 3 | 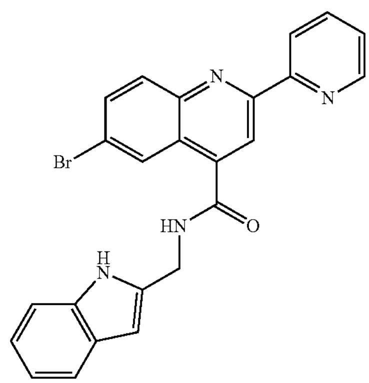 [SMILES: O=C(NCc1cc2ccccc2[nH]1)c1cc(-c2ccccn2)nc2ccc(Br)cc12] | 456.06 | +++ | ++++ |
| 4 | 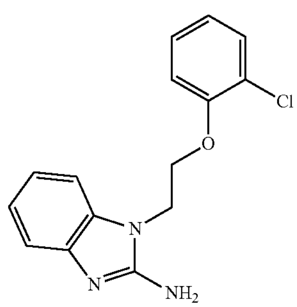 [SMILES: Nc1nc2ccccc2n1CCOc1ccccc1Cl] | 287.08 | +++ | +++ |

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

We claim:

1. A method for treating a subject suffering from a chronic itch condition, comprising: administering to the subject a small molecule MrgprX4 antagonist.

2. The method of claim 1, wherein the chronic itch condition is pruritus.

3. The method of claim 1, wherein the chronic itch condition is cholestatic pruritus.

* * * * *

```
                              SEQUENCE LISTING

<160> NUMBER OF SEQ ID NOS: 8

<210> SEQ ID NO 1
<211> LENGTH: 20
<212> TYPE: DNA
<213> ORGANISM: Homo sapiens

<400> SEQUENCE: 1
cagagatgat acagctggtg                                                 20

<210> SEQ ID NO 2
<211> LENGTH: 20
<212> TYPE: DNA
<213> ORGANISM: Homo sapiens

<400> SEQUENCE: 2
gactgggatg aaatctgacg                                                 20

<210> SEQ ID NO 3
<211> LENGTH: 23
<212> TYPE: DNA
<213> ORGANISM: Mus musculus

<400> SEQUENCE: 3
ttcccagcag cacctgtgca ggg                                             23

<210> SEQ ID NO 4
<211> LENGTH: 47
<212> TYPE: DNA
<213> ORGANISM: Mus musculus

<400> SEQUENCE: 4
gcagggtttc tagccctaaa cacatcggcc tcgccaacag cacccac                   47

<210> SEQ ID NO 5
<211> LENGTH: 45
<212> TYPE: DNA
<213> ORGANISM: Mus musculus

<400> SEQUENCE: 5
gcagggtttc tagccctaaa catcggcctc gccaacagca cccac                     45

<210> SEQ ID NO 6
<211> LENGTH: 75
<212> TYPE: DNA
<213> ORGANISM: Mus musculus

<400> SEQUENCE: 6 atggggaaa gcagcacctg tgcagggttt ctagccctaa acatcggcct cgccaacagc      60
acccacaaca actaa                                                      75

<210> SEQ ID NO 7
<211> LENGTH: 75
<212> TYPE: DNA
<213> ORGANISM: Mus musculus

<400> SEQUENCE: 7 taccccttt cgtcgtggac acgtcccaaa gatcgggatt tgtagccgga gcggttgtcg      60
```

```
tgggtgttgt tgatt                                                    75
```

<210> SEQ ID NO 8
<211> LENGTH: 24
<212> TYPE: PRT
<213> ORGANISM: Mus musculus

<400> SEQUENCE: 8

```
Met Gly Glu Ser Ser Thr Cys Ala Gly Phe Leu Ala Leu Asn Ile Gly
1               5                   10                  15

Leu Ala Asn Ser Thr His Asn Asn
            20
```